US012338242B2

(12) United States Patent
Masse

(10) Patent No.: US 12,338,242 B2
(45) Date of Patent: Jun. 24, 2025

(54) TYK2 INHIBITORS AND USES THEREOF

(71) Applicant: TAKEDA PHARMACEUTICAL COMPANY LIMITED, Osaka (JP)

(72) Inventor: Craig E. Masse, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 35 days.

(21) Appl. No.: 17/448,482

(22) Filed: Sep. 22, 2021

(65) Prior Publication Data
US 2022/0073528 A1 Mar. 10, 2022

Related U.S. Application Data

(62) Division of application No. 16/750,610, filed on Jan. 23, 2020, now Pat. No. 11,174,264.

(60) Provisional application No. 62/880,754, filed on Jul. 31, 2019, provisional application No. 62/795,735, filed on Jan. 23, 2019.

(51) Int. Cl.
C07D 487/04 (2006.01)
C07D 519/00 (2006.01)

(52) U.S. Cl.
CPC ......... C07D 487/04 (2013.01); C07D 519/00 (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,552,065 B2 | 4/2003 | Remiszewski et al. | |
| 7,390,799 B2 | 6/2008 | Bruncko et al. | |
| 8,138,347 B2 | 3/2012 | Knight et al. | |
| 2018/0155349 A1 | 6/2018 | Greenwood et al. | |
| 2018/0325899 A1 | 11/2018 | Weinstein et al. | |
| 2020/0231594 A1 | 7/2020 | Masse | |

FOREIGN PATENT DOCUMENTS

| | | |
|---|---|---|
| JP | 2009-509961 A | 3/2009 |
| WO | 2001042246 A2 | 6/2001 |
| WO | 2002088112 A1 | 11/2002 |
| WO | 2003063794 A2 | 8/2003 |
| WO | 2004019973 A1 | 3/2004 |
| WO | 2004089925 A1 | 10/2004 |
| WO | 2004106328 A1 | 12/2004 |
| WO | 2005007623 A2 | 1/2005 |
| WO | 2005113554 A2 | 12/2005 |
| WO | 2006078846 A1 | 7/2006 |
| WO | 2006122806 A2 | 11/2006 |
| WO | 2007016176 A2 | 2/2007 |
| WO | 2007038314 A2 | 4/2007 |
| WO | 2007044729 A2 | 4/2007 |
| WO | 2007053452 A1 | 5/2007 |
| WO | 2007070514 A1 | 6/2007 |
| WO | 2007084786 A1 | 7/2007 |
| WO | 2007129161 A2 | 11/2007 |
| WO | 2008039218 A2 | 4/2008 |
| WO | 2008109943 A1 | 9/2008 |
| WO | 2008118802 A1 | 10/2008 |
| WO | 2009100375 A1 | 8/2009 |
| WO | 2009114512 A1 | 9/2009 |
| WO | 2011090760 A1 | 7/2011 |
| WO | 2014074660 A1 | 5/2014 |
| WO | 2014074661 A1 | 5/2014 |
| WO | 2015026574 A1 | 2/2015 |
| WO | 2015089143 A1 | 6/2015 |
| WO | 2015131080 A1 | 9/2015 |
| WO | 2017087590 A1 | 5/2017 |
| WO | 2018067432 A1 | 4/2018 |
| WO | 2018093968 A1 | 5/2018 |

OTHER PUBLICATIONS

Choy "Clinical significance of Janus Kinase inhibitor selectivity" Rheumatology 2018, pp. 1-10.*
Barnes "Kinases as Novel Therapeutic Targets in Asthma and Chronic Obstructive Pulmonary Disease" Pharmacological Reviews 68:788-815, Jul. 2016.*
Thoma "Selective inhibitors of the Janus kinase Jak3—Are they effective?" Bioorganic & Medicinal Chemistry Letters 24 (2014) 4617-462.*
Lin "A Novel Selective JAK2 Inhibitor Identified Using Pharmacological Interactions" Frontiers in Pharmacology Dec. 2018 | vol. 9 | Article 1379 pp. 1-14.*
O'Shea "Janus kinase Inhibitors in autoimmune diseases" Ann Rheum Dis. Apr. 2013 ; 72(0 2): ii111-ii115.*
Liang "Lead Optimization of a 4-Aminopyridine Benzamide Scaffold To Identify Potent, Selective, and Orally Bioavailable TYK2 Inhibitors" J. Med. Chem. 2013, 56, 4521-4536.*
Vardiman "The World Health Organization (WHO) classification of the myeloid neoplasms" Blood (2002), 100(7), 2292-2302.*
Pui "Treatment of Acute Lymphoblastic Leukemia" New England Journal of Medicine 2006, 354, 166-78.*
FS14 Myelofibrosis Facts | p. 1 Revised Apr. 2012, pp. 1-9.*
Ocana, A. "Preclinical development of molecular targeted agents for cancer" Nat. Rev. Clin. Oncol. 2011, 8, 200-209.*
Johnson, et al. "Relationships between drug activity in NCI preclinical in vitro and in vivo models and early clinical trials." British Journal of Cancer 2001, 84, 1424-1431.*

(Continued)

Primary Examiner — Alicia L Otton
(74) Attorney, Agent, or Firm — Honigman LLP; Lucy X. Yang; Jonathan P. O'Brien

(57) ABSTRACT

The present invention provides compounds, compositions thereof, and methods of using the same for the inhibition of TYK2, and the treatment of TYK2-mediated disorders.

19 Claims, No Drawings

(56) References Cited

OTHER PUBLICATIONS

Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Bacon et al., "Interleukin 12 (IL-12) induces tyrosine phosphorylation of Jak2 and Tyk2: differential use of Janus family kinases by IL-2 and IL-12," The Journal of Experimental Medicine, vol. 181, No. 1, Jan. 1995 (pp. 399-404).
Ban et al., "Replication analysis identifies TYK2 as a multiple sclerosis susceptibility factor," European Journal of Human Genetics, vol. 17, No. 10, Oct. 2009 (pp. 1309-1313).
Berge et al., "Pharmaceutical salts," Journal Pharmaceutical Sciences, vol. 66, No. 1, Jan. 1977 (pp. 1-19).
Cho et al., "Genomics and the multifactorial nature of human auto-immune disease," The New England Journal Medicine, vol. 365, No. 17, Oct. 2011 (pp. 1612-1623).
Cortes et al., "Identification of multiple risk variants for ankylosing spondylitis through high-density genotyping of immune-related loci," Nature Genetics, vol. 45, No. 7, Jul. 2013 (pp. 730-738).
Duerr et al., "A Genome-Wide Association Study Identifies IL23R as an Inflammatory Bowel Disease Gene," Science, vol. 314, No. 5804, Dec. 2006 (pp. 1461-1463).
Finbloom et al., "IL-10 induces the tyrosine phosphorylation of Tyk2 and Jak1 and the differential assembly of Stat1 and Stat3 complexes in human T cells and monocytes," Journal immunology, vol. 155, No. 3, Aug. 1995 (pp. 1079-1090).
Fontan et al. "Discovering What Makes STAT Signaling TYK in T-ALL," Cancer Discovery, vol. 3, No. 5, May 2013 (pp. 494-496).
Graham et al., "Association of NCF2, IKZF1, IRF8, IFIH1, and TYK2 with Systemic Lupus Erythematosus," PLoS Genetics, vol. 7, No. 10, Oct. 2011 (9 pages).
Harel et al., "Pharmacologic inhibition of JAK-STAT signaling promotes hair growth," Science Advances, vol. 1, No. 9, Oct. 2015 (12 pages).
International Search Report and Written Opinion for Application No. PCT/US2020/014746, dated Apr. 14, 2020 (12 pages).
Ishizaki et al., "Tyk2 deficiency protects joints against destruction in anti-type II collagen antibody-induced arthritis in mice," International Immunology, vol. 23, No. 9, Sep. 2011 (pp. 575-582).
Ishizaki et al., "Tyk2 is a therapeutic target for psoriasis-like skin inflammation," International Immunology, vol. 26, No. 5, Dec. 2013 (pp. 257-267).
Moslin et al., "Identification of imidazo[1,2-b]pyridazine TYK2 pseudokinase ligands as potent and selective allosteric inhibitors of TYK2 signalling," Med. Chem. Commun., vol. 8, 2017, pp. 700-712.
Oyamada et al., "Tyrosine Kinase 2 Plays Critical Roles in the Pathogenic CD4 T Cell Responses for the Development of Experimental Autoimmune Encephalomyelitis," Journal of Immunology, vol. 183, No. 11, Dec. 2009 (pp. 7539-7546).
Parham et al., "A receptor for the heterodimeric cytokine IL-23 is composed of IL-12Rß1 and a novel cytokine receptor subunit, IL-23R," Journal of Immunology, vol. 168, No. 11, Jun. 2002 (pp. 5699-5708).
Ramirez et al., "Defining Causative Factors Contributing in the Activation of Hedgehog Signaling in Diffuse Large B-Cell Lymphoma," Leukemia Research, vol. 36, No. 10, Oct. 2012 (pp. 1267-1273).
Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).
Rostovtsev et al., "A Stepwise Huisgen Cycloaddition Process: Copper(I)-Catalyzed Regioselective "Ligation" of Azides and Terminal Alkynes," Angew. Chem. Int. Ed., vol. 41, No. 14, Jul. 2002 (pp. 2596-2599).
Sanda et al. "TYK2-STAT1-BCL2 Pathway Dependence in T-Cell Acute Lymphoblastic Leukemia," Cancer Discovery, vol. 3, No. 5, May 2013 (pp. 564-577).
Sigurdsson et al., "Polymorphisms in the Tyrosine Kinase 2 and Interferon Regulatory Factor 5 Genes Are Associated with Systemic Lupis Erythematosus," American Journal of Human Genetics, vol. 76, No. 3, Mar. 2005 (pp. 528-537).
Simma et al., "Identification of an Indispensable Role for Tyrosine Kinase 2 in CTL-Mediated Tumor Surveillance," Cancer Research, vol. 69, No. 1, Jan. 2009 (pp. 203-211).
Stahl et al., "Association and activation of Jak-Tyk kinases by CNTF-LIF-OSM-IL-6ß receptor components," Science, vol. 263, No. 5143, Jan. 1994 (pp. 92-95).
Strange et al., "A genome-wide association study identifies new psoriasis susceptibility loci and an interaction between HLA-C and ERAP1," Nature Genetics, vol. 42, No. 11, Nov. 2010 (pp. 985-990).
STN Registry database entry for CAS RN 1797511-85-3, Entered STN, Jul. 8, 2015, Accessed Feb. 13, 2021.
Sun et al., "Carbohydrate and protein immobilization onto solid surfaces by sequential Diels-Alder and azide-alkyne cycloadditions," Bioconjugate Chemistry, vol. 17, No. 1, Jan.-Feb. 2006 (52-57).
Velasquez et al., "A protein kinase in the interferon a/ß signaling pathway," Cell, vol. 70, No. 2, Jul. 1992 (pp. 313-322).
Wan et al. "Tyk/STAT3 Signaling Mediates ß-Amyloid-Induced Neuronal Cell Death: Implications in Alzheimer's Disease," Journal of Neuroscience, vol. 30, No. 20, May 2010 (pp. 6873-6881).
Welham et al., "Interleukin-13 signal transduction in lymphohemopoietic cells: similarities and differences in signal transduction with interleukin-4 and insulin," The Journal of Biological chemistry, vol. 270, No. 20, May 1995 (pp. 12286-12296).
Xing et al., "Alopecia areata is driven by cytotoxic T lymphocytes and is reversed by JAK inhibition," Nature Medicine, vol. 20, No. 9, Sep. 2014 (pp. 1043-1049).
Zhang et al., "Docking protein Gab2 regulates mucin expression and goblet cell hyperplasia through TYK2/STAT6 pathway," The FASEB Journal, vol. 26, No. 11, Nov. 2012 (pp. 4603-4613).

* cited by examiner

TYK2 INHIBITORS AND USES THEREOF

CROSS-REFERENCE TO RELATED APPLICATION

This application is a divisional of U.S. application Ser. No. 16/750,610, filed Jan. 23, 2020, which claims the benefit under 35 U.S.C. § 119 (e) of U.S. Provisional Application No. 62/795,735, filed Jan. 23, 2019 and U.S. Provisional Application No. 62/880,754, filed Jul. 31, 2019, the contents of each of which is incorporated herein in its entirety by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

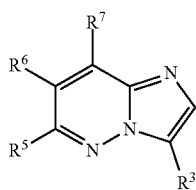

or a pharmaceutically acceptable salt thereof, wherein each of $R^3$, $R^5$, $R^6$, and $R^7$ is as defined below and described in embodiments herein, both singly and in combination.

In some embodiments, the present invention provides a pharmaceutical composition comprising a compound of formula I, and a pharmaceutically acceptable carrier, adjuvant, or diluent.

In some embodiments, the present invention provides a method of treating a TYK2-mediated disease, disorder, or condition, comprising administering to a patient in need thereof a a compound of formula I or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

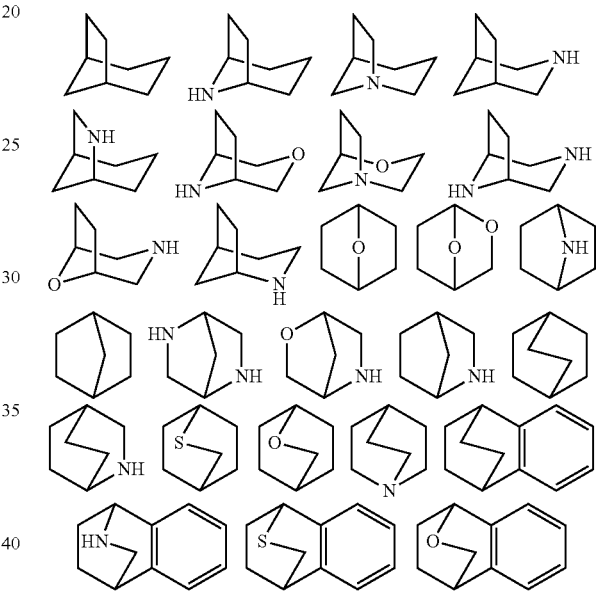

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3.

A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5-to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^°$; $-(CH_2)_{0-4}OR^°$; $-O(CH_2)_{0-4}R^°$, $-O-(CH_2)_{0-4}C(O)OR^°$; $-(CH_2)_{0-4}CH(OR^°)_2$; $-(CH_2)_{0-4}SR^°$; $-(CH_2)_{0-4}Ph$, which may be substituted with $R^°$; $-(CH_2)_{0-4}O(CH_2)_{0-1}Ph$ which may be substituted with $R^°$; $-CH=CHPh$, which may be substituted with $R^°$; $-(CH_2)_{0-4}O(CH_2)_{0-1}$-pyridyl which may be substituted with $R^°$; $-NO_2$; $-CN$; $-N_3$; $-(CH_2)_{0-4}N(R^°)_2$; $-(CH_2)_{0-4}N(R^°)C(O)R^°$; $-N(R^°)C(S)R^°$; $-(CH_2)_{0-4}N(R^°)C(O)NR^°_2$; $-N(R^°)C(S)NR^°_2$; $-(CH_2)_{0-4}N(R^°)C(O)OR^°$; $-N(R^°)N(R^°)C(O)R^°$; $-N(R^°)N(R^°)C(O)NR^°_2$; $-N(R^°N(R^°C(O)OR^°$; $-N(R^°)C(NR^°)N(R^°)_2$, $-(CH_2)_{0-4}C(O)R^°$; $-C(S)R^°$; $-(CH_2)_{0-4}C(O)OR^°$; $-(CH_2)_{0-4}C(O)SR^°$; $-(CH_2)_{0-4}C(O)OSiR^°_3$; $-(CH_2)_{0-4}OC(O)R^°$; $-OC(O)(CH_2)_{0-4}SR^°$; $-SC(S)SR^°$;

—(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, (haloR$^\bullet$), —(CH$_2$)$_{0-2}$OH, —(CH$_2$)$_{0-2}$R$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label," "fluorescent dye," and "fluorophore," as used herein, refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

In certain embodiments, the present invention provides a compound of formula I:

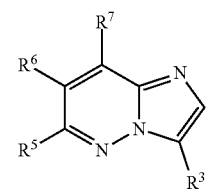

I or a pharmaceutically acceptable salt thereof, wherein:

$R^3$ is —C(O)NH$_2$, —C(O)NHR$^{3A}$, —C(O)N(R$^{3A}$)$_2$, —C(O)OR, —C(O)NHOR, or a 5-6 membered monocyclic heteroaryl ring having 1-4 heteroatoms independently selected from nitrogen, oxygen, and sulfur, wherein said ring is substituted with m instances of $R^{3B}$;

$R^5$ is hydrogen or -L$^1$-R$^{5A}$;

$R^6$ is hydrogen, $R^A$, or $R^B$;

or $R^5$ and $R^6$ are taken together with their intervening atoms to form a 4-7 membered partially unsaturated or heteroaryl ring having 0-3 heteroatoms independently selected from nitrogen, oxygen, and sulfur, wherein said ring is substituted by $R^{5A}$ and n instances of $R^C$;

$R^7$ is hydrogen, halogen, —NH$_2$, —NHR$^{7A}$, or —NHC(O)R$^{7A}$;

or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$;

$L^1$ is a covalent bond or a C$_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;

$R^{3A}$, $R^{3B}$, and $R^{7A}$ are each independently $R^B$, and are each substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur;

$R^{5A}$ and each instance of $R^{5B}$ are each independently $R^A$ or $R^B$, and are each substituted by r instances of $R^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently C$_{1-6}$ aliphatic, phenyl, a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring, a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4; provided that the compound is not

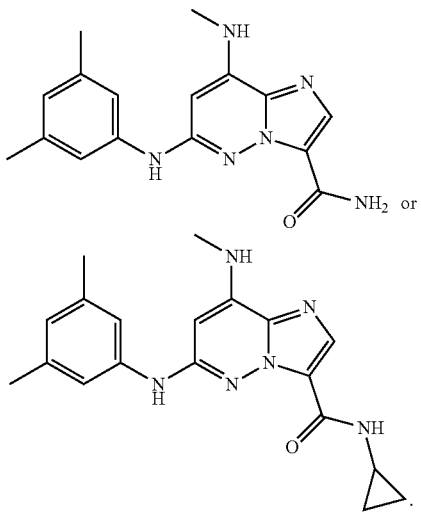

As defined generally above, $R^3$ is —C(O)NH$_2$, —C(O)NHR$^{3A}$, —C(O)N(R$^{3A}$)$_2$, —C(O)OR, —C(O)NOR, —C(O)NHOR, or a 5-6 membered monocyclic heteroaryl ring having 1-4 heteroatoms independently selected from nitrogen, oxygen, and sulfur, wherein said ring is substituted with m instances of $R^{3B}$. In some embodiments, $R^3$ is —C(O)NH$_2$, —C(O)NHR$^{3A}$, —C(O)N(R$^{3A}$)$_2$, or a 5-6 membered monocyclic heteroaryl ring having 1-4 heteroatoms independently selected from nitrogen, oxygen, and sulfur, wherein said ring is substituted with m instances of $R^{3B}$. In some embodiments, $R^3$ is —C(O)NH$_2$ or —C(O)NHR$^{3A}$. In some embodiments, $R^3$ is —C(O)NOR. In some embodiments, $R^3$ is —C(O)OR.

In some embodiments, $R^3$ is —C(O)N(R$^{3A}$)$_2$. In some embodiments, $R^3$ is —C(O)NHOR. In some embodiments, $R^3$ is a 5-6 membered monocyclic heteroaryl ring having 1-4 heteroatoms independently selected from nitrogen, oxygen, and sulfur, wherein said ring is substituted with m instances of $R^{3B}$.

In some embodiments, $R^3$ is —C(O)NH$_2$. In some embodiments, $R^3$ is —C(O)NHR$^{3A}$. In some embodiments, $R^3$ is —C(O)NHOR or —C(O)OR. In some embodiments, $R^3$ is —C(O)NH$_2$, —C(O)NHR$^{3A}$, —C(O)NHOR or —C(O)OR. In some embodiments, $R^3$ is —C(O)NH$_2$, —C(O)NHR$^{3A}$ or —C(O)NHOR.

In some embodiments, $R^3$ is selected from the following:

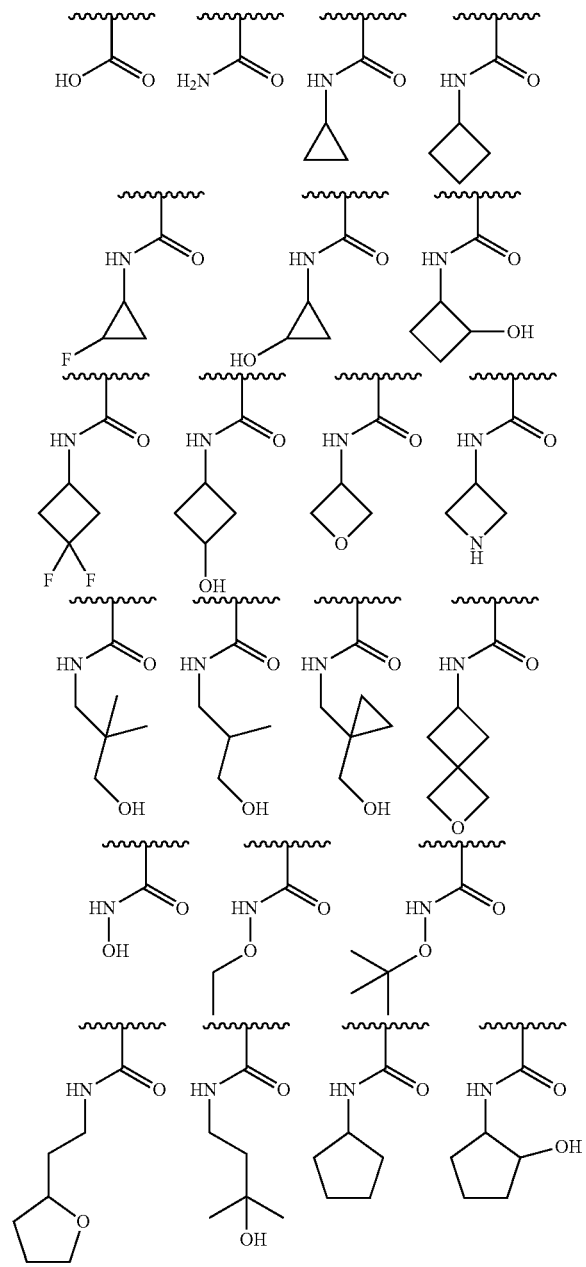

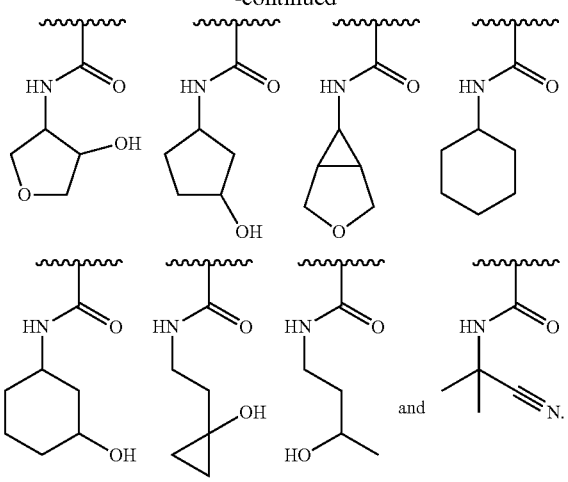

In some embodiments, $R^3$ is selected from the following:

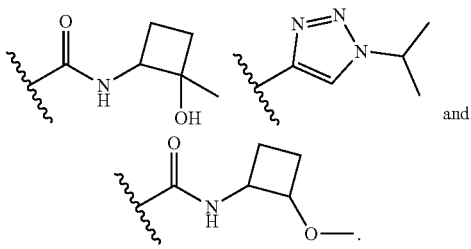

In some embodiments, $R^3$ is selected from the following:

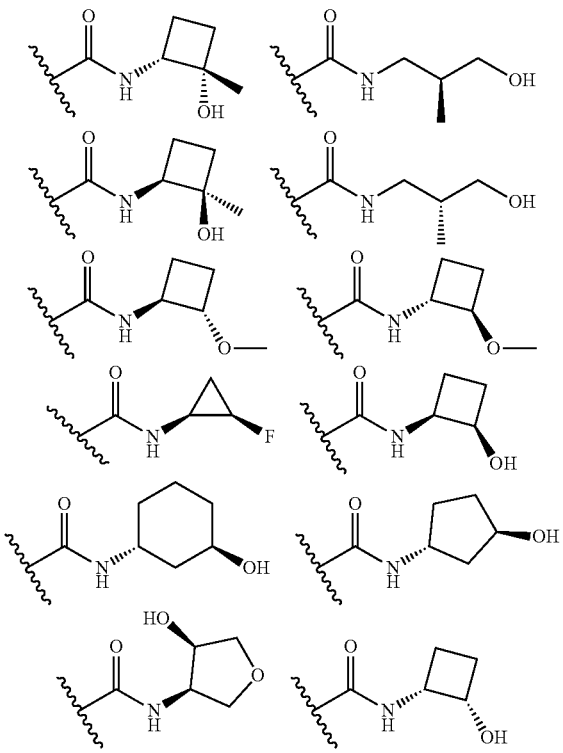

-continued
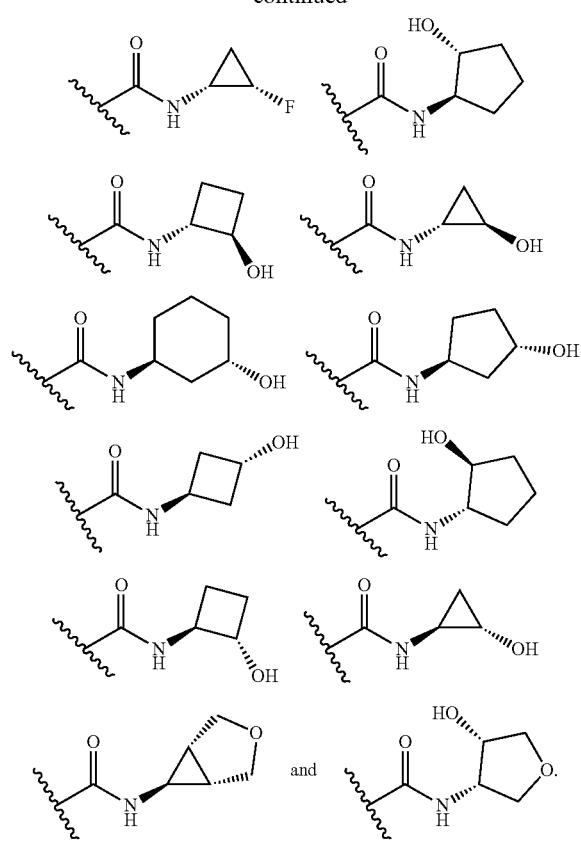
In some embodiments, R³ is selected from the following:
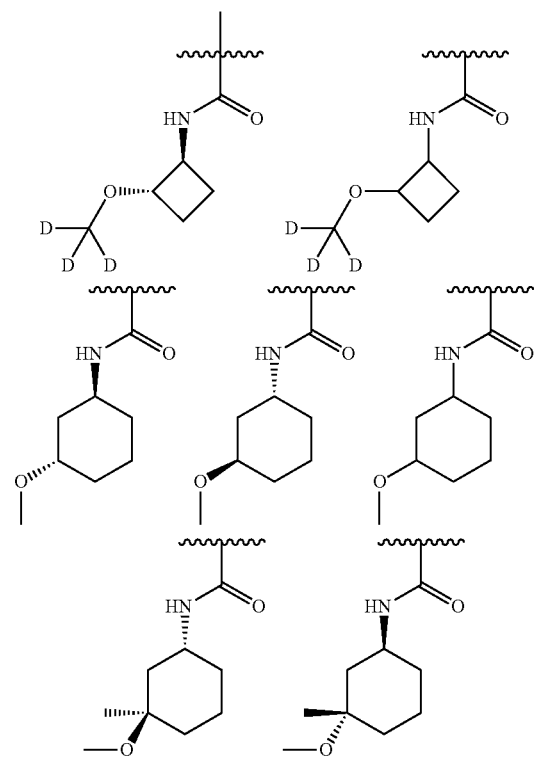
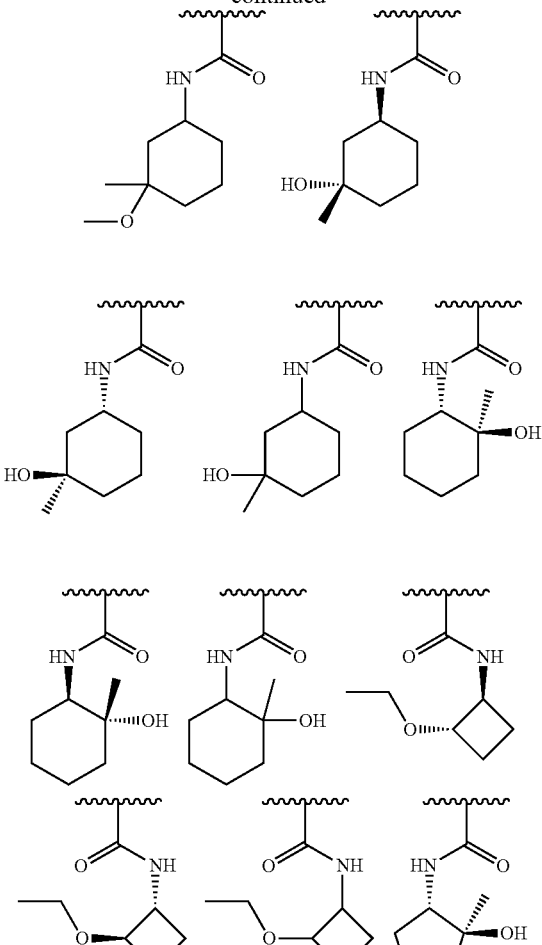

-continued

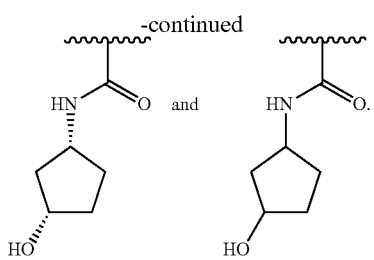

In some embodiments, $R^3$ is selected from those depicted in Table 1, below.

As defined generally above, $R^5$ is hydrogen, or -$L^1$-$R^{5A}$; or $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments, $R^5$ is hydrogen. In some embodiments, $R^5$ is -$L^1$-$R^{5A}$.

In some embodiments, $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments, $R^5$ is hydrogen or -$L^1$-$R^{5A}$.

In some embodiments, $R^5$ is selected from the following:

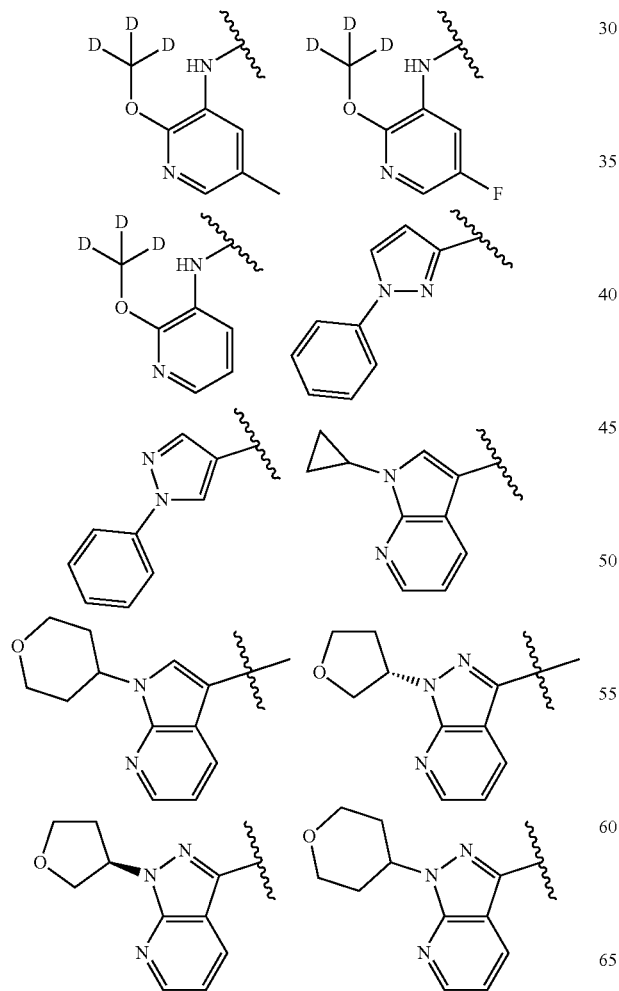

-continued

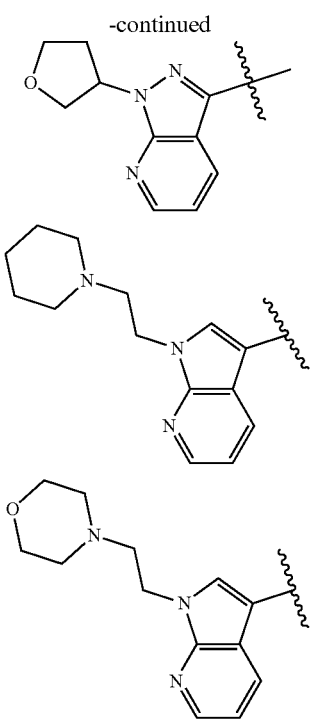

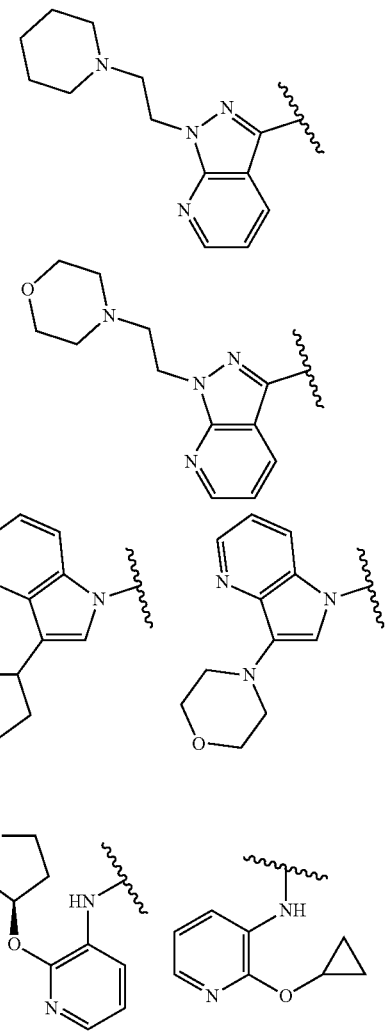

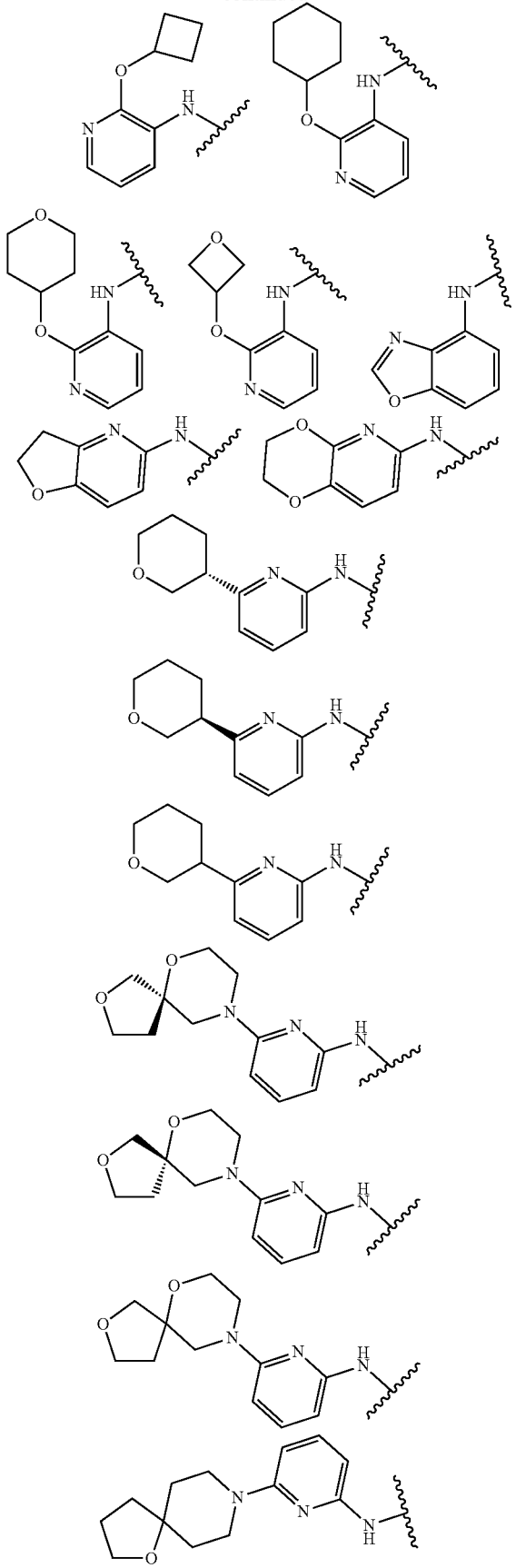
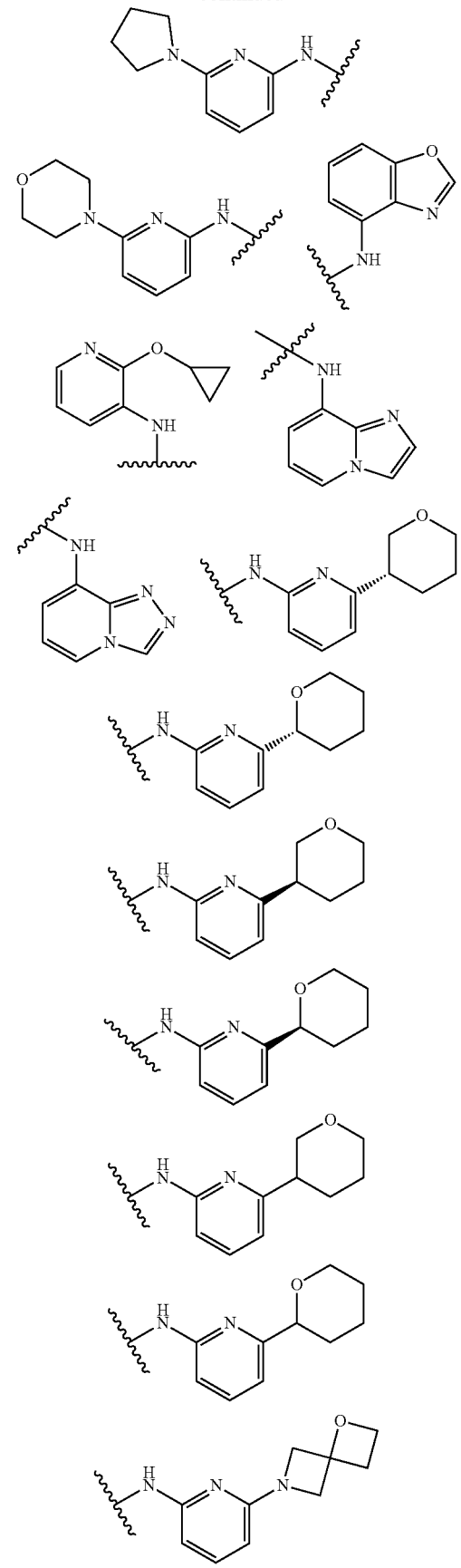

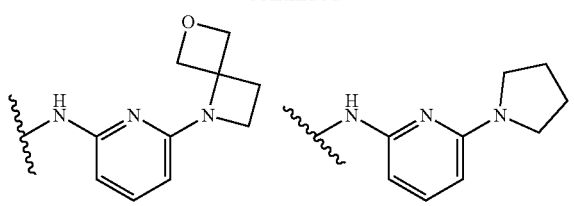
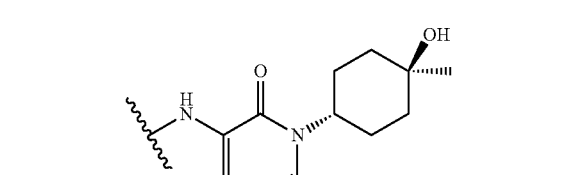
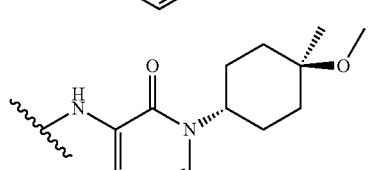
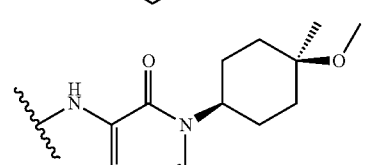
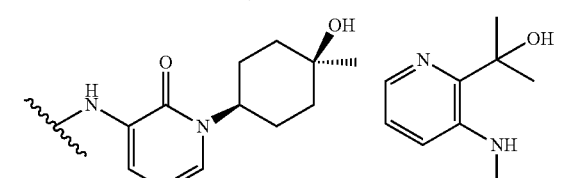
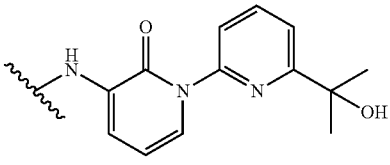
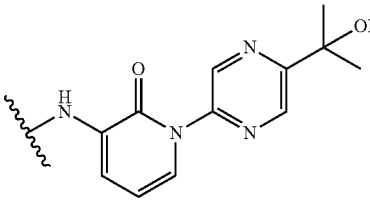
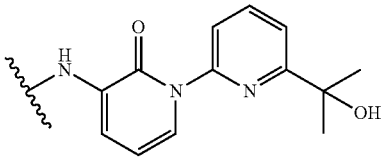
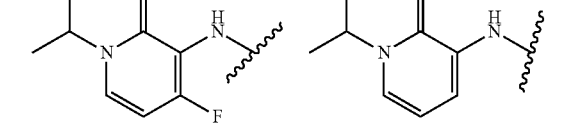
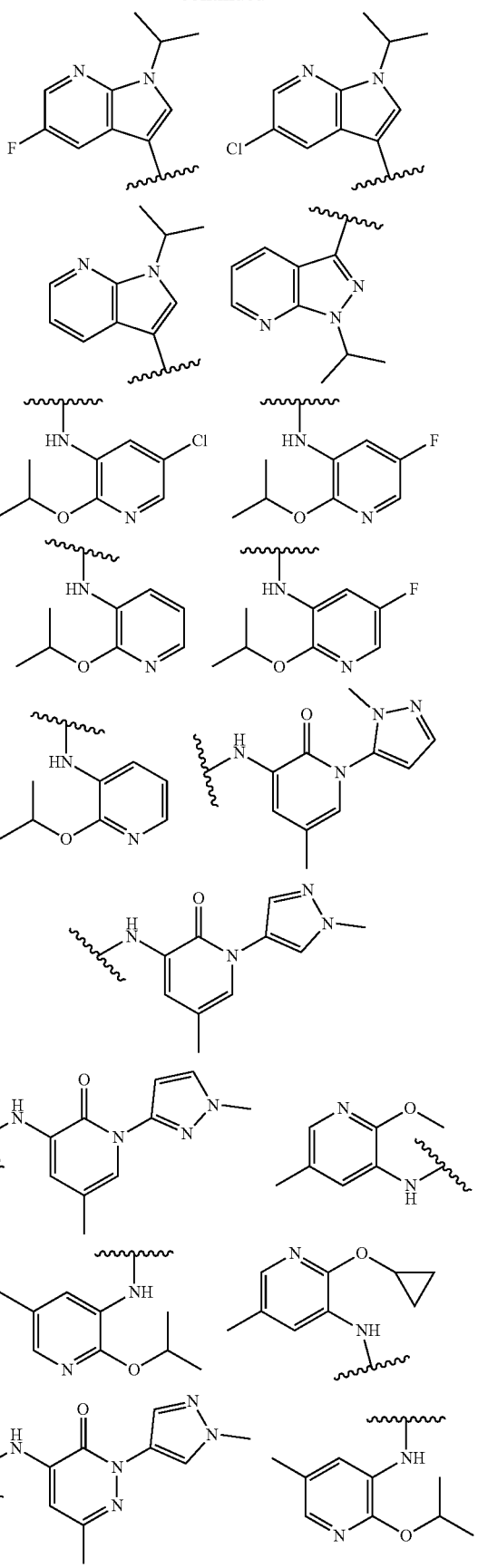

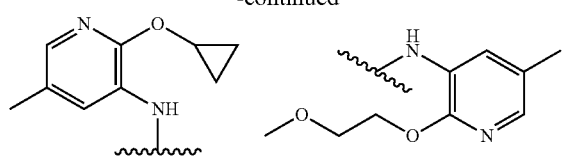
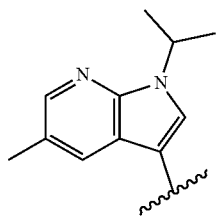
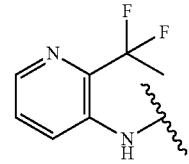
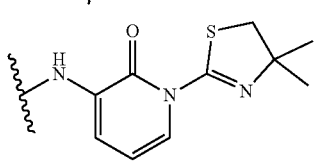
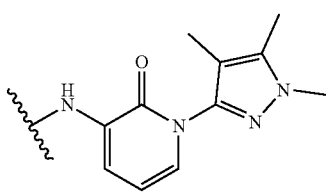
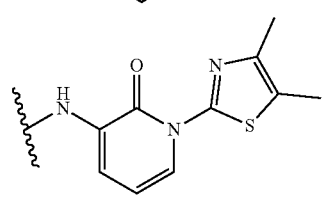
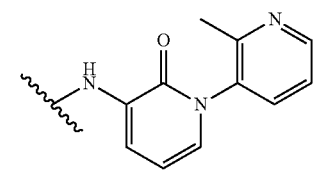
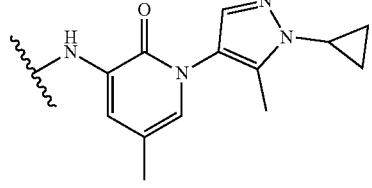
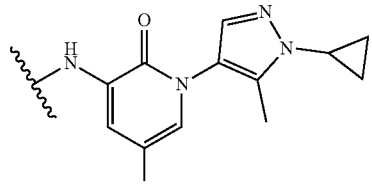
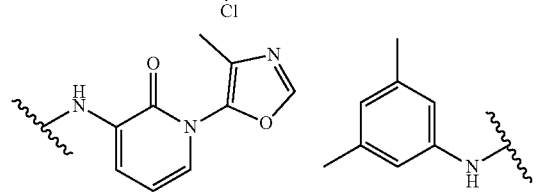
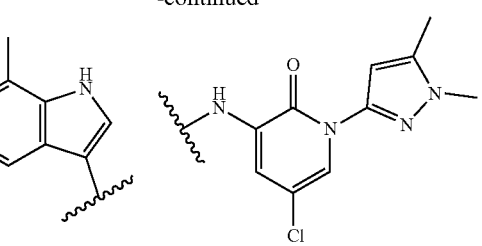
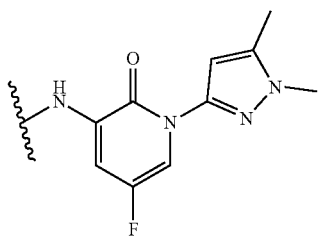
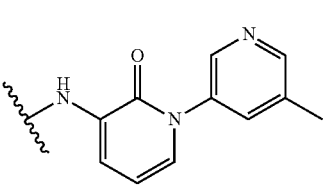
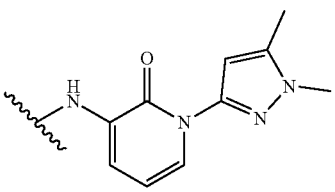
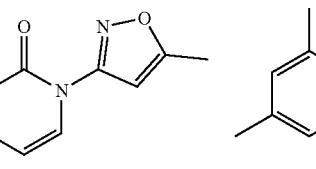
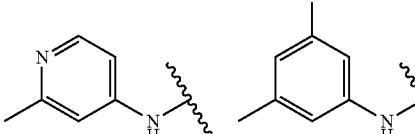
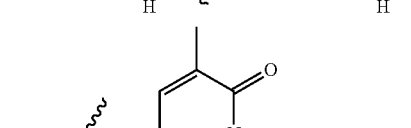
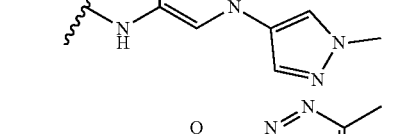
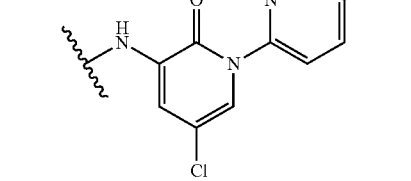

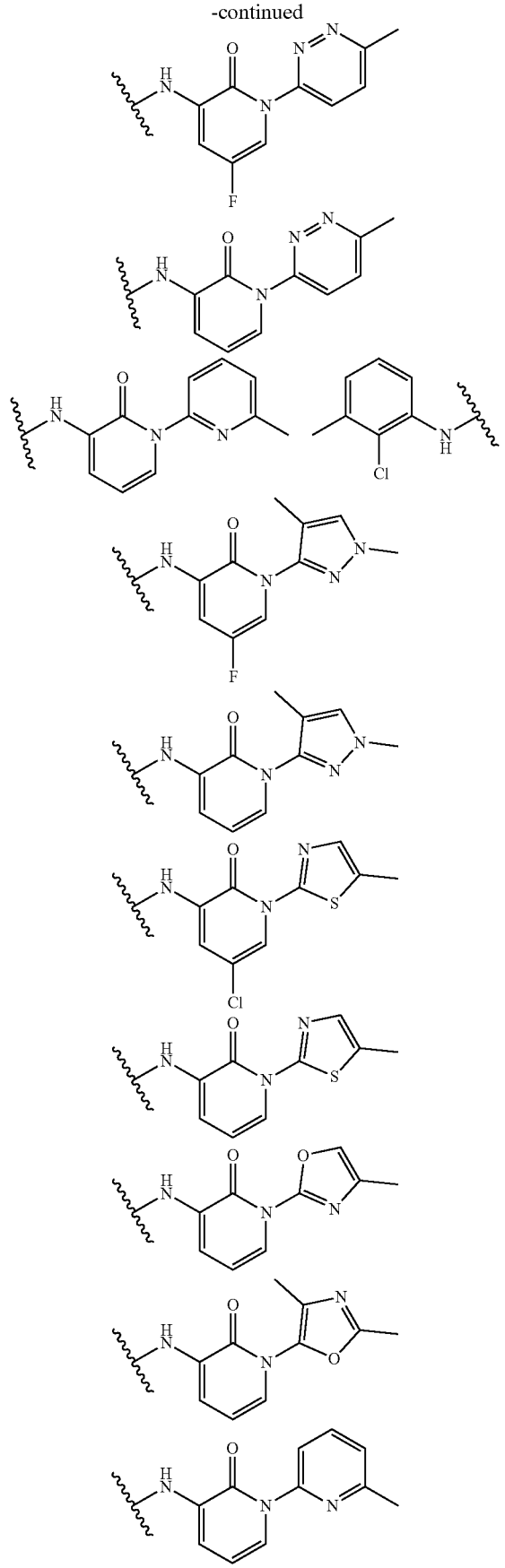
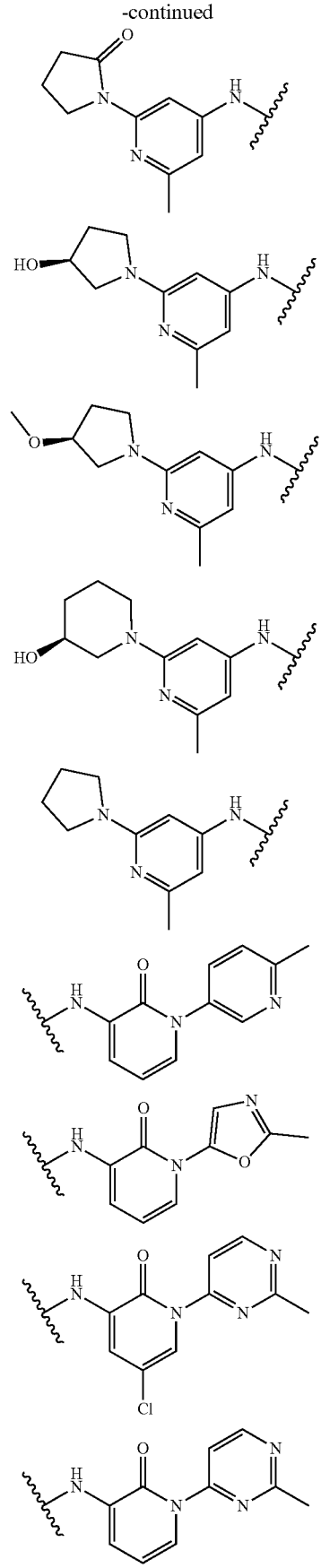

27
-continued
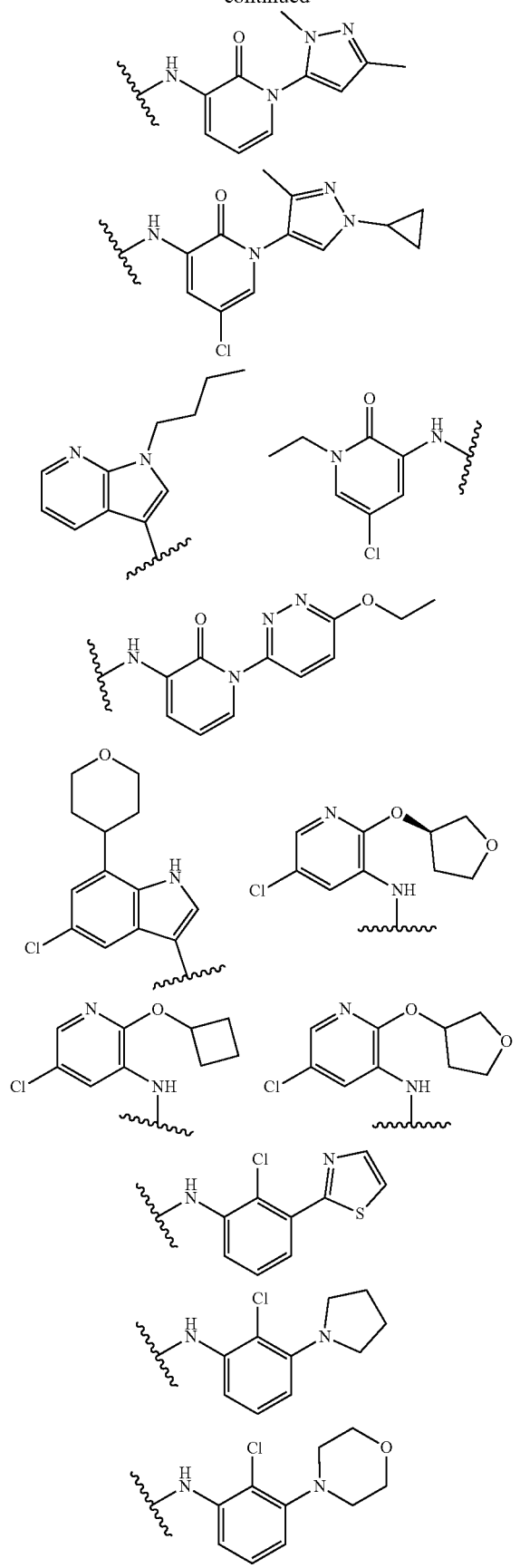
28
-continued
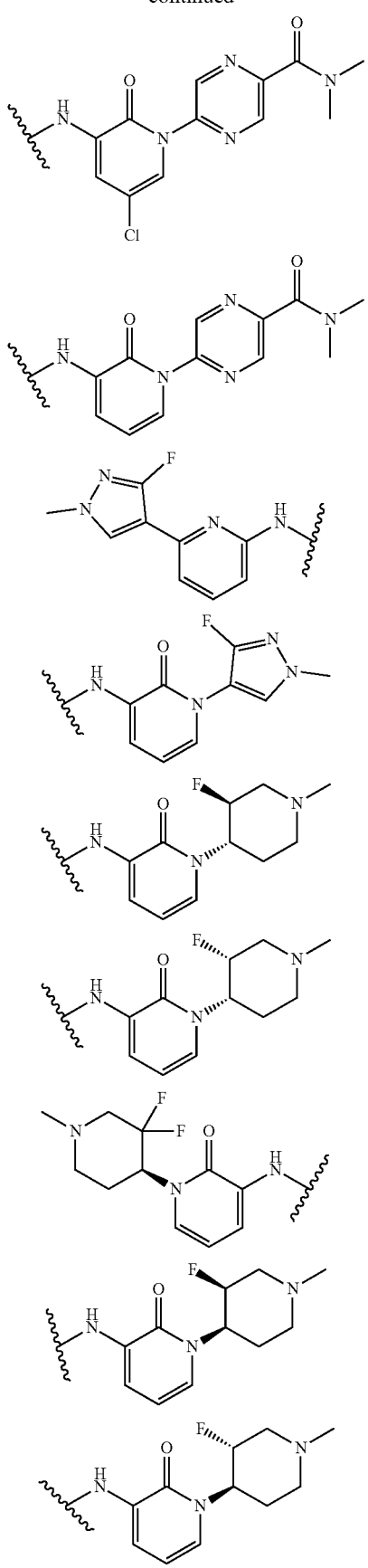

-continued
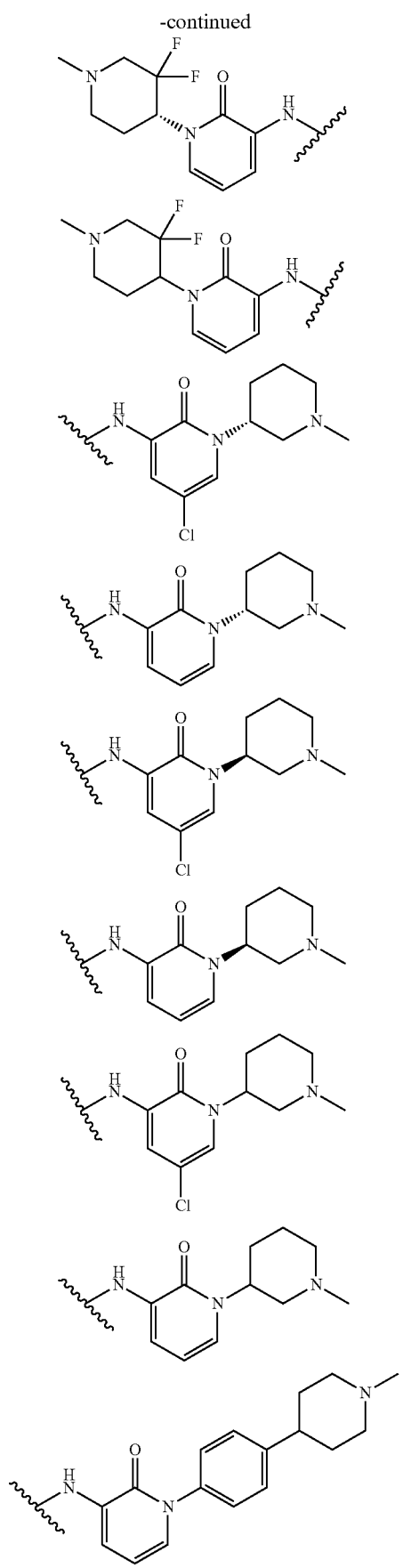
-continued
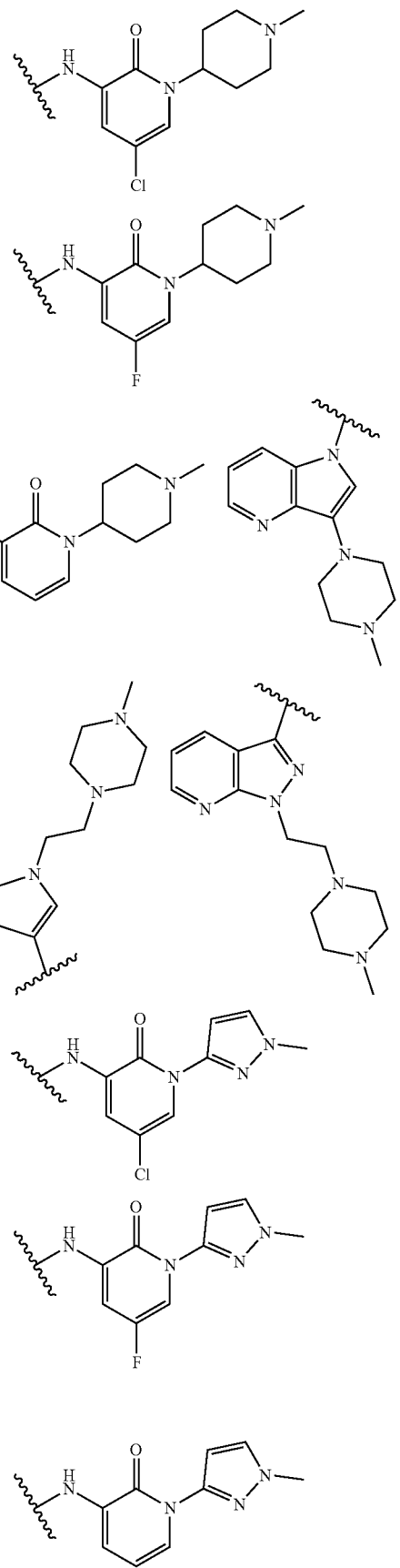

31
-continued
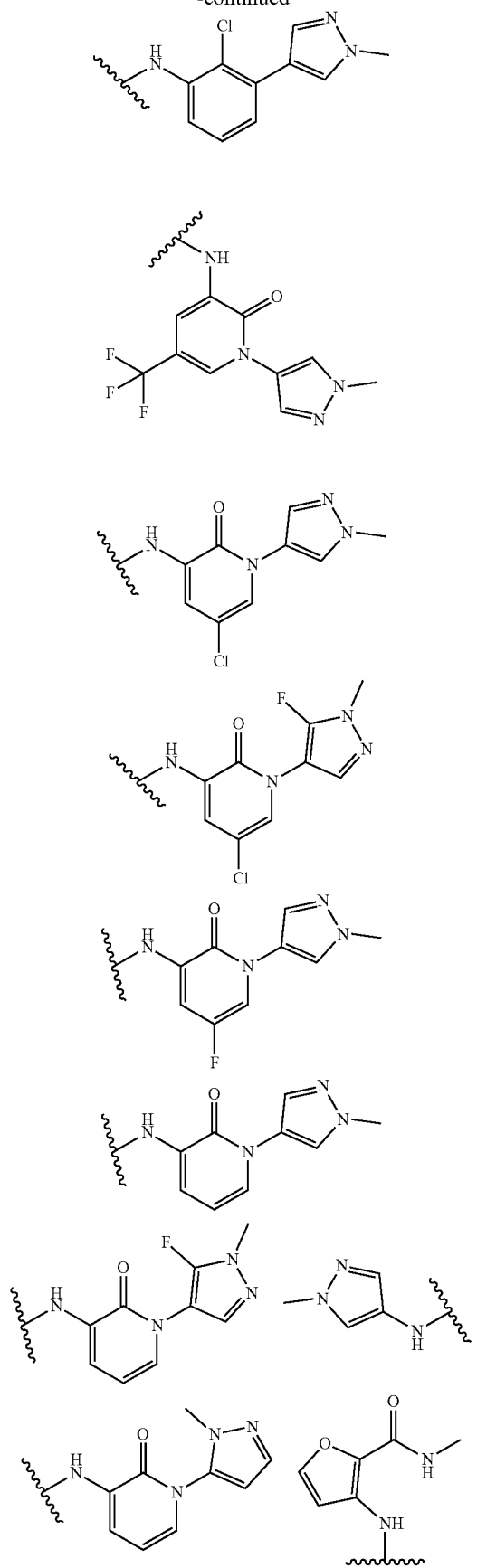
32
-continued
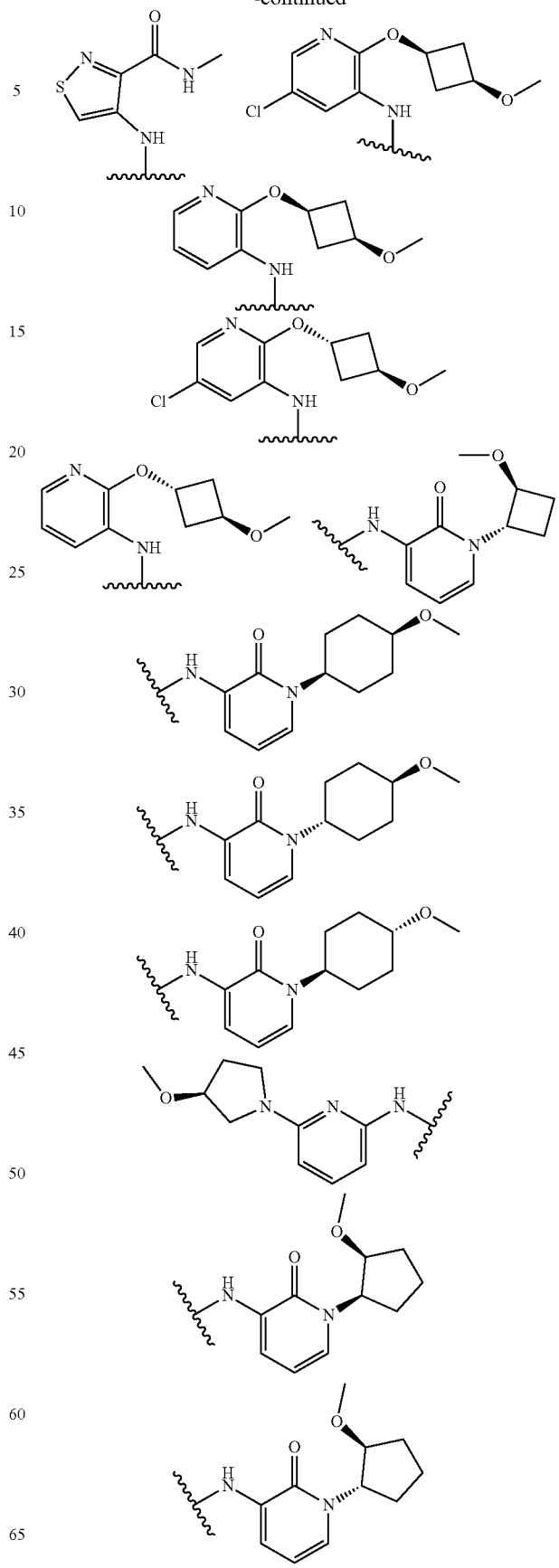

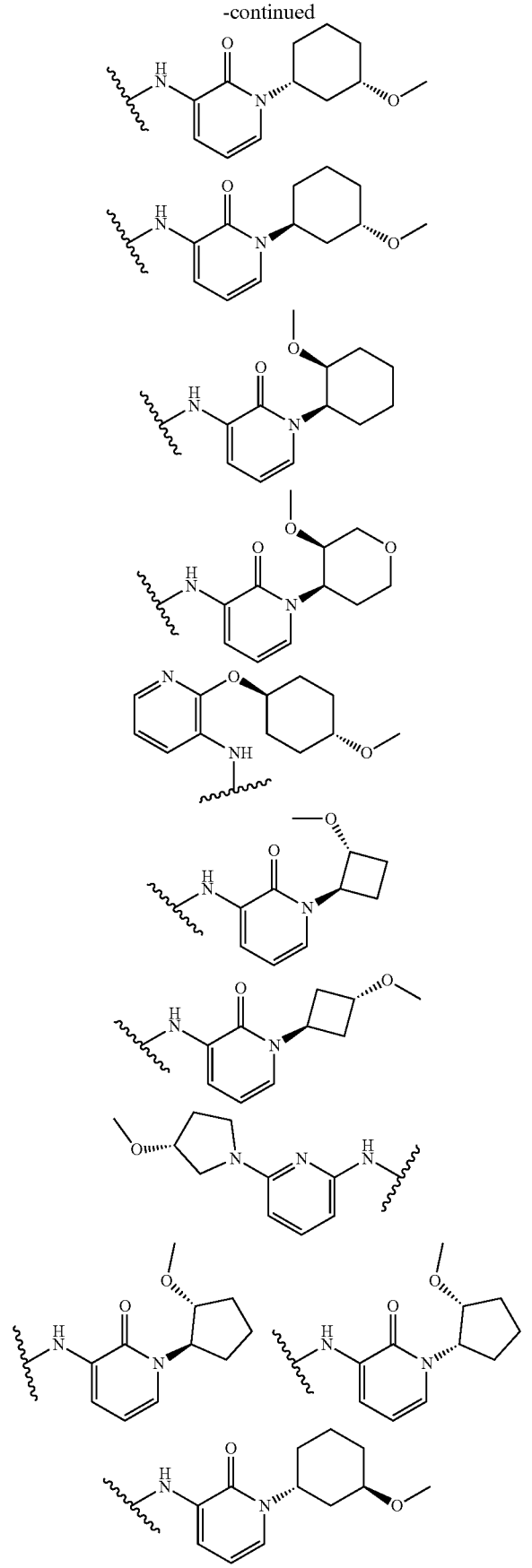
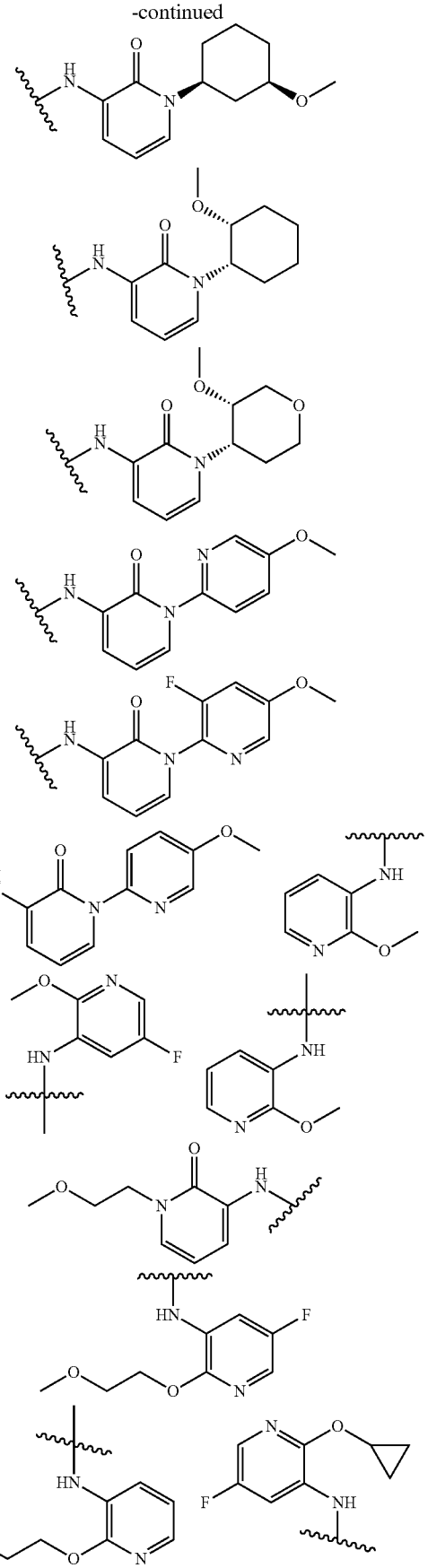

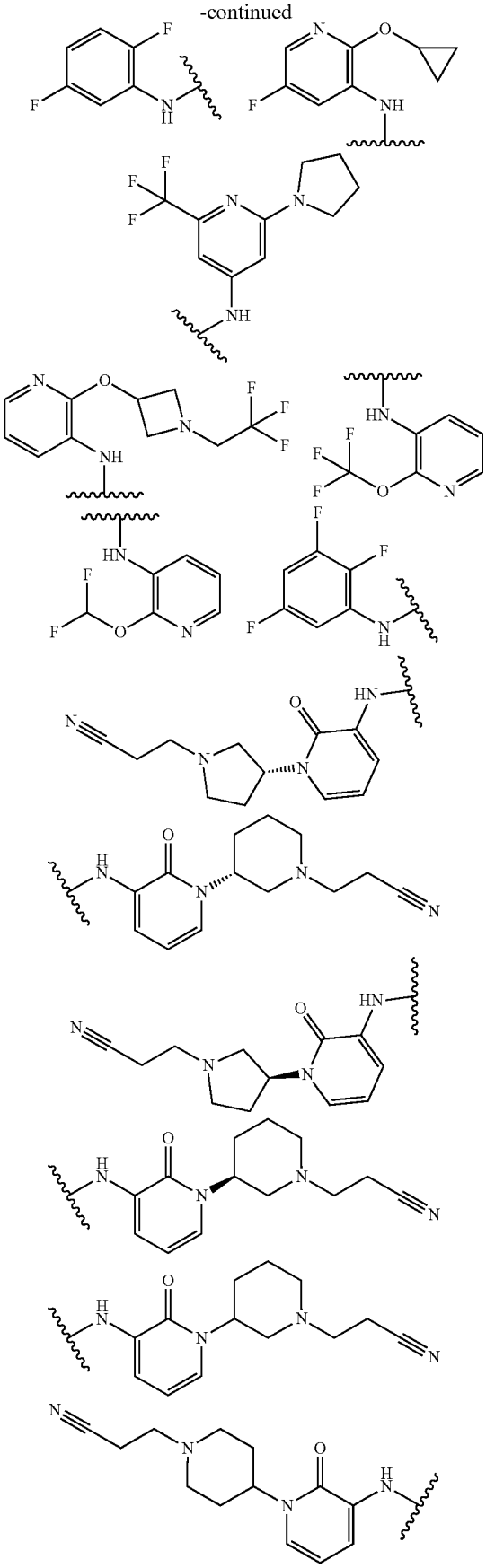
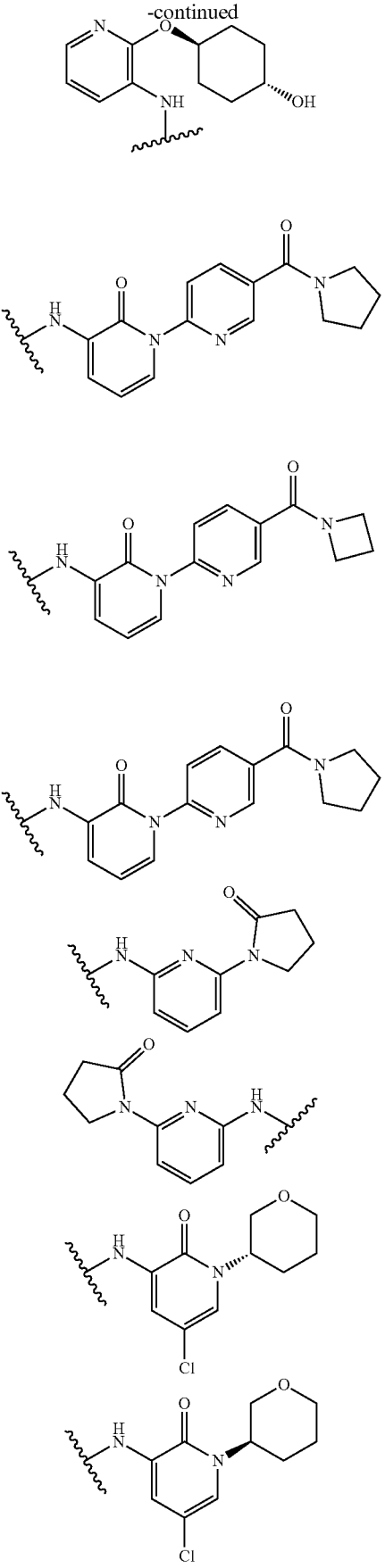

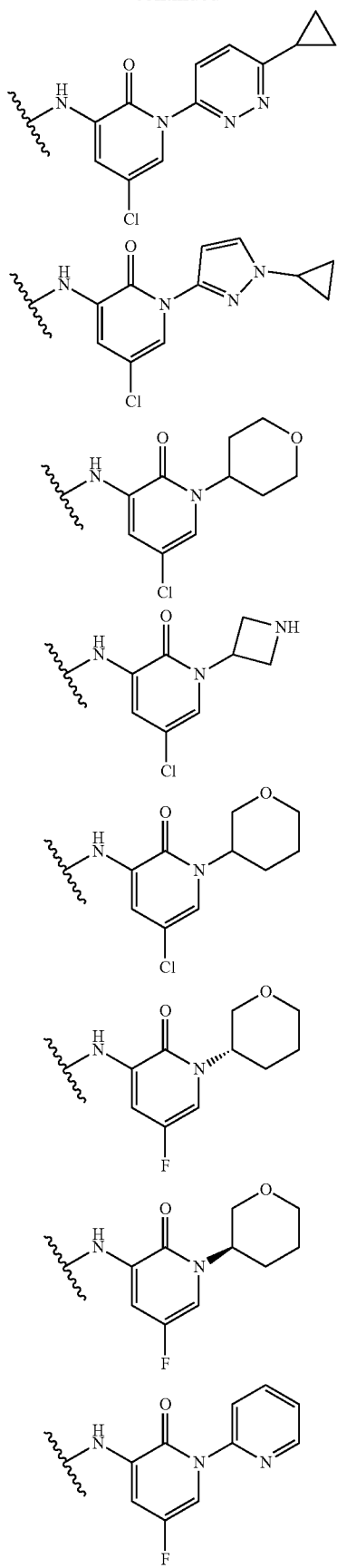
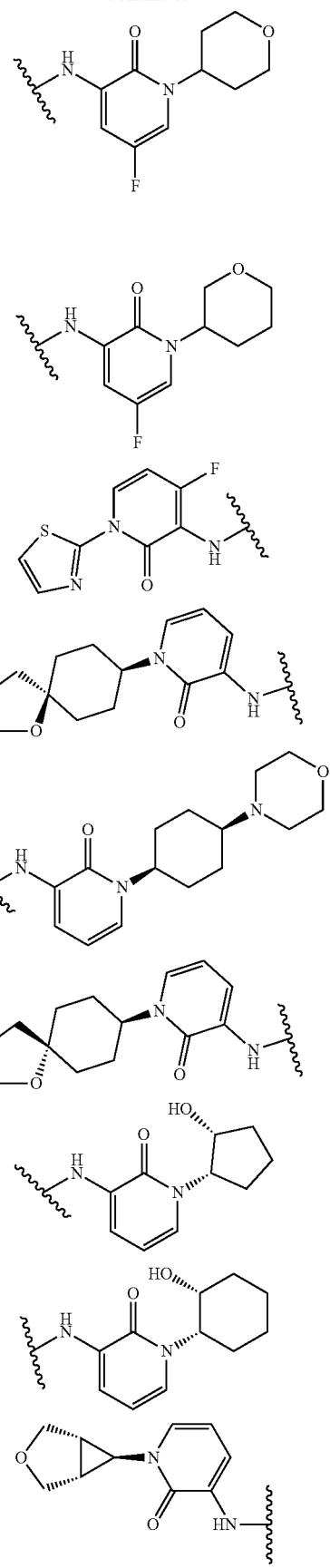

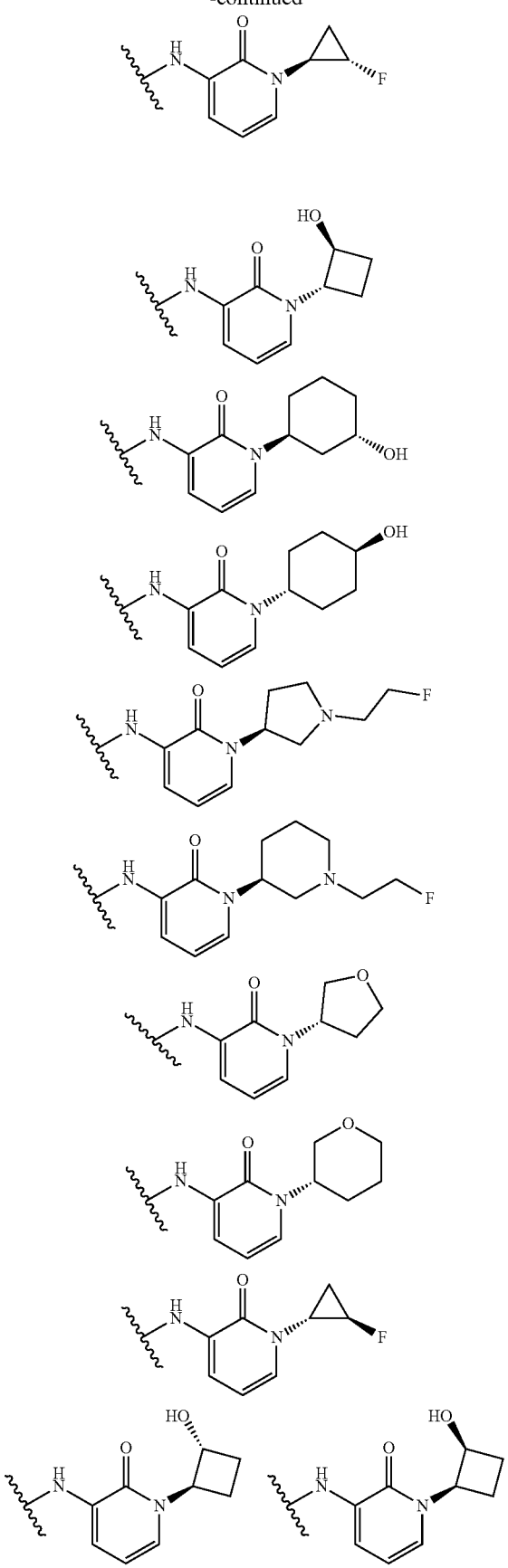
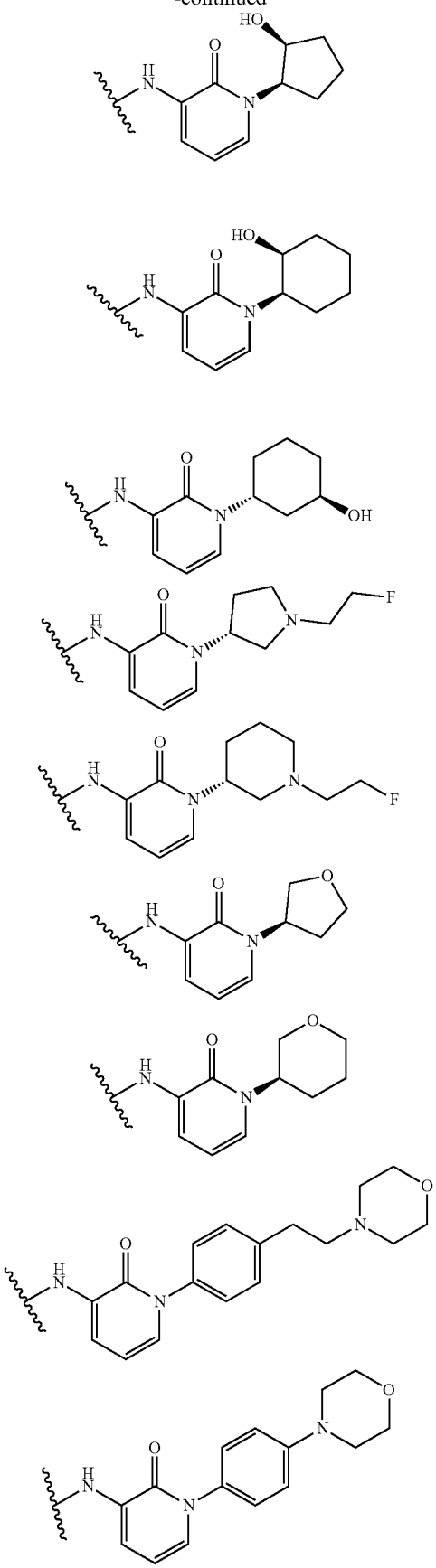

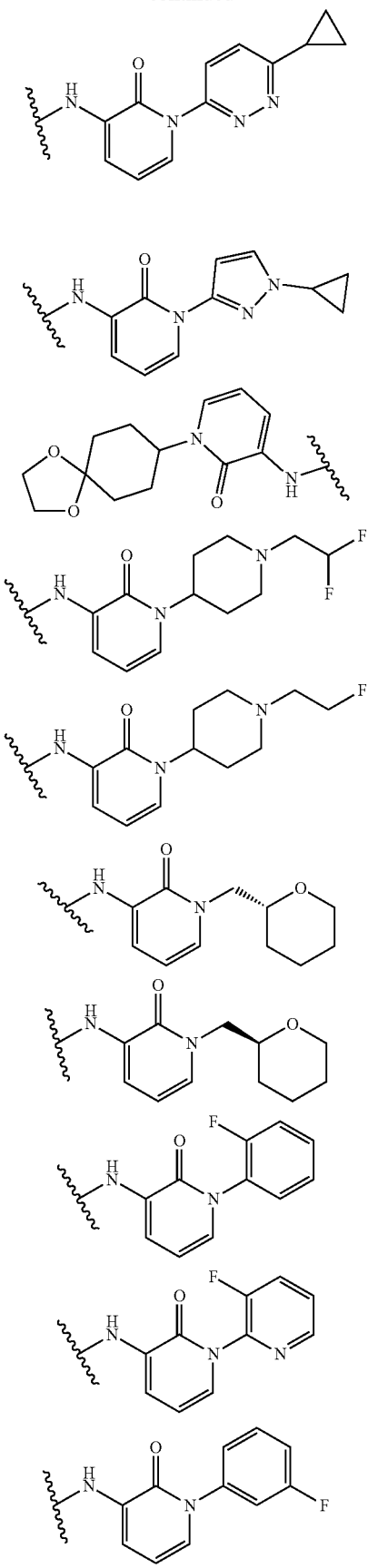
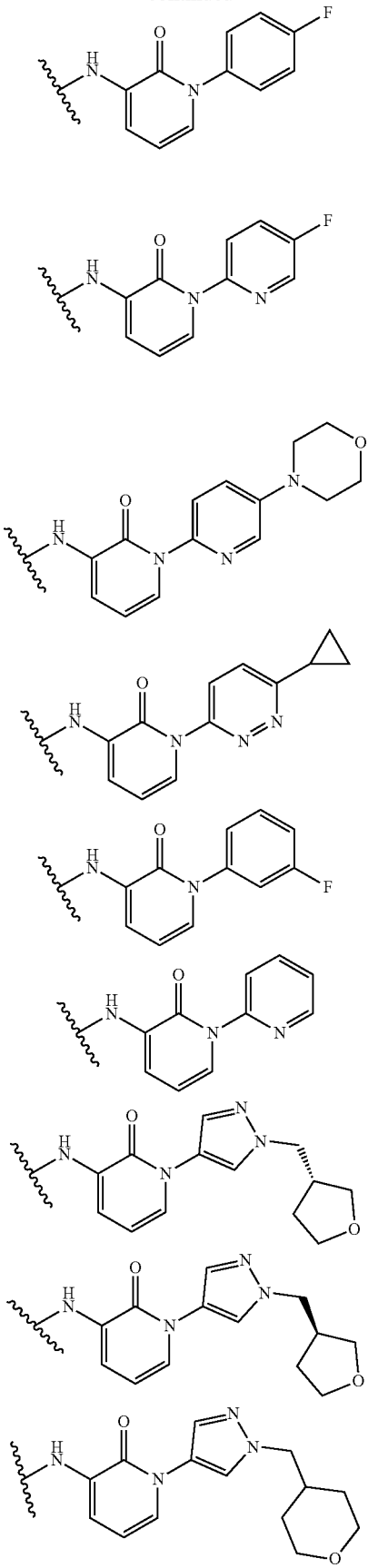

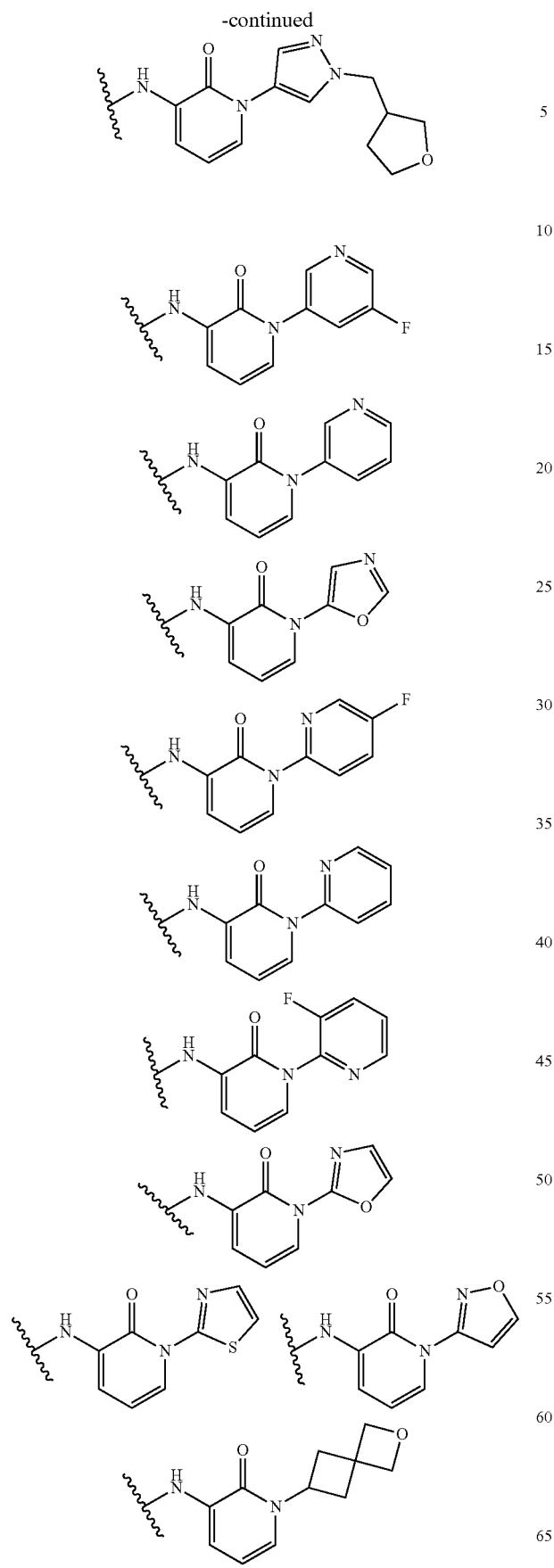
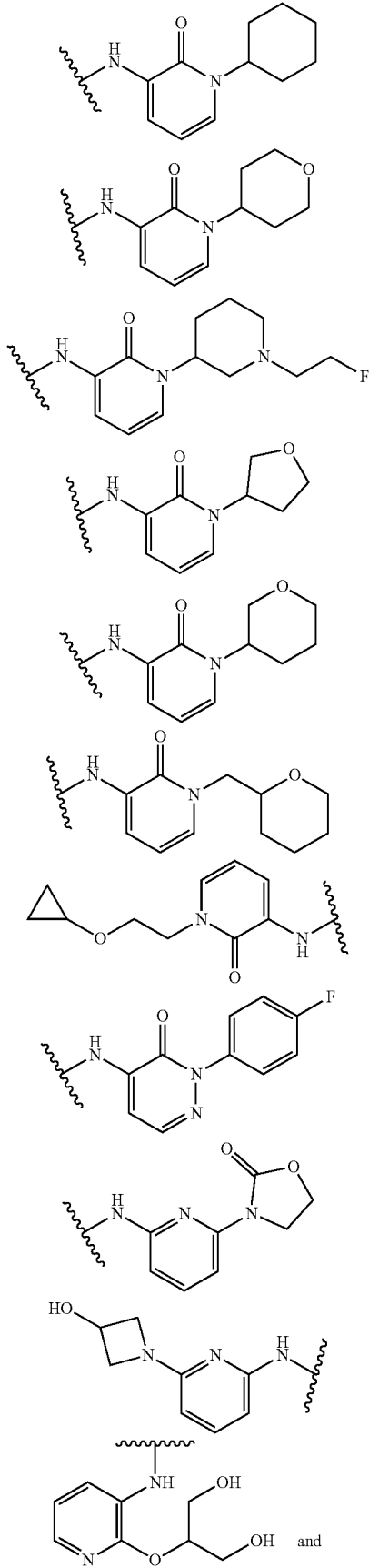

-continued
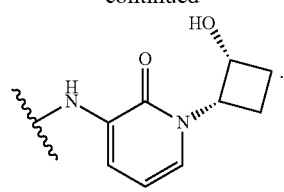
In some embodiments, $R^5$ is selected from the following:
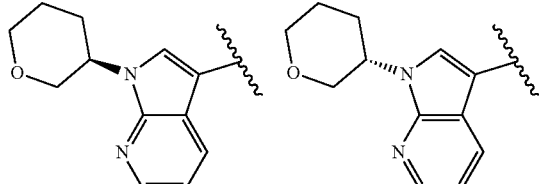
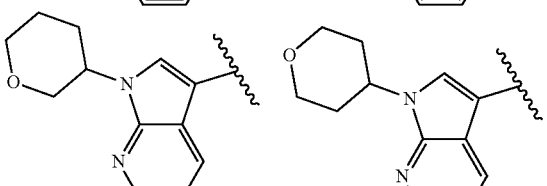
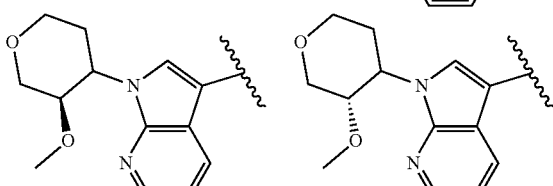
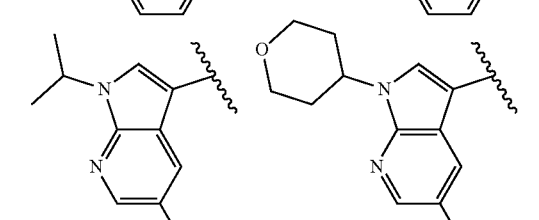
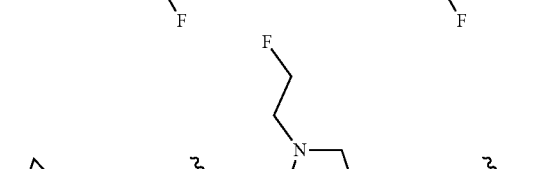
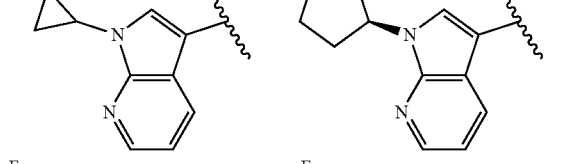
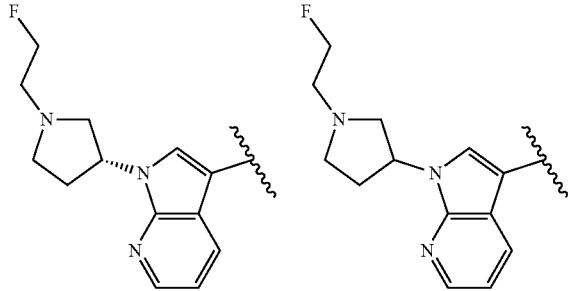
-continued
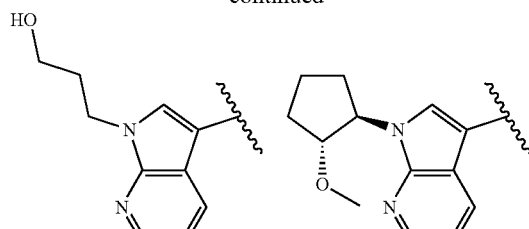
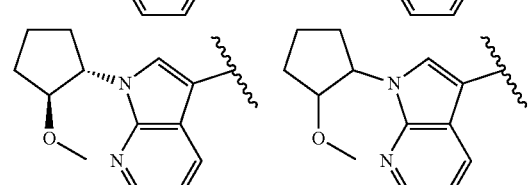
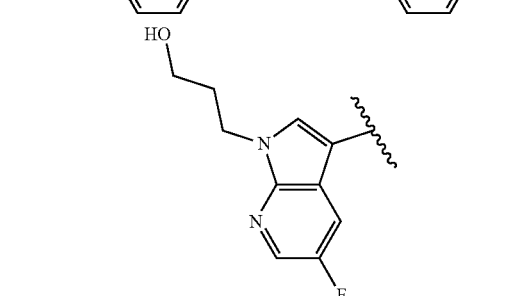
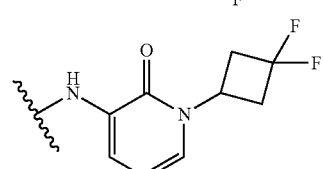
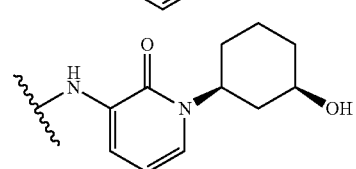
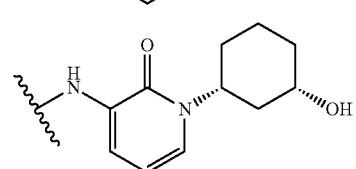
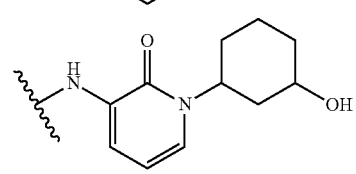
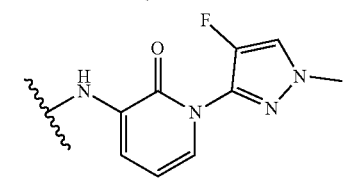
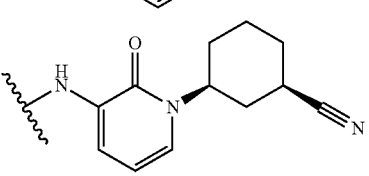

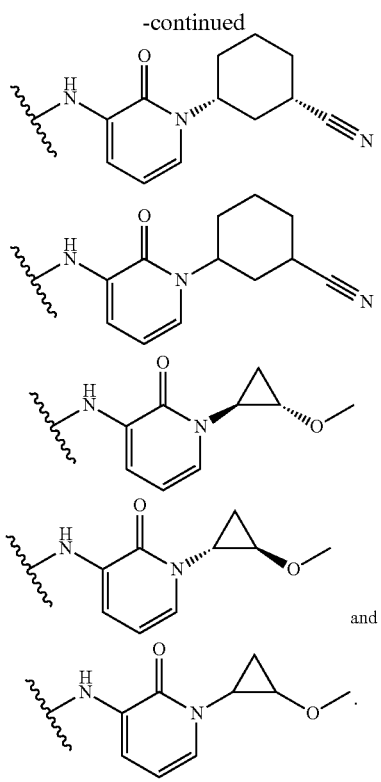

In some embodiments, $R^5$ is

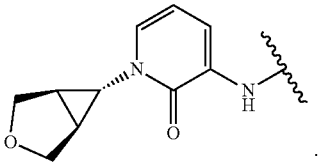 [SMILES: *Nc1cccn([C@H]2[C@@H]3COC[C@@H]32)c1=O]

In some embodiments, $R^5$ is selected from those depicted in Table 1, below.

As defined generally above, $R^6$ is hydrogen, $R^A$, or $R^B$, or $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments, $R^6$ is hydrogen.

In some embodiments, $R^6$ is $R^A$. In some embodiments, $R^6$ is $R^B$. In some embodiments, $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments $R^6$ is hydrogen, $R^A$ or $R^B$.

In some embodiments, $R^6$ is methyl.

In some embodiments, $R^6$ is selected from those depicted in Table 1, below.

As defined generally above, $R^7$ is hydrogen, halogen, $-NH_2$, $-NHR^{7A}$, or $-NHC(O)R^{7A}$; or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$. In some embodiments, $R^7$ is $-NH_2$ or $-NHR^{7A}$. In some embodiments, $R^7$ is $-NHMe$. In some embodiments, $R^7$ is $-NHCD_3$.

In some embodiments, $R^7$ hydrogen. In some embodiments, $R^7$ halogen. In some embodiments, $R^7$—$NH_2$. In some embodiments, $R^7$—$NHR^{7A}$. In some embodiments, $R^7$—$NHC(O)R^{7A}$. In some embodiments, $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$.

In some embodiments, $R^7$ is selected from the following:

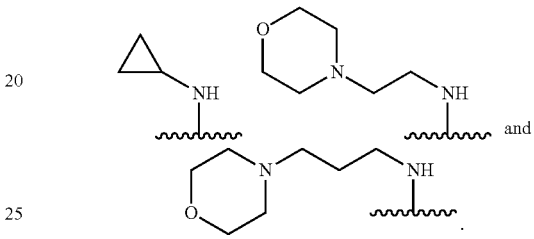

and

In some embodiments, $R^7$ is selected from those depicted in Table 1, below.

As defined generally above, $L^1$ is a covalent bond or a $C_{1-4}$ bivalent saturated or unsaturated, straight or branched hydrocarbon chain wherein one or two methylene units of the chain are optionally and independently replaced by $-C(R^{5B})_2-$, $-CH(R^{5B})-$, $-N(R)-$, $-N(R)C(O)-$, $-C(O)N(R)-$, $-N(R)S(O)_2-$, $-S(O)_2N(R)-$, $-O-$, $-C(O)-$, $-OC(O)-$, $-C(O)O-$, $-S-$, $-S(O)-$, or $-S(O)_2-$. In some embodiments, $L^1$ is $-N(R)-$. In some embodiments, $L^1$ is $-N(H)-$.

In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by $-C(R^{5B})_2-$, $-CH(R^{5B})-$, $-N(R)-$, $-N(R)C(O)-$, $-C(O)N(R)-$, $-N(R)S(O)_2-$, $-S(O)_2N(R)-$, $-O-$, $-C(O)-$, $-OC(O)-$, $-C(O)O-$, $-S-$, $-S(O)-$, or $-S(O)_2-$.

In some embodiments, $L^1$ is $-N(R)-$ or a covalent bond. In some embodiments, $L^1$ is $-N(H)-$ or a covalent bond.

In some embodiments, $L^1$ is selected from those depicted in Table 1, below.

As defined generally above, $R^{3A}$ is $R^B$, and is substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur. In some embodiments, $R^{3A}$ is $C_{1-6}$ aliphatic substituted by q instances of $R^C$. In some embodiments, $R^{3A}$ is a 3-7 membered saturated or partially unsaturated carbocyclic ring substituted by q instances of $R^C$. In some embodiments, $R^{3A}$ is cyclopropyl or cyclobutyl; each substituted by q instances of $R^C$. In some embodiments, $R^{3A}$ is cyclopropyl substituted by q instances of $R^C$. In some embodiments, $R^{3A}$ is cyclobutyl substituted by q instances of $R^C$. In some embodiments, $R^{3A}$ is $R^B$, and is substituted by q instances of $R^C$, provided that $R^{3A}$ is not phenyl.

In some embodiments, $R^{3A}$ is $R^B$, and is substituted by q instances of $R^C$, wherein two substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{3A}$ is $C_{1-6}$ aliphatic substituted by q instances of $R^C$ or a 3-7 membered saturated or partially unsaturated carbocyclic ring substituted by q instances of $R^C$.

In some embodiments, $R^{3A}$ is selected from the following:

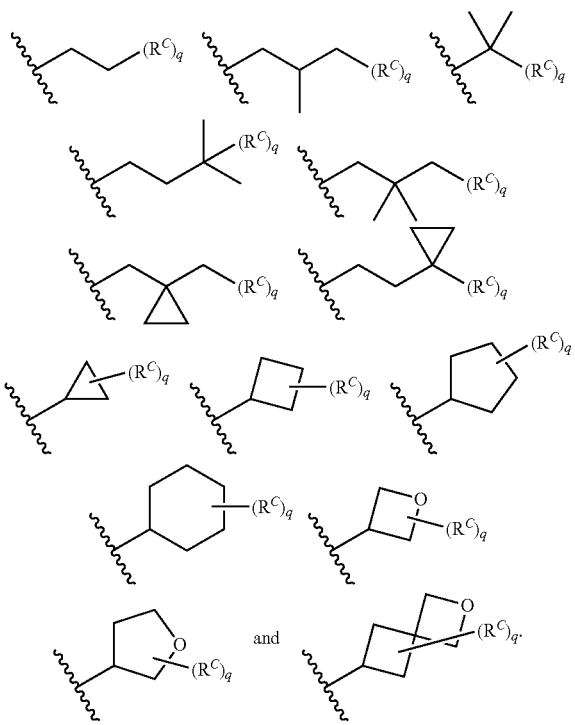

In some embodiments, $R^{3A}$ is selected from those depicted in Table 1, below.

As defined generally above, $R^{3B}$ is $R^B$, and is substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur. In some embodiments, $R^{3B}$ is $C_{1-6}$ aliphatic substituted by q instances of $R^C$. In some embodiments, $R^{3B}$ is a 3-7 membered saturated or partially unsaturated carbocyclic ring substituted by q instances of $R^C$. In some embodiments, $R^{3B}$ is cyclopropyl or cyclobutyl; each substituted by q instances of $R^C$. In some embodiments, $R^{3B}$ is cyclopropyl substituted by q instances of $R^C$. In some embodiments, $R^{3B}$ is cyclobutyl substituted by q instances of $R^C$. In some embodiments, $R^{3B}$ is $R^B$, and is substituted by q instances of $R^C$, provided that $R^{3B}$ is not phenyl.

In some embodiments, $R^{3B}$ is $R^B$, and is substituted by q instances of $R^C$, wherein two substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{3B}$ is $C_{1-6}$ aliphatic substituted by q instances of $R^C$ or a 3-7 membered saturated or partially unsaturated carbocyclic ring substituted by q instances of $R^C$.

In some embodiments, $R^{3B}$ is selected from the following:

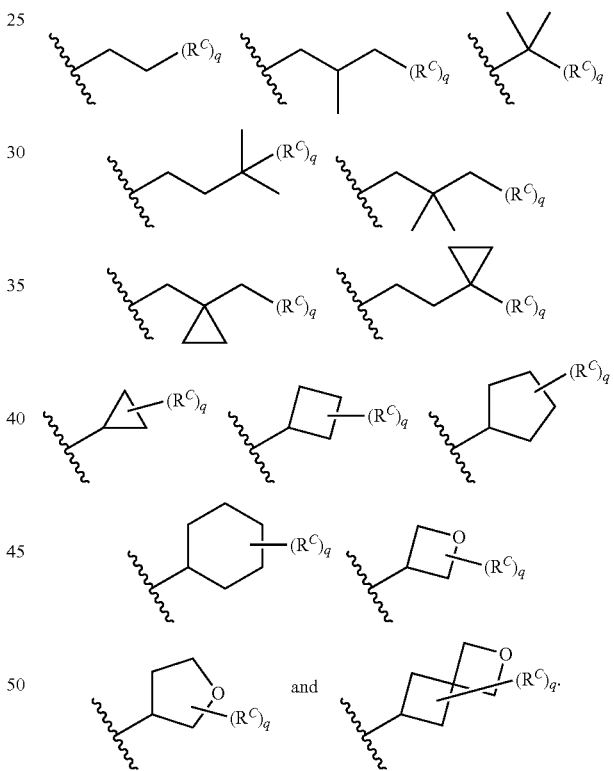

In some embodiments, $R^{3B}$ is selected from those depicted in Table 1, below.

As defined generally above, $R^{5A}$ is $R^A$ or $R^B$, and is substituted by r instances of $R^C$. In some embodiments, $R^{5A}$ is phenyl or a 5-6 membered monocyclic heteroaryl ring having 1-4 heteroatoms independently selected from nitrogen, oxygen, and sulfur; and is substituted by r instances of $R^C$.

In some embodiments, $R^{5A}$ is $R^A$ substituted by r instances of $R^C$. In some embodiments, $R^{5A}$ is $R^B$ substituted by r instances of $R^C$.

In some embodiments, $R^{5A}$ is selected from the following:

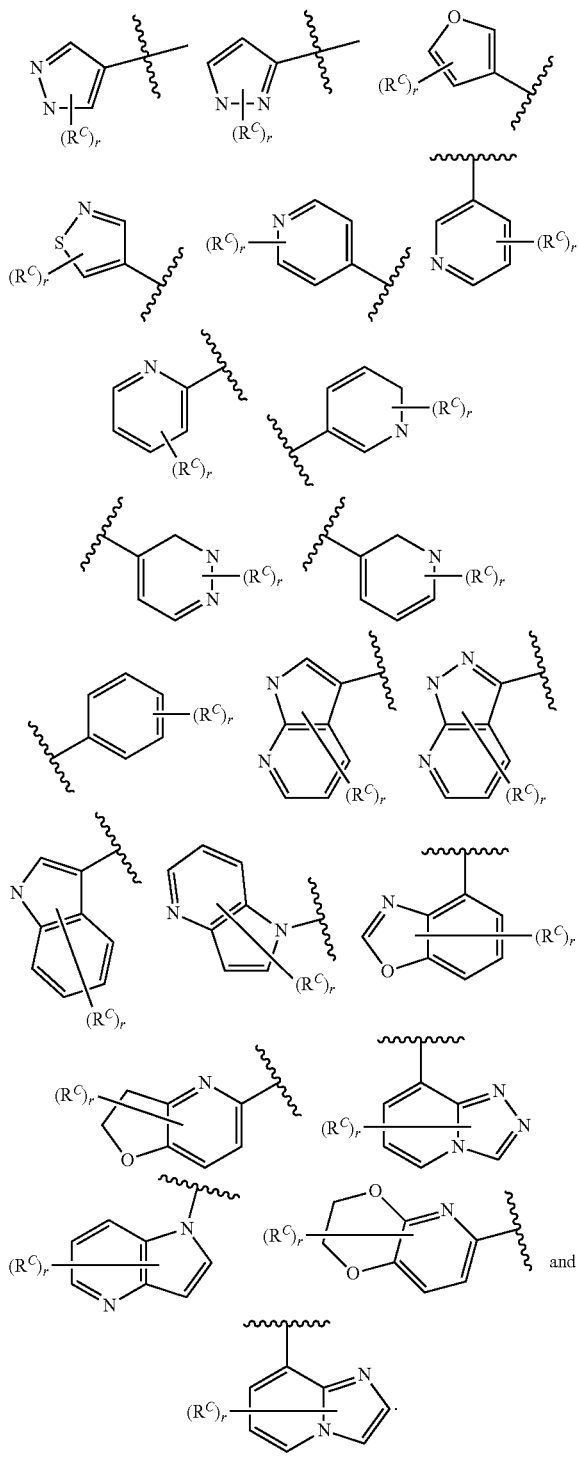

In some embodiments, $R^{5A}$ is selected from those depicted in Table 1, below.

As defined generally above, $R^{7A}$ is $R^B$, and is substituted by q instances of $R^C$. In some embodiments, $R^{7A}$ is $C_{1-6}$ aliphatic substituted by q instances of $R^C$. In some embodiments, $R^{7A}$ is methyl. In some embodiments, $R^{7A}$ is $R^B$, and is substituted by q instances of $R^C$, provided that $R^{7A}$ is not aromatic. In some embodiments, $R^{7A}$ is $R^B$, and is substituted by q instances of $R^C$, provided that $R^{7A}$ is not phenyl.

In some embodiments, $R^{7A}$ is $R^B$, and is substituted by q instances of $R^C$.

In some embodiments, $R^{7A}$ is hydrogen. In some embodiments, $R^{7A}$ is methyl.

In some embodiments, $R^{7A}$ is selected from the following:

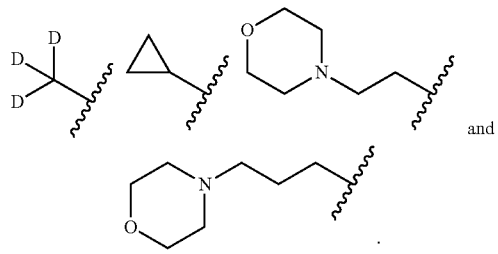

and

In some embodiments, $R^{7A}$ is selected from those depicted in Table 1, below.

As defined generally above, each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R) S(O)$_2$R.

In some embodiments, $R^A$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R) S(O)$_2$R.

In some embodiments, $R^A$ is selected from those depicted in Table 1, below.

As defined generally above, each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is methyl.

In some embodiments, $R^B$ is selected from those depicted in Table 1, below.

As defined generally above, each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, or —N(R)S(O)₂R, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, R$^C$ is oxo, halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, or —N(R)S(O)₂R, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, R$^C$ is oxo. In some embodiments, R$^C$ is methyl, ethyl, isopropyl, or n-butyl. In some embodiments, R$^C$ is fluoro. In some embodiments, R$^C$ is chloro. In some embodiments, R$^C$ is phenyl.

In some embodiments, R$^C$ is selected from the following:

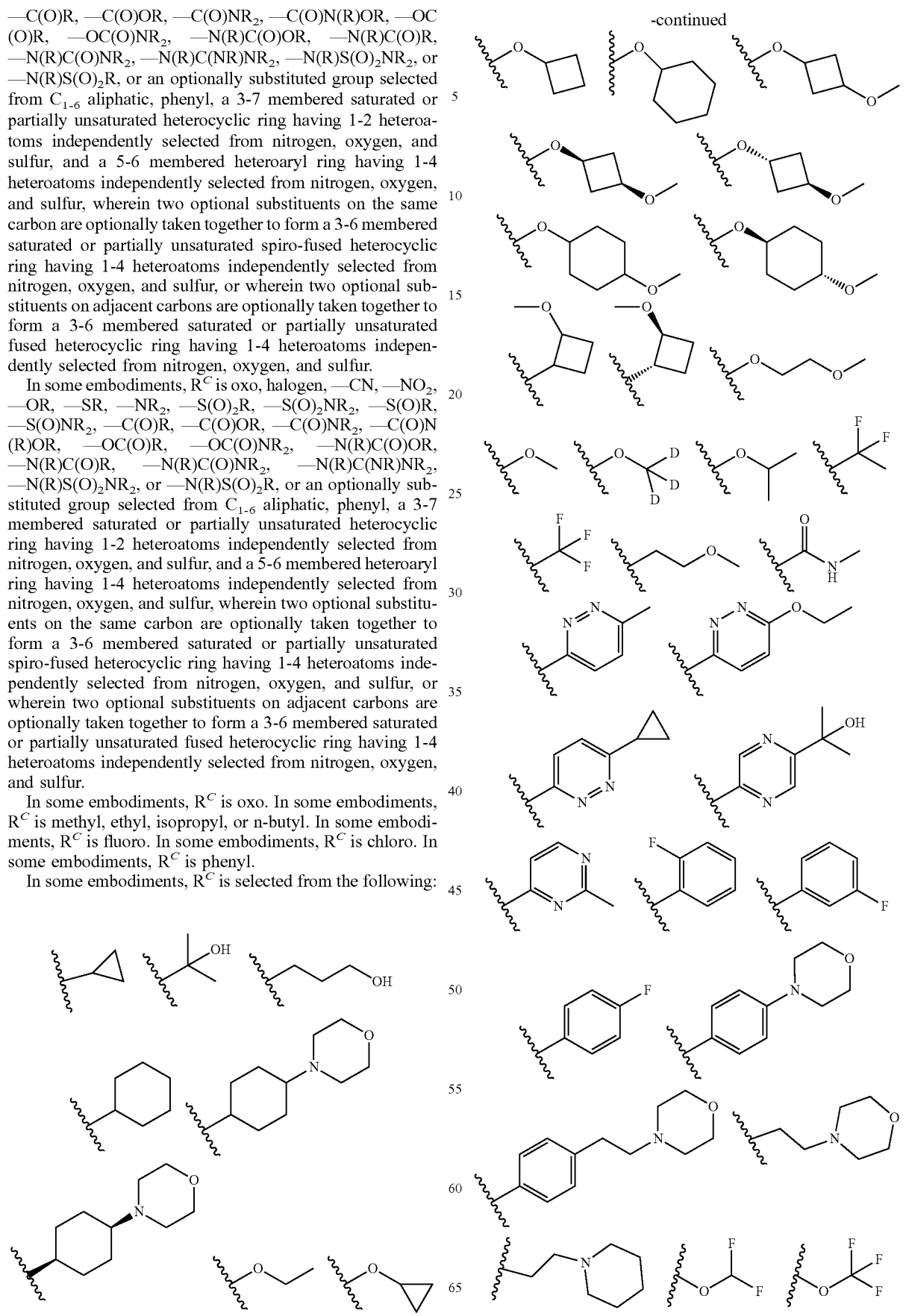

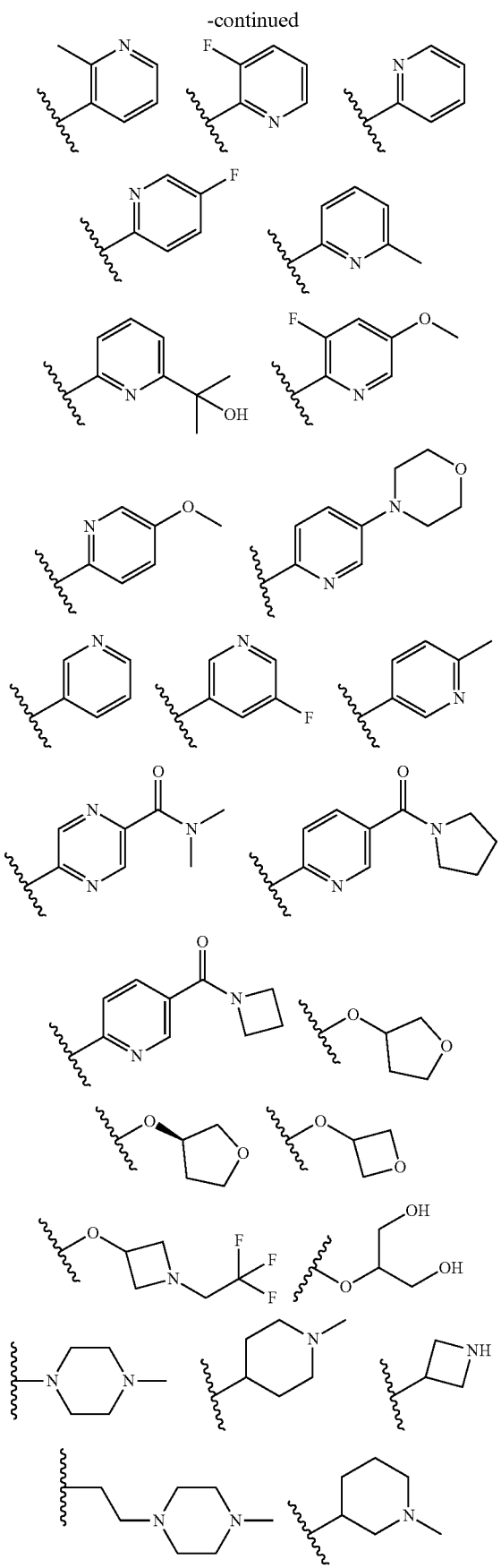
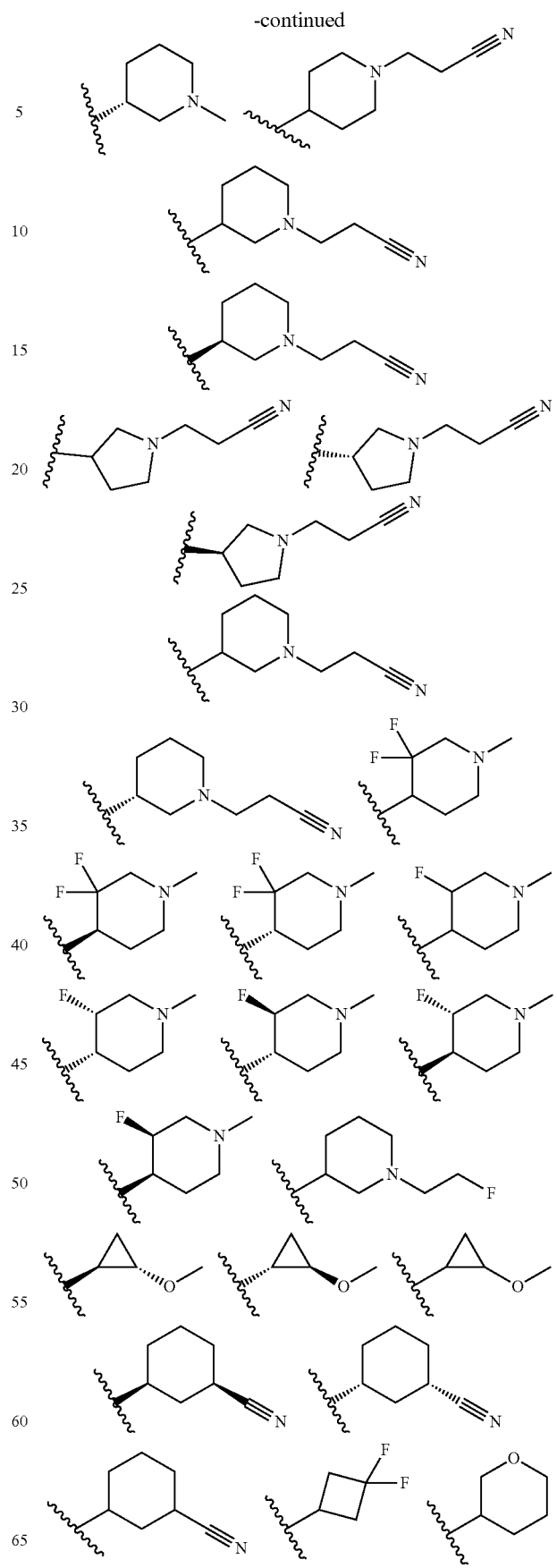

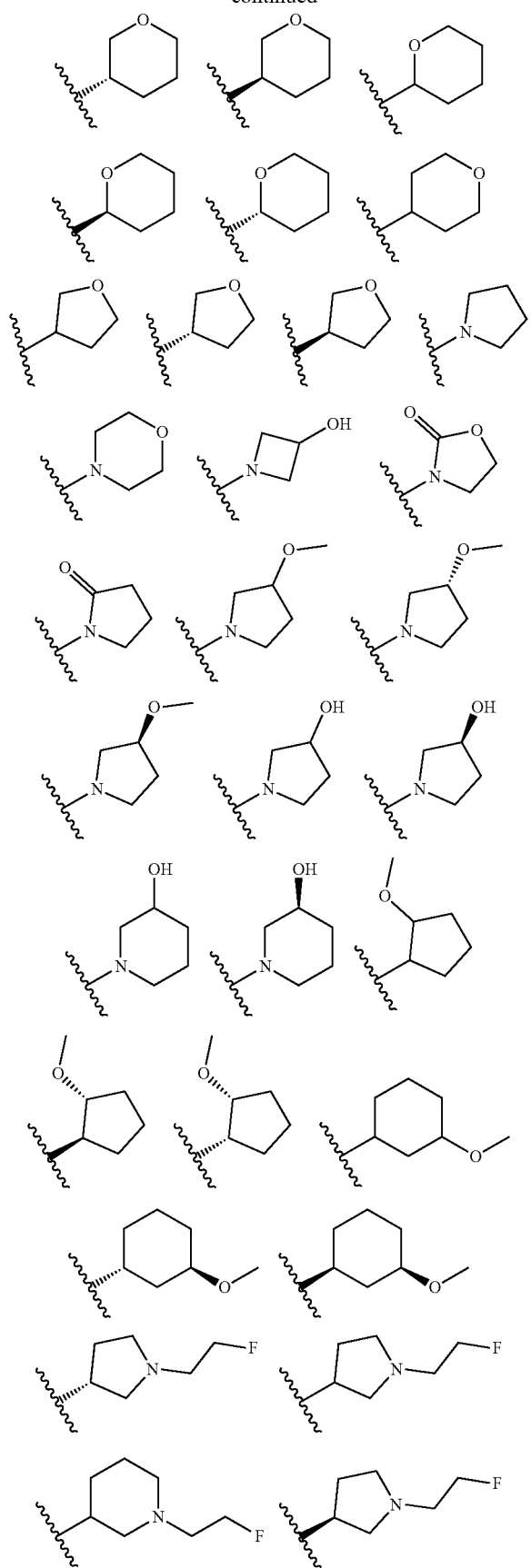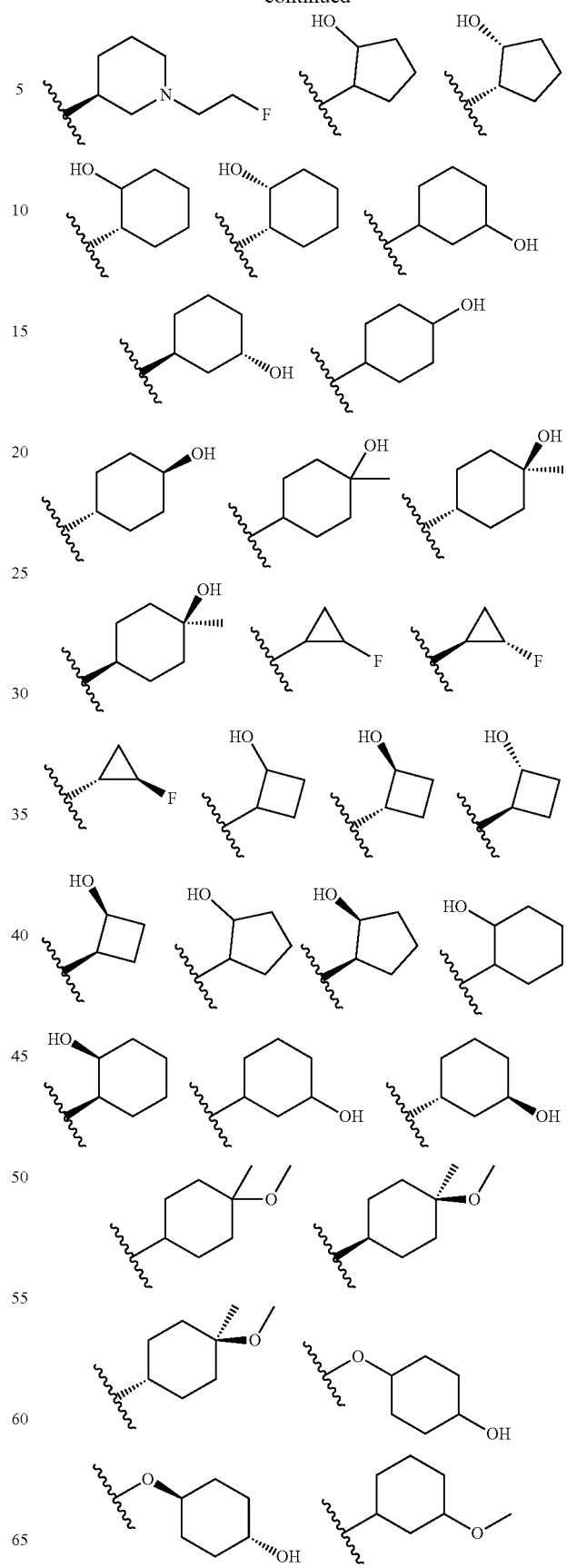

59
-continued
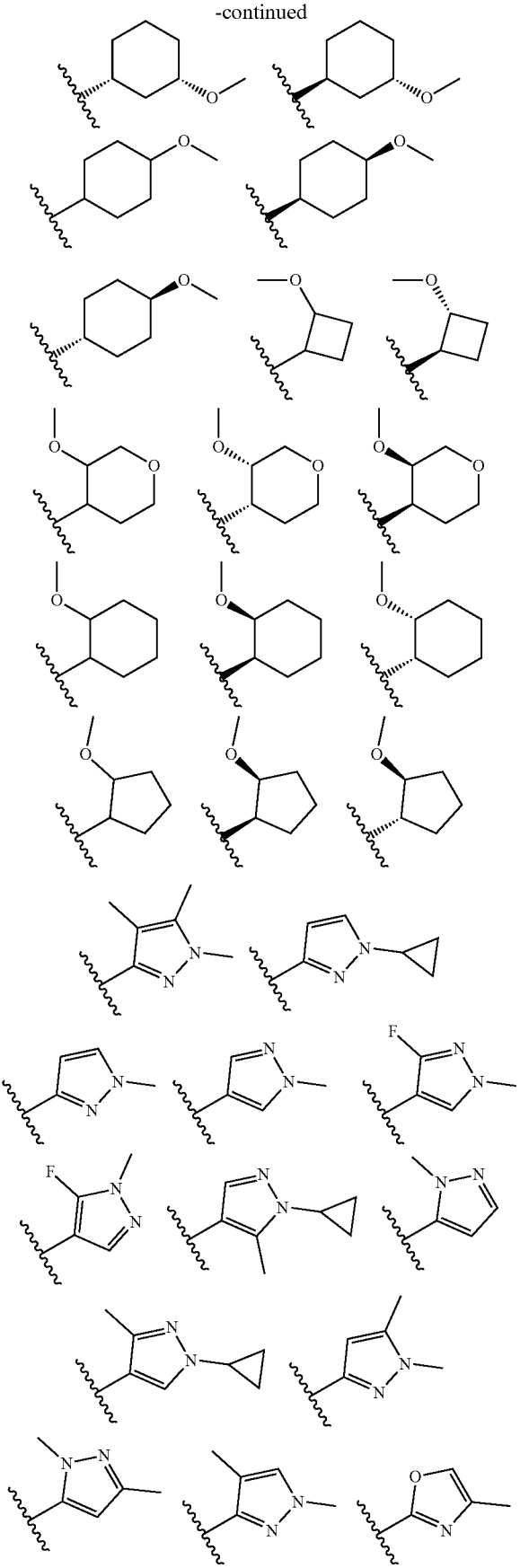
60
-continued
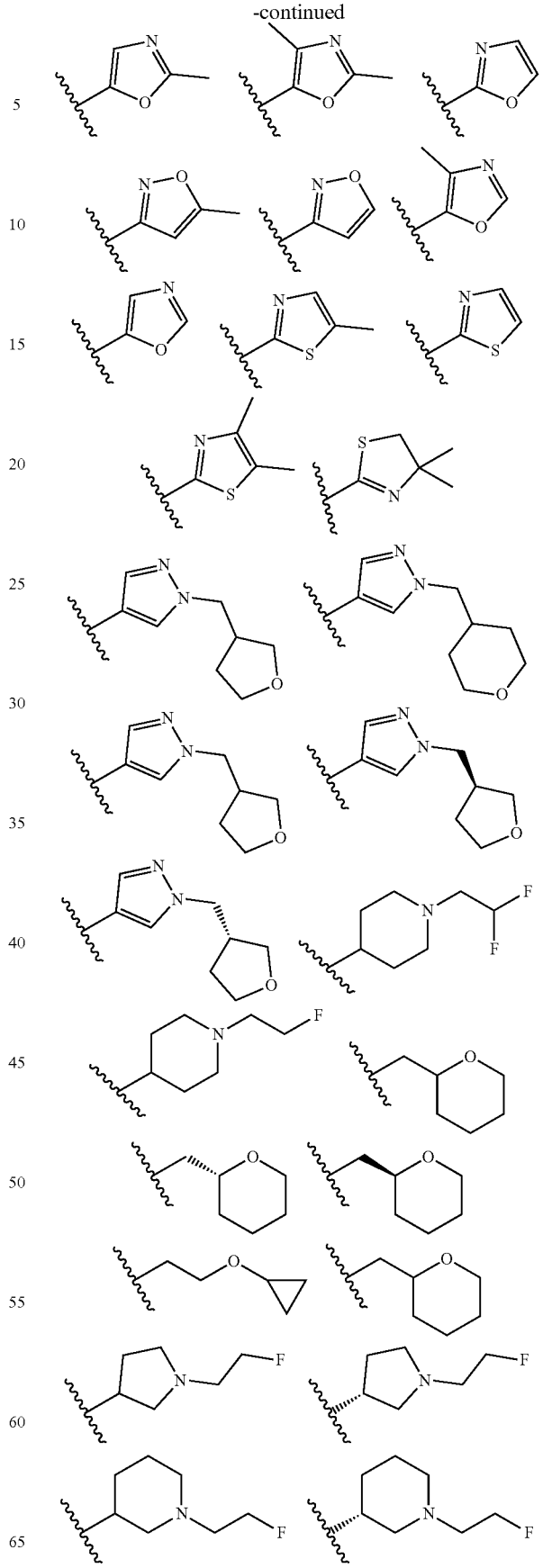

-continued

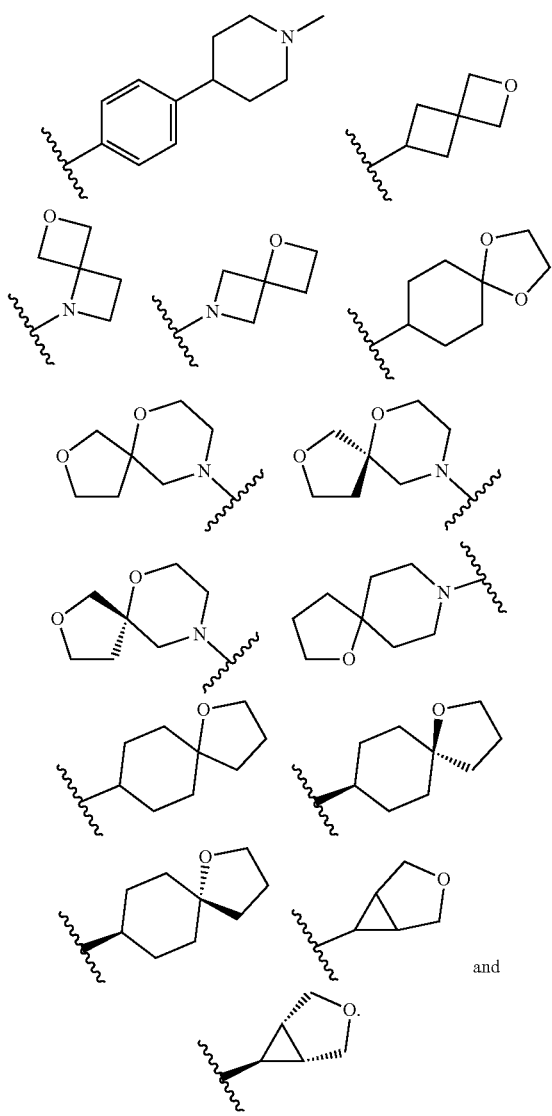

In some embodiments, $R^C$ is selected from the following:

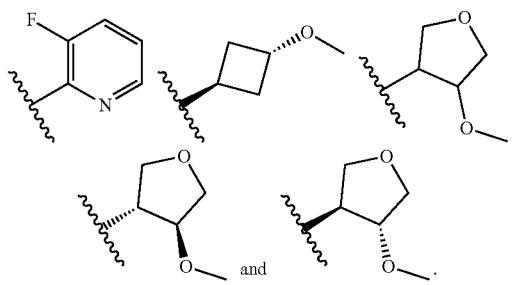

In some embodiments, $R^C$ is selected from those depicted in Table 1, below.

As defined generally above, each R is independently selected from hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined generally above, each hydrogen bound to carbon can be optionally and independently replaced by deuterium.

In some embodiments, a hydrogen bound to carbon is replaced by deuterium.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

In some embodiments, m is 1, 2, or 3. In some embodiments, m is 1 or 2. In some embodiments, m is 1 or 3. In some embodiments, m is 2 or 3. In some embodiments, m is 2 or 4. In some embodiments, m is 1, 2 or 4. In some embodiments, m is 1, 3 or 4. In some embodiments, m is 2, 3 or 4.

In some embodiments, m is selected from those depicted in Table 1, below.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

In some embodiments, n is 1, 2, or 3. In some embodiments, n is 1 or 2. In some embodiments, n is 1 or 3. In some embodiments, n is 2 or 3. In some embodiments, n is 2 or 4. In some embodiments, n is 1, 2 or 4. In some embodiments, n is 1, 3 or 4. In some embodiments, n is 2, 3 or 4.

In some embodiments, n is selected from those depicted in Table 1, below.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, p is 1, 2, or 3. In some embodiments, p is 1 or 2. In some embodiments, p is 1 or 3. In some embodiments, p is 2 or 3. In some embodiments, p is 2 or 4. In some embodiments, p is 1, 2 or 4. In some embodiments, p is 1, 3 or 4. In some embodiments, p is 2, 3 or 4.

In some embodiments, p is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is 1, 2, or 3. In some embodiments, q is 1 or 2. In some embodiments, q is 1 or 3. In some embodiments, q is 2 or 3. In some embodiments, q is 2 or 4. In some embodiments, q is 1, 2 or 4. In some embodiments, q is 1, 3 or 4. In some embodiments, q is 2, 3 or 4.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is 1, 2, or 3. In some embodiments, r is 1 or 2. In some embodiments, r is 1 or 3. In some embodiments, r is 2 or 3. In some embodiments, r is 2 or 4. In some embodiments, r is 1, 2 or 4. In some embodiments, r is 1, 3 or 4. In some embodiments, r is 2, 3 or 4.

In some embodiments, r is selected from those depicted in Table 1, below.

In some embodiments, the present invention provides a compound of formula I wherein $R^3$ is —C(O)NH$_2$ or —C(O)NHR$^{3A}$, thereby forming a compound of formulas II or III:

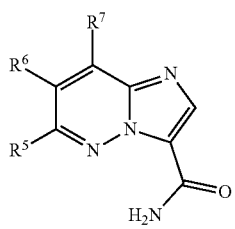

II

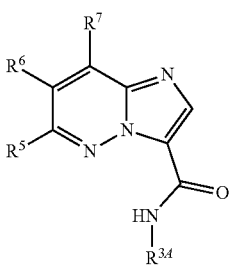

III or a pharmaceutically acceptable salt thereof, wherein each of $R^{3A}$, $R^5$, $R^6$, and $R^7$ is as defined above and described in embodiments herein, both singly and in combination.

In some embodiments, the present invention provides a compound of formula I, wherein $L^1$ is —N(R)—, thereby forming a compound of formula IV:

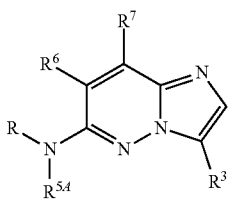

IV or a pharmaceutically acceptable salt thereof, wherein each of $R^3$, $R^{5A}$, $R^6$, and $R^7$ is as defined above and described in embodiments herein, both singly and in combination.

In some embodiments, the present invention provides a compound of formula II or III, wherein $L^1$ is —N(R)—, thereby forming a compound of formula V or VI respectively:

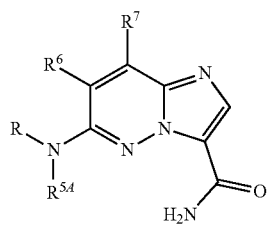

V

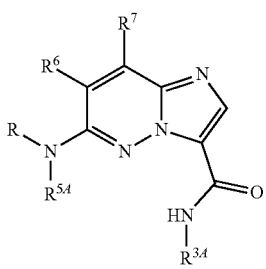

VI or a pharmaceutically acceptable salt thereof, wherein each of R, $R^{3A}$, $R^{5A}$, $R^6$, and $R^7$ is as defined above and described in embodiments herein, both singly and in combination.

In some embodiments, the present invention provides a compound of formula IV wherein $R^{5A}$ is phenyl or pyridin-3-yl, each substituted by r instances of $R^C$, thereby forming a compound of formula VII or VIII respectively:

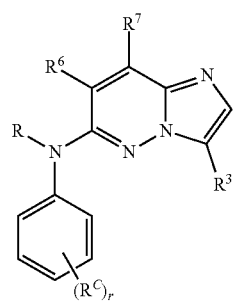

VII

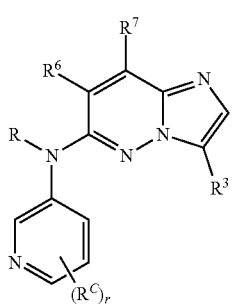

VIII or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula VIII wherein one instance of $R^C$ on $R^{5A}$ is oxo, thereby forming a compound of formula IX:

IX

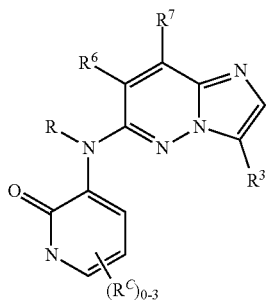

or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula IV, V, VI, VII, VIII, or IX, wherein R is hydrogen, thereby forming a compound of formula X, XI, XII, XIII, XIV, XV respectively:

X

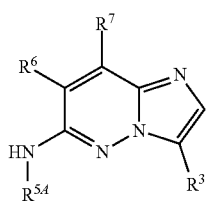

XI

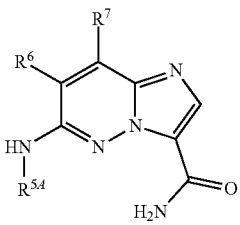

XII

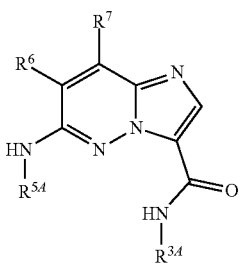

XIII

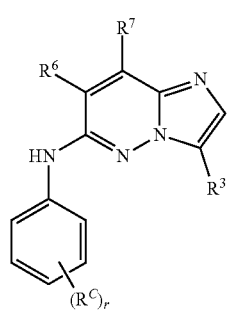

XIV

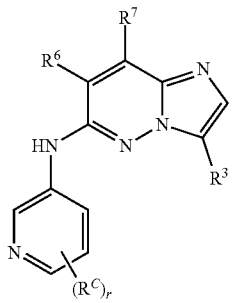

XV

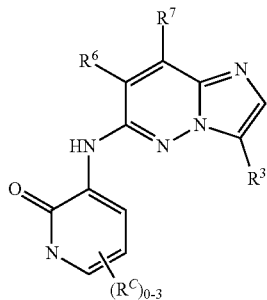

or a pharmaceutically acceptable salt thereof, wherein each of r, R, $R^C$, $R^3$, $R^{3A}$, $R^{5A}$, $R^6$, and $R^7$ is as defined above and described in embodiments herein, both singly and in combination.

In some embodiments, the present invention provides a compound of formula I, II, III, IV, V, VI, VII, VIII, IX, X, XI, XII, XIII, XIV, or XV, wherein $R^6$ is hydrogen, thereby forming a compound of formula I-a, II-a, III-a, IV-a, V-a, VI-a, VII-a, VIII-a, IX-a, X-a XI-a, XII-a, XIII-a, XIV-a, or XV-a respectively:

I-a

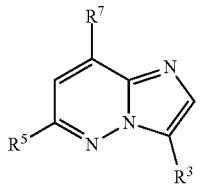

II-a

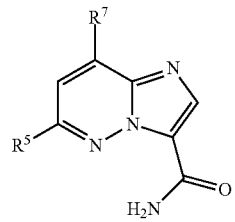

III-a

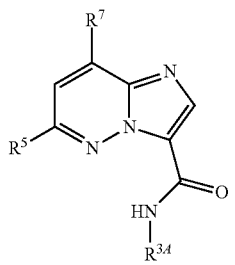

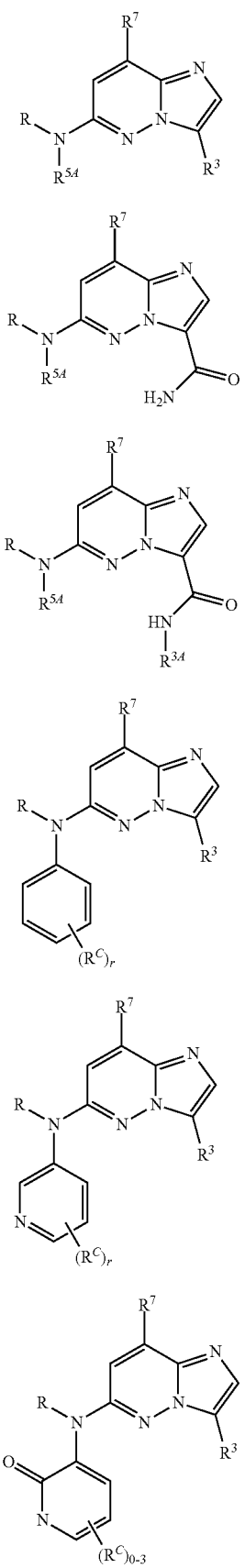
IV-a
V-a
VI-a
VII-a
VIII-a
IX-a
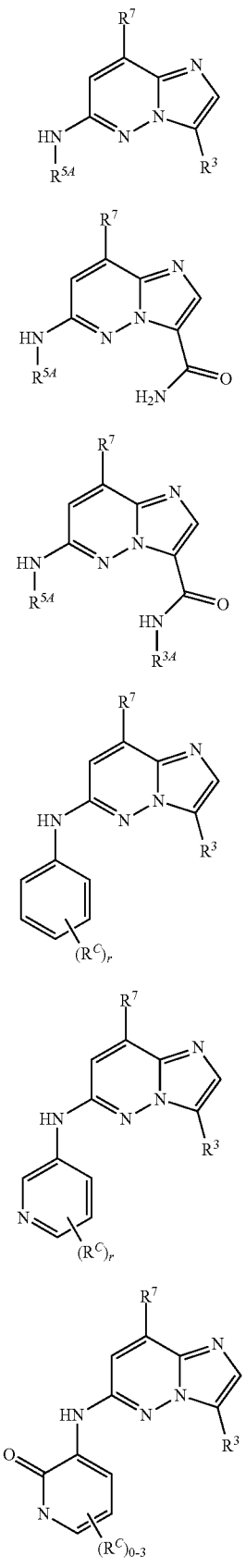
X-a
XI-a
XII-a
XIII-a
XIV-a
XV-a or a pharmaceutically acceptable salt thereof, wherein each of r, R, $R^C$, $R^3$, $R^{3A}$, $R^5$, $R^{5A}$, and $R^7$ is as defined above and described in embodiments herein, both singly and in combination.

In some embodiments, the present invention provides a compound of formula I, II, III, IV, V, VI, VII, VIII, IX, X, XI, XII, XIII, XIV, XV, I-a, II-a, III-a, IV-a, V-a, VI-a, VII-a, VIII-a, IX-a, X-a XI-a, XII-a, XIII-a, XIV-a, or XV-a wherein $R^7$ is —$NH_2$ or —$NHR^{7A}$.

In some embodiments, the present invention provides a compound of formula I, II, III, IV, V, VI, VII, VIII, IX, X, XI, XII, XIII, XIV, XV, I-a, II-a, III-a, IV-a, V-a, VI-a, VII-a, VIII-a, IX-a, X-a XI-a, XII-a, XIII-a, XIV-a, or XV-a wherein $R^7$ is —$NHR^{7A}$. thereby forming a compound of formula I-b, II-b, IV-b, V-b, VI-b, VII-b, VIII-b, IX-b, X-b, XI-b, XII-b, XIII-b, XIV-b, XV-b, I-c, II-c, IV-c, V-c, VI-c, VI-b, VIII-c, IX-c, X-c XI-c, XII-c, XIII-c, XIV-c, or XV-c respectively:

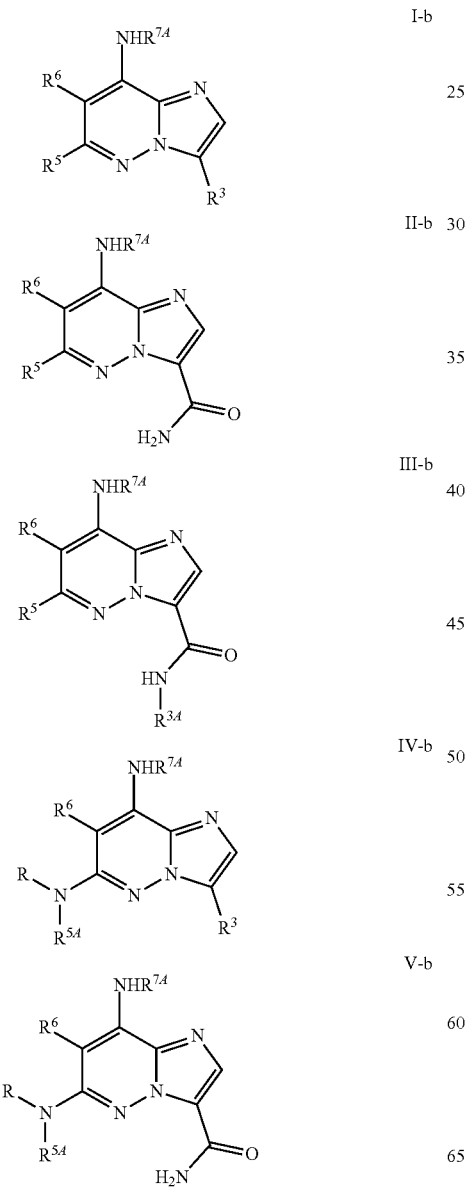
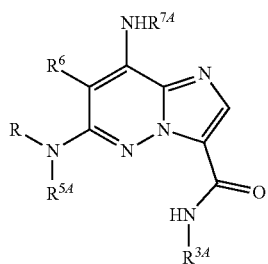
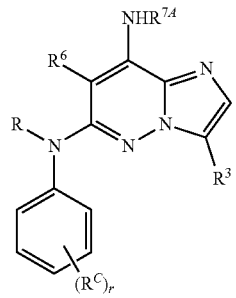
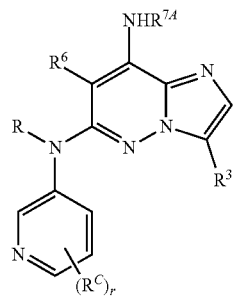
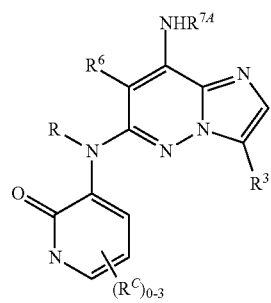
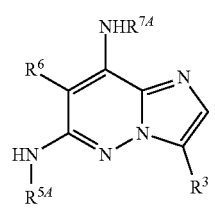
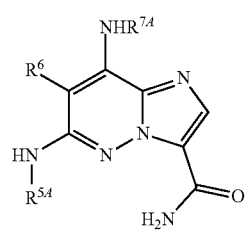

-continued
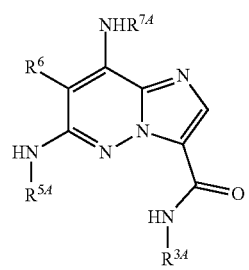
XII-b
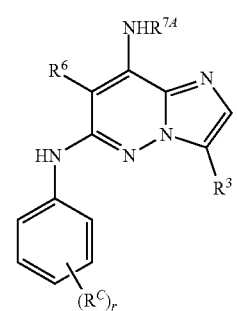
XIII-b
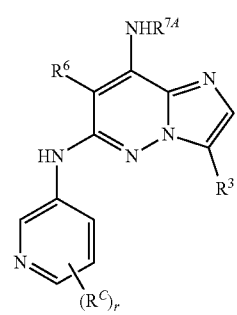
XIV-b
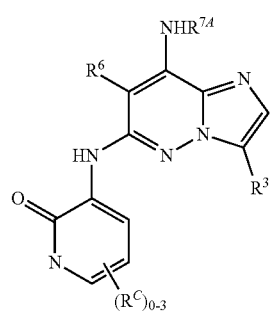
XV-b
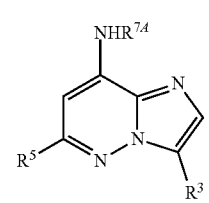
I-c
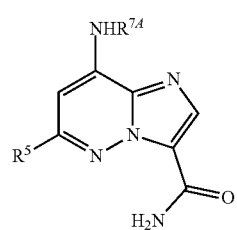
II-c
-continued
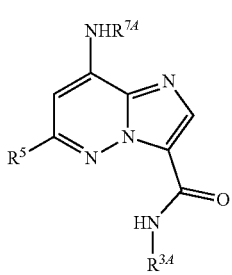
III-c
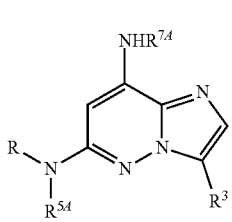
IV-c
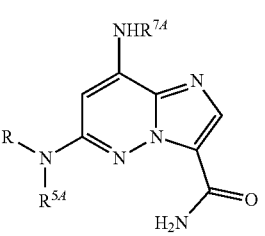
V-c
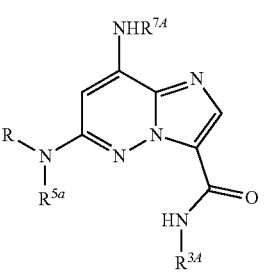
VI-c
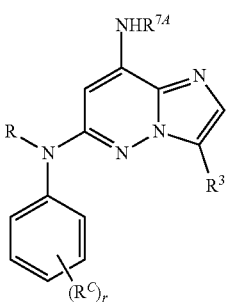
VII-c
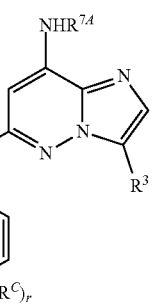
VIII-c -continued IX-c
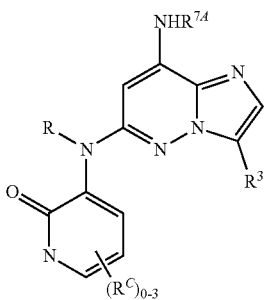

X-c
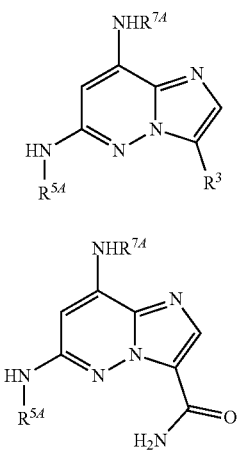

XI-c

XII-c

XIII-c

XIV-c
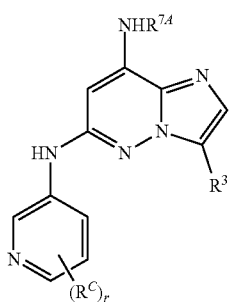

-continued

XV-c
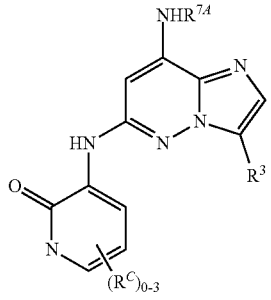

or a pharmaceutically acceptable salt thereof, wherein each of r, R, $R^C$, $R^3$, $R^{3A}$, $R^5$, $R^{5A}$, $R^6$, and $R^{7A}$ is as defined above and described in embodiments herein, both singly and in combination.

In some embodiments, the present invention provides a compound of formula I-b, II-b, IV-b, V-b, VI-b, VII-b, VIII-b, IX-b, X-b, XI-b, XII-b, XIII-b, XIV-b, XV-b, I-c, II-c, IV-c, V-c, VI-c, VII-c, VIII-c, IX-c, X-c XI-c, XII-c, XIII-c, XIV-c, or XV-c, wherein $R^{7A}$ is $R^B$, substituted by q instances of $R^C$, wherein $R^{7A}$ is not phenyl. In some embodiments, the present invention provides a compound of formula I-b, II-b, IV-b, V-b, VI-b, VII-b, VIII-b, IX-b, X-b, XI-b, XII-b, XIII-b, XIV-b, XV-b, I-c, II-c, IV-c, V-c, VI-c, VII-c, VIII-c, IX-c, X-c XI-c, XII-c, XIII-c, XIV-c, or XV-c, wherein $R^{7A}$ is methyl. In some embodiments, the present invention provides a compound of formula I-b, II-b, IV-b, V-b, VI-b, VII-b, VIII-b, IX-b, X-b, XI-b, XII-b, XIII-b, XIV-b, XV-b, I-c, II-c, IV-c, V-c, VI-c, VII-c, VIII-c, IX-c, X-c XI-c, XII-c, XIII-c, XIV-c, or XV-c, wherein $R^{7A}$ is -CD$_3$.

In some embodiments, the present invention provides a compound of formula I-b, III-b, IV-b, VI-b, VII-b, VIII-b, IX-b, X-b, XII-b, XIII-b, XIV-b, XV-b, I-c, IV-c, VI-c, VII-c, VIII-c, IX-c, X-c, XII-c, XIII-c, XIV-c, or XV-c, wherein $R^{3A}$ is $R^B$, and is substituted by q instances of $R^C$, provided that $R^{3A}$ is not phenyl.

In some embodiments, the present invention provides a compound of formula I-b, III-b, IV-b, VI-b, VII-b, VIII-b, IX-b, X-b, XII-b, XIII-b, XIV-b, XV-b, I-c, IV-c, VI-c, VII-c, VIII-c, IX-c, X-c, XII-c, XIII-c, XIV-c, or XV-c, wherein each of $R^{3A}$ and $R^{7A}$ is $R^B$, and is substituted by q instances of $R^C$, provided that neither $R^{3A}$ nor $R^{7A}$ is phenyl.

In some embodiments, the present invention provides a compound of formula IV wherein $R^{5A}$ is pyridin-2-yl substituted by r instances of $R^C$, thereby forming a compound of formula XVI:

XVI
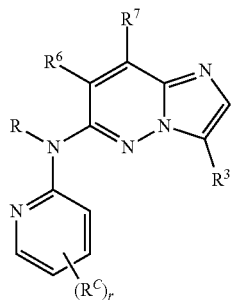

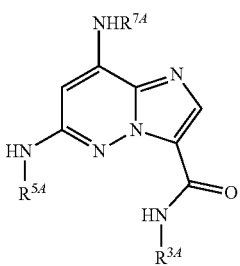

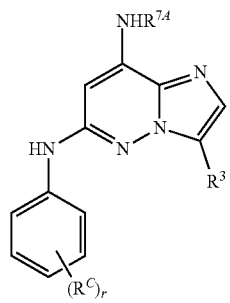

or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula I, wherein $R^5$ is -$L^1$-$R^{5A}$, $L^1$ is a covalent bond, and $R^{5A}$ is an 8-10 membered bicyclic heteroaryl ring having 1-4 heteroatoms independently selected from nitrogen, oxygen, and sulfur. In some embodiments, the present invention provides a compound of formula I, wherein $R^5$ is -$L^1$-$R^{5A}$, is a covalent bond, and $R^{5A}$ is an 8-10 membered bicyclic heteroaryl ring having 1-4 heteroatoms independently selected from nitrogen, oxygen, and sulfur.

In some embodiments, the present invention provides a compound of formula I, wherein $R^5$ is -$L^1$-$R^{5A}$, L' is a covalent bond, and $R^{5A}$ is indol-1-yl, indol-3-yl, 4-azaindol-1-yl, 7-azaindol-3-yl, or 7-azaindazol-3-yl, each $R^{5A}$ substituted by r instances of $R^C$, thereby providing a compound of formulas XVII, XVIII, XIX, XX, or XXI respectively:

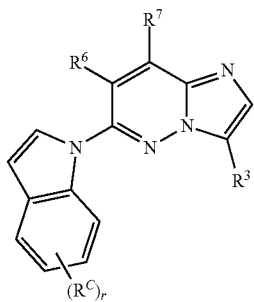

XVII

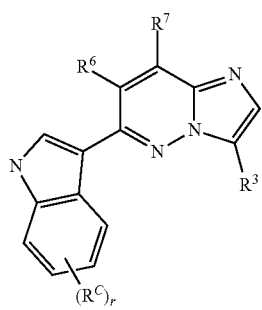

XVIII

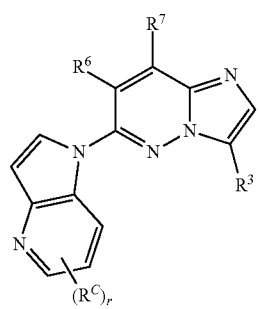
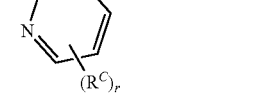

XIX

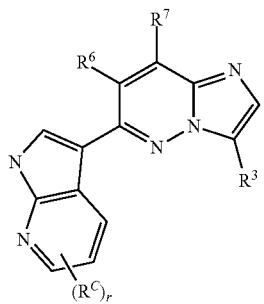

XX

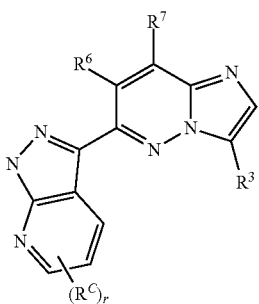

XXI or a pharmaceutically acceptable salt thereof, wherein each of r, $R^C$, $R^3$, $R^6$, and $R^7$ is as defined above and described in embodiments herein, both singly and in combination.

In some embodiments, the present invention provides a compound of formula XVII, XVIII, XIX, XX, or XXI wherein $R^6$ is hydrogen, thereby providing a compound of formulas XVII-a, XVIII-a, XIX-a, XX-a, or XXI-a respectively:

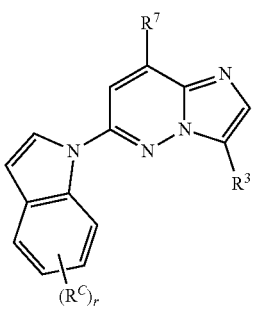

XVII-a

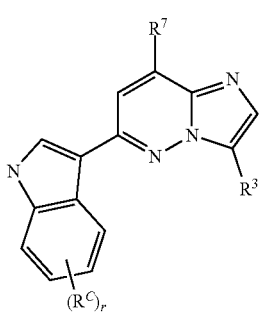

XVIII-a

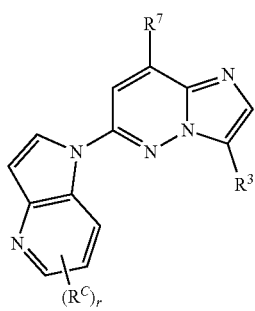
XIX-a

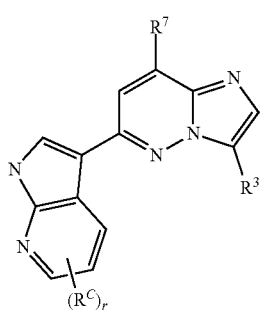
XX-a

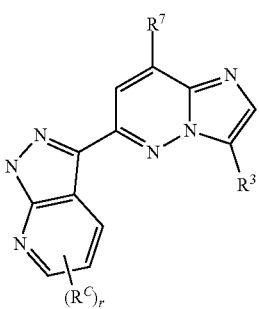
XXI-a or a pharmaceutically acceptable salt thereof, wherein each of r, R$^C$, R$^3$, and R$^7$ is as defined above and described in embodiments herein, both singly and in combination.

In some embodiments, the present invention provides a compound of formula XVII-a, XVIII-a, XIX-a, XX-a, or XXI-a wherein R$^7$ is —NHR$^{7A}$, thereby providing a compound of formulas XVII-b, XVIII-b, XIX-b, XX-b, or XXI-b respectively:

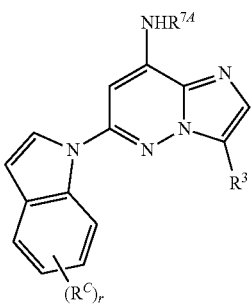
XVII-b

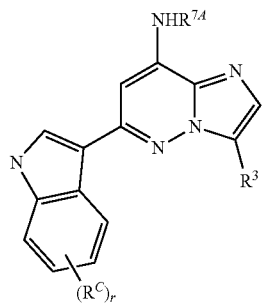
XVIII-b

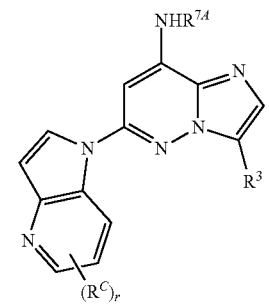
XIX-b

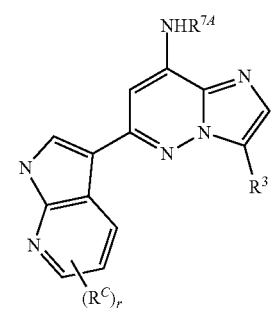
XX-b

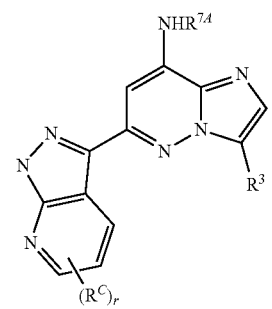
XXI-b or a pharmaceutically acceptable salt thereof, wherein each of r, R$^C$, R$^3$, and R$^{7A}$ is as defined above and described in embodiments herein, both singly and in combination.

In some embodiments, the present invention provides a compound of formula XVII-b, XVIII-b, XIX-b, XX-b, or XXI-b wherein R$^3$ is —C(O)NHR$^{3A}$, thereby providing a compound of formulas XVII-c, XVIII-c, XIX-c, XX-c, or XXI-c respectively:

XVII-c
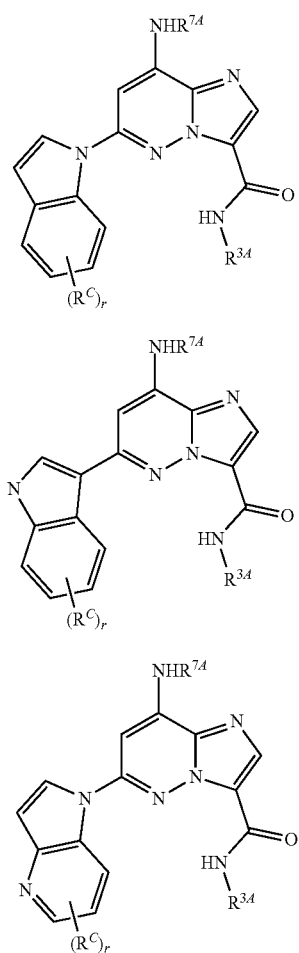
XVIII-c
XIX-c
-continued
XX-c
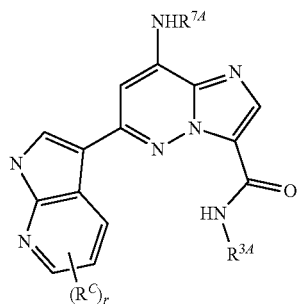
XXI-c
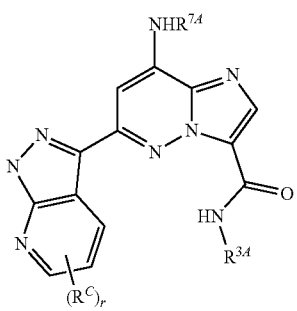
or a pharmaceutically acceptable salt thereof, wherein each of r, $R^C$, $R^3$, and $R^{7A}$ is as defined above and described in embodiments herein, both singly and in combination.
Exemplary compounds of the invention are set forth in Table 1, below.
TABLE 1
| Selected Compounds | |
|---|---|
| Compound | Structure |
| I-1 | 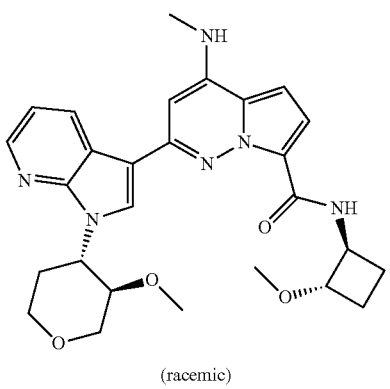 [SMILES: CNc1cc(-c2cn([C@H]3CCOC[C@@H]3OC)c3ncccc23)nn2c(C(=O)N[C@H]3CC[C@@H]3OC)ccc12] (racemic) |

TABLE 1-continued
Selected Compounds
| Compound | Structure |
|---|---|
| I-2 | 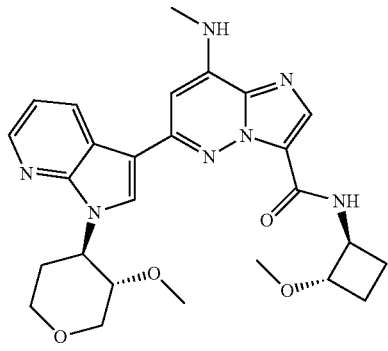<br>(racemic) |
| I-3 | 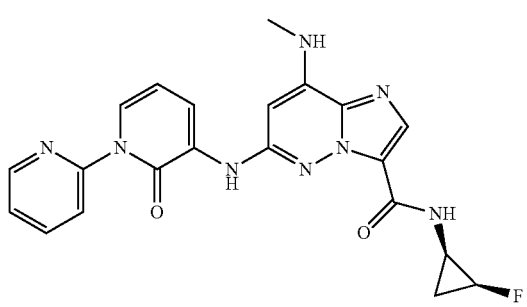 [SMILES: CNc1cc(Nc2cccn(-c3ccccn3)c2=O)nn2c(C(=O)N[C@@H]3C[C@@H]3F)cnc12] |
| I-4 | 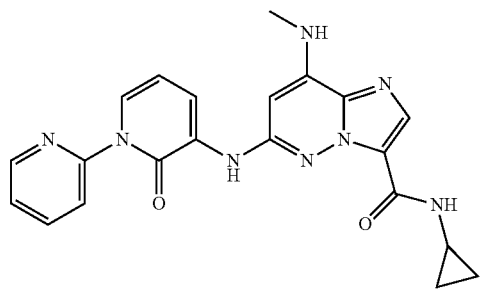 [SMILES: CNc1cc(Nc2cccn(-c3ccccn3)c2=O)nn2c(C(=O)NC3CC3)cnc12] |
| I-5 | 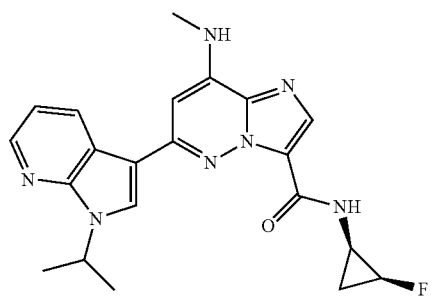 [SMILES: CNc1cc(-c2cn(C(C)C)c3ncccc23)nn2c(C(=O)N[C@@H]3C[C@@H]3F)cnc12] |

TABLE 1-continued
Selected Compounds
| Compound | Structure |
|---|---|
| I-6 | 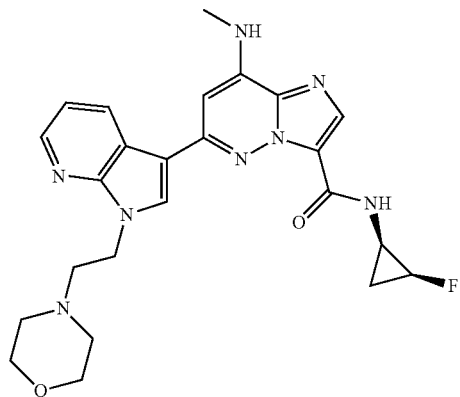 [SMILES: CNc1cc(-c2cn(CCN3CCOCC3)c3ncccc23)nn2c(C(=O)N[C@@H]3C[C@@H]3F)cnc12] |
| I-7 | 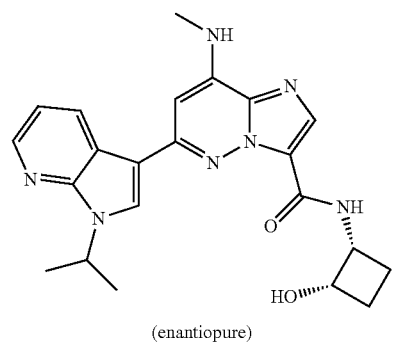 [SMILES: CNc1cc(-c2cn(C(C)C)c3ncccc23)nn2c(C(=O)N[C@@H]3CC[C@@H]3O)cnc12]<br>(enantiopure) |
| I-8 | 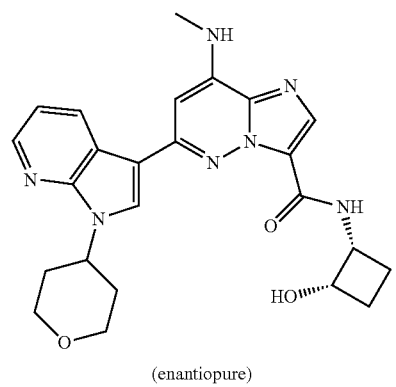 [SMILES: CNc1cc(-c2cn(C3CCOCC3)c3ncccc23)nn2c(C(=O)N[C@@H]3CC[C@@H]3O)cnc12]<br>(enantiopure) |

TABLE 1-continued
Selected Compounds
| Compound | Structure |
|---|---|
| I-9 | 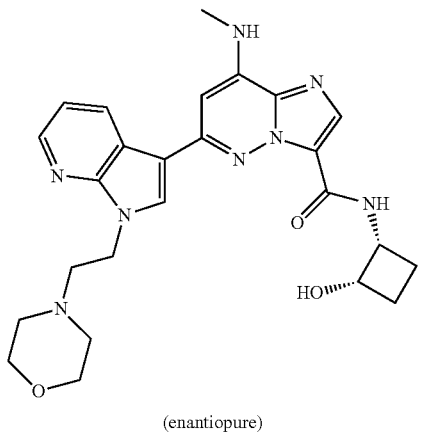 [SMILES: CNc1cc(-c2cn(CCN3CCOCC3)c3ncccc23)nn2c(C(=O)N[C@@H]3CC[C@@H]3O)cnc12]
(enantiopure) |
| I-10 | 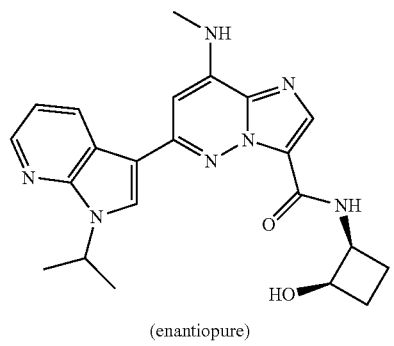 [SMILES: CNc1cc(-c2cn(C(C)C)c3ncccc23)nn2c(C(=O)N[C@H]3CC[C@H]3O)cnc12]
(enantiopure) |
| I-11 | 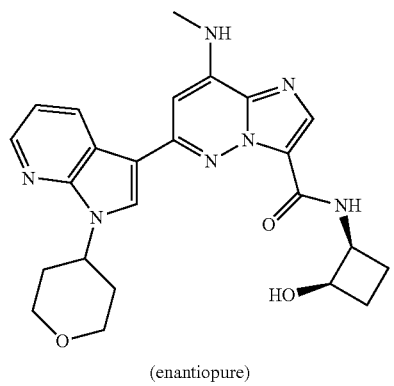 [SMILES: CNc1cc(-c2cn(C3CCOCC3)c3ncccc23)nn2c(C(=O)N[C@H]3CC[C@H]3O)cnc12]
(enantiopure) |

TABLE 1-continued
Selected Compounds
| Compound | Structure |
|---|---|
| I-12 | 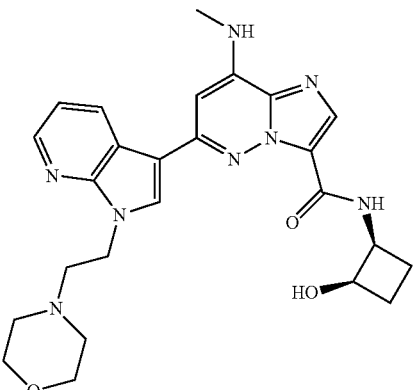<br>(enantiopure) |
| I-13 | 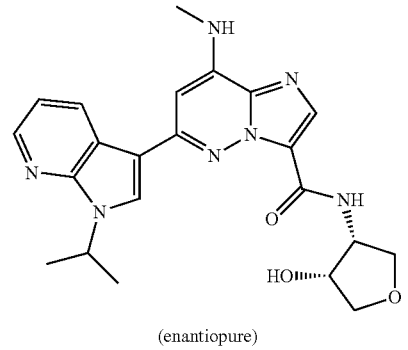 [SMILES: CNc1cc(-c2cn(C(C)C)c3ncccc23)nn2c(C(=O)N[C@@H]3COC[C@@H]3O)cnc12]<br>(enantiopure) |
| I-14 | 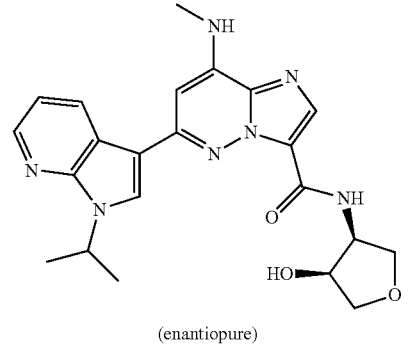 [SMILES: CNc1cc(-c2cn(C(C)C)c3ncccc23)nn2c(C(=O)N[C@H]3COC[C@H]3O)cnc12]<br>(enantiopure) |
| I-15 | 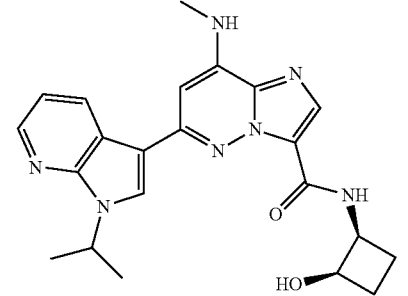<br>(racemic) |

TABLE 1-continued
| Selected Compounds | |
|---|---|
| Compound | Structure |
| I-16 | 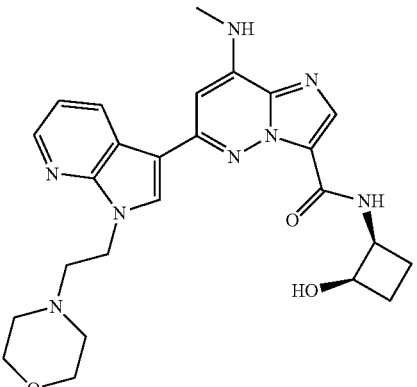<br>(racemic) |
| I-17 | 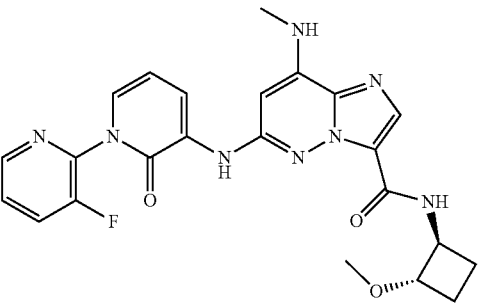 [SMILES: CNc1cc(Nc2cccn(-c3ncccc3F)c2=O)nn2c(C(=O)N[C@H]3CC[C@@H]3OC)cnc12] |
| I-18 | 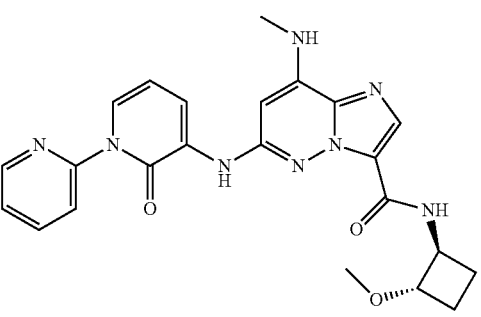 [SMILES: CNc1cc(Nc2cccn(-c3ccccn3)c2=O)nn2c(C(=O)N[C@H]3CC[C@@H]3OC)cnc12] |
| I-19 | 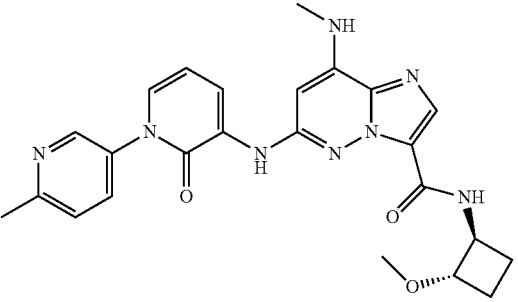 [SMILES: CNc1cc(Nc2cccn(-c3ccc(C)nc3)c2=O)nn2c(C(=O)N[C@H]3CC[C@@H]3OC)cnc12] |

TABLE 1-continued
Selected Compounds
| Compound | Structure |
|---|---|
| I-20 | 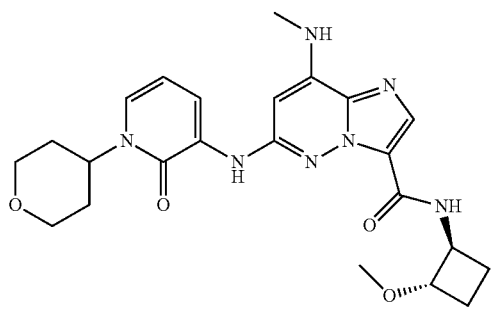 [SMILES: CNc1cc(Nc2cccn(C3CCOCC3)c2=O)nn2c(C(=O)N[C@H]3CC[C@@H]3OC)cnc12] |
| I-21 | 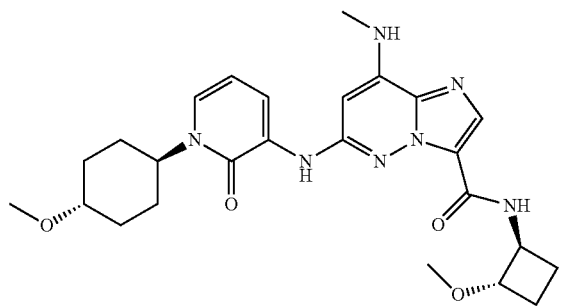 [SMILES: CNc1cc(Nc2cccn([C@H]3CC[C@H](OC)CC3)c2=O)nn2c(C(=O)N[C@H]3CC[C@@H]3OC)cnc12] |
| I-22 | 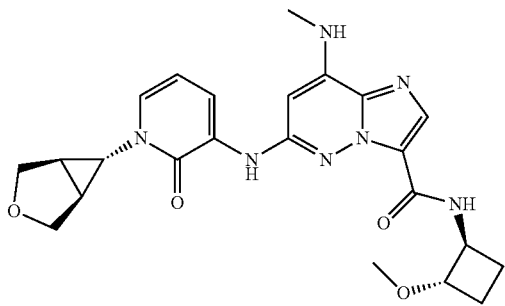 [SMILES: CNc1cc(Nc2cccn([C@H]3[C@@H]4COC[C@@H]43)c2=O)nn2c(C(=O)N[C@H]3CC[C@@H]3OC)cnc12] |
| I-23 | 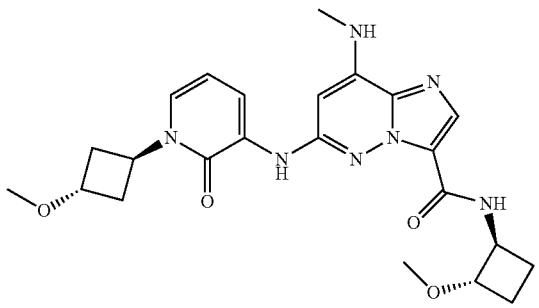 [SMILES: CNc1cc(Nc2cccn([C@H]3C[C@H](OC)C3)c2=O)nn2c(C(=O)N[C@H]3CC[C@@H]3OC)cnc12] |

TABLE 1-continued
Selected Compounds
| Compound | Structure |
|---|---|
| I-24 | 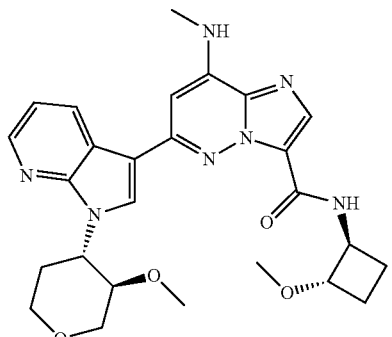<br>(enantiopure) |
| I-25 | 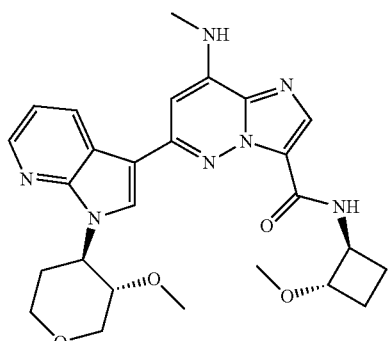<br>(enantiopure) |
| I-26 | 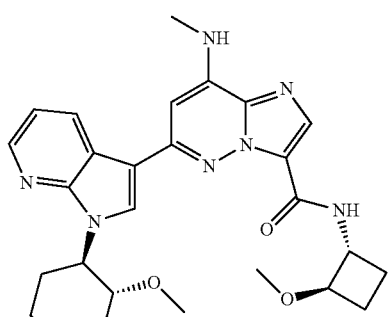<br>(enantiopure) |
| I-27 | 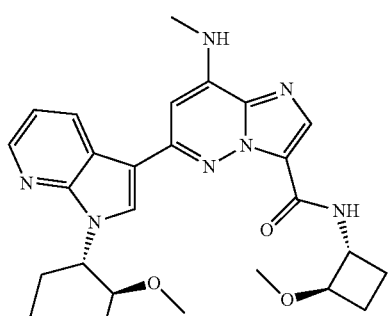<br>(enantiopure) |

TABLE 1-continued
Selected Compounds
| Compound | Structure |
|---|---|
| I-28 | 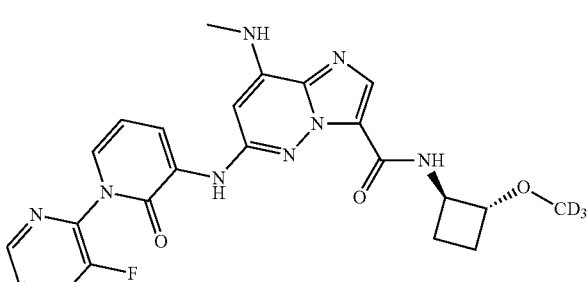<br>(enantiopure) |
| I-29 | 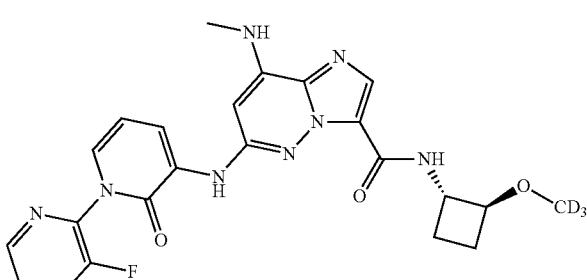<br>(enantiopure) |
| I-30 | 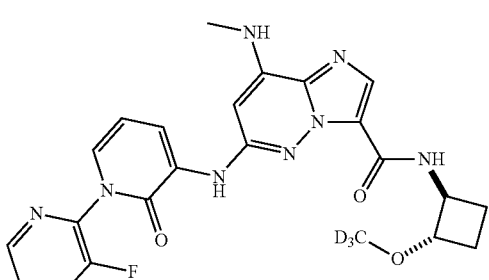<br>(racemic) |
| I-31 | 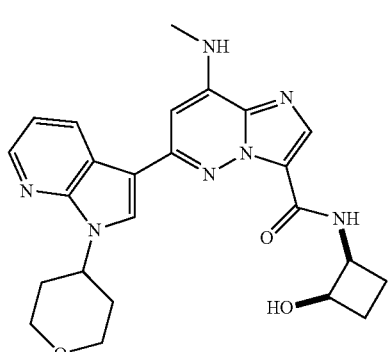<br>(racemic) |

TABLE 1-continued
Selected Compounds
| Compound | Structure |
|---|---|
| I-32 | 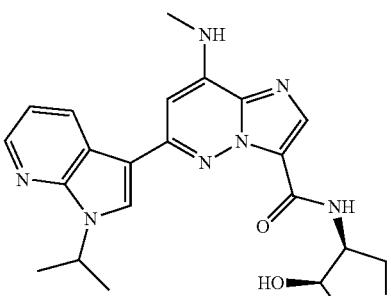<br>(racemic) |
| I-33 | 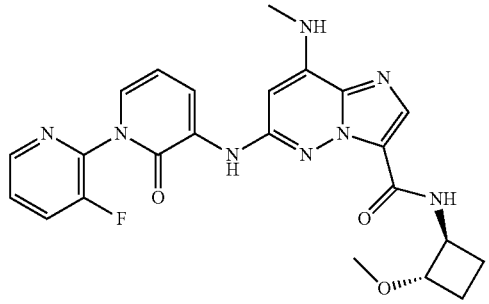<br>(enantiopure) |
| I-34 | 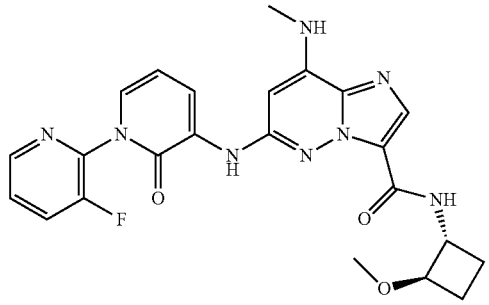<br>(enantiopure) |
| I-35 | 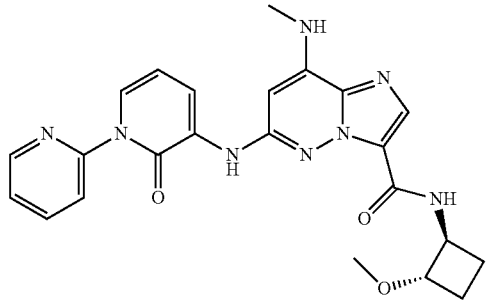<br>(enantiopure) |

TABLE 1-continued
Selected Compounds
| Compound | Structure |
|---|---|
| I-36 | 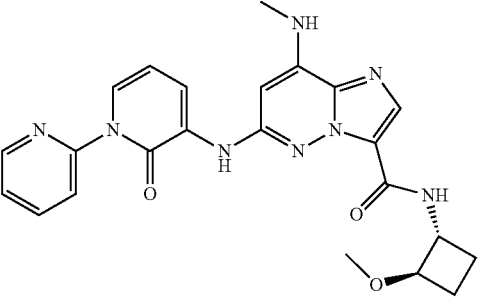<br>(enantiopure) |
| I-37 | 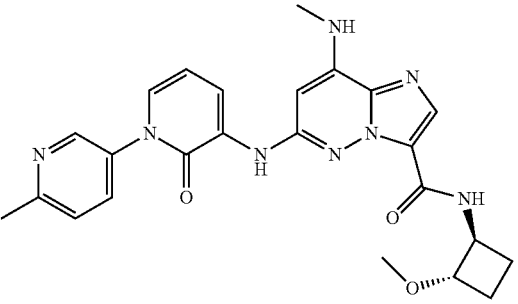<br>(enantiopure) |
| I-38 | 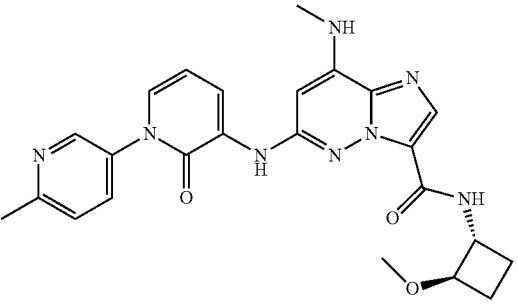<br>(enantiopure) |
| I-39 | 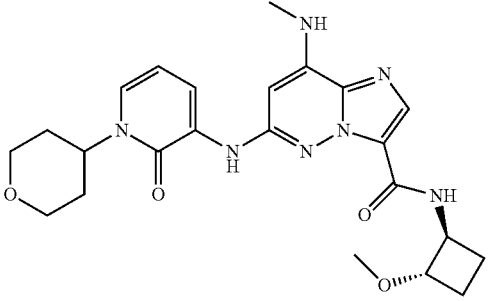<br>(enantiopure) |

TABLE 1-continued
| Selected Compounds | |
|---|---|
| Compound | Structure |
I-40
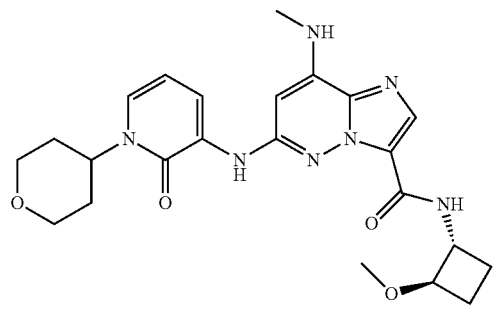
(enantiopure)
I-41
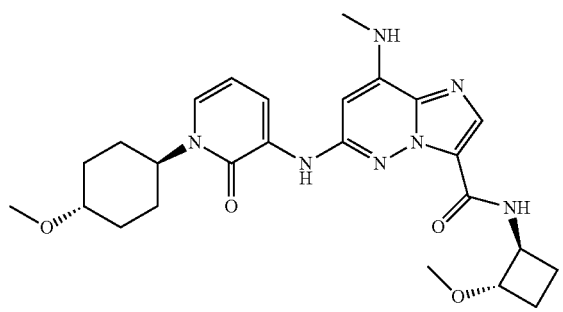
(enantiopure)
I-42
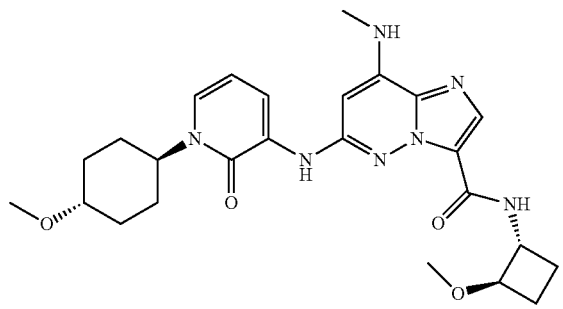
(enantiopure)
I-43
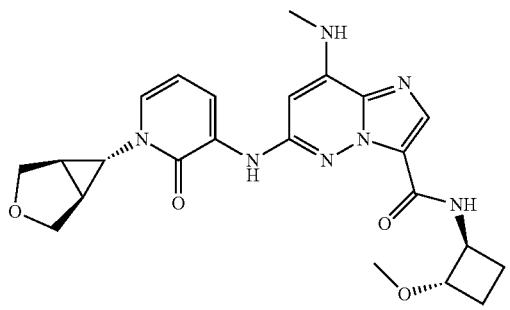
(enantiopure)

TABLE 1-continued
Selected Compounds
| Compound | Structure |
|---|---|
| I-44 | 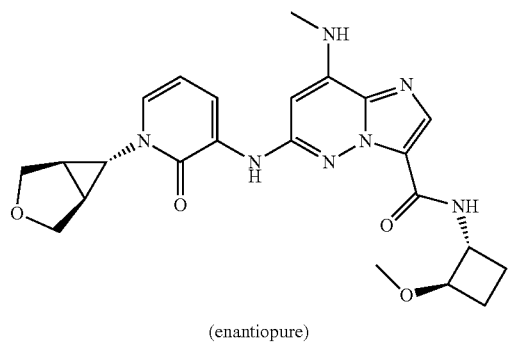 [SMILES: CNc1cc(Nc2cccn([C@H]3[C@@H]4COC[C@@H]43)c2=O)nn2c(C(=O)N[C@@H]3CC[C@H]3OC)cnc12]<br>(enantiopure) |
| I-45 | 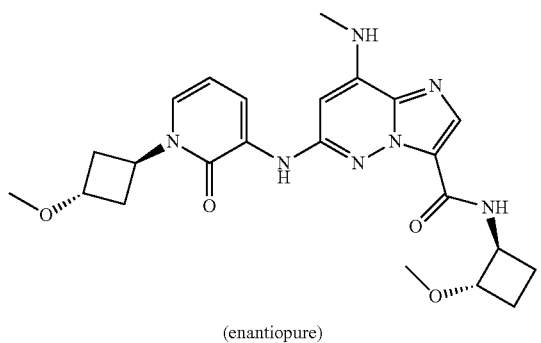 [SMILES: CNc1cc(Nc2cccn([C@H]3C[C@H](OC)C3)c2=O)nn2c(C(=O)N[C@H]3CC[C@@H]3OC)cnc12]<br>(enantiopure) |
| I-46 | 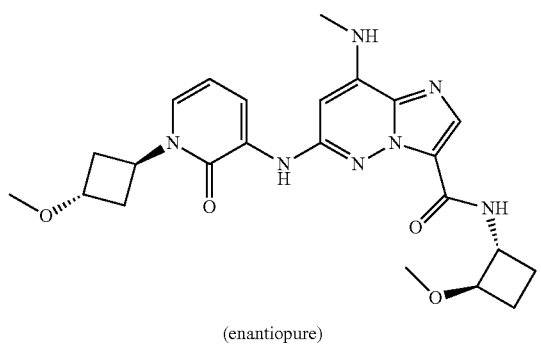 [SMILES: CNc1cc(Nc2cccn([C@H]3C[C@H](OC)C3)c2=O)nn2c(C(=O)N[C@@H]3CC[C@H]3OC)cnc12]<br>(enantiopure) |
| I-47 | 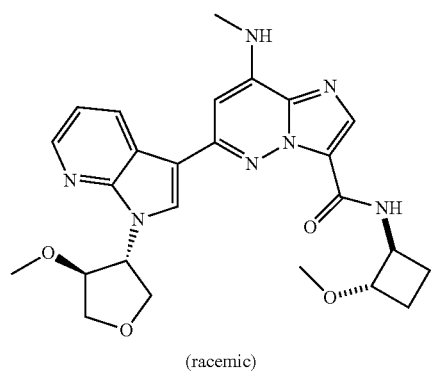<br>(racemic) |

TABLE 1-continued
Selected Compounds
| Compound | Structure |
|---|---|
| I-48 | 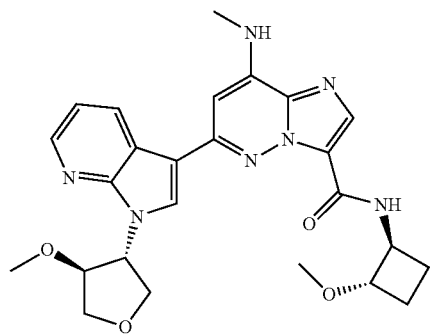<br>(enantiopure) |
| I-49 | 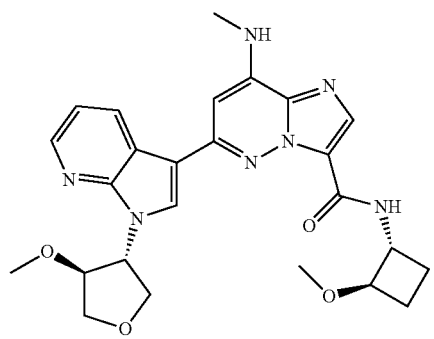<br>(enantiopure) |
| I-50 | 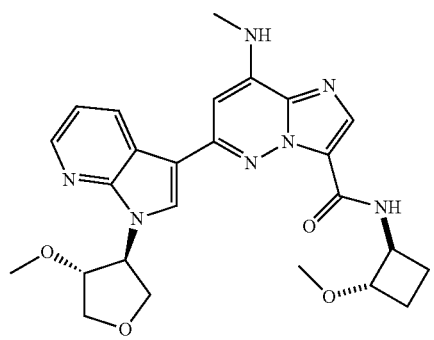<br>(racemic) |
| I-51 | 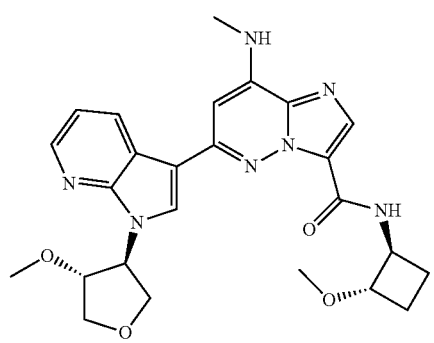<br>(enantiopure) |

TABLE 1-continued

Selected Compounds

| Compound | Structure |
|---|---|
| I-52 | 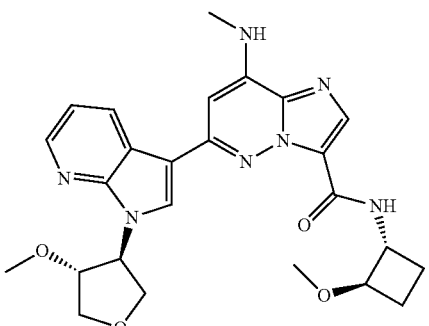<br>(enantiopure) |

In some embodiments, the method employs a compound set forth in Table 1, above, or a pharmaceutically acceptable salt thereof. In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as described above, wherein the compound is denoted as "A" as set forth in Table 2. In some embodiments, the present invention provides a compound of formula I as described above, wherein the compound is denoted as "B" as set forth in Table 2. In some embodiments, the present invention provides a compound of formula I as described above, wherein the compound is denoted as "C" as set forth in Table 2. In some embodiments, the present invention provides a compound of formula I as described above, wherein the compound is denoted as "D" as set forth in Table 2. In some embodiments, the present invention provides a compound of formula I as described above, wherein the compound is denoted as "A" or "B" as set forth in Table 2. In some embodiments, the present invention provides a compound of formula I as described above, wherein the compound is denoted as "A" or "B" or "C" as set forth in Table 2. In some embodiments, the present invention provides a compound of formula I as described above, wherein the compound is denoted as "A" or "B" or "C" or "D" as set forth in Table 2.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-$\alpha$, IFN-$\beta$, IFN-$\kappa$, IFN-$\delta$, IFN-$\epsilon$, IFN-$\tau$, IFN-$\omega$, and IFN-$\zeta$ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon $\alpha/\beta$ signaling pathway," Cell (1992) 70:313; Stahl et al., "Association and activation of Jak-Tyk kinases by CNTF-LIF-OSM-IL-6$\beta$ receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12R$\beta$1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT5.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behcet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behcet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11. Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmorterm brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, cutaneous lupus erythematosus, systemic lupus erythematosus, multiple sclerosis, psoriasis, Behcet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, cutaneous lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from cutaneous lupus erythematosus, Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid g), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthriti s, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-di hydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C$_{1-1033}$, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α-γ- or δ-tocopherol or α-γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and $2C_4$ Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGl antibody, Angiozyme (RPI 4610) and B vacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BILL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

The present invention is now further described by means of non-limiting embodiments 1-32:

Embodiment 1

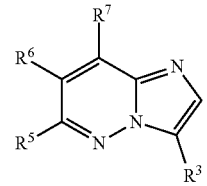

I

A compound of formula I:
or a pharmaceutically acceptable salt thereof, wherein:
$R^3$ is —C(O)NH$_2$, —C(O)NHR$^{3A}$, —C(O)N(R$^{3A}$)$_2$, —C(O)OR, —C(O)NHOR, or a 5-6 membered monocyclic heteroaryl ring having 1-4 heteroatoms independently selected from nitrogen, oxygen, and sulfur, wherein said ring is substituted with m instances of $R^{3B}$;
$R^5$ is hydrogen or -L$^1$-R$^{5A}$;
$R^6$ is hydrogen, $R^A$, or $R^B$;
or $R^5$ and $R^6$ are taken together with their intervening atoms to form a 4-7 membered partially unsaturated or heteroaryl ring having 0-3 heteroatoms independently selected from nitrogen, oxygen, and sulfur, wherein said ring is substituted by $R^{5A}$ and n instances of $R^C$;
$R^7$ is hydrogen, halogen, —NH$_2$, —NHR$^{7A}$, or —NHC(O)R$^{7A}$;
or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$;
$L^1$ is a covalent bond or a $C_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;
$R^{3A}$, $R^{3B}$, and $R^{7A}$ are each independently $R^B$, and are each substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur;
$R^{5A}$ and each instance of $R^{5B}$ are each independently $R^A$ or $R^B$, and are each substituted by r instances of $R^C$;
each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;
each instance of $R^B$ is independently $C_{1-6}$ aliphatic, phenyl, a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring, a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4; provided that the compound is not

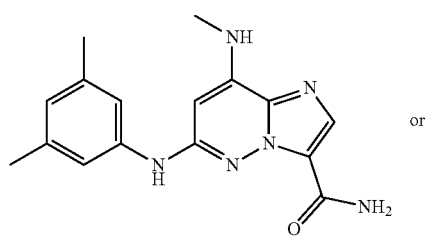

or

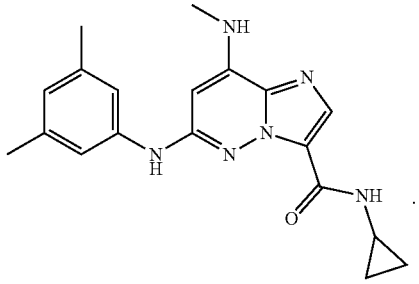

Embodiment 2

The compound of embodiment 1 of one of formulas II or III:

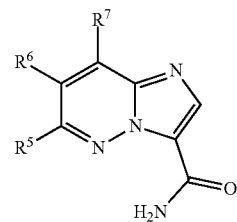

II

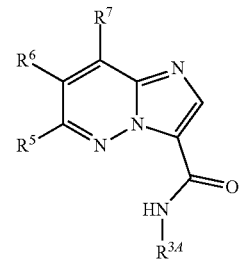

III or a pharmaceutically acceptable salt thereof.

Embodiment 3

The compound of any one of embodiments 1 or 2 of formula V or VI:

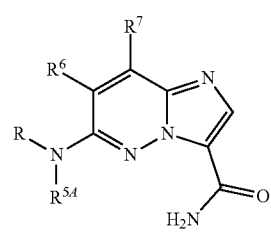

V

VI

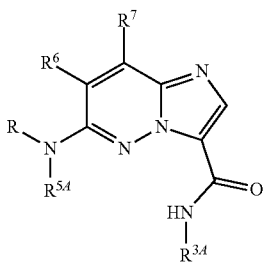

or a pharmaceutically acceptable salt thereof.

Embodiment 4

The compound of any one of embodiments 1-3 of formula V-a or VI-a:

V-a

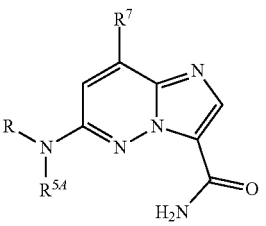

VI-a

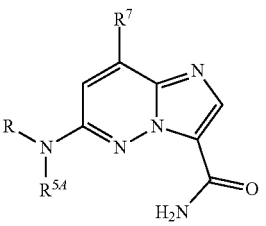

or a pharmaceutically acceptable salt thereof.

Embodiment 5

The compound of any one of embodiments 1-4 wherein $R^7$ is —NH$_2$ or —NHR$^{7A}$, or a pharmaceutically acceptable salt thereof.

Embodiment 6

The compound of any one of embodiments 1-5 of one of formulas V-c or VI-c:

V-c

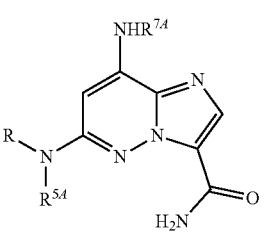

VI-c

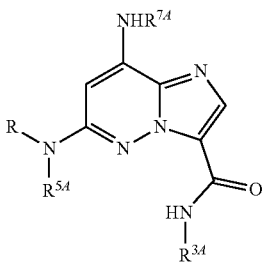

or a pharmaceutically acceptable salt thereof.

Embodiment 7

The compound of any one of embodiments 1-6 wherein each of $R^{3A}$ and $R^{7A}$ is independently $R^B$, and is substituted by q instances of $R^C$, provided that neither of $R^{3A}$ or $R^{7A}$ is phenyl.

Embodiment 8

The compound of any one of embodiments 1-7 wherein $R^{7A}$ is $C_{1-6}$ aliphatic.

Embodiment 9

The compound of any one of embodiments 1-8 wherein $R^{7A}$ is methyl.

Embodiment 10

The compound of any one of embodiments 1-9, selected from those depicted in Table 1 of the specification, or a pharmaceutically acceptable salt thereof.

Embodiment 11

A pharmaceutical composition comprising a compound according to any one of embodiments 1-10, or a pharmaceutically acceptable salt thereof, and a pharmaceutically acceptable carrier, adjuvant, or vehicle.

Embodiment 12

The compound of embodiments 1 to 10, or the pharmaceutical composition of embodiment 11 for use as a medicament.

Embodiment 13

A method, optionally an in-vitro method, of inhibiting TYK2 in a biological sample comprising contacting the sample with the compound of any one of embodiments 1-10, or a pharmaceutically acceptable salt thereof, or a pharmaceutical composition of embodiment 11.

Embodiment 14

The compound of any one of embodiments 1-10 or the pharmaceutical composition of embodiment 11 for use in the treatment of an TYK2-mediated disorder, disease, or condition in a patient comprising administering to said patient the compound of any one of embodiments 1-10 or the pharmaceutical composition of embodiment 11.

Embodiment 15

The compound of any one of embodiments 1-10 or the pharmaceutical composition of embodiment 11 for use according to embodiment 14, wherein the disorder is selected from an autoimmune disorder, an inflammatory disorder, a proliferative disorder, an endocrine disorder, a neurological disorder, or a disorder associated with transplantation.

Embodiment 16

The compound of any one of embodiments 1-10 or the pharmaceutical composition of embodiment 11 for use according to embodiment 15, wherein the disorder is an autoimmune disorder.

Embodiment 17

The compound of any one of embodiments 1-10 or the pharmaceutical composition of embodiment 11 for use according to embodiment 16, wherein the autoimmune disorder is selected from type 1 diabetes, ankylosing spondylitis, cutaneous lupus erythematosus, systemic lupus erythematosus, multiple sclerosis, systemic sclerosis, psoriasis, Crohn's disease, ulcerative colitis, and inflammatory bowel disease.

Embodiment 18

The compound of any one of embodiments 1-10 or the pharmaceutical composition of embodiment 11 for use according to embodiment 15, wherein the disorder is an inflammatory disorder.

Embodiment 19

The compound of any one of embodiments 1-10 or the pharmaceutical composition of embodiment 11 for use according to embodiment 18, wherein the inflammatory disorder is selected from rheumatoid arthritis, asthma, chronic obstructive pulmonary disease, psoriasis, Crohn's disease, ulcerative colitis, and inflammatory bowel disease.

Embodiment 20

The compound of any one of embodiments 1-10 or the pharmaceutical composition of embodiment 11 for use according to embodiment 15, wherein the disorder is a proliferative disorder.

Embodiment 21

The compound of any one of embodiments 1-10 or the pharmaceutical composition of embodiment 11 for use according to embodiment 20, wherein the proliferative disorder is a hematological cancer.

Embodiment 22

The compound of any one of embodiments 1-10 or the pharmaceutical composition of embodiment 11 for use according to embodiment 20, wherein the proliferative disorder is a leukemia.

Embodiment 23

The compound of any one of embodiments 1-10 or the pharmaceutical composition of embodiment 11 for use according to embodiment 22, wherein the leukemia is a T-cell leukemia.

Embodiment 24

The compound of any one of embodiments 1-10 or the pharmaceutical composition of embodiment 11 for use according to embodiment 23, wherein the T-cell leukemia is T-cell acute lymphoblastic leukemia (T-ALL).

Embodiment 25

The compound of any one of embodiments 1-10 or the pharmaceutical composition of embodiment 11 for use according to embodiment 20, wherein the proliferative disorder is associated with one or more activating mutations in TYK2.

Embodiment 26

The compound of any one of embodiments 1-10 or the pharmaceutical composition of embodiment 11 for use according to embodiment 15, wherein the disorder is associated with transplantation.

Embodiment 27

The compound of any one of embodiments 1-10 or the pharmaceutical composition of embodiment 11 for use according to embodiment 26, wherein the disorder is transplant rejection or graft versus host disease.

Embodiment 28

The compound of any one of embodiments 1-10 or the pharmaceutical composition of embodiment 11 for use according to embodiment 15, wherein the disorder is an endocrine disorder.

Embodiment 29

The compound of any one of embodiments 1-10 or the pharmaceutical composition of embodiment 11 for use according to embodiment 28, wherein the endocrine disorder is polycystic ovary syndrome, Crouzon's syndrome, or type 1 diabetes.

Embodiment 30

The compound of any one of embodiments 1-10 or the pharmaceutical composition of embodiment 11 for use according to embodiment 15, wherein the disorder is a neurological disorder.

Embodiment 31

The compound of any one of embodiments 1-10 or the pharmaceutical composition of embodiment 11 for use according to embodiment 30, wherein the neurological disorder is Alzheimer's disease.

Embodiment 32

The compound of any one of embodiments 1-10 or the pharmaceutical composition of embodiment 11 for use according to embodiment 14, wherein the disorder is associated with type I interferon, IL-10, IL-12, or IL-23 signaling.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Example 1. General Synthetic Procedures and Synthesis of N-((1R,2S)-2-fluorocyclopropyl)-6-(1-isopropyl-1H-pyrrolo[2,3-b]pyridin-3-yl)-8-(methylamino)imidazo[1,2-b]pyridazine-3-carboxamide (I-5)

Synthesis General Procedure A (Buchwald Amination)

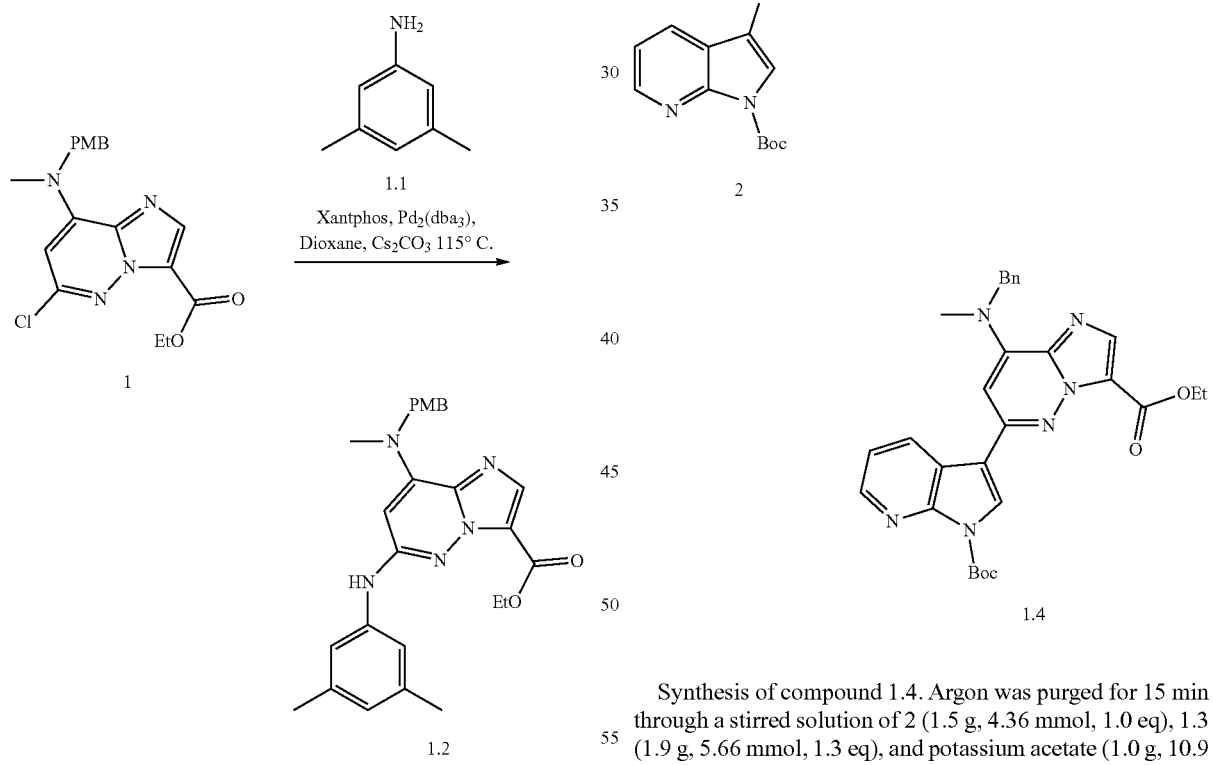

Synthesis of compound 1.2. To a solution of 1 (0.5 g, 1.33 mmol, 1.0 eq) in 1,4-dioxane (8 mL) was added 1.1 (0.193 g, 1.59 mmol, 1.2 eq), cesium carbonate (0.866 g, 2.66 mmol, 2.0 eq). The reaction mixture was degassed for 10 min. under argon atmosphere, then tris(dibenzylideneacetone)dipalladium(O) (0.060 g, 0.066 mmol, 0.05 eq) and 4,5-Bis(diphenylphosphino)-9,9-dimethylxanthene (0.076 g, 0.13 mmol, 0.1 eq) were added, again degassed for 5 min. The reaction mixture was stirred at 115° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane (DCM or MDC) as eluant to obtain pure 1.2 (0.140 g, Yield: 22.84%). MS(ES): m/z=460.23 [M+H]$^+$.

General Procedure B: (Suzuki Coupling)

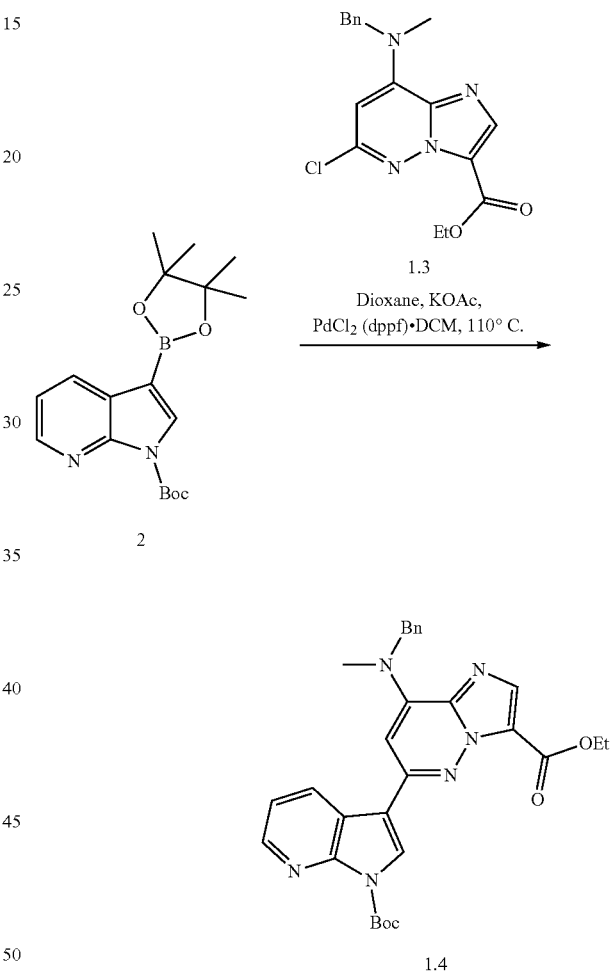

Synthesis of compound 1.4. Argon was purged for 15 min through a stirred solution of 2 (1.5 g, 4.36 mmol, 1.0 eq), 1.3 (1.9 g, 5.66 mmol, 1.3 eq), and potassium acetate (1.0 g, 10.9 mmol, 2.5 eq) in 1,4-dioxane:water (75 mL, 9:1), and [1,1'-bis(diphenylphosphino) ferrocene]palladium(II) dichloride (0.318 g, 0.43 mmol, 0.1 eq) was added to it and further purging was done for 10 min. The reaction mixture was allowed to stir at 110° C. for 5 h. After completion of the reaction, reaction mixture was transferred into water and product was extracted with ethyl acetate. The organic layers were combined, washed with brine solution, dried over sodium sulphate and concentrated under reduced pressure to obtain 1.4 (0.8 g, yield: 34.86%). MS (ES): m/z 527.24 [M+H]$^+$.

General Procedure C (Acid-Amine Coupling)

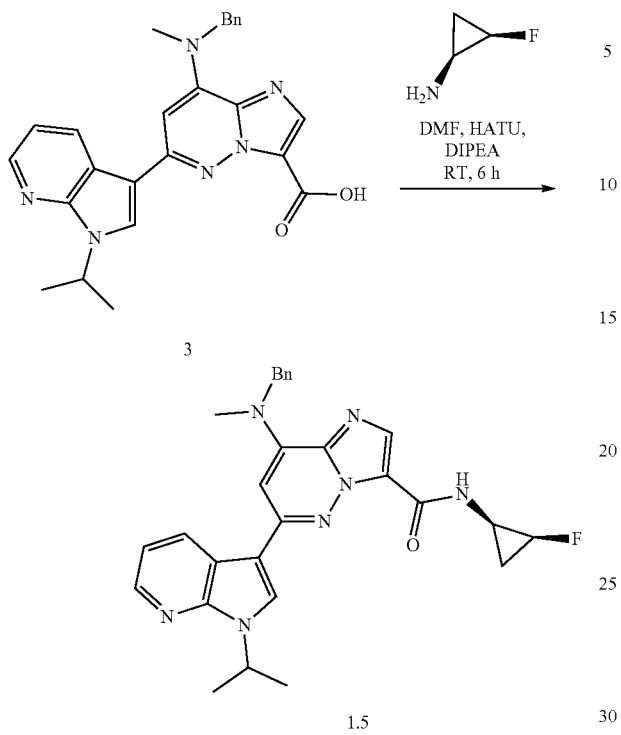

Synthesis of compound 1.5. To a solution of 3 (0.060 g, 0.13 mmol, 1.0 eq), in N,N-dimethylformamide (1 mL) was added 1-[Bis(dimethylamino)methylene]-1H-1,2,3-triazolo[4,5-b]pyridinium 3-oxid hexafluorophosphate (0.098 g, 0.26 mmol, 2.0 eq) and stirred at room temperature for 15 min. To this was added diisopropylethylamine (0.06 mL, 0.39 mmol, 3.0 eq) followed by addition of (1S, 2R)-2-fluorocyclopropan-1-amine (0.010 g, 0.13 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.5 (0.055 g, yield: 81.15%). MS(ES): m/z 498.24 [M+H]$^+$.

General Procedure D (Deprotection by Triflic Acid)

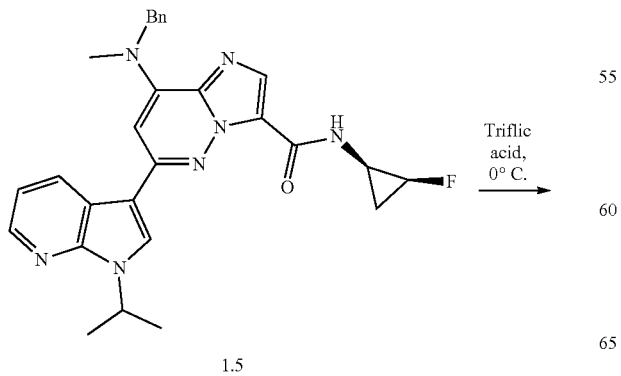

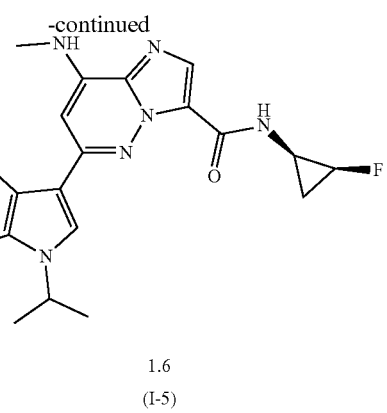

Synthesis of compound 1.6 (compound I-5). To a cooled solution of 1.5 (0.055 g, 0.11 mmol, 1.0 eq) in dichloromethane (DCM or MDC) (1 mL), triflic acid (0.5 mL) was added at 0° C. Reaction mixture was stirred at same temperature for 10 min. After completion of the reaction, the reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 1.6 (compound I-5) (0.030 g, yield: 66.61%), MS (ES): m/z 408.19 [M+H]$^+$.

General Procedure: Synthesis of Ethyl-8-(benzyl (methyl) amino)-6-chloroimidazo[1,2-b]pyridazine-3-carboxylate Applicable to Related Compounds Containing a Benzyl Protecting Group

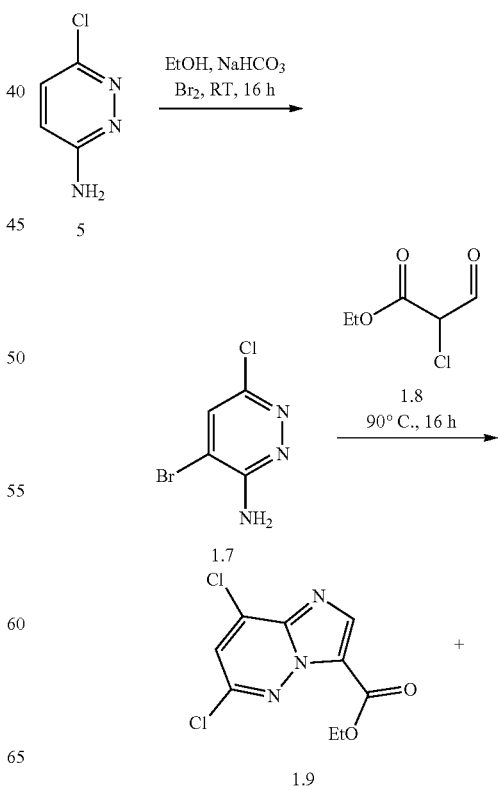

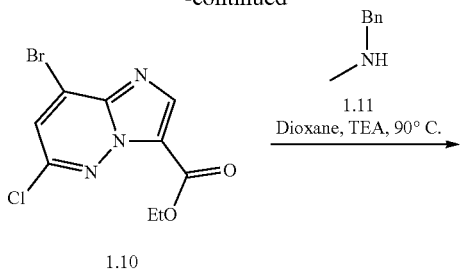

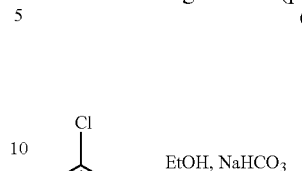

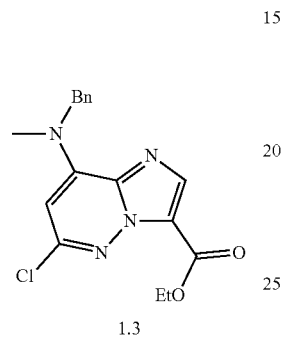

Synthesis of compound 1.7. To a mixture of 5 (10.0 g, 77.51 mmol, 1.0 eq) and sodium bicarbonate (13.0 g, 155 mmol, 2.0 eq) in ethanol (150 mL) was added bromine (12.4 g, 77.51 mmol, 1.0 eq) at 0° C. Reaction mixture was stirred at room temperature for 16 h. After completion of reaction, reaction mixture was transferred into water and solid precipitated was collected using filtration, dried well to obtain 1.7 (7.0 g, yield: 43.50%). MS(ES): m/z 208.92 [M+H]$^+$.

Synthesis of compounds 1.9 and 1.10. A mixture of compound 1.7 (5.0 g, 24.03 mmol, 1.0 eq) and 1.8 (3.9 g, 26.43 mmol, 1.1 eq) was heated at 90° C. for 18 h. After completion of reaction, reaction mixture was transferred into water and product was extracted with ethyl acetate. The organic layers were combined, washed with brine solution, dried over sodium sulphate and concentrated under reduced pressure to obtain crude material. This was further purified by column chromatography and the compound was eluted in 2% methanol in dichloromethane to obtain 1.9 and 1.10 (1.3 g, yield: 20.84%). MS(ES): m/z 260.99 [M+H]$^+$.

Synthesis of compound 1.3. To a mixture of 1.9+1.10 (1.3 g, 5.0 mmol, 1.0 eq) in 1,4-dioxane (15 mL) were added 1.11 (0.665 g, 5.5 mmol, 1.1 eq) and triethylamine (0.858 g, 8.5 mmol, 1.7 eq). Reaction mixture stirred at 90° C. for 3 h. After completion of reaction, the reaction mixture was cooled to room temperature and concentrated under reduced pressure to obtained residue which was triturated with water to obtain solid which was filtered, washed with water and dissolved in dichloromethane. The solution was dried over sodium sulphate and concentrated under reduced pressure to obtain 1.3 (1.28 g, yield: 86.96%). MS(ES): m/z 345.11 [M+H]$^+$.

General Procedure: Synthesis of Ethyl 6-chloro-8-((4-methoxybenzyl)(methyl)amino)imidazo[1,2-b]pyridazine-3-carboxylate and Related Compounds Containing a PMB (p-Methoxybenzyl) Protecting Group

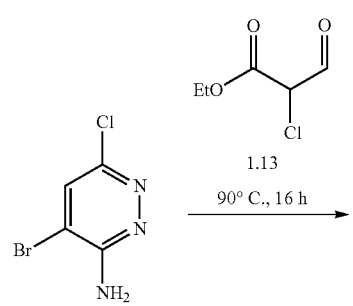

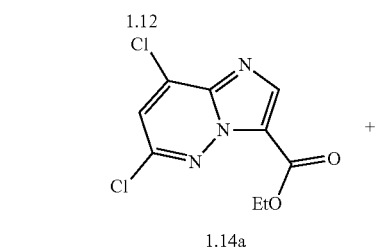

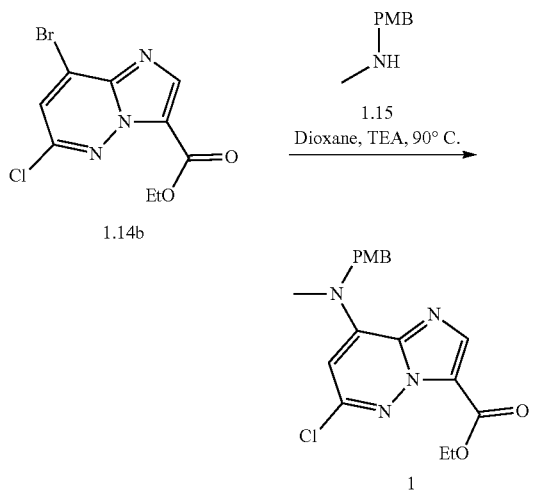

Synthesis of compound 1.12. To a mixture of 6 (10.0 g, 77.51 mmol, 1.0 eq) and sodium bicarbonate (13.0 g, 155 mmol, 2.0 eq) in ethanol (150 mL) was added bromine (12.4 g, 77.51 mmol, 1.0 eq) at 0° C. Reaction mixture was stirred at room temperature for 16 h. After completion of the reaction, the reaction mixture was transferred into water and the solid precipitated was collected using filtration, and dried well to obtain 1.12 (7.0 g, yield: 43.50%). MS(ES): m/z 208.92 [M+H]$^+$.

Synthesis of compounds 1.14a and 1.14b. A mixture of compound 1.12 (5.0 g, 24.03 mmol, 1.0 eq) and 1.13 (3.9 g, 26.43 mmol, 1.1 eq) was heated at 90° C. for 18 h. After completion of the reaction, the reaction mixture was transferred into water and the product was extracted with ethyl acetate. The organic layers were combined, washed with brine solution, dried over sodium sulphate and concentrated under reduced pressure to obtain crude material. This was further purified by column chromatography and the compound was eluted in 2% methanol in dichloromethane to obtain 1.14a and 1.14b (1.3 g, yield: 20.84%). MS(ES): m/z 260.99 [M+H]⁺.

Synthesis of compound 1. To a mixture of 1.14a+1.14b (0.9 g, 3.46 mmol, 1.0 eq) in 1,4-dioxane (10 mL) were added 1.15 (0.573 g, 3.80 mmol, 1.1 eq) and triethylamine (0.593 g, 5.88 mmol, 1.7 eq). The reaction mixture was stirred at 90° C. for 3 h. After completion of the reaction, the reaction mixture was cooled to room temperature and concentrated under reduced pressure to obtain a crude residue, which was triturated with water to obtain a solid, which was then filtered, washed with water, and dissolved in dichloromethane. The solution was dried over sodium sulphate and concentrated under reduced pressure to obtain 1 (0.7 g, yield: 53.97%). MS(ES): m/z 375.12 [M+H]⁺.

Synthesis of N-((1R,2S)-2-fluorocyclopropyl)-6-(1-isopropyl-1H-pyrrolo[2,3-b]pyridin-3-yl)-8-(methylamino)imidazo[1,2-b]pyridazine-3-carboxamide (I-5)

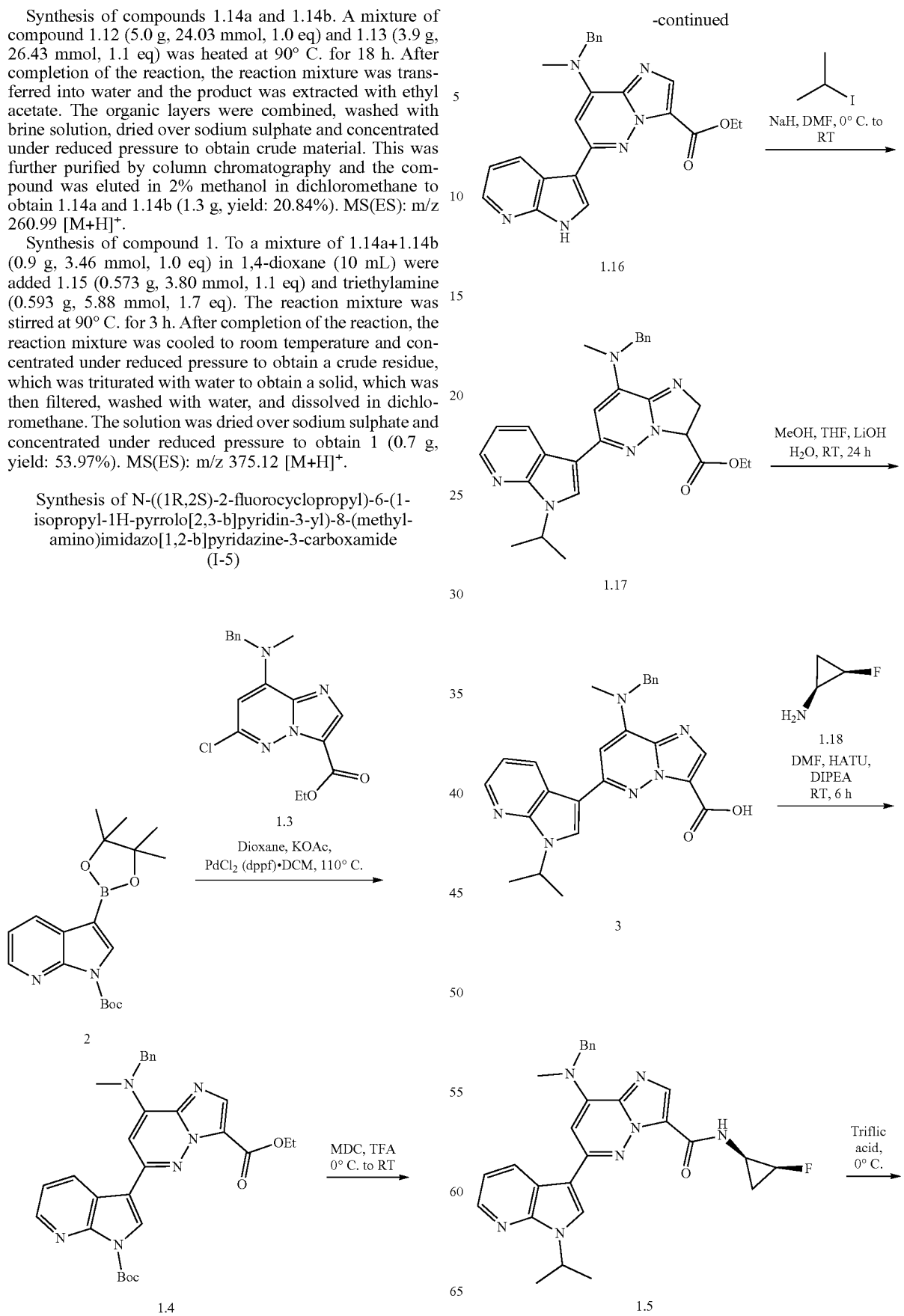

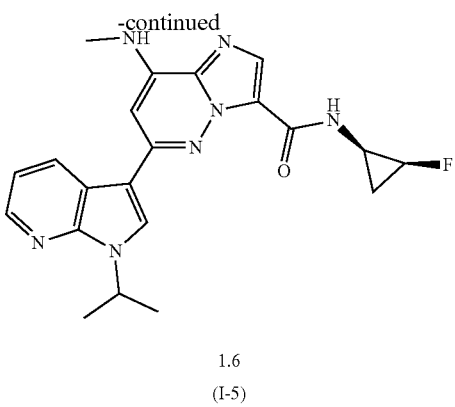

1.6
(I-5)

Synthesis of compound 1.3. Compound was synthesized using general procedure of core synthesis above to obtain 1.3. (Yield: 86.96%), MS (ES): m/z 345.11 [M+H]$^+$.

Synthesis of compound 1.4. Argon was purged for 15 min through a stirred mixture of 2 (1.5 g, 4.36 mmol, 1.0 eq), 1.3 (1.9 g, 5.66 mmol, 1.3 eq) and potassium acetate (1.0 g, 10.9 mmol, 2.5 eq) in 1,4-dioxane (35 mL), then [1,1'-Bis(diphenylphosphino) ferrocene]palladium(II) dichloride (0.318 g, 0.43 mmol, 0.1 eq) was added to it and further purging done for 10 min. Reaction was allowed to stir at 100° C. for 5 h. After completion of the reaction, the reaction mixture was transferred into water and product was extracted with ethyl acetate. The organic layer were combined, washed with brine solution, dried over sodium sulphate and concentrated under reduced pressure to obtain 1.4 (0.8 g, Yield: 34.86%). MS (ES): m/z 527.24 [M+H]$^+$.

Synthesis of compound 1.16. Compound 1.4 (0.8 g, 1.52 mmol, 1.0 eq) was dissolved in dichloromethane (15 mL) and trifluoroacetic acid (1 mL) was added to the reaction mixture. The reaction was stirred at room temperature for 1 h. After completion of the reaction, the reaction mixture was transferred into saturated bicarbonate solution and product was extracted with dichloromethane. The organic layers were combined and dried over sodium sulphate and concentrated under reduced pressure to obtain crude material. This was further purified by trituration with diethyl ether to obtain pure 1.16 (0.6 g, Yield: 92.61%). MS(ES): m/z 427.18 [M+H]$^+$.

Synthesis of compound 1.17. To a suspension of sodium hydride (0.043 g, 1.82 mmol, 2 eq) in dimethylformamide (4 mL) at 0° C. was added 1.16 (0.39 g, 0.91 mmol, 1.0 eq) and the mixture stirred for 15 min followed by addition of 2-iodopropane (0.170 g, 1.00 mmol, 1.1 eq). The reaction mixture was stirred at room temperature for 2 h. After completion of the reaction, the reaction mixture was diluted with water extracted with diethyl ether. The organic layers were combined, dried over sodium sulphate, and concentrated under reduced pressure to obtain solid which was. This was further purified by distillation to obtain pure 1.17 (0.250 g, Yield: 58.35%). MS (ES): m/z 469.23 [M+H]$^+$.

Synthesis of compound 3. To a solution of 1.17 (0.250 g, 0.53 mmol, 1.0 eq), in methanol:tetrahydrofuran:water (8 mL, 2:2:1) was added lithium hydroxide (0.127 g, 5.3 mmol, 10 eq). The reaction was stirred at temperature for 24 h. After completion of the reaction, the reaction mixture was concentrated under reduced pressure to obtain a residue. To this was added water and the mixture was acidified with 1N hydrochloric acid to adjust to pH-6-6.5 at 10° C. Product was extracted with dichloromethane. The organic layers were combined, washed with brine solution, dried over sodium sulphate, and concentrated under reduced pressure to obtain crude material. This was further purified by column chromatography and compound was eluted in 2.1% methanol in dichloromethane to obtain pure 3 (0.210 g, Yield: 89.35%). MS(ES): m/z 441.20 [M+H]$^+$.

Synthesis of compound 1.5. To a solution of 3 (0.060 g, 0.13 mmol, 1.0 eq), in N,N-dimethylformamide (2 mL) was added 1-[Bis(dimethylamino)methylene]-1H-1,2,3-triazolo [4,5-b]pyridinium 3-oxid hexafluorophosphate (0.098 g, 0.26 mmol, 2.0 eq) and the mixture stirred at room temperature for 15 min. To this was added diisopropylethylamine (0.06 mL, 0.39 mmol, 3.0 eq) followed by addition of 1.18 (0.011 g, 0.15 mmol, 1.2 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.5 (0.055 g, Yield: 81.15%). MS(ES): m/z 498.24 [M+H]$^+$.

Synthesis of compound 1.6 (I-5). A solution of 1.5 (0.055 g, 0.11 mmol, 1.0 eq) in dichloromethane (1 mL) was cooled to 0° C. and triflic acid (1 mL) was added. The reaction mixture was stirred at the same temperature for 10 min. After completion of the reaction, the reaction mixture was transferred into 1N sodium hydroxide solution and the product was extracted with dichloromethane. The organic layers were combined, dried over sodium sulphate and concentrated under reduced pressure to obtain crude material. This was further purified by trituration with diethyl ether to a obtain I-5 (0.030 g, Yield: 66.61%). MS (ES): m/z 408.27 [M+H]$^+$; LCMS purity: 97.21%; HPLC purity: 99.34%; $^1$H NMR (DMSO-$d_6$, 400 MHZ): 9.09-9.08 (d, J=4.4 Hz, 1H), 8.59 (bs, 1H), 8.51-8.49 (d, J=8 Hz, 1H), 8.40-8.39 (d, J=4.8 Hz, 1H), 8.06 (s, 1H), 7.79-7.78 (d, J=4.8 Hz, 1H), 7.29-7.26 (m, 1H), 6.73 (s, 1H), 5.23-5.20 (m, 1H), 5.02 (bs, 1H), 4.86 (bs, 1H), 3.06-3.05 (d, J=4.8 Hz, 3H), 1.59-1.57 (d, J=6.4 Hz, 6H), 1.31-1.24 (m, 1H), 1.06-1.00 (m, 1H).

Example 2. Synthesis of N-((1R,2S)-2-fluorocyclopropyl)-8-(methylamino)-6-((2-oxo-2[1-[1,2'-bipyridin]-3-yl)amino)imidazo[1,2-b]pyridazine-3-carboxamide (I-3)

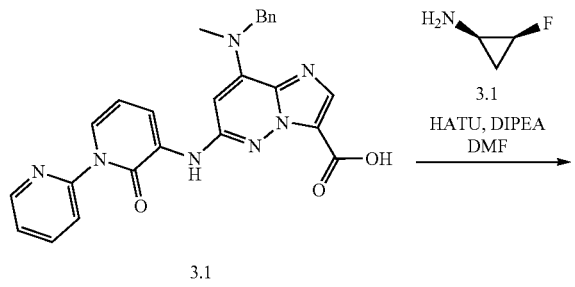

3.1

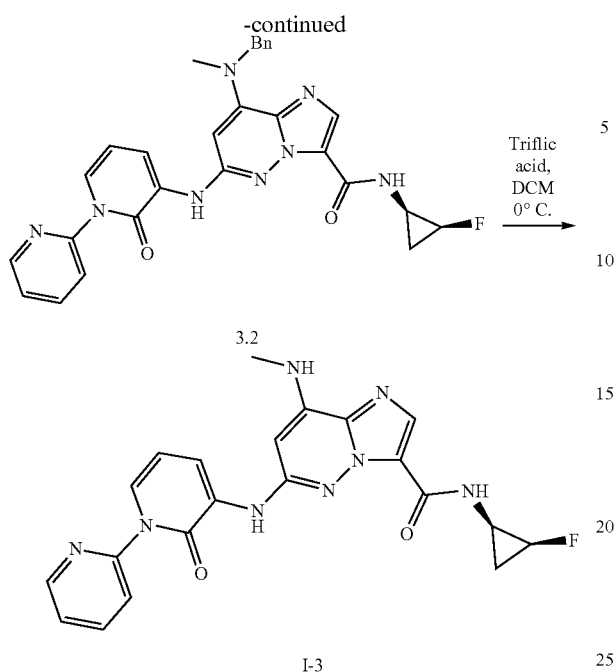

3.2

I-3

Synthesis of compound 3.1. Compound was synthesized as per experimental protocol used for preparing intermediates in the synthesis of compound I-4, described below in Example 3 (Yield: 65.23%), MS (ES): m/z 468.17 [M+H]$^+$.

Synthesis of compound 3.2. To a solution of 3.1 (0.1 g, 0.21 mmol, 1.0 eq), in N,N-dimethylformamide (2 mL) was added 1-[Bis(dimethylamino)methylene]-1H-1,2,3-triazolo[4,5-b]pyridinium 3-oxid hexafluorophosphate (0.159 g, 0.42 mmol, 2.0 eq) and the mixture stirred at room temperature for 15 min. To this was added diisopropylethylamine (0.1 mL, 0.63 mmol, 3.0 eq), followed by addition of 3.1 (0.018 g, 0.25 mmol, 1.2 eq). The reaction mixture was stirred at room temperature for 5 min. After completion of the reaction, the reaction mixture was transferred into water and the product was extracted with ethyl acetate. The organic layers were combined, washed with brine solution, dried over sodium sulphate, and concentrated under reduced pressure to obtain crude material. This was further purified by column chromatography and the compound was eluted in 40% ethyl acetate in hexane to obtain 3.2 (0.086 g, Yield: 76.64%). MS(ES): m/z 425.21[M+H]$^+$.

Synthesis of compound I-3: A solution of 3.2 (0.086 g, 0.20 mmol, 1.0 eq) in dichloromethane (1 mL) was cooled to 0° C. and triflic acid (1 mL) was added. The reaction mixture was stirred at the same temperature for 10 min. After completion of the reaction, the reaction mixture was transferred into a 1 M sodium hydroxide solution and the product was extracted with dichloromethane. The organic layers were combined, dried over sodium sulphate, and concentrated under reduced pressure to obtain crude material. This was further purified by trituration with diethyl ether to a obtain I-3 (0.042 g, Yield: 58.97%). MS (ES): m/z 435.52 [M+H]$^+$ LCMS purity: 98.97%, HPLC purity: 97.10%, $^1$H NMR (DMSO-d$_6$, 400 MHZ): 8.66 (bs, 3H), 8.06-8.03 (t, J=6.8 Hz, 2H), 7.92 (s, 1H), 7.85-7.83 (d, J=8 Hz, 1H), 7.54 (bs, 3H), 6.40 (bs, 2H), 4.96 (bs, 1H), 4.80 (bs, 1H), 2.99 (bs, 1H), 2.87-2.86 (d, J=4.8 Hz, 1H), 1.24 (bs, 2H), 1.02-0.96 (m, 1H).

Example 3. Synthesis of N-cyclopropyl-8-(methylamino)-6-((2-oxo-2H-[1,2'-bipyridin]-3-yl)amino)imidazo[1,2-b]pyridazine-3-carboxamide (I-4)

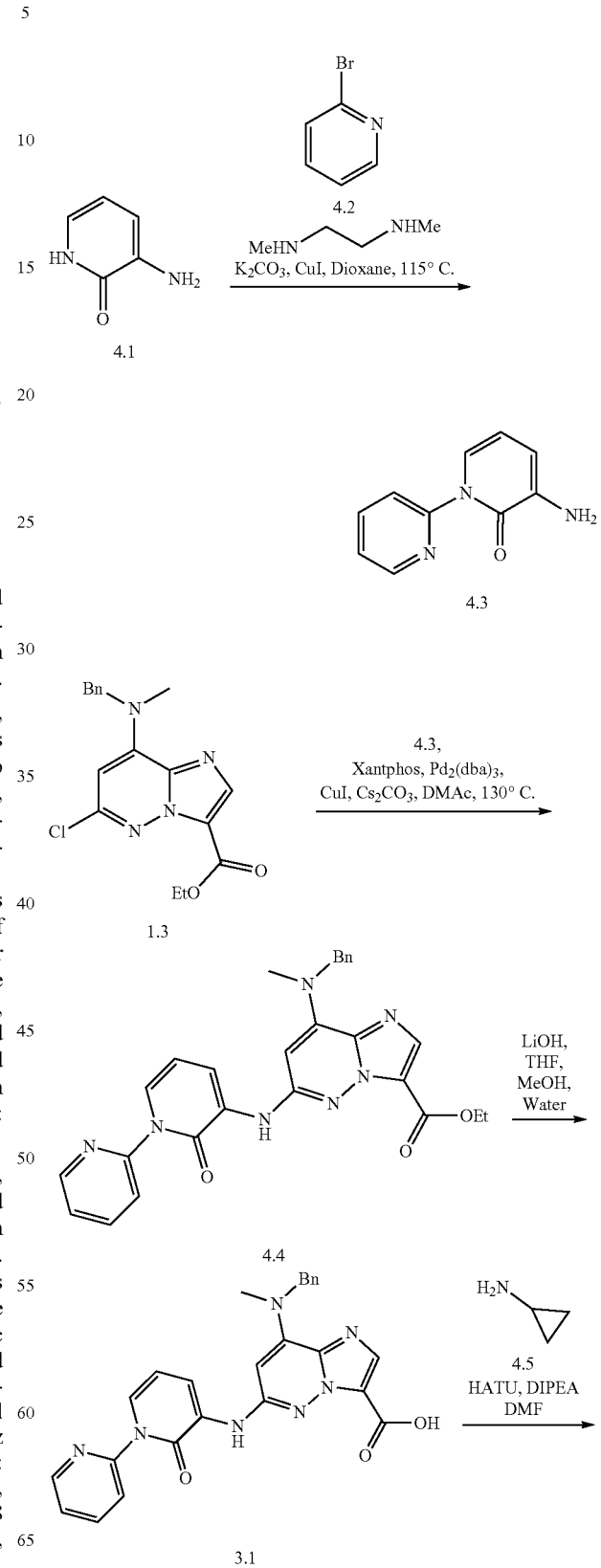

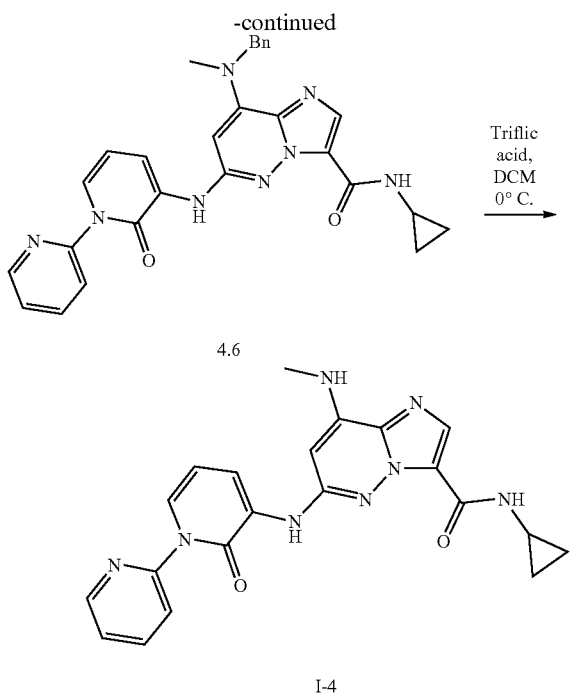

Synthesis of compound 4.3. To a solution of 4.1 (2 g, 18.18 mmol, 1.0 eq) in 1,4-dioxane (40 mL), 4.2 (7.2 g, 45.45 mmol, 2.5 eq) was added. The reaction mixture was degassed for 10 min under argon atmosphere followed by addition of potassium carbonate (7.5 g, 54.54 mmol, 3.0 eq), N,N-dimethylethylenediamine (0.640 g, 7.27 mmol, 0.4 eq), and copper iodide (0.692 g, 3.636 mmol, 0.2 eq). The reaction mixture was heated at 110° C. for 12 h. After completion of the reaction, the reaction mixture was transferred to ice cold water and the product was extracted with ethyl acetate. The organic layer was combined, washed with brine solution, dried over sodium sulphate, and concentrated under reduced pressure to obtain crude material. This was further purified by 3% methanol in dichloromethane to obtain 4.3 (2 g, Yield: 58.82%). MS (ES): m/z 188.20 [M+H]+.

Synthesis of compound 1.3. Compound was synthesized using general procedure of core synthesis to obtain 1.3 (Yield: 86.96%). MS (ES): m/z 345.11 [M+H]+.

Synthesis of compound 4.4. To a solution of 1.3 (1.2 g, 3.48 mmol, 1.0 eq) in 1,4-dioxane (20 mL) was added 4.3 (0.779 g, 4.17 mmol, 1.2 eq), Cesium carbonate (2.2 g, 6.96 mmol, 2.0 eq). The reaction mixture was degassed for 10 min under argon atmosphere, then copper(I) iodide (0.132 g, 4.17 mmol, 0.2 eq), tris(dibenzylideneacetone)dipalladium (O) (0.159 g, 0.69 mmol, 0.05 eq) and 4,5-bis(diphenylphosphino)-9,9-dimethylxanthene (0.201 g, 0.34 mmol, 0.1 eq) were added, followed by further degassing for 5 min. The reaction was stirred at 100° C. for 4 h. After completion of the reaction, the reaction mixture was cooled to room temperature, transferred into water and product was extracted with ethyl acetate. The organic layer was combined, washed with brine solution, dried over sodium sulphate and concentrated under reduced pressure to obtain crude material. This was further purified by combi flash using 3% methanol in dichloromethane as eluant to obtain pure 4.4. (0.650 g, 37.69%). MS(ES): m/z 496.21 [M+H]+.

Synthesis of compound 3.1. To a solution of 4.4 (0.260 g, 1.31 mmol, 1.0 eq), in methanol:tetrahydrofuran:water (12 mL, 2:2:1) was added lithium hydroxide (0.314 g, 13.1 mmol, 10 eq). The reaction was stirred at room temperature for 24 h. After completion of reaction, reaction mixture was concentrated under reduced pressure to obtain residue. To this added water and acidified with 1N hydrochloric acid to adjust pH-6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 3.1 (0.4 g, Yield: 65.23%). MS(ES): m/z 468.17 [M+H]+.

Synthesis of compound 4.6. To a solution of 3.1 (0.1 g, 0.21 mmol, 1.0 eq), in N,N-dimethylformamide (2 mL) was added 1-[bis(dimethylamino)methylene]-1H-1,2,3-triazolo[4,5-b]pyridinium 3-oxid hexafluorophosphate (0.159 g, 0.42 mmol, 2.0 eq) and the mixture was stirred at room temperature for 15 min. To this was added diisopropylethylamine (0.1 mL, 0.63 mmol, 3.0 eq) followed by addition of 4.5 (0.015 g, 0.25 mmol, 1.2 eq). The reaction mixture was stirred at room temperature for 5 min. After completion of the reaction, the reaction mixture was transferred into water and the product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 4.6 (0.080 g, Yield: 73.83%). MS(ES): m/z 507.22 [M+H]+.

Synthesis of compound I-4: A solution of 4.6 (0.080 g, 0.15 mmol, 1.0 eq) in dichloromethane (1 mL) was cooled to 0° C. and triflic acid (1 mL) was added. The reaction mixture was stirred at the same temperature for 10 min. After completion of the reaction, the reaction mixture was transferred into 1N sodium hydroxide solution and the product was extracted with dichloromethane. The organic layer was combined, dried over sodium sulphate, and concentrated under reduced pressure to obtain crude material. This was further purified by trituration with diethyl ether to a obtain I-4 (0.030 g, Yield: 45.62%). MS (ES): m/z 417.60 [M+H]+ LCMS purity: 98.89%, HPLC purity: 99.38%, 1H NMR (DMSO-d6, 400 MHZ): 8.67-8.66 (d, J=4 Hz, 2H), 8.61 (bs, 1H), 8.05-8.00 (d, J=12.4 Hz, 2H), 7.86 (bs, 1H), 7.84 (bs, 1H), 7.56-7.49 (m, 3H), 6.46-6.45 (t, J=7.2 Hz, 1H), 6.38 (bs, 1H), 3.17 (bs, 1H), 2.86-2.85 (d, J=4.4 Hz, 3H), 0.81-0.80 (d, J=5.6 Hz, 2H), 0.57 (bs, 2H).

Example 4. Synthesis of N-((1R,2S)-2-fluorocyclopropyl)-8-(methylamino)-6-(1-(2-morpholinoethyl)-1H-pyrrolo[2,3-b]pyridin-3-yl)imidazo[1,2-b]pyridazine-3-carboxamide (I-6)

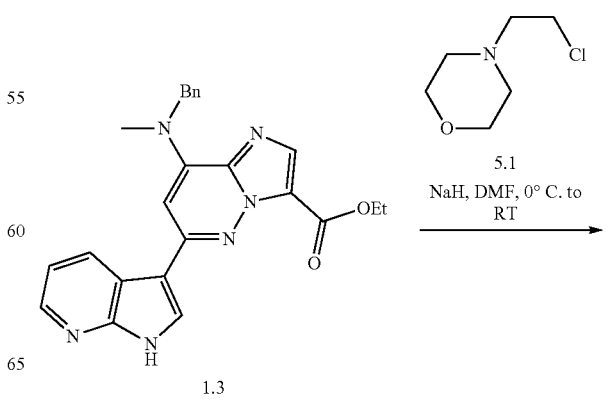

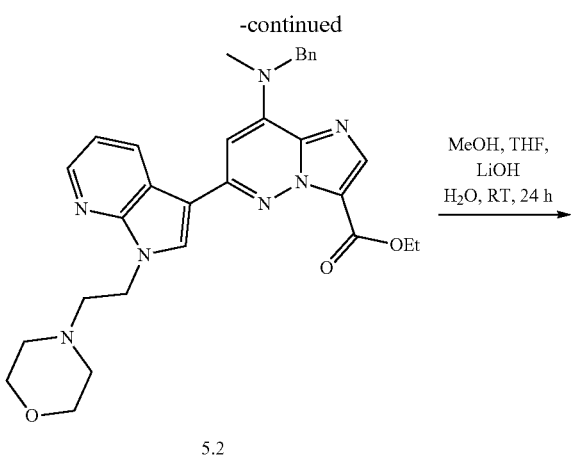

5.2

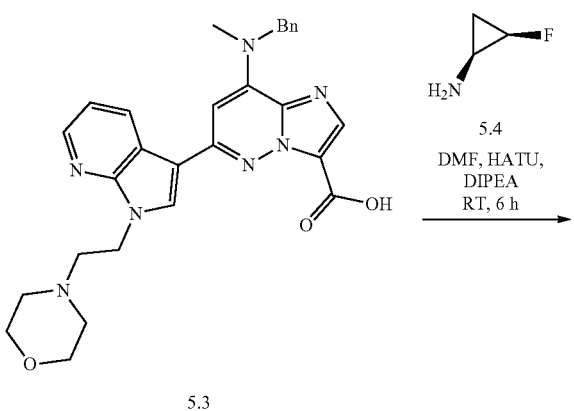

5.3

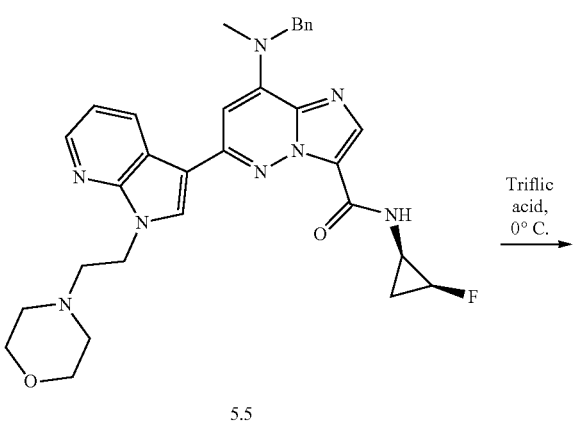

5.5

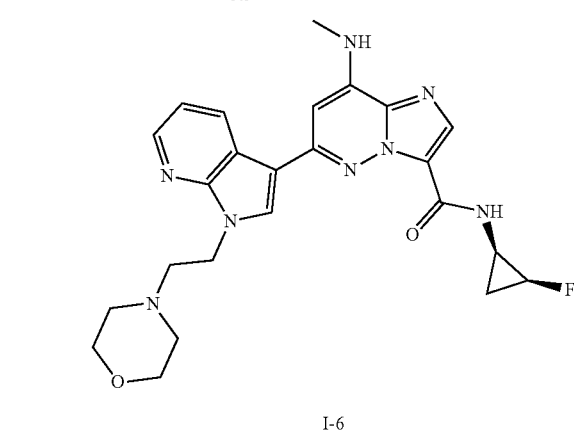

I-6

Synthesis of compound 1.3. Compound was synthesized as per experimental protocol described above for compound I-5 in Example 1 to obtain 1.3 (Yield: 92.61%), MS (ES): m/z 427.18 [M+H]+.

Synthesis of compound 5.2. To a suspension of sodium hydride (0.027 g, 1.16 mmol, 2.0 eq) in dimethylformamide (3 mL) at 0° C. was added 1.3 (0.250 g, 0.58 mmol, 1.0 eq) and the mixture stirred for 15 min followed by addition of 5.1 (0.095 g, 0.63 mmol, 1.1 eq). Reaction mixture was stirred at room temperature for 2 h. After completion of the reaction, the reaction mixture was diluted with water extracted with diethyl ether. The organic layer was combined, dried over sodium sulphate, and concentrated under reduced pressure to obtain a solid. This was further purified by distillation to obtain pure 5.2 (0.260 g, Yield: 82.19%). MS (ES): m/z 540.27 [M+H]+.

Synthesis of compound 5.3. To a solution of 5.2 (0.260 g, 0.48 mmol, 1.0 eq), in methanol:tetrahydrofuran:water (6 mL, 2:2:1) was added lithium hydroxide (0.115 g, 4.8 mmol, 10 eq). The reaction was stirred at room temperature for 24 h. After completion of the reaction, the reaction mixture was concentrated under reduced pressure to obtain a residue. To this was added water and the mixture acidified with 1N hydrochloric acid to adjust to pH~6-6.5 at 10° C. Product was extracted with dichloromethane. The organic layer was combined, washed with brine solution, dried over sodium sulphate, and concentrated under reduced pressure to obtain a crude material. This was further purified by column chromatography and compound was eluted in 2.1% methanol in dichloromethane to obtain pure 5.3 (0.190 g, Yield: 77.08%). MS(ES): m/z 512.24 [M+H]+.

Synthesis of compound 5.5. To a solution of 5.3 (0.050 g, 0.097 mmol, 1.0 eq), in N,N-dimethylformamide (1 mL) was added 1-[bis(dimethylamino)methylene]-1H-1,2,3-triazolo[4,5-b]pyridinium 3-oxid hexafluorophosphate (0.073 g, 0.19 mmol, 2.0 eq) and the mixture stirred at room temperature for 15 min. To this was added diisopropylethylamine (0.05 mL, 0.291 mmol, 3.0 eq) followed by addition of 5.4 (0.010 g, 0.11 mmol, 1.2 eq). The reaction mixture was stirred at room temperature for 5 min. After completion of the reaction, the reaction mixture was transferred into water and the product was extracted with ethyl acetate. The organic layer was combined, washed with brine solution, dried over sodium sulphate and concentrated under reduced pressure to obtain crude material. This was further purified by column chromatography and the compound was eluted in 40% ethyl acetate in hexane to obtain 5.5 (0.050 g, Yield: 89.96%). MS(ES): m/z 569.27 [M+H]+.

Synthesis of compound I-6: A solution of 5.5 (0.050 g, 0.087 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-6 (0.028 g, Yield: 66.55%). MS (ES): m/z 479.56 [M+H]+ LCMS purity: 97.73%, HPLC purity: 95.42%, CHIRAL HPLC: 99.15% 1H NMR (DMSO-$d_6$, 400 MHZ): 9.07 (bs, 1H), 8.51-8.49 (d, J=10 Hz, 2H), 8.40 (bs, 1H), 8.07 (s, 1H), 7.82 (bs, 1H), 7.27 (bs, 1H), 6.63 (bs, 1H), 5.02 (bs, 1H), 4.86 (bs, 1H), 4.49 (bs, 3H), 3.55 (bs, 4H), 3.04-3.03 (d, J=4 Hz, 4H), 2.68 (bs, 2H), 1.31-1.26 (bs, 2H), 1.10-1.06 (bs, 2H).

Example 5. Synthesis of N-(2-hydroxycyclobutyl)-6-(1-isopropyl-1H-pyrrolo[2,3-b]pyridin-3-yl)-8-(methylamino)imidazo[1,2-b]pyridazine-3-carboxamide (I-15), N-((1S,2R)-2-hydroxycyclobutyl)-6-(1-isopropyl-1H-pyrrolo[2,3-b]pyridin-3-yl)-8-(methylamino)imidazo[1,2-b]pyridazine-3-carboxamide (I-10), and N-((1R,2S)-2-hydroxycyclobutyl)-6-(1-isopropyl-1H-pyrrolo[2,3-b]pyridin-3-yl)-8-(methylamino)imidazo[1,2-b]pyridazine-3-carboxamide (I-7)

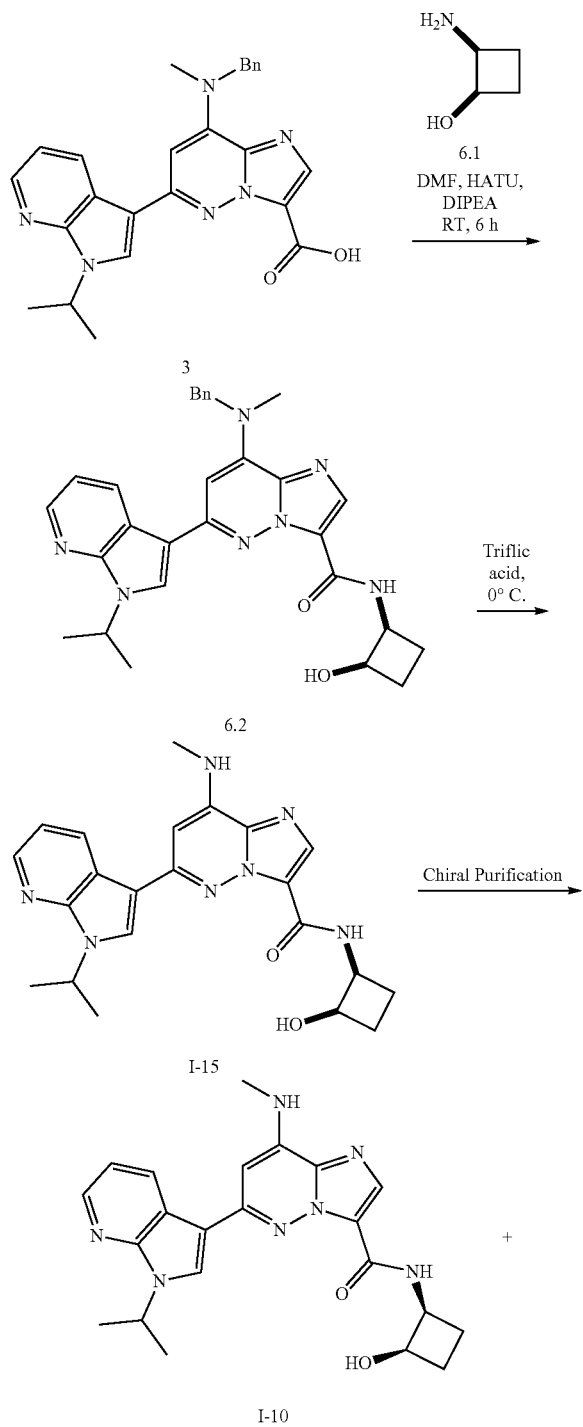
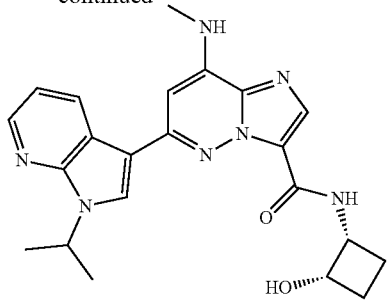

Synthesis of compound 3. Compound was synthesized as per experimental protocol for compound 3 in Example 1 to obtain 3 (Yield: 89.35%), MS (ES): 111/Z 441.20 [M+H]⁺.

Synthesis of compound 6.2. To a solution of 3 (0.1 g, 0.22 mmol, 1.0 eq), in N,N-dimethylformamide (1 mL) was added 1-[bis(dimethylamino)methylene]-1H-1,2,3-triazolo[4,5-b]pyridinium 3-oxid hexafluorophosphate (0.167 g, 0.44 mmol, 2.0 eq) and the mixture was stirred at room temperature for 15 min. To this was added diisopropylethylamine (0.1 mL, 0.66 mmol, 3.0 eq) followed by addition of 6.1 (0.022 g, 0.26 mmol, 1.2 eq). The reaction mixture was stirred at room temperature for 5 min. After completion of the reaction, the reaction mixture was transferred into water and the product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 6.2 (0.115 g, Yield: 99.41%). MS(ES): m/z 510.26 [M+H]⁺.

Synthesis of compound I-15: A solution of 6.2 (0.115 g, 0.22 mmol, 1.0 eq) in dichloromethane (1 mL) was cooled to 0° C. and triflic acid (1 mL) was added. The reaction mixture was stirred at same temperature for 10 min. After completion of the reaction, the reaction mixture was transferred into 1N sodium hydroxide solution and the product was extracted with dichloromethane. The organic layer was combined, dried over sodium sulphate, and concentrated under reduced pressure to obtain crude material. This was further purified by trituration with diethyl ether to a obtain I-15 (0.080 g, Yield: 84.51%). MS(ES): m/z 420.27 [M+H]⁺ LCMS purity: 97.92%, HPLC purity: 95.0%, CHIRAL HPLC purity: 35%, 62%, ¹H NMR (DMSO-d₆, 400 MHZ): 9.35-9.33 (d, J=8.4 Hz, 1H), 8.75-8.74 (d, J=7.6 Hz, 1H), 8.68 (s, 1H), 8.40-8.39 (d, J=3.2 Hz, 1H), 8.02 (s, 1H), 7.78-7.77 (d, J=4.8 Hz, 1H), 7.31-7.28 (m, 1H), 6.72 (s, 1H), 5.51-5.50 (d, J=4 Hz, 1H), 5.26-5.21 (m, 1H), 4.63-4.60 (t, J=6.4 Hz, 1H), 4.42 (bs, 1H), 3.08-3.06 (d, J=4.8 Hz, 3H), 1.79 (bs, 1H), 1.59-1.57 (d, J=6.4 Hz, 6H), 1.24 (bs, 1H), 1.06-1.04 (d, J=6 Hz, 2H).

Synthesis of compounds I-10 and I-7. Isomers of I-15 (0.080 g) were separated out using a chiral column (CHIRAL PAK OX-H 250×4.6 mm, 5 u) and 0.1% DEA in HEX IPA-MEOH (50-50) as co-solvent with a flow rate of 4 mL/min to get pure fraction-1 (FR-a) and fraction-2 (FR-b). FR-a was concentrated under reduced pressure at 30° C. to afford pure I-10 (0.024 g). MS(ES): m/z 420.62 [M+H]⁺, LCMS purity: 100%, HPLC purity: 97.0%, CHIRAL HPLC purity: 99.78%, ¹H NMR (DMSO-d₆, 400 MHZ): 9.35-9.33 (d, J=8.4 Hz, 1H), 8.75-8.74 (d, J=7.6 Hz, 1H), 8.68 (s, 1H), 8.40-8.39 (d, J=3.2 Hz, 1H), 8.02 (s, 1H), 7.78-7.77 (d, J=4.8

Hz, 1H), 7.31-7.28 (m, 1H), 6.72 (s, 1H), 5.51-5.50 (d, J=4 Hz, 1H), 5.26-5.21 (m, 1H), 4.63-4.60 (t, J=6.4 Hz, 1H), 4.42 (bs, 1H), 3.08-3.06 (d, J=4.8 Hz, 3H), 1.79 (bs, 1H), 1.59-1.57 (d, J=6.4 Hz, 6H), 1.24 (bs, 1H), 1.06-1.04 (d, J=6 Hz, 2H).

FR-b was concentrated under reduced pressure at 30° C. to afford pure I-7 (0.043 g). MS(ES): m/z 420.57 [M+H]$^+$, LCMS purity: 100%, HPLC purity: 96.86%, CHIRAL HPLC purity: 99.83%, $^1$H NMR (DMSO-d$_6$, 400 MHZ): 9.35-9.33 (d, J=8.4 Hz, 1H), 8.75-8.74 (d, J=7.6 Hz, 1H), 8.68 (s, 1H), 8.40-8.39 (d, J=3.2 Hz, 1H), 8.02 (s, 1H), 7.78-7.77 (d, J=4.8 Hz, 1H), 7.31-7.28 (m, 1H), 6.72 (s, 1H), 5.51-5.50 (d, J=4 Hz, 1H), 5.26-5.21 (m, 1H), 4.63-4.60 (t, J=6.4 Hz, 1H), 4.42 (bs, 1H), 3.08-3.06 (d, J=4.8 Hz, 3H), 1.79 (bs, 1H), 1.59-1.57 (d, J=6.4 Hz, 6H), 1.24 (bs, 1H), 1.06-1.04 (d, J=6 Hz, 2H).

Example 6. Synthesis of rac-N-((1S,2R)-2-hydroxycyclobutyl)-8-(methylamino)-6-(1-(tetrahydro-2H-pyran-4-yl)-1H-pyrrolo[2,3-b]pyridin-3-yl)imidazo[1,2-b]pyridazine-3-carboxamide (I-31), N-((1S,2R)-2-hydroxycyclobutyl)-8-(methylamino)-6-(1-(tetrahydro-2H-pyran-4-yl)-1H-pyrrolo[2,3-b]pyridin-3-yl)imidazo[1,2-b]pyridazine-3-carboxamide (I-11) and N-((1R,2S)-2-hydroxycyclobutyl)-8-(methylamino)-6-(1-(tetrahydro-2H-pyran-4-yl)-1H-pyrrolo[2,3-b]pyridin-3-yl)imidazo[1,2-b]pyridazine-3-carboxamide (I-8)

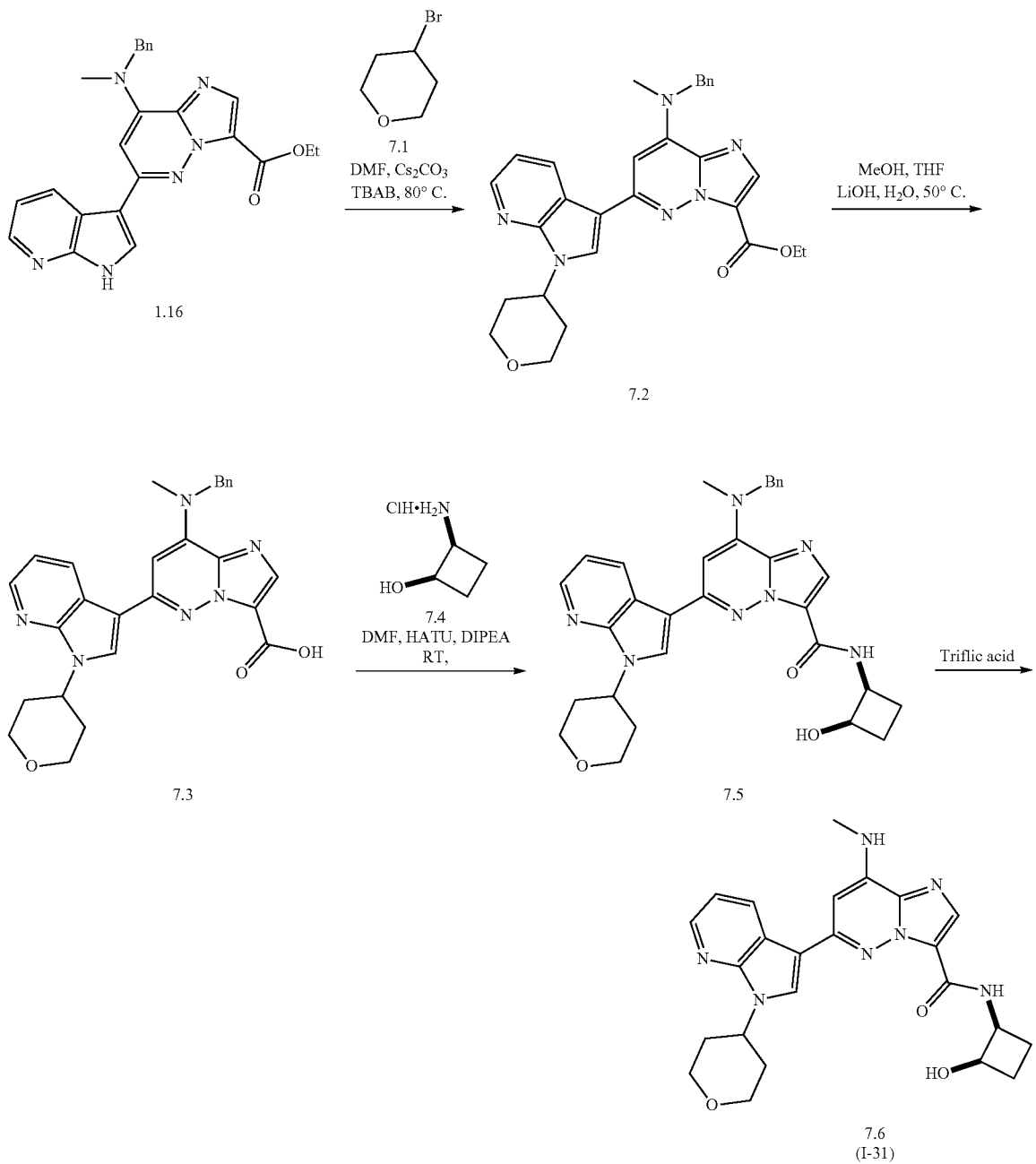

-continued

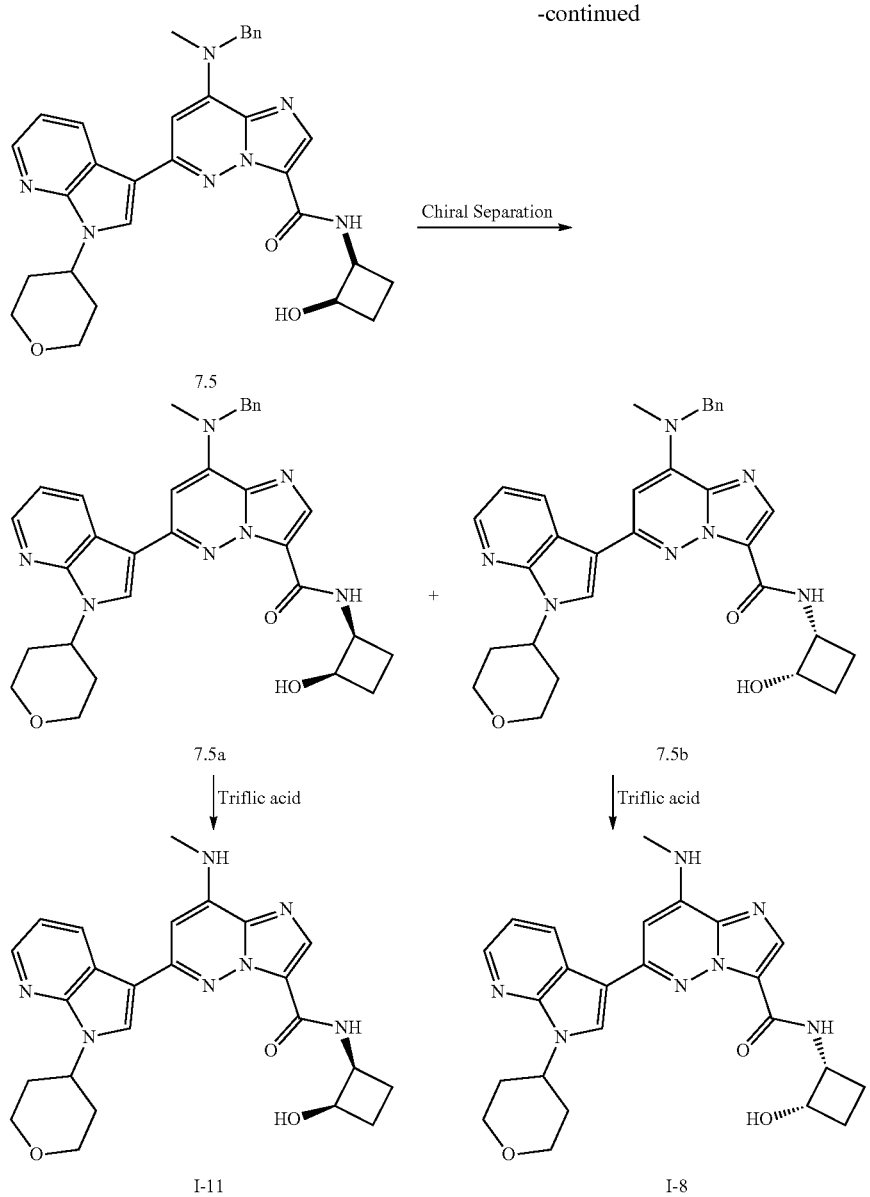

Synthesis of compound 1.16. Compound was synthesized as per experimental protocol described above in Example 1 to obtain 1.16 (Yield: 92.61%). MS (ES): m/z 427.18 [M+H]⁺.

Synthesis of compound 7.2. To a solution of 7.2 (0.3 g, 0.70 mmol, 1.0 eq), in dimethylformamide (3 mL) was added 7.1 (1.1 g, 7.0 mmol, 10.0 eq), Cesium carbonate (0.682 g, 2.1 mmol, 3.0 eq) and tetra-n-butylammonium bromide (0.112 g, 0.35 mmol, 0.5 eq). The reaction mixture was stirred at 80° C. for 16 h. After completion of the reaction, the reaction mixture was transferred into water and the product was extracted with ethyl acetate. The organic layer was combined, washed with brine solution, dried over sodium sulphate, and concentrated under reduced pressure to obtain crude material. This was further purified by column chromatography and the compound was eluted in 1% methanol in dichloromethane to obtain 7.2 (0.220 g, Yield: 61.25%). MS(ES): m/z 511.24 [M+H]⁺

Synthesis of compound 7.3. To a solution of 7.2 (0.510 g, 0.43 mmol, 1.0 eq), in tetrahydrofuran:methanol:water (10 mL, 2:1:1) was added lithium hydroxide (0.103 g, 4.3 mmol, 10.0 eq). The reaction mixture was stirred at 50° C. for 16 h. After completion of the reaction, the reaction mixture was concentrated under reduced pressure to obtain a residue. To this was added water and the mixture was acidified with 1N hydrochloric acid to adjust to pH-6-6.5 at 10° C. The product was extracted with dichloromethane. The organic layer was combined, washed with brine solution, dried over sodium sulphate, and concentrated under reduced pressure to obtain crude material. This was further purified by column chromatography and compound was eluted in 2.1% methanol in dichloromethane to obtain pure 7.3 (0.170 g, Yield: 81.77%). MS(ES): m/z 483.21 [M+H]⁺.

Synthesis of compound 7.5. Compound was synthesized using general procedure C to obtain 7.5 (0.150 g, Yield: 77.18%). MS(ES): m/z 552.27 [M+H]⁺.

Synthesis of compound 7.6 (I-31): Compound was synthesized using general procedure D to obtain 7.6 (0.025 g, Yield: 59.76%). MS (ES): m/z 462.32 [M+H]⁺; LCMS purity: 100%; HPLC purity: 98.52%, CHIRAL HPLC:

50.05%, 49.94%, $^1$H NMR (DMSO-$d_6$, 400 MHz): 9.26-9.24 (d, J=8.4 Hz, 1H), 8.78-8.77 (d, J=6.8 Hz, 1H), 8.73 (s, 1H), 8.39-8.38 (d, J=3.6 Hz, 1H), 8.01 (s, 1H), 7.76-7.75 (d, J=4.8 Hz, 1H), 7.31-7.28 (m, 1H), 6.74 (s, 1H), 5.11-5.05 (m, 1H), 4.64-4.60 (d, J=7.2 Hz, 2H), 3.63-3.57 (t, J=12 Hz, 2H), 3.05-3.04 (d, J=3.6 Hz, 3H), 2.25-2.21 (m, 3H), 2.11-2.05 (m, 2H), 1.79 (bs, 1H), 1.54 (bs, 2H), 0.88-0.80 (m, 3H).

Synthesis of compound 7.5a and 7.5b: Isomers of 7.5 (0.1 g) were separated using a chiral column CHIRALPAK AD-H (250 mm*4.6 mm, 5 u) and 0.1% DEA MEOH:ACN (50:50) as co-solvent with flow rate of 4 mL/min to get pure fraction-1 (FR-a) and fraction-2 (FR-b). FR-a was concentrated under reduced pressure at 30° C. to afford pure 7.5a (0.045 g). MS(ES): m/z 552.27 [M+H]$^+$. FR-b was concentrated under reduced pressure at 30° C. to afford pure 7.5b (0.044 g). MS(ES): m/z 552.27 [M+H]$^+$.

Synthesis of compound I-11: Compound was synthesized using general procedure D to obtain I-11 (0.032 g, Yield: 85%). MS (ES): m/z 462.41 [M+H]$^+$ LCMS purity: 100%, HPLC purity: 99.21%, CHIRAL HPLC: 100%, $^1$H NMR (DMSO-$d_6$, 400 MHZ): 9.26-9.24 (d, J=8.4 Hz, 1H), 8.78-8.76 (d, J=6.8 Hz, 1H), 8.72 (s, 1H), 8.38-8.37 (d, J=3.6 Hz, 1H), 8.00 (s, 1H), 7.76-7.75 (d, J=4.8 Hz, 1H), 7.31-7.28 (m, 1H), 6.73 (s, 1H), 5.45-5.44 (d, J=4 Hz, 1H), 5.11-5.05 (m, 1H), 4.63-4.60 (d, J=6.4 Hz, 1H), 4.39 (bs, 1H), 3.63-3.57 (t, J=11.6 Hz, 2H), 3.05-3.04 (d, J=3.6 Hz, 3H), 2.23-2.21 (m, 3H), 2.11-2.05 (m, 3H), 1.78 (bs, 1H), 1.22 (bs, 1H), 0.88-0.85 (m, 2H).

Synthesis of compound I-8: Compound was synthesized using general procedure D to obtain I-8 (0.032 g, Yield: 86%). MS (ES): m/z 462.41 [M+H]$^+$ LCMS purity: 100%; HPLC purity: 100%, CHIRAL HPLC: 100%; $^1$H NMR (DMSO-$d_6$, 400 MHZ): 9.26-9.24 (d, J=8.4 Hz, 1H), 8.78-8.76 (d, J=6.8 Hz, 1H), 8.72 (s, 1H), 8.38-8.37 (d, J=3.6 Hz, 1H), 8.00 (s, 1H), 7.76-7.74 (d, J=4.8 Hz, 1H), 7.31-7.28 (m, 1H), 6.73 (s, 1H), 5.45-5.44 (d, J=4 Hz, 1H), 5.11-5.05 (m, 1H), 4.63-4.60 (d, J=6.4 Hz, 1H), 4.39 (bs, 1H), 3.63-3.57 (t, J=11.6 Hz, 2H), 3.05-3.04 (d, J=3.6 Hz, 3H), 2.23-2.21 (m, 3H), 2.11-2.03 (m, 3H), 1.78 (bs, 1H), 1.22 (bs, 1H), 0.88-0.85 (m, 2H).

Example 7. Synthesis of N-((1S,2R)-2-hydroxycyclobutyl)-8-(methylamino)-6-(1-(2-morpholinoethyl)-1H-pyrrolo[2,3-b]pyridin-3-yl)imidazo[1,2-b]pyridazine-3-carboxamide (I-16), N-((1S,2R)-2-hydroxycyclobutyl)-8-(methylamino)-6-(1-(2-morpholinoethyl)-1H-pyrrolo[2,3-b]pyridin-3-yl)imidazo[1,2-b]pyridazine-3-carboxamide (I-12), N-((1R,2S)-2-hydroxycyclobutyl)-8-(methylamino)-6-(1-(2-morpholinoethyl)-1H-pyrrolo[2,3-b]pyridin-3-yl)imidazo[1,2-b]pyridazine-3-carboxamide (I-9)

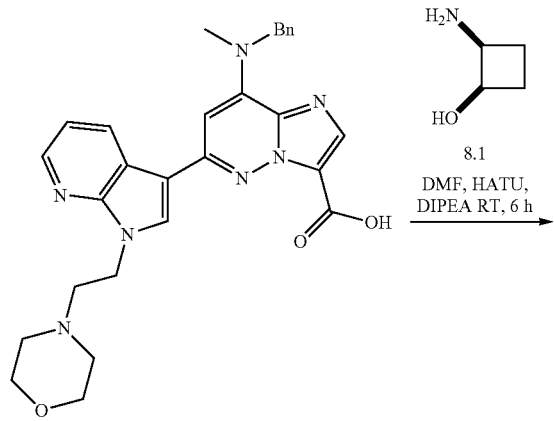

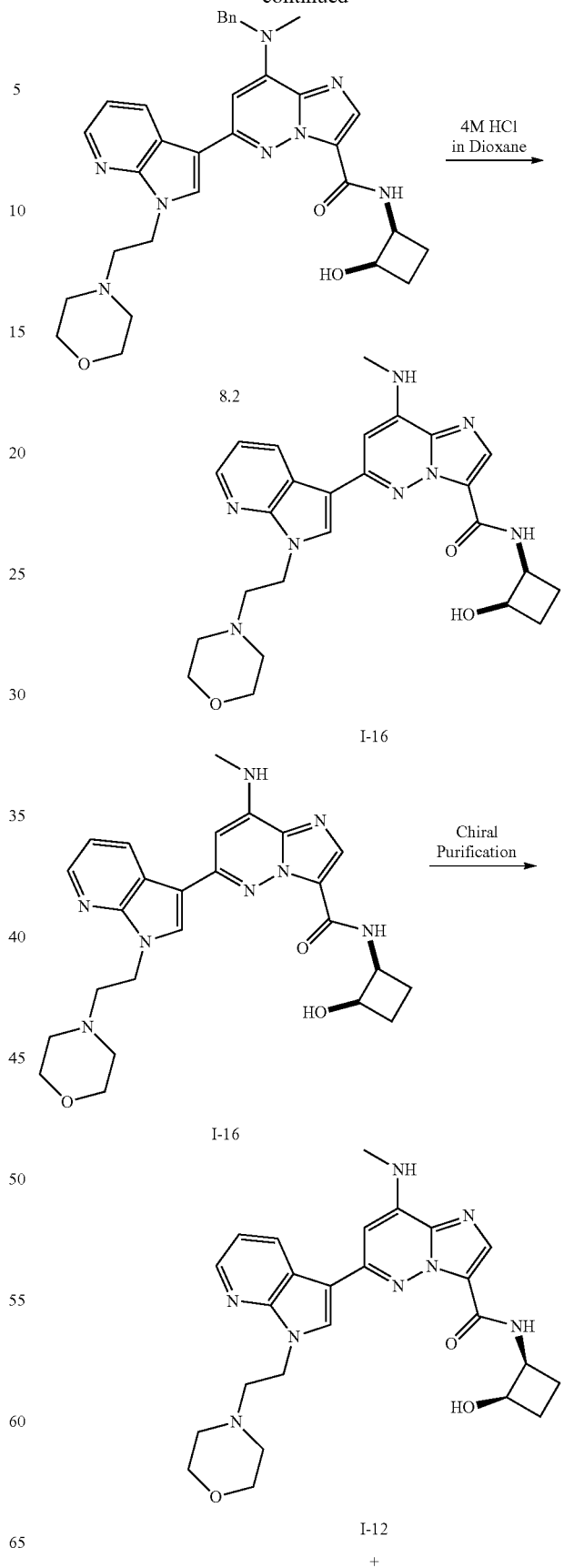

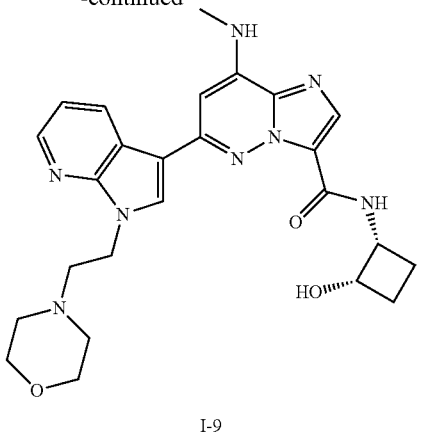

I-9

Synthesis of compound 5.3. Compound was synthesized as per experimental protocol in Example 4 to obtain 5.3 (Yield: 77.08%), MS (ES): m/z 512.24 [M+H]$^+$.

Synthesis of compound 8.2. To a solution of 5.3 (0.1 g, 0.19 mmol, 1.0 eq), in N,N-dimethylformamide (1 mL) was added 1-[Bis(dimethylamino)methylene]-1H-1,2,3-triazolo[4,5-b]pyridinium 3-oxid hexafluorophosphate (0.144 g, 0.38 mmol, 2.0 eq) and the mixture stirred at room temperature for 15 min. To this was added diisopropylethylamine (0.1 mL, 0.57 mmol, 3.0 eq) followed by addition of 8.1 (0.019 g, 0.22 mmol, 1.2 eq). The reaction mixture was stirred at room temperature for 5 min. After completion of the reaction, the reaction mixture was transferred into water and the product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 8.2. (0.110 g, Yield: 96.91%). MS(ES): m/z 581.29 [M+H]$^+$.

Synthesis of compound I-16. To the compound 8.2 (0.110 g, 0.18 mmol, 1.0 eq) was added 4M hydrochloric acid in 1,4-dioxane (3 mL) and the mixture stirred at room temperature for 4 h. After completion of the reaction, the reaction mixture was concentrated under reduced pressure, and the residue was stirred with saturated sodium bicarbonate solution and extracted with dichloromethane. The organic layer was combined, washed with brine, dried over sodium sulphate, and concentrated under reduced pressure to obtain a residue, which was triturated with diethyl ether to obtain I-16 (0.075 g, Yield: 80.71%). MS (ES): m/z 491.36 [M+H]$^+$; LCMS purity: 97.26%, HPLC purity: 96.14%, CHIRAL HPLC purity: 34%, 63%. $^1$H NMR (DMSO-d$_6$, 400 MHZ): 9.33-9.31 (d, J=8 Hz, 1H), 8.76-8.74 (d, J=6 Hz, 1H), 8.57 (s, 1H), 8.40-8.38 (d, J=4.4 Hz, 1H), 8.02 (s, 1H), 7.80-7.79 (d, J=4.8 Hz, 1H), 7.31-7.28 (m, 1H), 6.65 (s, 1H), 5.54-5.53 (d, J=3.6 Hz, 1H), 4.61 (bs, 1H), 4.51-4.48 (t, J=6.4 Hz, 2H), 4.42 (bs, 1H), 3.52 (s, 4H), 3.06-3.05 (d, J=4.8 Hz, 3H), 2.84-2.81 (t, J=6.4 Hz, 2H), 2.14-2.06 (m, 2H), 1.78 (bs, 1H), 1.57 (bs, 1H), 1.24 (bs, 2H), 0.90 (bs, 2H).

Synthesis of compound I-12 and I-9. Isomers of I-16 (0.080 g) were separated out using column (CHIRAL PAK OX-H 250×4.6 mm, 5 u) and 0.1% DEA in Hexanes/i-PrOH-MeOH (50-50) as co-solvent with flow rate of 4 mL/min to get pure fraction-1 (FR-a) and fraction-2 (FR-b). FR-a was concentrated under reduced pressure at 30° C. to afford pure I-12 (0.010 g). MS(ES): m/z 491.52 [M+H]$^+$, LCMS purity: 95.31%, HPLC purity: 95.00%, CHIRAL HPLC purity: 95.28%, $^1$H NMR (DMSO-d$_6$, 400 MHZ): 9.33-9.31 (d, J=8 Hz, 1H), 8.76-8.74 (d, J=6 Hz, 1H), 8.57 (s, 1H), 8.40-8.38 (d, J=4.4 Hz, 1H), 8.02 (s, 1H), 7.80-7.79 (d, J=4.8 Hz, 1H), 7.31-7.28 (m, 1H), 6.65 (s, 1H), 5.54-5.53 (d, J=3.6 Hz, 1H), 4.61 (bs, 1H), 4.51-4.48 (t, J=6.4 Hz, 2H), 4.42 (bs, 1H), 3.52 (s, 4H), 3.06-3.05 (d, J=4.8 Hz, 3H), 2.84-2.81 (t, J=6.4 Hz, 2H), 2.14-2.06 (m, 2H), 1.78 (bs, 1H), 1.57 (bs, 1H), 1.24 (bs, 2H), 0.90 (bs, 2H).

FR-b was concentrated under reduced pressure at 30° C. to afford pure I-9 (0.030 g). MS(ES): m/z 491.67 [M+H]$^+$, LCMS purity: 100%, HPLC purity: 98.71%, CHIRAL HPLC purity: 100%, $^1$H NMR (DMSO-d$_6$, 400 MHZ): 9.33-9.31 (d, J=8 Hz, 1H), 8.76-8.74 (d, J=6 Hz, 1H), 8.61 (s, 1H), 8.45 (bs, 2H), 8.39-8.38 (d, J=4 Hz, 1H), 8.02 (s, 1H), 7.80-7.79 (d, J=4.4 Hz, 1H), 7.31-7.28 (m, 1H), 6.65 (s, 1H), 4.61 (bs, 1H), 4.50-4.48 (t, J=6.4 Hz, 2H), 4.43 (bs, 1H), 3.55 (s, 4H), 3.06-3.05 (d, J=4.8 Hz, 3H), 2.84-2.81 (t, J=6.4 Hz, 2H), 2.13-2.06 (m, 2H), 1.81 (bs, 2H), 1.57 (bs, 1H), 1.24 (bs, 2H).

Example 8. Synthesis of rac-N-((3S,4S)-4-hydroxytetrahydrofuran-3-yl)-6-(1-isopropyl-1H-pyrrolo[2,3-b]pyridin-3-yl)-8-(methylamino)imidazo[1,2-b]pyridazine-3-carboxamide (I-32), N-((3S,4S)-4-hydroxytetrahydrofuran-3-yl)-6-(1-isopropyl-1H-pyrrolo[2,3-b]pyridin-3-yl)-8-(methylamino)imidazo[1,2-b]pyridazine-3-carboxamide (I-14) and N-((3R,4R)-4-hydroxytetrahydrofuran-3-yl)-6-(1-isopropyl-1H-pyrrolo[2,3-b]pyridin-3-yl)-8-(methylamino)imidazo[1,2-b]pyridazine-3-carboxamide (I-13)

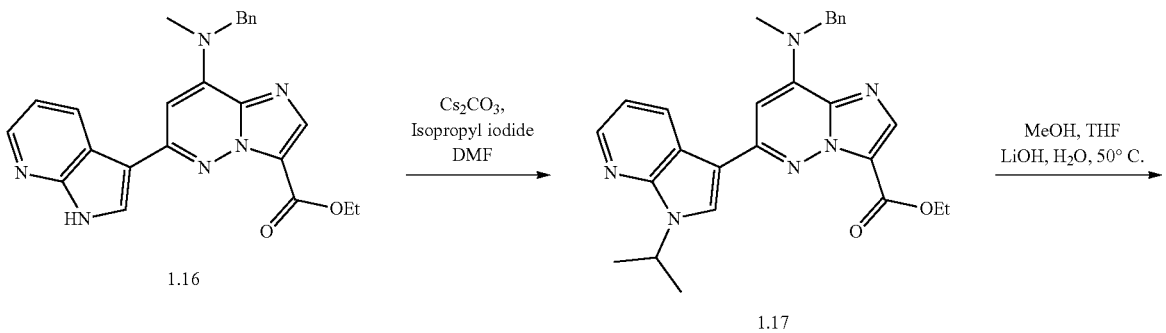

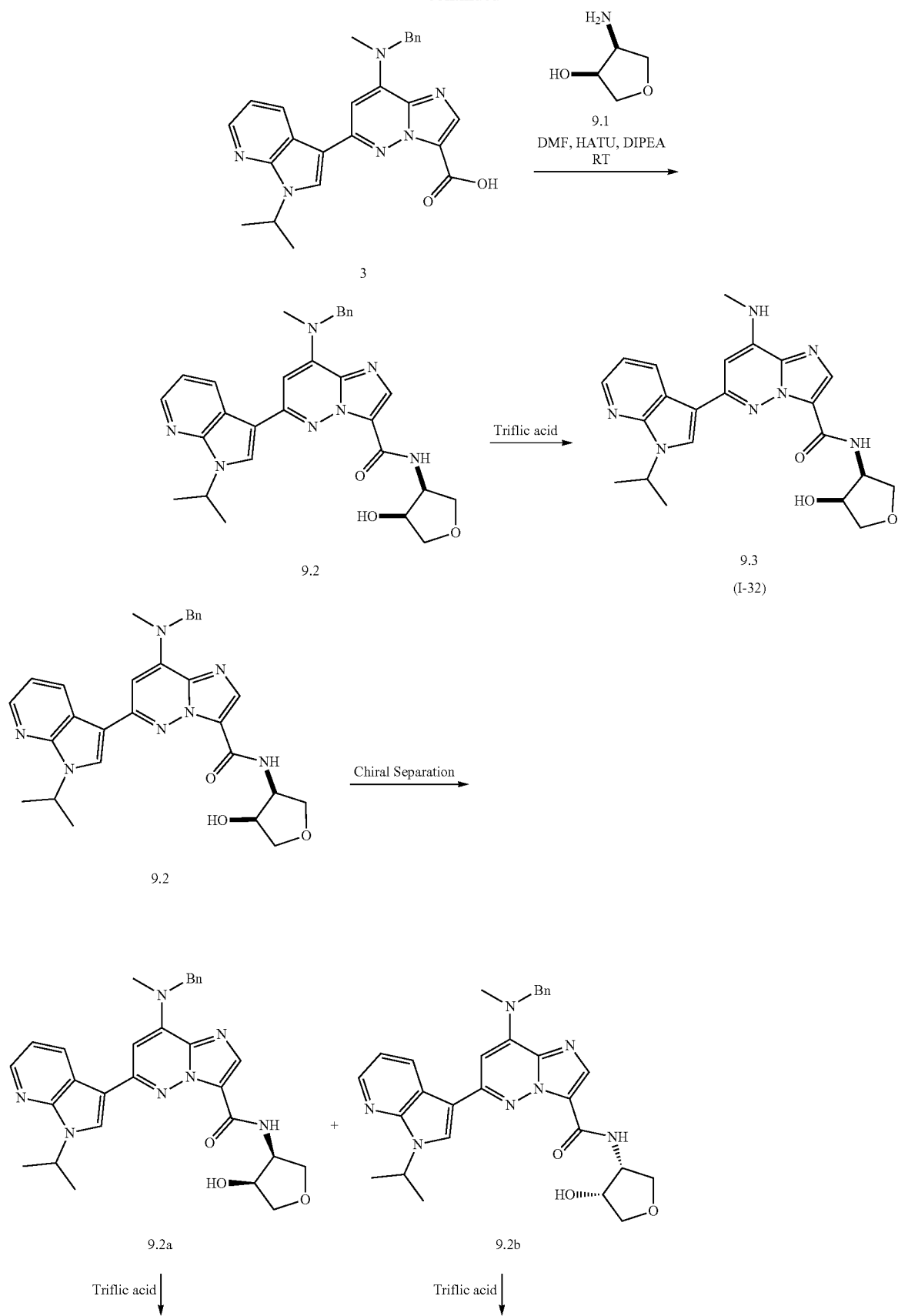

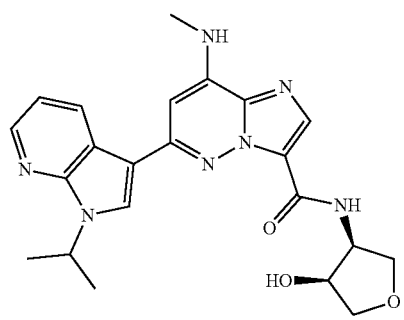

I-14

-continued

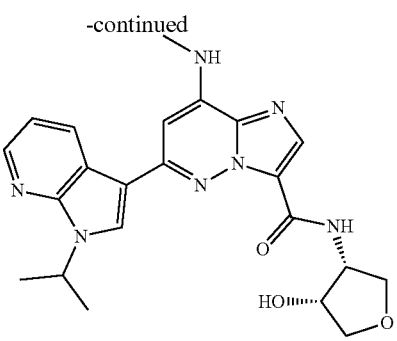

I-13

Synthesis of compound 1.16. Compound was synthesized as per experimental protocol described above in Example 1 to obtain 1.16 (Yield: 92.61%). MS (ES): m/z 427.18 [M+H]$^+$.

Synthesis of compound 1.17. To a solution of 1.16 (0.4 g, 0.82 mmol, 1.0 eq), in dimethylformamide (6 mL) was added isopropyl iodide (0.2 mL, 2.05 mmol, 2.5 eq) and cesium carbonate (1.3 g, 4.1 mmol, 5.0 eq). The reaction mixture was stirred at 110° C. for 3 h. After completion of the reaction, the reaction mixture was transferred into water and the product was extracted with ethyl acetate. The organic layer was combined, washed with brine solution, dried over sodium sulphate, and concentrated under reduced pressure to obtain crude material. This was further purified by column chromatography and the compound was eluted in 20% ethyl acetate in hexane to obtain 1.17 (0.3 g, Yield: 78.02%). MS(ES): m/z 426.23 [M+H]$^+$.

Synthesis of compound 3. To a solution of 1.17 (0.3 g, 0.64 mmol, 1.0 eq), in tetrahydrofuran:methanol:water (8 mL, 2:1:1) was added lithium hydroxide (0.153 g, 6.4 mmol, 10.0 eq). The reaction was stirred at 50° C. for 16 h. After completion of the reaction, the reaction mixture was concentrated under reduced pressure to obtain a residue. To this was added water and the mixture acidified with 1N hydrochloric acid to adjust to pH-6-6.5 at 10° C. Product was extracted with dichloromethane. The organic layer was combined, washed with brine solution, dried over sodium sulphate, and concentrated under reduced pressure to obtain crude material. This was further purified by column chromatography and compound was eluted in 2.1% methanol in dichloromethane to obtain pure 3 (0.262 g, Yield: 92.90%). MS(ES): m/z 441.20 [M+H]$^+$.

Synthesis of compound 9.2. Compound was synthesized using general procedure C to obtain 9.2 (0.250 g, Yield: 79.97%). MS(ES): m/z 526.25 [M+H]$^+$.

Synthesis of compound 9.3 (I-32). Compound was synthesized using general procedure D to obtain 9.3 (I-32) (0.030 g, Yield: 72.42%). MS (ES): m/z 436.41 [M+H]$^+$ LCMS purity: 100%, HPLC purity: 99.46%, CHIRAL HPLC: 49.39%, 49.28%, $^1$H NMR (DMSO-d$_6$, 400 MHz): 9.20-9.18 (d, J=7.6 Hz, 1H), 8.67-8.65 (d, J=7.6 Hz, 1H), 8.63 (s, 1H), 8.39-8.38 (d, J=3.6 Hz, 1H), 8.05 (s, 1H), 7.80-7.79 (d, J=4.8 Hz, 1H), 7.28-7.25 (m, 1H), 6.71 (s, 1H), 5.64-5.63 (d, J=4 Hz, 1H), 5.23-5.20 (m, 1H), 4.33 (s, 1H), 4.05-3.98 (m, 3H), 3.61-3.57 (t, J=8 Hz, 1H), 3.07-3.06 (d, J=4 Hz, 3H), 1.58-1.57 (d, J=4.8 Hz, 6H), 1.25 (bs, 1H).

Synthesis of compound 9.2a and 9.2b. Isomers of 9.2 (0.2 g) were separated out using column CHIRALPAK AD-H (250 mm*4.6 mm, 5 u) and 0.1% DEA MEOH:MeCN (50:50) as co-solvent with flow rate of 4 mL/min to get pure fraction-1 (FR-a) and fraction-2 (FR-b). FR-a was concentrated under reduced pressure at 30° C. to afford pure 9.2a (0.070 g). MS(ES): m/z 526.25 [M+H]$^+$. FR-b was concentrated under reduced pressure at 30° C. to afford pure 9.2b (0.072 g). MS(ES): m/z 526.25 [M+H]$^+$.

Synthesis of compound I-14. Compound was synthesized using general procedure D to obtain I-14 (0.030 g, Yield: 51.73%). MS (ES): m/z 436.30 [M+H]$^+$ LCMS purity: 100%, HPLC purity: 100%, CHIRAL HPLC: 100%, $^1$H NMR (DMSO-d$_6$, 400 MHz): 9.18-9.16 (d, J=7.6 Hz, 1H), 8.65-8.63 (d, J=7.6 Hz, 1H), 8.61 (s, 1H), 8.37-8.36 (d, J=3.6 Hz, 1H), 8.03 (s, 1H), 7.78-7.76 (d, J=4.8 Hz, 1H), 7.26-7.23 (m, 1H), 6.69 (s, 1H), 5.62-5.61 (d, J=4.4 Hz, 1H), 5.23-5.16 (m, 1H), 4.32 (bs, 1H), 4.05-3.98 (m, 3H), 3.59-3.55 (t, J=8.4 Hz, 1H), 3.05-3.04 (d, J=4 Hz, 3H), 1.55-1.57 (d, J=4.8 Hz, 6H), 1.22 (bs, 1H).

Synthesis of compound I-13. Compound was synthesized using general procedure D to obtain I-13 (0.031 g, Yield: 51.97%). MS (ES): m/z 436.33 [M+H]$^+$ LCMS purity: 100%, HPLC purity: 99.76%, CHIRAL HPLC: 98.59%; $^1$H NMR (DMSO-d$_6$, 400 MHz): 9.18-9.16 (d, J=7.6 Hz, 1H), 8.65-8.63 (d, J=7.6 Hz, 1H), 8.61 (s, 1H), 8.37-8.36 (d, J=3.6 Hz, 1H), 8.03 (s, 1H), 7.78-7.77 (d, J=4.8 Hz, 1H), 7.26-7.23 (m, 1H), 6.69 (s, 1H), 5.62-5.61 (d, J=4.4 Hz, 1H), 5.23-5.16 (m, 1H), 4.32 (bs, 1H), 4.05-3.98 (m, 3H), 3.59-3.55 (t, J=8.4 Hz, 1H), 3.05-3.04 (d, J=4 Hz, 3H), 1.55-1.57 (d, J=4.8 Hz, 6H), 1.22 (bs, 1H).

Example 9. Synthesis of 6-((3'-fluoro-2-oxo-2H-[1,2'-bipyridin]-3-yl)amino)-N-(2-methoxycyclobutyl)-8-(methylamino)imidazo[1,2-b]-3-carboxamide
(I-17)

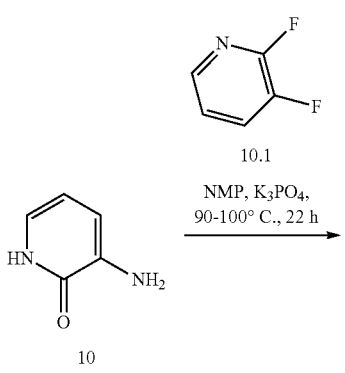

175
-continued

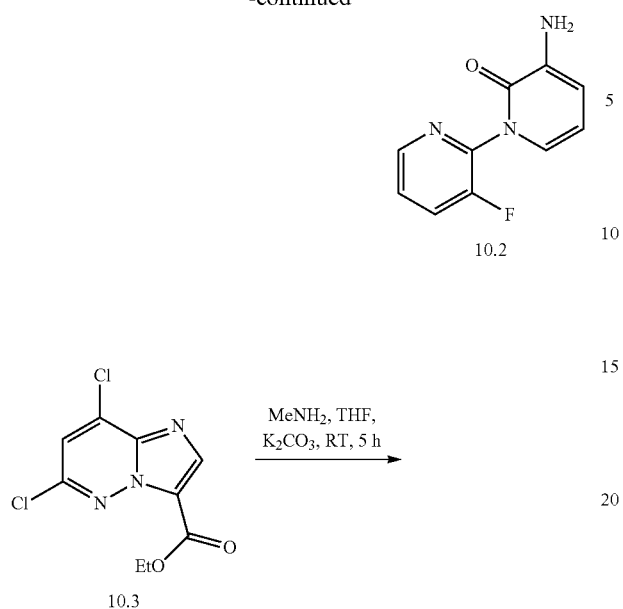

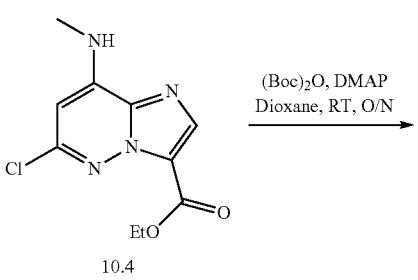

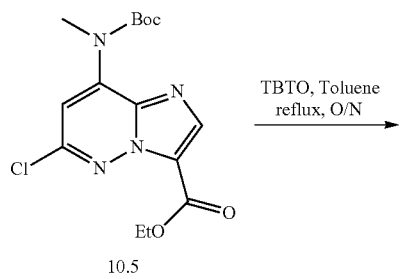

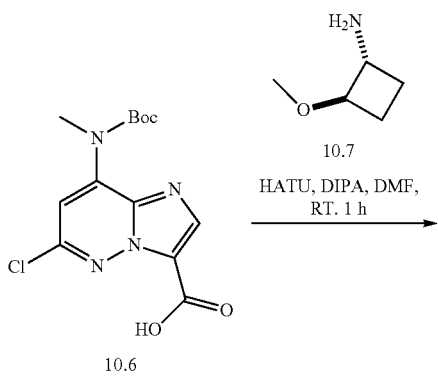

176
-continued

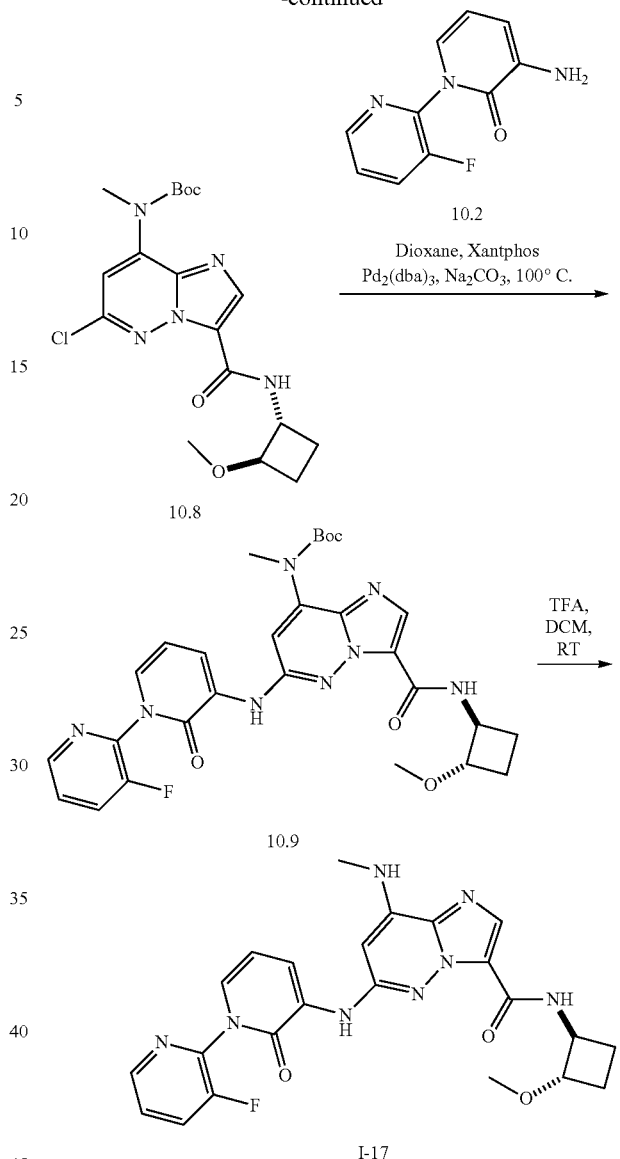

Synthesis of compound 10.2. To a solution of 10 (2.5 g, 22.70 mmol, 1.0 eq) in 1-methylpyrrolidin-2-one (50 mL), 10.1 (3.4 g, 29.51 mmol, 1.3 eq) was added followed by addition of potassium phosphate tribasic (12.04 g, 56.80 mmol, 2.5 eq). The reaction mixture was heated at 90-100° C. for 22 h. After completion of the reaction, the reaction mixture was cooled to room temperature, transferred into cold water and product was extracted with ethyl acetate. The organic layer was combined, washed with brine solution followed by water, dried over sodium sulphate, and concentrated under reduced pressure to obtain crude material. This was further purified column chromatography using 2.0% methanol in dichloromethane as eluant to obtain 10.2 (2.3 g, 49.37%). MS (ES): m/z 206.02 [M+H]⁺.

Synthesis of compound 10.3. Compound was synthesized as per experimental protocol of core synthesis described above to obtain 10.3. (Yield: 20.84%), MS (ES): m/z 260.99 [M+H]⁺.

Synthesis of compound 10.4. To a solution of 10.3 (8.0 g, 30.76 mmol, 1.0 eq) in tetrahydrofuran (100 mL) was added potassium carbonate (8.4 g, 61.52 mmol, 2.0 eq) followed by addition of Methylamine (2.0 g, 30.76 mmol, 2.0 eq). The reaction mixture was heated at room temperature for 5 h. After completion of the reaction, the reaction mixture was cooled to room temperature, transferred into cold water and product was extracted with ethyl acetate. The organic layer was combined, washed with brine solution followed by water, dried over sodium sulphate, and concentrated under reduced pressure to obtain 10.4 (5.0 g, Yield: 63.83%). MS (ES): m/z 255.06 [M+H]$^+$.

Synthesis of compound 10.5. To a solution of 10.4 (0.5 g, 1.96 mmol, 1.0 eq) in 1,4-dioxane (8 mL) were added di-tert-butyl dicarbonate (0.769 g, 3.52 mmol, 1.8 eq) and 4-dimethylaminopyridine (0.025 g, 0.19 mmol, 0.1 eq) and the mixture was stirred at room temperature for 8 h. After completion of the reaction, the reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 10.5 (0.480 g, Yield: 68.91%). MS(ES): m/z 355.11[M+H]$^+$.

Synthesis of compound 10.6. To a suspension of 10.5 (0.480 g, 1.35 mmol, 1.0 eq) in toluene (5 mL) was added tributyltin oxide (1.6 g, 2.7 mmol, 2.0) and reaction mixture was heated at 120° C. for 12 h. After completion of the reaction, the reaction mixture was concentrated under reduced pressure to obtain residue which was dissolved in saturated sodium bicarbonate solution and washed with hexane. The aqueous layer was separated and acidified with 1N hydrochloric acid to pH-5-6 and extracted with ethyl acetate. The organic layer was combined, dried over sodium sulphate, and concentrated under reduced pressure to obtain solid which was triturated with hexane to obtain pure 10.6 (0.350 g, Yield: 79.18%), MS (ES): m/z 327.08 [M+H]$^+$.

Synthesis of compound 10.8. To a solution of 10.6 (2.0 g, 6.13 mmol, 1.0 eq), in N,N-dimethylformamide was added 1-[bis(dimethylamino)methylene]-1H-1,2,3-triazolo[4,5-b]pyridinium 3-oxid hexafluorophosphate (4.65 g, 12.26 mmol, 2.0 eq) and stirred at room temperature for 15 min. To this added diisopropylethylamine (3.2 mL, 18.39 mmol, 3.0 eq) followed by addition of 10.7 (0.619 g, 6.13 mmol, 1.0 eq). The reaction mixture was stirred at room temperature for 5 min. After completion of the reaction, the reaction mixture was transferred into water and product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 10.8. (1.6 g, Yield: 63.77%), MS (ES): m/z 410.16 [M+H]$^+$.

Synthesis of compound 10.9. To a solution of 10.8 (0.175 g, 0.42 mmol, 1.0 eq) in 1,4-dioxane (3 mL) was added 10.2 (0.103 g, 0.50 mmol, 1.2 eq), sodium carbonate (0.088 g, 0.84 mmol, 2.0 eq). The reaction mixture was degassed for 10 min. under argon atmosphere, then tris(dibenzylideneacetone)dipalladium(O) (0.019 g, 0.021 mmol, 0.05 eq) and 4,5-Bis(diphenylphosphino)-9,9-dimethylxanthene (0.024 g, 0.042 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 10.9 (0.160 g, 64.77%). MS(ES): m/z 579.24 [M+H]$^+$.

Synthesis of compound I-17. The compound 10.9 (0.025 g, 0.043 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-17 (0.015 g, 72.55%). MS(ES): m/z 479.56 [M+H]$^+$ LCMS purity: 100%, HPLC purity: 95.00%, CHIRAL HPLC: 48.97%, 49.70%, $^1$H NMR (DMSO-d$_6$, 400 MHz): 8.87-8.85 (d, J=8.8 Hz, 1H), 8.72 (s, 1H), 8.53-8.52 (d, J=4.4 Hz, 1H), 8.17-8.15 (d, J=6.8 Hz, 1H), 8.10-8.06 (d, J=9.2 Hz, 1H), 7.89 (s, 1H), 7.75-7.74 (d, J=4.4 Hz, 1H), 7.54-7.53 (d, J=4.8 Hz, 1H), 7.45-7.44 (d, J=6.4 Hz, 1H), 6.48-6.45 (t, J=10.8 Hz, 1H), 6.38 (s, 1H), 4.38-4.34 (t, J=8.8 Hz, 1H), 3.18 (s, 3H), 2.88-2.87 (d, J=4 Hz, 3H), 2.15-2.07 (m, 3H), 1.57-1.51 (m, 2H).

Example 10. Synthesis of N-(2-methoxycyclobutyl)-8-(methylamino)-6-((2-oxo-2H-[1,2'-bipyridin]-3-yl)amino)imidazo[1,2-b]pyridazine-3-carboxamide (I-18)

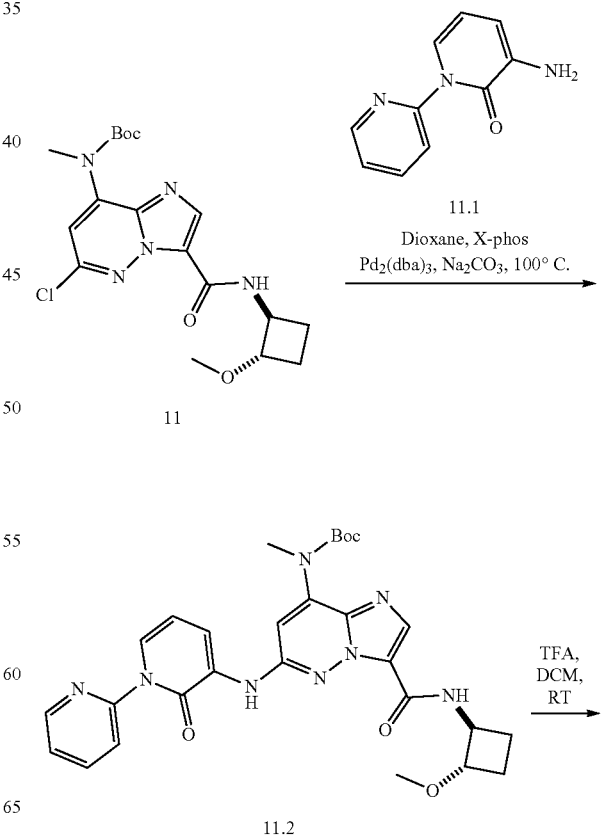

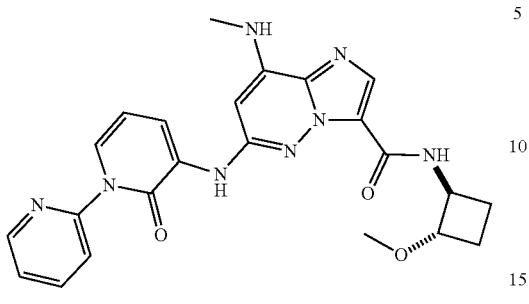

I-18

Synthesis of compound 11. Compound was synthesized as per experimental protocol above in Example 9 to obtain 11 (Yield: 63.77%). MS (ES): m/z 410.16 [M+H]⁺.

Synthesis of compound 11.1. Compound was synthesized as per experimental protocol described above in Example 3 to obtain 11.1 (Yield: 58.82%). MS (ES): m/z 188.20 [M+H]⁺.

Synthesis of compound 11.2. To a solution of 11 (0.175 g, 0.42 mmol, 1.0 eq) in 1,4-dioxane (3 mL) was added 11.1 (0.103 g, 0.50 mmol, 1.2 eq), sodium carbonate (0.088 g, 0.84 mmol, 2.0 eq). The reaction mixture was degassed for 10 min under argon atmosphere, then tris(dibenzylideneacetone)dipalladium(O) (0.019 g, 0.021 mmol, 0.05 eq) and 2-dicyclohexylphosphino-2',4',6'-triisopropylbiphenyl (0.020 g, 0.042 mmol, 0.1 eq) were added, and the mixture was again degassed for 5 min. The reaction was stirred at 100° C. for 4 h. After completion of reaction, the reaction mixture was cooled to room temperature, transferred into water and the product was extracted with ethyl acetate. The organic layer was combined, washed with brine solution, dried over sodium sulphate, and concentrated under reduced pressure to obtain crude material. This was further purified by combi flash using 3% methanol in dichloromethane as eluant to obtain pure 11.2 (0.170 g, Yield: 71.02%). MS(ES): m/z 561.25 [M+H]⁺.

Synthesis of compound I-18. The compound 11.2 (0.030 g, 0.053 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-18 (0.018 g, Yield: 73.04%). MS(ES): m/z 461.77 [M+H]⁺; LCMS purity: 99.33%, HPLC purity: 99.59%, CHIRAL HPLC: 47.01%, 48.01%; ¹H NMR (DMSO-d₆, 400 MHz): 8.88-8.86 (d, J=8.8 Hz, 1H), 8.70 (s, 1H), 8.66-8.65 (d, J=3.6 Hz, 1H), 8.13-8.11 (d, J=7.2 Hz, 1H), 8.08-8.04 (t, J=7.6 Hz, 1H), 7.89 (bs, 1H), 7.86 (s, 1H), 7.60-7.52 (m, 3H), 6.47-6.44 (t, J=7.2 Hz, 1H), 6.40 (s, 1H), 4.39-4.35 (m, 1H), 3.22 (s, 3H), 2.89-2.88 (d, J=4.4 Hz, 3H), 2.14-2.07 (m, 2H), 1.57-1.51 (m, 3H).

Example 11. Synthesis of N-(2-methoxycyclobutyl)-6-((6'-methyl-2-oxo-2H-[1,3'-bipyridin]-3-yl)amino)-8-(methylamino)imidazo[1,2-b]pyridazine-3-carboxamide (I-19)

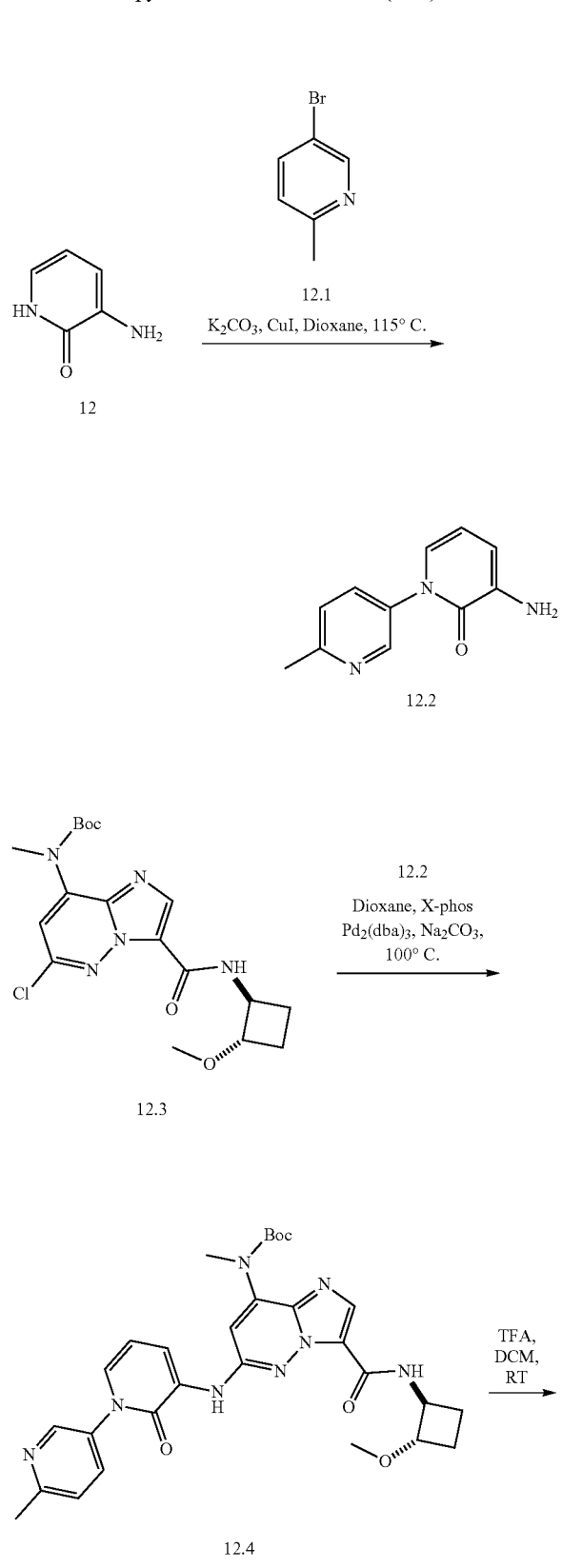

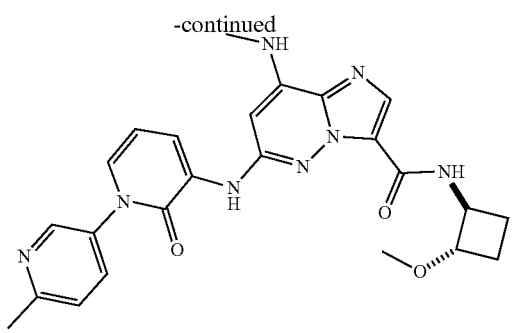

I-19

Synthesis of compound 12.2. To a solution of 12 (3.0 g, 17.44 mmol, 1 eq) in 1,4-dioxane (150 mL), 12.1 (2.30 g, 20.92 mmol, 1.2 eq) was added. The reaction mixture was degassed for 10 min under argon atmosphere followed by addition of potassium carbonate (6.0 g, 43.6 mmol, 2.5 eq), N,N-dimethylethylenediamine (0.384 g, 4.36 mmol, 0.25 eq), and copper iodide (0.497 g, 2.61 mmol, 0.15 eq). The reaction mixture was heated at 115° C. for 12 h. After completion of the reaction, the reaction mixture was transferred to ice cold water and product was extracted with ethyl acetate. The organic layer was combined, washed with brine solution, dried over sodium sulphate and concentrated under reduced pressure to obtain crude material. This was further purified by 5% methanol in dichloromethane to obtain 12.2 (1.56 g, Yield: 44.45%). MS (ES): m/z 202.09 [M+H]$^+$.

Synthesis of compound 12.3. Compound was synthesized as per experimental protocol described above in Example 9 to obtain 12.3 (Yield: 63.77%). MS (ES): m/z 410.16 [M+H]$^+$.

Synthesis of compound 12.4. To a solution of 12.3 (0.175 g, 0.42 mmol, 1.0 eq) in 1,4-dioxane (3 mL) was added 12.2 (0.103 g, 0.50 mmol, 1.2 eq), sodium carbonate (0.088 g, 0.84 mmol, 2.0 eq). The reaction mixture was degassed for 10 min under argon atmosphere, then tris(dibenzylideneacetone)dipalladium(O) (0.019 g, 0.021 mmol, 0.05 eq) and 2-dicyclohexylphosphino-2',4',6'-triisopropylbiphenyl (0.020 g, 0.042 mmol, 0.1 eq) were added, and the mixture again degassed for 5 min. The reaction was stirred at 100° C. for 4 h. After completion of the reaction, the reaction mixture was cooled to room temperature, transferred into water and the product was extracted with ethyl acetate. The organic layer was combined, washed with brine solution, dried over sodium sulphate, and concentrated under reduced pressure to obtain crude material. This was further purified by combi flash using 3% methanol in dichloromethane as eluent to obtain pure 12.4. (0.160 g, Yield: 65.21%). MS(ES): m/z 575.27 [M+H]$^+$.

Synthesis of compound I-19. The compound 12.4 (0.025 g, 0.043 mmol, 1.0 eq) was dissolved in dichloromethane (1 mL) and trifluoroacetic acid (0.09 mL) was added to the reaction mixture. The reaction was stirred at room temperature for 1 h. After completion of reaction, the reaction mixture was transferred into saturated bicarbonate solution and the product was extracted with dichloromethane. The organic layer was combined and dried over sodium sulphate and concentrated under reduced pressure to obtain crude material. This was further purified by trituration with diethyl ether to obtain pure I-19 (0.015 g, Yield: 72.66%). MS(ES): m/z 475.77 [M+H]$^+$; LCMS purity: 100%, HPLC purity: 100%, CHIRAL HPLC: 46.44%, 47.34%, $^1$H NMR (DMSO-d$_6$, 400 MHZ): 8.85 (s, 1H), 8.83-8.81 (d, J=8.8 Hz, 1H), 8.73 (s, 1H), 8.24-8.22 (d, J=7.2 Hz, 1H), 8.17-8.16 (d, J=6.8 Hz, 1H), 7.94 (bs, 1H), 7.74-7.72 (d, J=8.4 Hz, 1H), 7.49 (bs, 1H), 7.42-7.41 (d, J=6.8 Hz, 1H), 6.47 (s, 1H), 6.45-6.43 (t, J=6 Hz, 1H), 3.80-3.77 (m, 1H), 3.22 (s, 3H), 2.87 (s, 3H), 2.66 (bs, 3H), 2.16-2.05 (m, 2H), 1.57-1.45 (m, 2H), 1.23 (bs, 1H).

Example 12. Synthesis of N-(2-methoxycyclobutyl)-8-(methylamino)-6-((2-oxo-1-(tetrahydro-2H-pyran-4-yl)-1,2-dihydropyridin-3-yl)amino)imidazo[1,2-b]pyridazine-3-carboxamide (I-20)

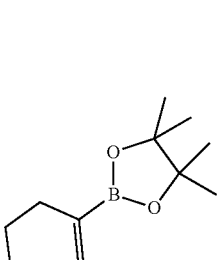

13

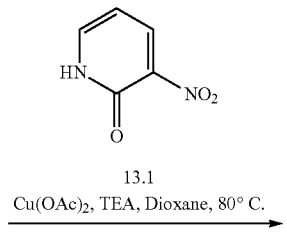

13.1
Cu(OAc)$_2$, TEA, Dioxane, 80° C.

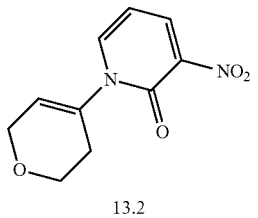

13.2

Pd/C, MeOH, H$_2$

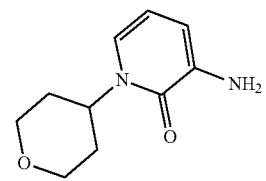

13.3

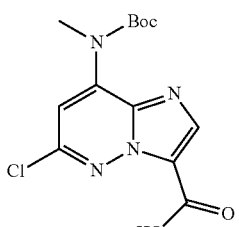

13.4

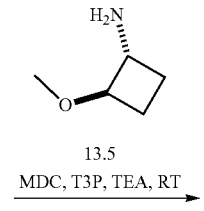

13.5
MDC, T3P, TEA, RT

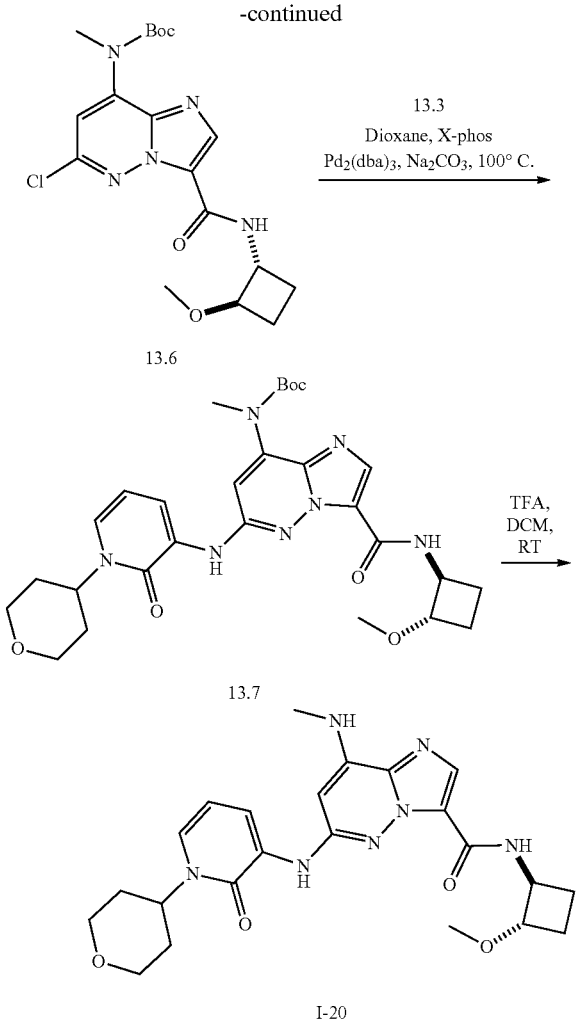

Synthesis of compound 13.2. To a solution of 13 (3.0 g, 14.28 mmol, 1.0 eq) and 13.1 (2.4 g, 17.14 mmol, 1.2 eq) in dioxane (30 mL) was added copper acetate (2.60 g, 14.28 mmol, 1.0 eq) and triethylamine (5.00 mL, 35.7 mmol, 2.5 eq) under nitrogen. The reaction was stirred at 80° C. for 5 h. After completion of the reaction, the reaction mixture was transferred into ice cold water and product was extracted with ethyl acetate. The organic layer was combined and dried over sodium sulphate and concentrated under reduced pressure to obtain crude material. This was further purified by column chromatography and compound was eluted in 10% ethyl acetate in hexane to obtain pure 13.2 (0.380 g, 11.98%), MS (ES): m/z 222.20 [M+H]$^+$.

Synthesis of compound 13.3. To a solution of 13.1 (0.380 g, 1.71 mmol, 1.0 eq) in methanol (4 ml), palladium on charcoal (0.100 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 1.4% methanol in dichloromethane to obtain pure 13.3 (0.120 g, 36.13%). MS (ES): m/z 195.23 [M+H]$^+$.

Synthesis of compound 13.4. Compound was synthesized using general procedure of core synthesis described above to obtain 13.4. (Yield: 71.67%). MS (ES): m/z 327.08 [M+H]$^+$.

Synthesis of compound 13.6. To a solution of 13.4 (2.0 g, 6.11 mmol, 1.0 eq), in dichloromethane (30 mL) was added propylphosphonic anhydride (3.8 g, 12.22 mmol, 2.0 eq) and stirred at room temperature for 15 min. To this added triethylamine (1.8 g, 18.33 mmol, 3.0 eq) followed by addition of 13.5 (0.740 g, 7.33 mmol, 1.2 eq). The reaction mixture was stirred at room temperature for 5 min. After completion of the reaction, the reaction mixture was transferred into water and product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 13.6 (1.6 g, Yield: 63.77%). MS(ES): m/z 410.16 [M+H]$^+$.

Synthesis of compound 13.7. To a solution of 13.6 (0.175 g, 0.42 mmol, 1.0 eq) in 1,4-dioxane (3 mL) was added 13.3 (0.097 g, 0.50 mmol, 1.2 eq), sodium carbonate (0.088 g, 0.84 mmol, 2.0 eq). The reaction mixture was degassed for 10 min. under argon atmosphere, then tris(dibenzylideneacetone)dipalladium(O) (0.020 g, 0.021 mmol, 0.05 eq) and 2-dicyclohexylphosphino-2',4',6'-triisopropylbiphenyl (0.019 g, 0.042 mmol, 0.1 eq) were added, again degassed for 5 min. The reaction mixture was stirred at 100° C. for 4 h. After completion of reaction, reaction mixture was cooled to room temperature, transferred into water and product was extracted with ethyl acetate. The organic layer was combined, washed with brine solution, dried over sodium sulphate, and concentrated under reduced pressure to obtain crude material. This was further purified by combi flash using 3% methanol in dichloromethane as eluent to obtain pure 13.7 (0.150 g, Yield: 61.89%). MS(ES): m/z 568.28 [M+H]$^+$.

Synthesis of compound I-20. The compound 13.7 (0.025 g, 0.044 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-20 (0.015 g, 72.85%). MS(ES): m/z 468.77 [M+H]$^+$; LCMS purity: 100%, HPLC purity: 100%, Chiral HPLC purity: 47.30%, 49.03%; $^1$H NMR (DMSO-d$_6$, 400 MHz): 8.83-8.80 (d, J=8.8 Hz, 1H), 8.54 (s, 1H), 7.98-7.96 (d, J=6.4 Hz, 1H), 7.85 (s, 1H), 7.50-7.45 (m, 2H), 6.36-6.33 (t, J=6.8 Hz, 1H), 6.31 (s, 1H), 5.76 (s, 1H), 5.03 (bs, 1H), 4.33-4.31 (m, 1H), 3.99 (bs, 2H), 3.76-3.70 (m, 2H), 3.53-3.47 (t, J=11.2 Hz, 3H), 3.18 (s, 3H), 2.86-2.85 (d, J=4.8 Hz, 3H), 2.10-2.03 (m, 3H), 1.76 (bs, 2H).

Example 13. Synthesis of N-(2-methoxycyclobutyl)-6-((1-((1r,4S)-4-methoxycyclohexyl)-2-oxo-1,2-dihydropyridin-3-yl)amino)-8-(methylamino)imidazo[1,2-b]pyridazine-3-carboxamide (I-21)

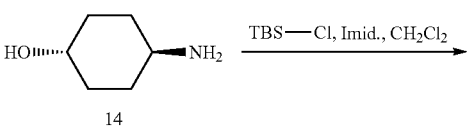

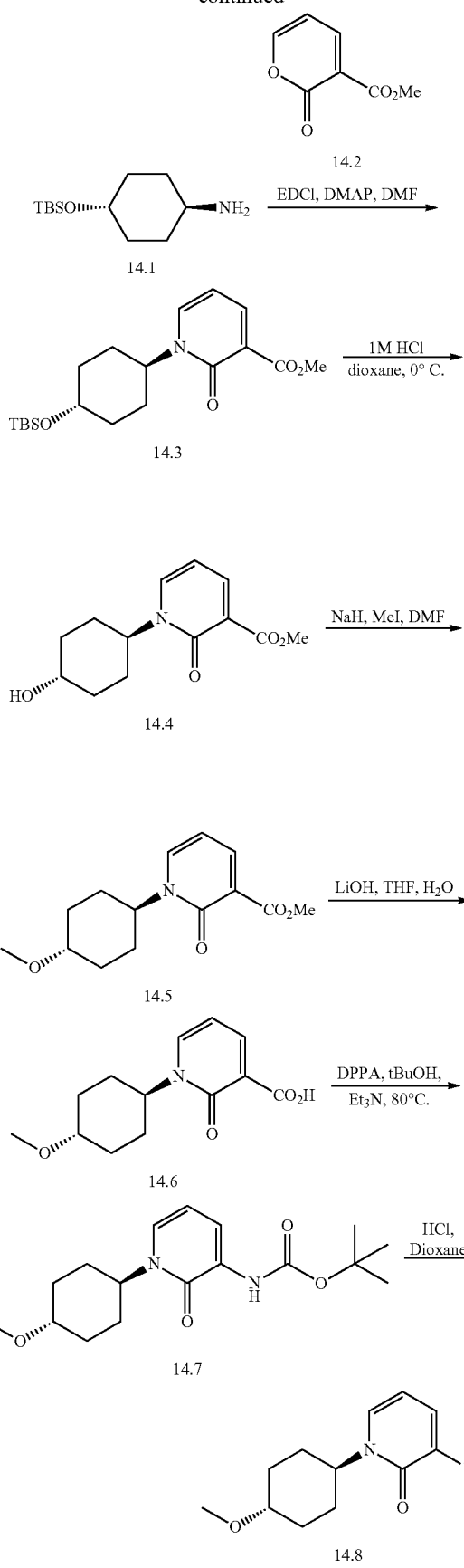

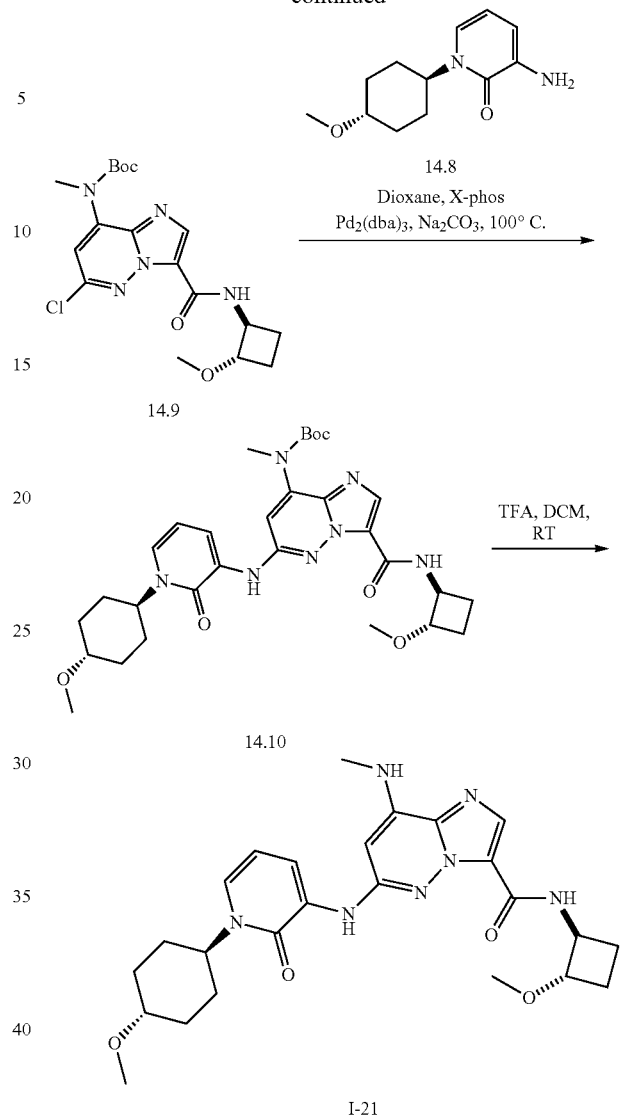

Synthesis of compound 14.1. To a solution of 14 (4 g, 34.73 mmol, 1.0 eq) in dichloromethane (40 mL), imidazole (7 g, 104.19 mmol, 3.0 eq), tert-butyldimethylsilyl chloride (7.8 g, 52.09 mmol, 1.5 eq) was added at 0° C. The reaction mixture was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 5% methanol in dichloromethane as eluent to 14.1 (5.2 g, 65.26%). MS(ES): m/z 230.44 [M+H]$^+$.

Synthesis of compound 14.3. To a solution of 14.1 (5.2 g, 22.66 mmol, 1.0 eq) in dimethylformamide (50 mL) was added 14.2 (3.4 g, 22.66 mmol, 1.0 eq). The reaction mixture was stirred at room temperature for 1 h followed by addition of N-Ethyl-N'-(3-dimethylaminopropyl) carbodiimide hydrochloride (6.5 g, 33.99 mol, 1.5 eq) and 4-dimethyl-aminopryidine (0.69 g, 5.66 mmol, 0.25 eq). The reaction was stirred at room temperature for 16 h. After completion of the reaction, the reaction mixture was transferred into ice cold water and the product was extracted with ethyl acetate. The organic layer was combined, washed with brine solution, dried over sodium sulphate and concentrated under reduced pressure to obtain crude material. This was further purified by combi flash using 30% ethylacetate in hexane as eluent to 14.3 (1.8 g, 21.73%). MS(ES): m/z 366.55 [M+H]+.

Synthesis of compound 14.4. To 14.3 (1.8 g, 4.92 mmol, 1.0 eq) was added hydrochloric acid in 1,4-dioxane (10 mL). The reaction mixture was stirred at room temperature for 1 h. After completion of the reaction, the reaction mixture was concentrated under reduced pressure to obtain residue which was stirred with diethyl ether and filtered to obtain pure 14.4 (1.2 g, 96.98%). MS (ES): m/z 252.28 [M+H]+.

Synthesis of compound 14.5. To a solution of 14.4. (1.2 g, 4.78 mmol, 1.0 eq) in tetrahydrofuran (10 mL), sodium hydride (0.10 g, 7.17 mmol, 1.5 eq), was added 0° C. followed by addition of methyl iodide (0.67 g, 4.78 mmol, 1.0 eq). The reaction mixture was stirred at room temperature for 16 h. After completion of the reaction, the reaction mixture was transferred into ice cold water and product was extracted with ethylacetate. Organic layer was combined, washed with brine solution, dried over sodium sulphate and concentrated under reduced pressure to obtain crude material. This was further purified by combi flash using 1.4% methanol in dichloromethane as eluent to 14.5 (0.78 g, 61.56%). MS(ES): m/z 266.31 [M+H]+.

Synthesis of compound 14.6. To a solution of 14.5 (0.78 g, 2.94 mmol, 1.0 eq), in tetrahydrofuran:methanol:water (5 mL, 1:1:1) was added lithium hydroxide (1.2 g, 29.4 mmol, 10 eq). The reaction was stirred at 70° C. for 3 h. After completion of the reaction, the reaction mixture was concentrated under reduced pressure to obtain residue. To this was added water and the mixture was acidified with 1N hydrochloric acid to adjust to pH-6-6.5 at 10° C. Product was extracted with dichloromethane. The organic layer was combined, washed with brine solution, dried over sodium sulphate and concentrated under reduced pressure to obtain 14.6 (0.65 g, 87.99%). MS(ES): m/z: 252.28 [M+H]+.

Synthesis of compound 14.7. To a solution of 14.6 (0.65 g, 2.59 mmol, 1.0 eq) in tert-butanol (6 mL) was added diphenylphosphorylazide (1.1 g, 4.14 mmol, 1.6 eq), trimethylamine (10 mL, 7.7 mmol, 3.0 eq). The reaction mixture was heated at 80° C. for 18 h. After completion of reaction, reaction mixture was transferred into ice cold water and product was extracted with ethylacetate. Organic layer was combined, washed with brine solution, dried over sodium sulphate, and concentrated under reduced pressure to obtain crude material. This was further purified by combi flash using 5% ethyl acetate in hexane as eluent to 14.7 (0.38 g, 45.56%). MS(ES): m/z 323.41 [M+H]+.

Synthesis of compound 14.8. To 14.7 (0.38 g, 1.18 mmol, 1.0 eq) was added hydrochloric acid in 1,4-dioxane (1 mL). The reaction mixture was stirred at room temperature for 1 h. After completion of the reaction, the reaction mixture was concentrated under reduced pressure to obtain residue which was stirred with diethyl ether and filtered to obtain pure 14.8 (0.20 g, 76.34%). MS (ES): m/z 223.29 [M+H]+.

Synthesis of compound 14.9. Compound was synthesized as per the experimental protocol described above in Example 12 to obtain 14.9 (Yield: 63.77%). MS (ES): m/z 410.16 [M+H]+.

Synthesis of compound 14.10. To a solution of 14.9 (0.175 g, 0.42 mmol, 1.0 eq) in 1,4-dioxane (3 mL) was added 14.8 (0.111 g, 0.50 mmol, 1.2 eq), sodium carbonate (0.088 g, 0.84 mmol, 2.0 eq). The reaction mixture was degassed for 10 min under argon atmosphere, then tris (dibenzylideneacetone)dipalladium(O) (0.020 g, 0.021 mmol, 0.05 eq) and 2-Dicyclohexylphosphino-2',4',6'-triisopropylbiphenyl (0.019 g, 0.042 mmol, 0.1 eq) were added, again degassed for 5 min. The reaction mixture was stirred at 100° C. for 4 h. After completion of the reaction, the reaction mixture was cooled to room temperature, transferred into water and product was extracted with ethyl acetate. The organic layer was combined, washed with brine solution, dried over sodium sulphate, and concentrated under reduced pressure to obtain crude material. This was further purified by combi flash using 3% methanol in dichloromethane as eluent to obtain pure 14.10 (0.153 g, Yield: 60.16%). MS(ES): m/z 596.32 [M+H]+.

Synthesis of compound I-21. The compound 14.10 (0.025 g, 0.042 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-21 (0.018 g, 86.55%). MS(ES): m/z 496.61 [M+H]+ LCMS purity: 100%, HPLC purity: 98.43%, Chiral HPLC purity: 47.08%, 48.92%, 1H NMR (DMSO-d6, 400 MHz): 8.83-8.81 (d, J=8.8 Hz, 1H), 8.52 (s, 1H), 8.96-8.94 (d, J=6.4 Hz, 1H), 7.85 (s, 1H), 7.49-7.48 (d, J=4.8 Hz, 1H), 7.42-7.40 (d, J=6 Hz, 1H), 6.35-6.31 (t, J=7.2 Hz, 1H), 6.29 (s, 1H), 4.79 (bs, 1H), 4.35-4.30 (m, 1H), 3.76-3.72 (m, 1H), 3.22 (s, 4H), 3.18 (s, 3H), 2.86-2.85 (d, J=4.8 Hz, 3H), 2.15-2.08 (m, 4H), 1.80 (bs, 3H), 1.52 (bs, 2H), 1.23 (bs, 3H).

Example 14. Synthesis of 6-((1-((1R,5S,6r)-3-oxabicyclo[3.1.0]hexan-6-yl)-2-oxo-1,2-dihydropyridin-3-yl)amino)-N-(2-methoxycyclobutyl)-8-(methylamino)imidazo[1,2-b]pyridazine-3-carboxamide (I-22)

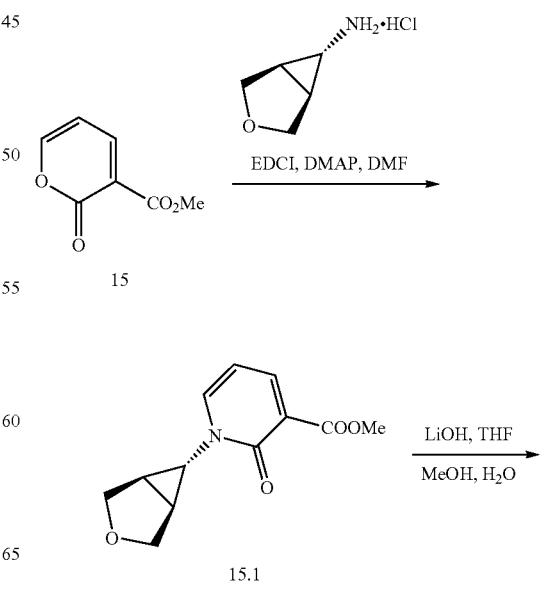

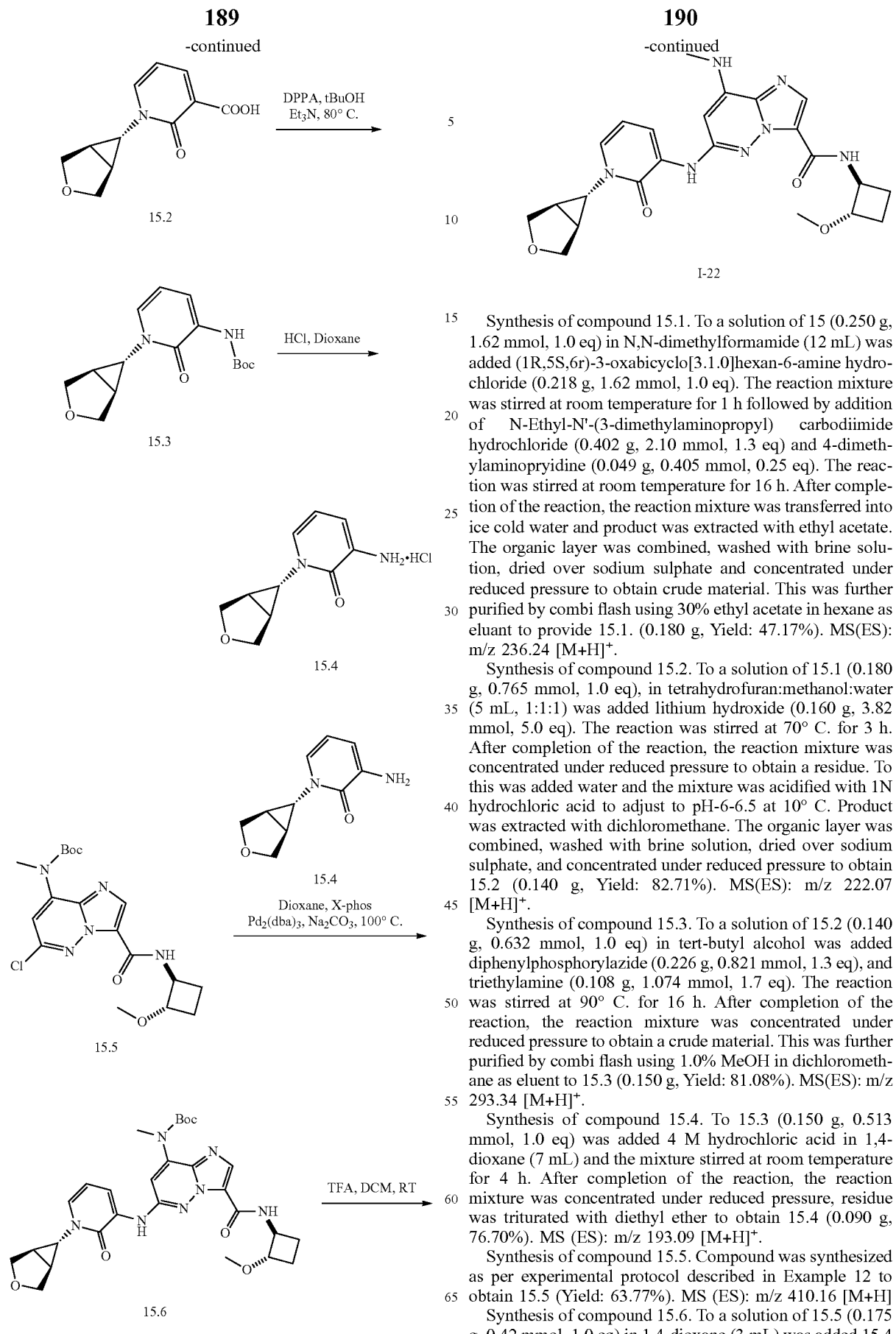

Synthesis of compound 15.1. To a solution of 15 (0.250 g, 1.62 mmol, 1.0 eq) in N,N-dimethylformamide (12 mL) was added (1R,5S,6r)-3-oxabicyclo[3.1.0]hexan-6-amine hydrochloride (0.218 g, 1.62 mmol, 1.0 eq). The reaction mixture was stirred at room temperature for 1 h followed by addition of N-Ethyl-N'-(3-dimethylaminopropyl) carbodiimide hydrochloride (0.402 g, 2.10 mmol, 1.3 eq) and 4-dimethylaminopryidine (0.049 g, 0.405 mmol, 0.25 eq). The reaction was stirred at room temperature for 16 h. After completion of the reaction, the reaction mixture was transferred into ice cold water and product was extracted with ethyl acetate. The organic layer was combined, washed with brine solution, dried over sodium sulphate and concentrated under reduced pressure to obtain crude material. This was further purified by combi flash using 30% ethyl acetate in hexane as eluant to provide 15.1. (0.180 g, Yield: 47.17%). MS(ES): m/z 236.24 [M+H]$^+$.

Synthesis of compound 15.2. To a solution of 15.1 (0.180 g, 0.765 mmol, 1.0 eq), in tetrahydrofuran:methanol:water (5 mL, 1:1:1) was added lithium hydroxide (0.160 g, 3.82 mmol, 5.0 eq). The reaction was stirred at 70° C. for 3 h. After completion of the reaction, the reaction mixture was concentrated under reduced pressure to obtain a residue. To this was added water and the mixture was acidified with 1N hydrochloric acid to adjust to pH-6-6.5 at 10° C. Product was extracted with dichloromethane. The organic layer was combined, washed with brine solution, dried over sodium sulphate, and concentrated under reduced pressure to obtain 15.2 (0.140 g, Yield: 82.71%). MS(ES): m/z 222.07 [M+H]$^+$.

Synthesis of compound 15.3. To a solution of 15.2 (0.140 g, 0.632 mmol, 1.0 eq) in tert-butyl alcohol was added diphenylphosphorylazide (0.226 g, 0.821 mmol, 1.3 eq), and triethylamine (0.108 g, 1.074 mmol, 1.7 eq). The reaction was stirred at 90° C. for 16 h. After completion of the reaction, the reaction mixture was concentrated under reduced pressure to obtain a crude material. This was further purified by combi flash using 1.0% MeOH in dichloromethane as eluent to 15.3 (0.150 g, Yield: 81.08%). MS(ES): m/z 293.34 [M+H]$^+$.

Synthesis of compound 15.4. To 15.3 (0.150 g, 0.513 mmol, 1.0 eq) was added 4 M hydrochloric acid in 1,4-dioxane (7 mL) and the mixture stirred at room temperature for 4 h. After completion of the reaction, the reaction mixture was concentrated under reduced pressure, residue was triturated with diethyl ether to obtain 15.4 (0.090 g, 76.70%). MS (ES): m/z 193.09 [M+H]$^+$.

Synthesis of compound 15.5. Compound was synthesized as per experimental protocol described in Example 12 to obtain 15.5 (Yield: 63.77%). MS (ES): m/z 410.16 [M+H]

Synthesis of compound 15.6. To a solution of 15.5 (0.175 g, 0.42 mmol, 1.0 eq) in 1,4-dioxane (3 mL) was added 15.4

(0.096 g, 0.50 mmol, 1.2 eq), sodium carbonate (0.088 g, 0.84 mmol, 2.0 eq). The reaction mixture was degassed for 10 min under argon atmosphere, then tris(dibenzylideneacetone)dipalladium(O) (0.020 g, 0.021 mmol, 0.05 eq) and 2-dicyclohexylphosphino-2',4',6'-triisopropylbiphenyl (0.019 g, 0.042 mmol, 0.1 eq) were added, and the mixture was again degassed for 5 min. The reaction mixture was stirred at 100° C. for 4 h. After completion of reaction, reaction mixture was cooled to room temperature, transferred into water and product was extracted with ethyl acetate. The organic layer was combined, washed with brine solution, dried over sodium sulphate, and concentrated under reduced pressure to obtain crude material. This was further purified by combi flash using 3% methanol in dichloromethane as eluent to obtain pure 15.6 (0.140 g, Yield: 57.97%). MS(ES): m/z 566.27 [M+H]⁺.

Synthesis of compound I-22. The compound 15.6 (0.025 g, 0.044 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-22 (0.016 g, 77.76%). MS(ES): m/z 466.86 [M+H]⁺ LCMS purity: 100%, HPLC purity: 97.40%, CHIRAL HPLC: 49.41%, 49.24%, ¹H NMR (DMSO-$d_6$, 400 MHz): 8.82-8.80 (d, J=8.8 Hz, 1H), 8.61 (s, 1H), 7.96-7.94 (d, J=6.8 Hz, 1H), 7.85 (s, 1H), 7.50-7.48 (d, J=5.2 Hz, 1H), 7.28-7.27 (d, J=6 Hz, 1H), 6.34 (s, 1H), 6.26-6.23 (t, J=7.2 Hz, 1H), 4.35-4.31 (t, J=8.4 Hz, 1H), 3.98 (bs, 2H), 3.71 (s, 3H), 3.19 (bs, 2H), 3.14 (bs, 2H), 2.86-2.84 (d, J=4.8 Hz, 3H), 2.27 (bs, 2H), 2.13-2.00 (m, 2H), 1.55-1.50 (m, 1H), 1.42-1.37 (m, 1H).

Example 15. Synthesis of N-((1S,2S)-2-methoxycyclobutyl)-6-((1-((1r,3S)-3-methoxycyclobutyl)-2-oxo-1,2-dihydropyridin-3-yl)amino)-8-(methylamino)imidazo[1,2-b]pyridazine-3-carboxamide (I-23)

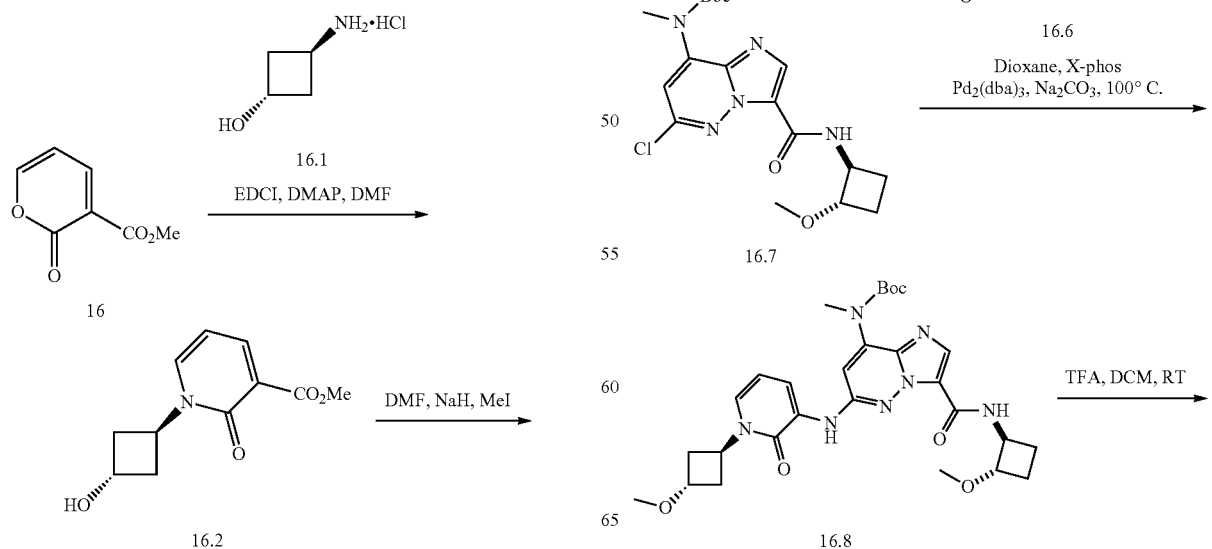

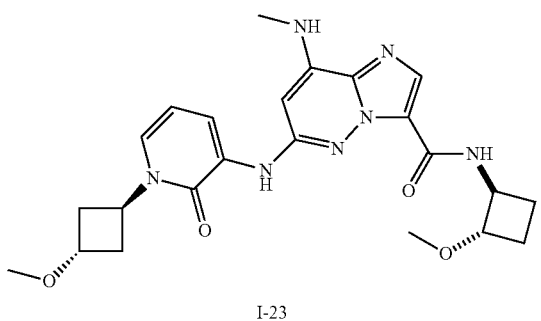

I-23

Synthesis of compound 16.2. To a cooled solution of 16 (5.0 g, 32.44 mmol, 1.0 eq), in N,N-dimethylformamide (50 mL) was added 16.1 (3.99 g, 32.44 mmol, 1.0 eq). The reaction mixture was stirred at 0° C. for 30 min and further stirred at room temperature for 15 min. N-Ethyl-N'-(3-dimethylaminopropyl)carbodiimide hydrochloride (6.5 g, 42.17 mmol, 1.3 eq) and 4-Dimethylaminopyridine (0.790 g, 6.48 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 16.2 (3.35 g, 46.26%). MS(ES): m/z 224.09 [M+H]$^+$.

Synthesis of compound 16.3. To a cooled solution of 16.2 (3.35 g, 15.02 mmol, 1.0 eq), in N,N-dimethylformamide (35 mL) was added sodium hydride (1.44 g, 6.08 mmol, 4.0 eq) at 0° C. portion wise and allowed to stir for 30 min followed by dropwise addition of methyl iodide (2.7 g, 19.52 mmol, 1.3 eq). The reaction mixture was stirred at same temperature for 20 min and the mixture was allowed to stir at room temperature for 6 h. After completion of the reaction, the reaction mixture was transferred into ice water and product was extracted with ethyl acetate. Organic layer was combined, washed with brine solution, dried over sodium sulphate and concentrated under reduced pressure to obtain crude product which was purified by column chromatography eluting pure compound in 2-2.5% methanol in dichloromethane to obtain pure 16.3 (2.85 g, 80.04%). MS (ES): m/z 238.10 [M+H]$^+$.

Synthesis of compound 16.4. To a solution of 16.3 (2.85 g, 12.02 mmol, 1.0 eq), in tetrahydrofuran:water (30 mL, 2:1) was added lithium hydroxide (2.88 g, 120.2 mmol, 10 eq). The reaction was stirred at 60° C. for 16 h. After completion of the reaction, the reaction mixture was concentrated under reduced pressure to obtain a residue. To this was added water and the mixture was acidified with 1 N hydrochloric acid to adjust to pH-6-6.5 at 10° C. The product was extracted with dichloromethane. The organic layer was combined, washed with brine solution, dried over sodium sulphate and concentrated under reduced pressure to obtain crude material. This was further purified by column chromatography and compound was eluted in 2.1% methanol in dichloromethane to obtain pure 16.4. (2.4 g, 89.50%). MS(ES): m/z 224.09 [M+H]$^+$.

Synthesis of compound 16.5. To a solution of 16.4 (2.4 g, 10.76 mmol, 1.0 eq) in tert-butanol (25 mL) was added triethylamine (1.84 g, 18.29 mmol, 1.7 eq) and diphenyl phosphoryl azide (3.84 g, 13.98 mmol, 1.3 eq) under nitrogen followed by heating at 80° C. for 16 h. After completion of the reaction, the reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 16.5 (2.0 g, 63.20%). MS(ES): m/z 295.16 [M+H]$^+$.

Synthesis of compound 16.6. A cooled solution of 16.5 (2.0 g, 6.80 mmol, 1 eq) in dioxane (20 mL) was added 4N hydrochloric acid in dioxane (22 mL) dropwise. The reaction mixture was stirred at room temperature for 2 h. After completion of reaction, reaction mixture was concentrated under reduced pressure to obtain pure 16.6 (1.4 g, 89.32%). MS(ES): m/z 195.11 [M+H]$^+$.

Synthesis of compound 16.7. Compound was synthesized as per experimental protocol described above in Example 12 to obtain 16.7 (Yield: 63.77%). MS (ES): m/z 410.16 [M+H]$^+$.

Synthesis of compound 16.8. To a solution of 16.7 (0.175 g, 0.42 mmol, 1.0 eq) in 1,4-dioxane (3 mL) was added 16.6 (0.097 g, 0.50 mmol, 1.2 eq), sodium carbonate (0.088 g, 0.84 mmol, 2.0 eq). The reaction mixture was degassed for 10 min under argon atmosphere, then tris(dibenzylideneacetone)dipalladium(O) (0.020 g, 0.021 mmol, 0.05 eq) and 2-dicyclohexylphosphino-2',4',6'-triisopropylbiphenyl (0.019 g, 0.042 mmol, 0.1 eq) were added, and the mixture was again degassed for 5 min. The reaction mixture was stirred at 100° C. for 4 h. After completion of the reaction, the reaction mixture was cooled to room temperature, transferred into water and the product was extracted with ethyl acetate. The organic layer was combined, washed with brine solution, dried over sodium sulphate and concentrated under reduced pressure to obtain crude material. This was further purified by combi flash using 3% methanol in dichloromethane as eluent to obtain pure 16.8 (0.145 g, Yield: 59.83%). MS(ES): m/z 568.28 [M+H]$^+$.

Synthesis of compound I-23. The compound 16.8 (0.025 g, 0.044 mmol, 1.0 eq) was dissolved in dichloromethane (1 mL) and trifluoroacetic acid (0.09 mL) was added to the reaction mixture. The reaction was stirred at room temperature for 1 h. After completion of the reaction, the reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-23 (0.016 g, 77.70%). MS(ES): m/z 468.91 [M+H]$^+$; LCMS purity: 98.64%, HPLC purity: 98.37%, CHIRAL HPLC purity: 49.08%, 48.92%, $^1$H NMR (DMSO-$d_6$, 400 MHz): 8.83-8.81 (d, J=8.8 Hz, 1H), 8.57 (s, 1H), 7.98-7.97 (d, J=6.4 Hz, 1H), 7.85 (s, 1H), 7.50-7.49 (d, J=5.2 Hz, 2H), 6.36 (s, 1H), 6.33-6.31 (t, J=7.2 Hz, 1H), 5.31-5.27 (t, J=8.4 Hz, 1H), 4.35-4.31 (t, J=8 Hz, 1H), 4.05 (bs, 1H), 3.76-3.70 (m, 1H), 3.21 (s, 3H), 3.19 (s, 3H), 2.85-2.84 (d, J=4.8 Hz, 3H), 2.13-2.01 (m, 2H), 1.55-1.50 (m, 1H), 1.45-1.40 (m, 1H), 1.22 (bs, 3H), 1.10-1.07 (m, 1H).

Example 16. Synthesis of rac-N-((1S,2S)-2-methoxycyclobutyl)-6-(1-((3R,4S)-3-methoxytetrahydro-2H-pyran-4-yl)-1H-pyrrolo[2,3-b]pyridin-3-yl)-8-(methylamino)imidazo[1,2-b]pyridazine-3-carboxamide (I-1), N-((1S,2S)-2-methoxycyclobutyl)-6-(1-((3R,4S)-3-methoxytetrahydro-2H-pyran-4-yl)-1H-pyrrolo[2,3-b]pyridin-3-yl)-8-(methylamino)imidazo[1,2-b]pyridazine-3-carboxamide (I-24) and N-((1R,2R)-2-methoxycyclobutyl)-6-(1-((3R,4S)-3-methoxytetrahydro-2H-pyran-4-yl)-1H-pyrrolo[2,3-b]pyridin-3-yl)-8-(methylamino)imidazo[1,2-b]pyridazine-3-carboxamide (I-27)

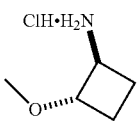

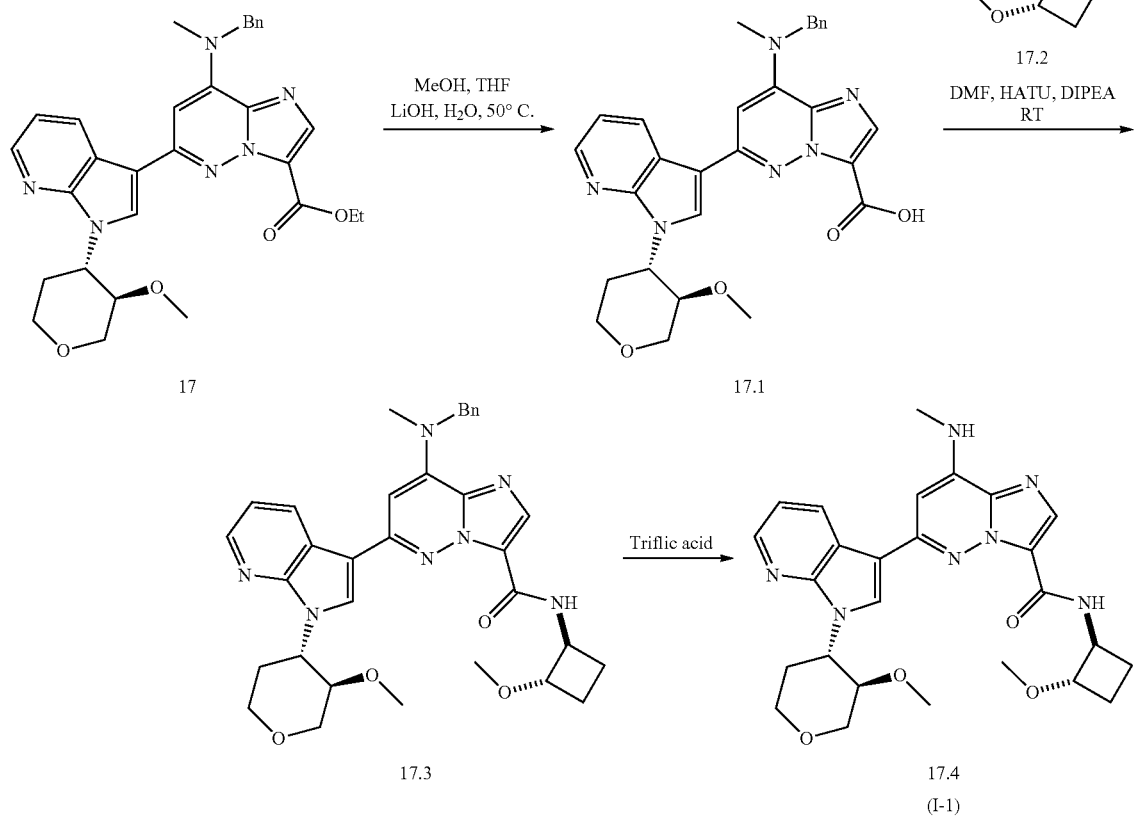

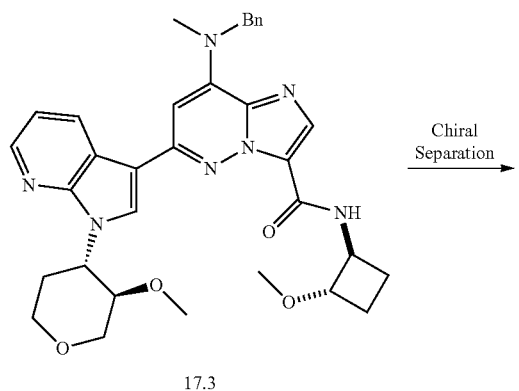

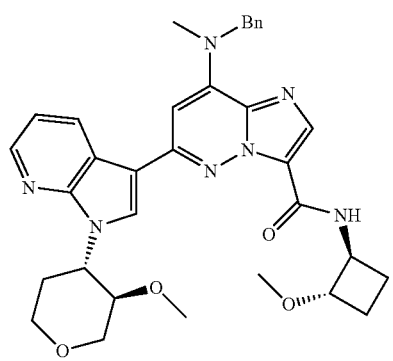

17.3a

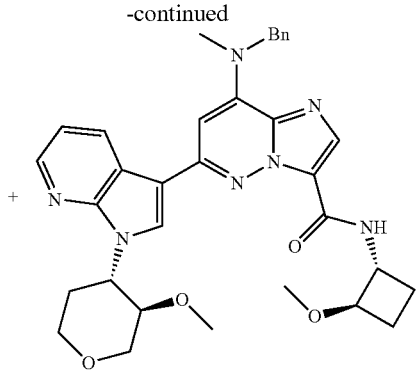

-continued 17.3b

|Triflic acid

|Triflic acid

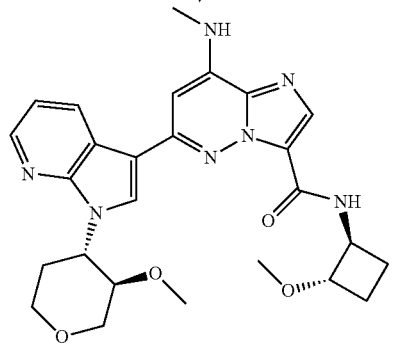

I-24

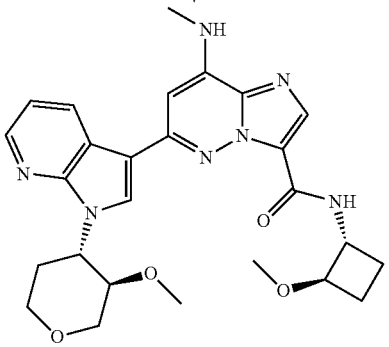

I-27

Synthesis of compound 17. Compound was synthesized as per experimental protocol described above to obtain 17 (MS (ES): m/z 541.25 [M+H]$^+$.

Synthesis of compound 17.1. To a solution of 17 (0.250 g, 0.46 mmol, 1.0 eq), in tetrahydrofuran:methanol:water (4 mL, 2:1:1) was added lithium hydroxide (0.110 g, 4.6 mmol, 10.0 eq). The reaction was stirred at 50° C. for 16 h. After completion of reaction, reaction mixture was concentrated under reduced pressure to obtain residue. To this added water and acidified with 1N hydrochloric acid to adjust pH-6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 17.1 (0.195 g, Yield: 82.27%). MS(ES): m/z 513.22 [M+H]$^+$.

Synthesis of compound 17.3. Compound was synthesized using general procedure C to obtain 17.3 (0.155 g, Yield: 68.39%). MS(ES): m/z 596.29 [M+H]$^+$.

Synthesis of compound 17.4 (I-1). Compound was synthesized using general procedure D to obtain 17.4 (0.025 g, Yield: 65.46%). MS (ES): m/z 506.25 [M+H]$^+$ LCMS purity: 99.00%, HPLC purity: 97.89%, CHIRAL HPLC: 50.05%, 49.94%; $^1$H NMR (DMSO-d$_6$, 400 MHz): 9.26-9.24 (d, J=8.8 Hz, 1H), 8.80-8.78 (d, J=7.6 Hz, 1H), 8.50 (bs, 2H), 7.99 (s, 1H), 7.72-7.70 (d, J=7.2 Hz, 1H), 7.29-7.26 (t, J=6.8 Hz, 1H), 6.67 (s, 1H), 5.45 (bs, 1H), 4.49 (bs, 1H), 4.42-4.38 (m, 1H), 4.13-4.04 (m, 3H), 3.84-3.80 (m, 1H), 3.66-3.60 (t, J=10.8 Hz, 1H), 3.24 (s, 3H), 3.21 (s, 3H), 3.03-3.02 (d, J=4.8 Hz, 3H), 2.20-2.18 (m, 1H), 2.10-2.08 (m, 1H), 1.54 (bs, 3H), 1.23 (bs, 1H).

Synthesis of compound 17.3a and 17.3b. Isomers of 17.3 (0.115 g) were separated out using column CHIRALCEL OJ-H (250 mm*4.6 mm, 5 u) and 0.1% DEA in MEOH as co-solvent with flow rate of 4 mL/min to get pure fraction-1 (FR-a) and fraction-2 (FR-b). FR-a was concentrated under reduced pressure at 30° C. to afford pure 17.3b (0.045 g). MS(ES): m/z 596.29 [M+H]$^+$. FR-b was concentrated under reduced pressure at 30° C. to afford pure 17.3a. (0.046 g). MS(ES): m/z 596.29 [M+H]$^+$.

Synthesis of compound I-24. Compound was synthesized using general procedure D to obtain I-24 (0.030 g, Yield: 78.55%). MS (ES): m/z 506.64 [M+H]$^+$ LCMS purity: 100%, HPLC purity: 97.60%, CHIRAL HPLC: 97.55%, $^1$H NMR (DMSO-d$_6$, 400 MHz): 9.25-9.22 (d, J=8.8 Hz, 1H), 8.78-8.76 (d, J=7.2 Hz, 1H), 8.48 (bs, 2H), 7.97 (s, 1H), 7.64-7.63 (d, J=4.8 Hz, 1H), 7.28-7.24 (t, J=6.8 Hz, 1H), 6.65 (s, 1H), 5.44 (bs, 1H), 4.47 (bs, 1H), 4.43-4.37 (m, 1H), 4.13-4.04 (m, 3H), 3.84-3.80 (m, 1H), 3.64-3.58 (t, J=11.2 Hz, 1H), 3.22 (s, 3H), 3.13 (s, 3H), 3.02-3.00 (d, J=4.8 Hz, 3H), 2.19-2.16 (m, 1H), 1.98 (bs, 1H), 1.54-1.47 (m, 3H), 1.23 (bs, 1H).

Synthesis of compound I-27. Compound was synthesized using general procedure D to obtain I-27 (0.032 g, Yield: 81.97%). MS (ES): m/z 506.64 [M+H]$^+$ LCMS purity: 100%, HPLC purity: 98.98%, CHIRAL HPLC: 100%, $^1$H NMR (DMSO-d$_6$, 400 MHz): 9.25-9.22 (d, J=8.8 Hz, 1H), 8.78-8.76 (d, J=7.2 Hz, 1H), 8.48 (bs, 2H), 7.97 (s, 1H), 7.64-7.63 (d, J=4.8 Hz, 1H), 7.27-7.24 (t, J=6.4 Hz, 1H), 6.65 (s, 1H), 5.44 (bs, 1H), 4.47 (bs, 1H), 4.43-4.37 (m, 1H), 4.13-4.04 (m, 3H), 3.84-3.80 (m, 1H), 3.64-3.59 (t, J=11.2 Hz, 1H), 3.22 (s, 3H), 3.13 (s, 3H), 3.02-3.01 (d, J=4.8 Hz, 3H), 2.21-2.16 (m, 1H), 2.09-2.05 (m, 1H), 1.54-1.47 (m, 3H), 1.22 (bs, 1H).

Example 17. Synthesis of rac-N-((1S,2S)-2-methoxycyclobutyl)-6-(1-((3S,4R)-3-methoxytetrahydro-2H-pyran-4-yl)-1H-pyrrolo[2,3-b]pyridin-3-yl)-8-(methylamino)imidazo[1,2-b]pyridazine-3-carboxamide (I-2), N-((1S,2S)-2-methoxycyclobutyl)-6-(1-((3S,4R)-3-methoxytetrahydro-2H-pyran-4-yl)-1H-pyrrolo[2,3-b]pyridin-3-yl)-8-(methylamino)imidazo[1,2-b]pyridazine-3-carboxamide (I-25) and N-((1R,2R)-2-methoxycyclobutyl)-6-(1-((3S,4R)-3-methoxytetrahydro-2H-pyran-4-yl)-1H-pyrrolo[2,3-b]pyridin-3-yl)-8-(methylamino)imidazo[1,2-b]pyridazine-3-carboxamide (I-26)

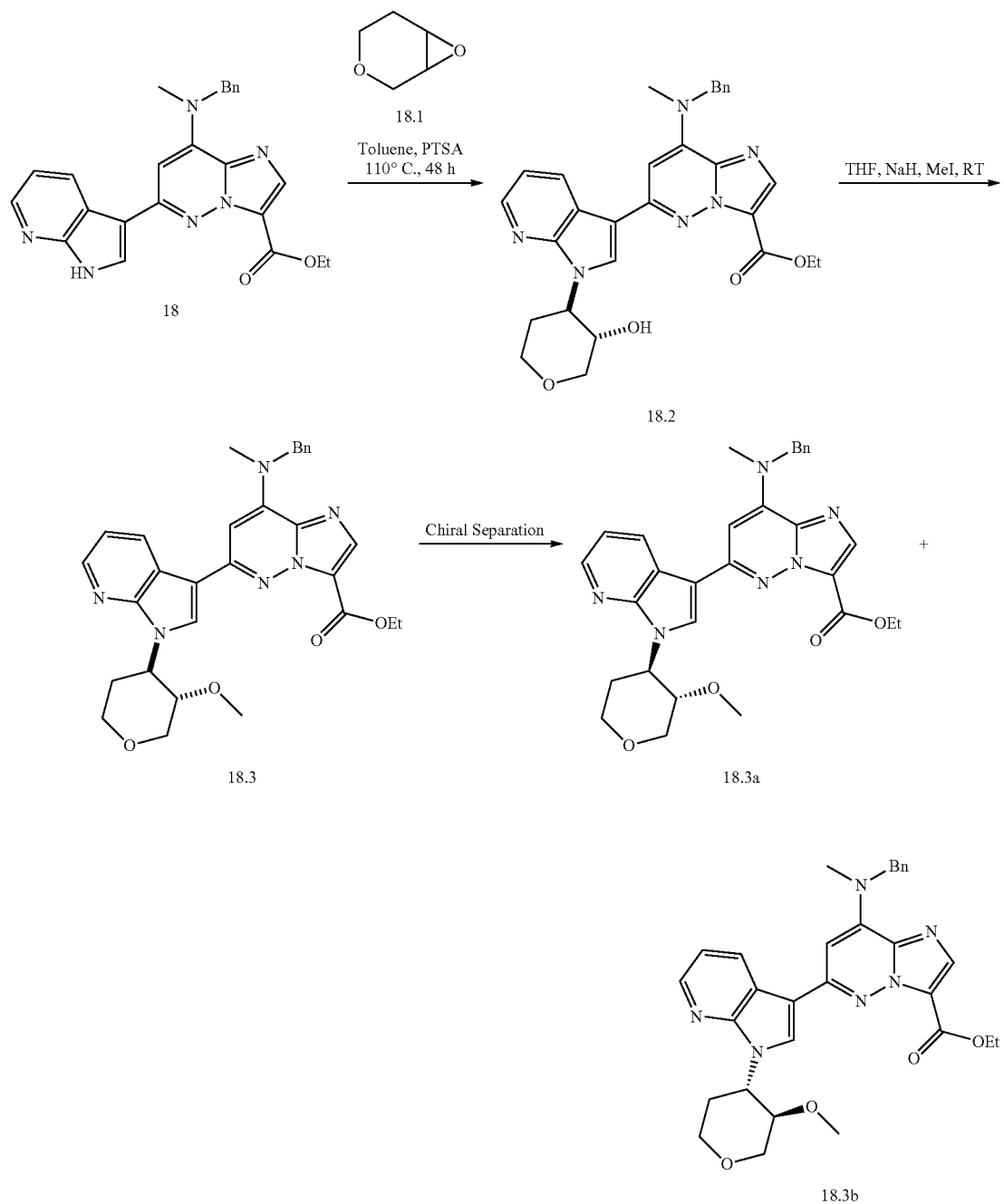

-continued
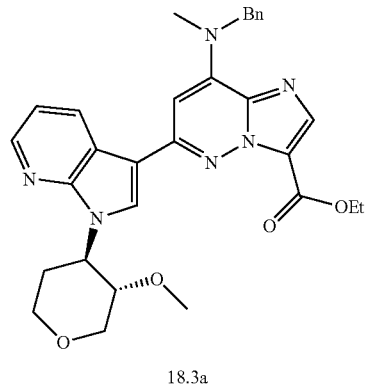# 18.3a
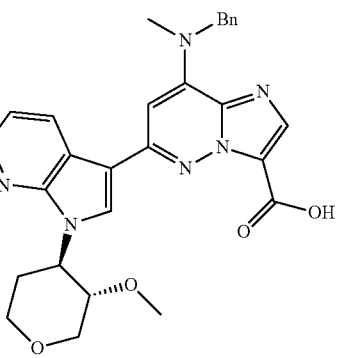# 18.4
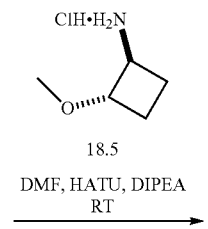# 18.5
MeOH, THF
LiOH, H₂O, 50° C.
DMF, HATU, DIPEA
RT
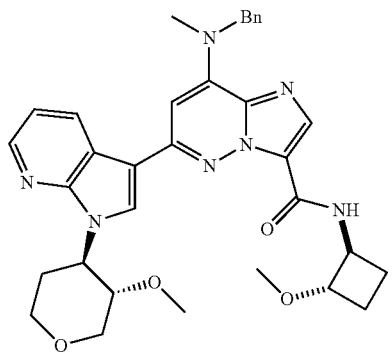# 18.6
Triflic acid
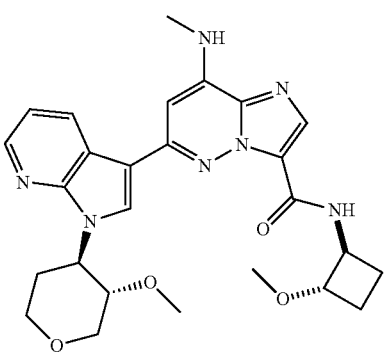# 18.7 (I-2)
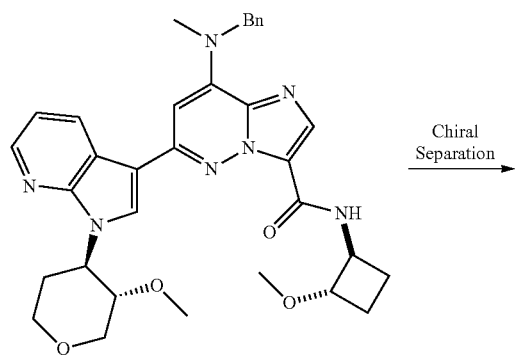# 18.6
Chiral Separation -continued

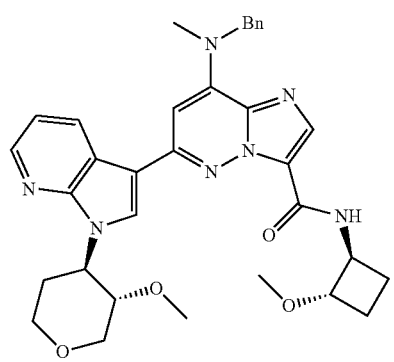

18.6a

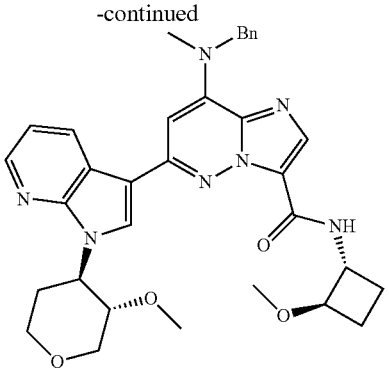

18.6b

Triflic acid, MDC

Triflic acid, MDC

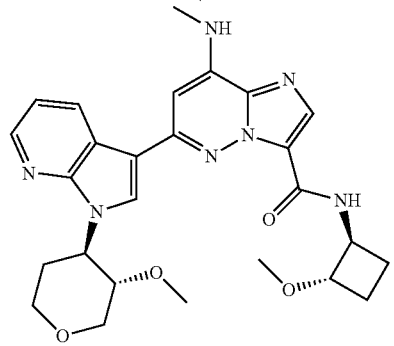

I-25

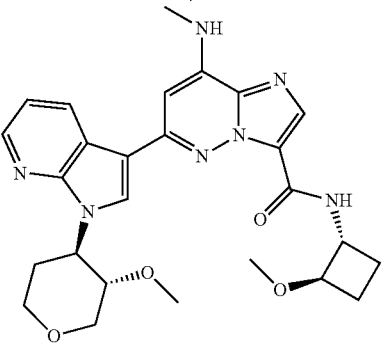

I-26

Synthesis of compound 18. Compound was synthesized as per experimental protocol described above in Example 1 to obtain 18 (Yield: 92.61%). MS (ES): m/z 427.18 [M+H]$^+$.

Synthesis of compound 18.2. To a solution of 18 (1.1 g, 2.58 mmol, 1.0 eq) in toluene (15 mL) was added 18.1 (0.387 g, 3.87 mmol, 1.5 eq) and p-toluene sulfonic acid (0.044 g, 0.25 mmol, 0.1 eq). The reaction mixture was refluxed at 110° C. for 48 h. After completion of the reaction, the reaction mixture was transferred into water and product was extracted with dichloromethane. The organic layer was combined, washed with brine solution, dried over sodium sulphate and concentrated under reduced pressure to obtain a crude material. This was further purified by column chromatography and the compound was eluted in 2.1% methanol in dichloromethane to obtain 18.2 (0.8 g, Yield: 58.90%). MS(ES): m/z 527.24 [M+H]$^+$.

Synthesis of compound 18.3. To a solution of compound 18.2 (0.8 g, 1.52 mmol, 1.0 eq) in dimethylformamide (10 mL), was added sodium hydride (0.072 g, 3.04 mmol, 2.0 eq) at 0° C. and stirred for 20 min. Methyl iodide (0.237 g, 1.67 mmol, 1.1 eq) was added and reaction mixture was stirred at room temperature for 2 h. After completion of the reaction, the reaction mixture was transferred into ice, stirred and extracted with diethyl ether. Organic layer was combined, dried over sodium sulphate and concentrated under reduced pressure to obtain crude material. This was further purified by column chromatography and the compound was eluted in 2.0% methanol in dichloromethane to obtain 18.3 (0.640 g, Yield: 77.92%). MS (ES): m/z 541.25 [M+H]$^+$.

Synthesis of compound 18.3a and 18.3b. Isomers of 18.3 (0.640 g) were separated out using column CHIRALCEL OJ-H (250 mm*4.6 mm, 5 u) and 0.1% DEA in MEOH as co-solvent with flow rate of 4 mL/min to get pure fraction-1 (FR-a) and fraction-2 (FR-b). FR-a was concentrated under reduced pressure at 30° C. to afford pure 18.3a (0.242 g). MS(ES): m/z 541.25 [M+H]$^+$. FR-b was concentrated under reduced pressure at 30° C. to afford pure 18.3b (0.250 g). MS(ES): m/z 541.25 [M+H]$^+$.

Synthesis of compound 18.4. To a solution of 18.3a (0.242 g, 0.44 mmol, 1.0 eq), in tetrahydrofuran:methanol:water (4 mL, 2:1:1) was added lithium hydroxide (0.105 g, 4.4 mmol, 10.0 eq). The reaction was stirred at 50° C. for 16 h. After completion of the reaction, the reaction mixture was concentrated under reduced pressure to obtain a residue. To this was added water and the mixture was acidified with 1N hydrochloric acid to adjust to pH-6-6.5 at 10° C. Product was extracted with dichloromethane. The organic layer was combined, washed with brine solution, dried over sodium sulphate, and concentrated under reduced pressure to obtain crude material. This was further purified by column chromatography and compound was eluted in 2.5% methanol in dichloromethane to obtain pure 18.4 (0.185 g, Yield: 80.63%). MS(ES): m/z 513.22 [M+H]$^+$.

Synthesis of compound 18.6. Compound was synthesized using general procedure C to obtain 18.6 (0.150 g, Yield: 69.77%). MS(ES): m/z 596.29 [M+H]$^+$.

Synthesis of compound 18.7 (I-2). Compound was synthesized using general procedure D to obtain 18.7 (0.025 g, Yield: 73.64%). MS (ES): m/z 506.25 [M+H]$^+$ LCMS purity: 100%, HPLC purity: 98.30%, CHIRAL HPLC: 50.05%, 49.94%, $^1$H NMR (DMSO-d$_6$, 400 MHZ): 9.26-9.24 (d, J=8.8 Hz, 1H), 8.78-8.77 (d, J=7.2 Hz, 1H), 8.49 (bs, 2H), 7.98 (s, 1H), 7.64-7.63 (d, J=4.8 Hz, 1H), 7.27-7.24

(t, J=6.8 Hz, 1H), 6.65 (s, 1H), 5.44 (bs, 1H), 4.47 (bs, 1H), 4.43-4.37 (m, 1H), 4.13-4.04 (m, 3H), 3.84-3.80 (m, 1H), 3.64-3.59 (t, J=11.2 Hz, 1H), 3.22 (s, 3H), 3.13 (s, 3H), 3.02-3.01 (d, J=4.8 Hz, 3H), 2.21-2.16 (m, 1H), 1.98 (bs, 1H), 1.54-1.47 (m, 3H), 1.23 (bs, 1H).

Synthesis of compound 18.6a and 18.6b. Isomers of 18.5 (0.110 g) were separated out using column CHIRALCEL OJ-H (250 mm*4.6 mm, 5 u) and 0.1% DEA in MEOH as co-solvent with flow rate of 4 mL/min to get pure fraction-1 (FR-a) and fraction-2 (FR-b). FR-a was concentrated under reduced pressure at 30° C. to afford pure 18.6b (0.045 g). MS(ES): m/z 596.29 [M+H]$^+$. FR-b was concentrated under reduced pressure at 30° C. to afford pure 18.6b (0.045 g). MS(ES): m/z 596.29 [M+H]$^+$.

Synthesis of compound I-25. Compound was synthesized using general procedure D to obtain I-25 (0.030 g, Yield: 78.55%). MS (ES): m/z 506.37 [M+H]$^+$; LCMS purity: 100%, HPLC purity: 98.22%, CHIRAL HPLC: 96.41%, $^1$H NMR (DMSO-d$_6$, 400 MHz): 9.25-9.22 (d, J=8.8 Hz, 1H), 8.78-8.77 (d, J=7.2 Hz, 1H), 8.49 (bs, 2H), 7.97 (s, 1H), 7.64-7.63 (d, J=4.8 Hz, 1H), 7.27-7.24 (t, J=6.8 Hz, 1H), 6.65 (s, 1H), 5.44 (bs, 1H), 4.47 (bs, 1H), 4.43-4.37 (m, 1H), 4.13-4.04 (m, 3H), 3.84-3.80 (m, 1H), 3.64-3.59 (t, J=11.2 Hz, 1H), 3.22 (s, 3H), 3.13 (s, 3H), 3.02-3.01 (d, J=4.8 Hz, 3H), 2.21-2.16 (m, 1H), 1.98 (bs, 1H), 1.54-1.47 (m, 3H), 1.22 (bs, 1H).

Synthesis of compound I-26. Compound was synthesized using general procedure D to obtain I-26 (0.031 g, Yield: 81.17%). MS (ES): m/z 506.37 [M+H]$^+$; LCMS purity: 100%, HPLC purity: 98.92%, CHIRAL HPLC: 100%, $^1$H NMR (DMSO-d$_6$, 400 MHz): 9.25-9.22 (d, J=8.8 Hz, 1H), 8.78-8.76 (d, J=7.2 Hz, 1H), 8.48 (bs, 2H), 7.97 (s, 1H), 7.64-7.63 (d, J=4.8 Hz, 1H), 7.28-7.24 (t, J=6.4 Hz, 1H), 6.65 (s, 1H), 5.44 (bs, 1H), 4.47 (bs, 1H), 4.43-4.37 (m, 1H), 4.13-4.04 (m, 3H), 3.84-3.80 (m, 1H), 3.64-3.59 (t, J=11.2 Hz, 1H), 3.22 (s, 3H), 3.13 (s, 3H), 3.02-3.01 (d, J=4.8 Hz, 3H), 2.21-2.16 (m, 1H), 1.98 (bs, 1H), 1.54-1.47 (m, 3H), 1.22 (bs, 1H).

Example 18. Synthesis of 6-((3'-fluoro-2-oxo-2H-[1,2'-bipyridin]-3-yl)amino)-N-(2-(methoxy-d3)cyclobutyl)-8-(methylamino)imidazo[1,2-b]pyridazine-3-carboxamide (I-30)

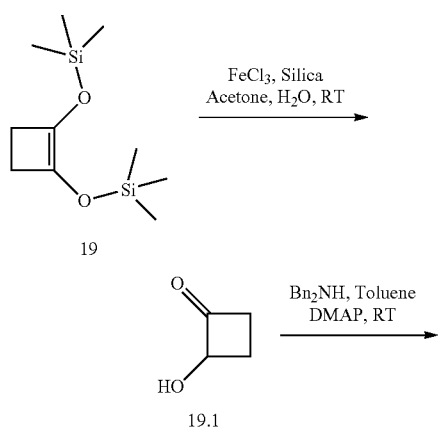

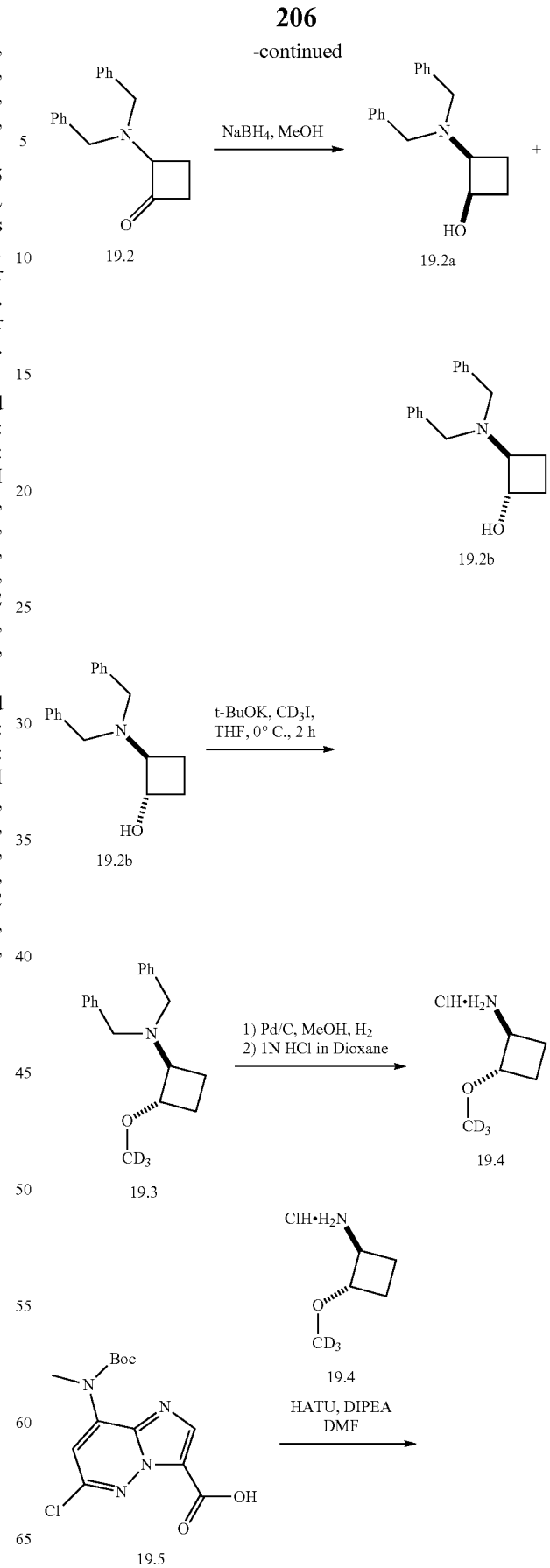

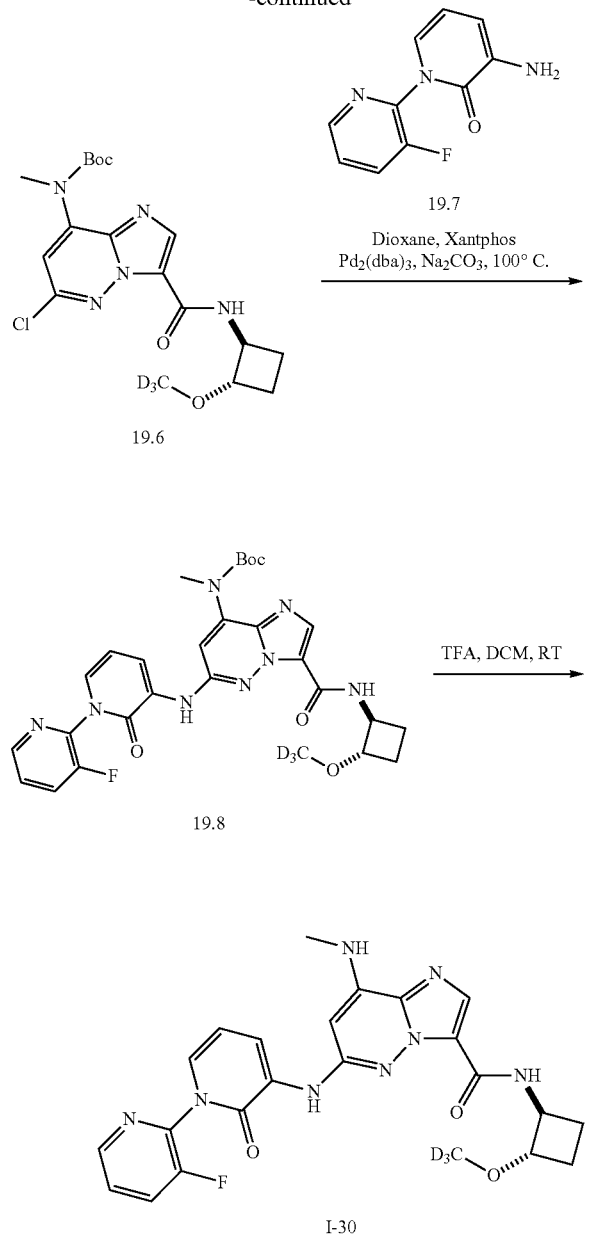

Synthesis of compound 19.1. To a cooled solution of 19 (100 g, 434.78 mmol, 1.0 eq) in acetone (300 mL) and water (15.6 mL) was added catalytic iron (III) chloride on silica gel (500 mg). The reaction mixture at was stirred at room temperature for 2 h. After completion of reaction, reaction mixture was concentrated under reduced pressure to obtain crude material. This was further purified by column chromatography and compound was eluted in 60% ethyl acetate in hexane to obtain pure 19.1 (32 g, Yield: 85.66%). MS (ES): m/z 87.04 [M+H]$^+$.

Synthesis of compound 19.2. To a cooled solution of 19.1 (32 g, 372.09 mmol, 1.0 eq) in toluene (320 mL) was added 4-dimethylaminopyridine (4.53 g, 37.20 mmol, 0.1 eq). Then dibenzylamine (73.30 g, 372.09 mmol, 1.0 eq) was added to the reaction mixture. The reaction mixture was stirred at room temperature for 16 h. After completion of the reaction, the reaction mixture was concentrated under reduced pressure to obtain crude material. This was further purified by column chromatography and the compound was eluted in 5% ethyl acetate in hexane to obtain pure 19.2 (74 g, Yield: 75.02%). MS (ES): m/z 266.15 [M+H]$^+$.

Synthesis of compound 19.2a and 19.2b. To a cooled solution of 19.2 (74 g, 279.24 mmol, 1.0 eq) in methanol (750 mL) was added portionwise sodium borohydride (10.5 g, 279.24 mmol, 1.0 eq) at 0° C. The reaction mixture was stirred at 0° C. for 2 h. After completion of the reaction, the reaction mixture was concentrated under reduced pressure to obtain crude material. This was further purified by column chromatography and compound 19.2a was eluted in 30% ethyl acetate in hexane and 19.2b was eluted in 40% ethyl acetate in hexane to obtain 19.2a (32 g, Yield: 42.92%), and 19.2b (24.7 g, Yield: 33.13%). MS (ES): m/z 268.17 [M+H]$^+$.

Synthesis of compound 19.3. To a cooled solution of 19.2b (0.6 g, 2.24 mmol, 1.0 eq) in tetrahydrofuran (6 mL) was added potassium tert-butoxide (1M in tetrahydrofuran) (2.68 mL, 2.68 mmol, 1.2 eq). The reaction was stirred at 0° C. for 30 min. Then methyl-d$_3$ iodide (0.357 g, 2.46 mmol, 1.1 eq) was added to the reaction mixture at 0° C. and reaction was stirred at 0° C. for 2 h. After completion of reaction, reaction mixture was transferred into water and product was extracted with ethyl acetate. The organic layer was combined, dried over sodium sulphate and concentrated under reduced pressure to obtain crude material. This was further purified by column chromatography and compound was eluted in 30% ethyl acetate in hexane to obtain pure 19.3 (0.4 g, Yield: 62.67%). MS (ES): m/z 285.20 [M+H]$^+$.

Synthesis of compound 19.4. To a solution of 19.3 (0.4 g, 1.40 mmol, 1.0 eq) in methanol (8 mL), 10% palladium on carbon (0.2 g) was added. Hydrogen was purged through reaction mixture for 4 h at room temperature. After completion of the reaction, the reaction mixture was filtered through a celite-bed and washed with methanol. The filtrate was concentrated under reduced pressure to obtain a crude material. To this filtrate was added 1N hydrochloric acid in dioxane (2 mL) and stirred at 0° C. for 1 h. After completion of reaction, reaction mixture was concentrated under reduced pressure to obtain crude material. This was further purified by trituration with n-pentane to obtain pure 19.4 (0.1 g, Yield: 50.56%), MS (ES): 105.13 [M–HCl]$^+$.

Synthesis of compound 19.5. Compound was synthesized as per experimental protocol above in Example 9 to obtain 19.5 (Yield: 79.18%). MS (ES): m/z 327.08 [M+H]$^+$.

Synthesis of compound 19.6. To a solution of 19.5 (0.1 g, 0.30 mmol, 1.0 eq), in N,N-dimethylformamide (1 mL) was added 1-[bis(dimethylamino)methylene]-1H-1,2,3-triazolo[4,5-b]pyridinium 3-oxid hexafluorophosphate (0.228 g, 0.6 mmol, 2.0 eq) and stirred at room temperature for 15 min. To this added diisopropylethylamine (0.15 mL, 0.9 mmol, 3.0 eq) followed by addition of 19.4 (0.042 g, 0.30 mmol, 1.0 eq). The reaction mixture was stirred at room temperature for 5 min. After completion of the reaction, the reaction mixture was transferred into water and product was extracted with ethyl acetate. The organic layer was combined, washed with brine solution, dried over sodium sulphate, and concentrated under reduced pressure to obtain crude material. This was further purified by column chromatography and the compound was eluted in 40% ethyl acetate in hexane to obtain 19.6 (0.220 g, Yield: 74.93%). MS(ES): m/z 413.17 [M+H]$^+$.

Synthesis of compound 19.7. Compound was synthesized as per experimental protocol above in Example 9 to obtain 19.7 (Yield: 49.37%). MS (ES): m/z 206.02 [M+H]$^+$.

Synthesis of compound 19.8. To a solution of 19.6 (0.220 g, 0.53 mmol, 1.0 eq) in 1,4-dioxane (4 mL) was added 19.7

(0.130 g, 0.63 mmol, 1.2 eq), sodium carbonate (0.112 g, 1.06 mmol, 2.0 eq). The reaction mixture was degassed for 10 min under argon atmosphere, then tris(dibenzylideneacetone)dipalladium(0) (0.023 g, 0.026 mmol, 0.05 eq) and 4,5-Bis(diphenylphosphino)-9,9-dimethylxanthene (0.030 g, 0.053 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 19.8. (0.150 g, Yield: 48.40%). MS(ES): m/z 582.26 [M+H]$^+$.

Synthesis of compound I-30. The compound 19.6 (0.040 g, 0.068 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated bicarbonate solution and product was extracted with dichloromethane. The organic layer was combined and dried over sodium sulphate and concentrated under reduced pressure to obtain crude material. This was further purified by trituration with diethyl ether to obtain pure I-30 (0.025 g, Yield: 75.50%). MS(ES): m/z 482.56 [M+H]$^+$ LCMS purity: 97.46%, HPLC purity: 50.17%, CHIRAL HPLC: 50.17%, 49.46%; $^1$H NMR (DMSO-d$_6$, 400 MHz): 8.86-8.83 (d, J=8.8 Hz, 1H), 8.71 (s, 1H), 8.51 (bs, 1H), 8.15-8.13 (d, J=7.2 Hz, 1H), 8.09-8.04 (t, J=8.8 Hz, 1H), 7.87 (s, 1H), 7.72 (bs, 1H), 7.53 (bs, 1H), 7.44-7.42 (d, J=6.8 Hz, 1H), 6.48-6.44 (t, J=7.2 Hz, 1H), 6.36 (s, 1H), 4.34 (bs, 1H), 3.78-3.76 (m, 2H), 2.88-2.86 (d, J=4 Hz, 3H), 2.12-2.05 (m, 1H), 1.23 (bs, 2H).

Example 19. Synthesis of 6-((3'-fluoro-2-oxo-2H-[1,2'-bipyridin]-3-yl)amino)-N-((1R,2R)-2-(methoxy-d$_3$)cyclobutyl)-8-(methylamino)imidazo[1,2-b]pyridazine-3-carboxamide (I-28), 6-((3'-fluoro-2-oxo-2H-[1,2'-bipyridin]-3-yl)amino)-N-((1S,2S)-2-(methoxy-d3)cyclobutyl)-8-(methylamino)imidazo[1,2-b]pyridazine-3-carboxamide (I-29)

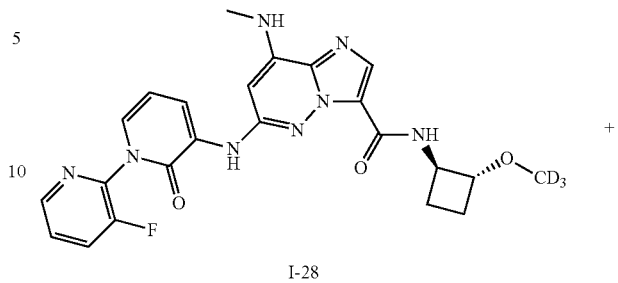

Isolation of compounds I-28 and I-29 from mixture of trans diasteriomers I-30. Isomers of I-30 (0.090 g) were separated on a Shimadzu LC-20AP and UV detector. The column used was CHIRALCEL OX-H (250*21.0) mm, 5 micron, column flow was 18.0 ml/min. Mobile phase were used (A) 0.1% diethylamine in n-Hexane and (B) 0.1% Diethylamine in Propan-2-ol:Acetonitrile (70:30). The UV spectra were recorded at 275 nm Lambdamax. Isocratic ratio was, as described below.

| Time (min) | % A | % B |
|---|---|---|
| 0.01 | 50 | 50 |
| 28 | 50 | 50 | to get pure fraction-1 (FR-a) and fraction-2 (FR-b).

FR-a was concentrated under reduced pressure at 30° C. to afford pure I-28 (0.030 g). MS(ES): m/z 482.72 [M+H]$^+$, LCMS purity: 100%, HPLC purity: 97.29%, CHIRAL HPLC purity: 99.50%, $^1$H NMR (DMSO-d$_6$, 400 MHZ): 8.85-8.83 (d, J=8.8 Hz, 1H), 8.70 (s, 1H), 8.51-8.50 (d, J=4.4 Hz, 1H), 8.14-8.13 (d, J=7.2 Hz, 1H), 8.08-8.04 (t, J=8.4 Hz, 1H), 7.87 (s, 1H), 7.74-7.70 (m, 1H), 7.52-7.51 (t, J=4.8 Hz, 1H), 7.43-7.42 (d, J=5.6 Hz, 1H), 6.48-6.44 (t, J=7.2 Hz, 1H), 6.36 (s, 1H), 4.36-4.32 (m, 1H), 3.80-3.74 (m, 1H), 2.86-2.85 (d, J=4.4 Hz, 3H), 2.14-2.03 (m, 2H), 1.17-1.13 (m, 1H), 1.04-1.02 (d, J=6.4 Hz, 1H).

FR-b was concentrated under reduced pressure at 30° C. to afford pure I-29 (0.030 g). MS(ES): m/z 482.67 [M+H]$^+$, LCMS purity: 100%, HPLC purity: 98.53%, CHIRAL HPLC purity: 96.77%, $^1$H NMR (DMSO-d$_6$, 400 MHz): 8.85-8.83 (d, J=8.8 Hz, 1H), 8.70 (s, 1H), 8.51-8.50 (d, J=4.4 Hz, 1H), 8.15-8.13 (d, J=7.2 Hz, 1H), 8.08-8.04 (t, J=8.4 Hz, 1H), 7.87 (s, 1H), 7.74-7.70 (m, 1H), 7.52-7.51 (t, J=4.8 Hz, 1H), 7.43-7.42 (d, J=5.6 Hz, 1H), 6.48-6.44 (t, J=7.2 Hz, 1H), 6.36 (s, 1H), 4.36-4.32 (m, 1H), 3.80-3.74 (m, 1H), 2.86-2.85 (d, J=4.4 Hz, 3H), 1.04-1.02 (d, J=6 Hz, 4H).

Example 20: 6-((3'-fluoro-2-oxo-2H-[1,2'-bipyridin]-3-yl)amino)-N-((1S,2S)-2-methoxycyclobutyl)-8-(methylamino)imidazo[1,2-b]pyridazine-3-carboxamide (I-33), 6-((3'-fluoro-2-oxo-2H-[1,2'-bipyridin]-3-yl)amino)-N-((1R,2R)-2-methoxycyclobutyl)-8-(methylamino)imidazo[1,2-b]pyridazine-3-carboxamide (I-34)

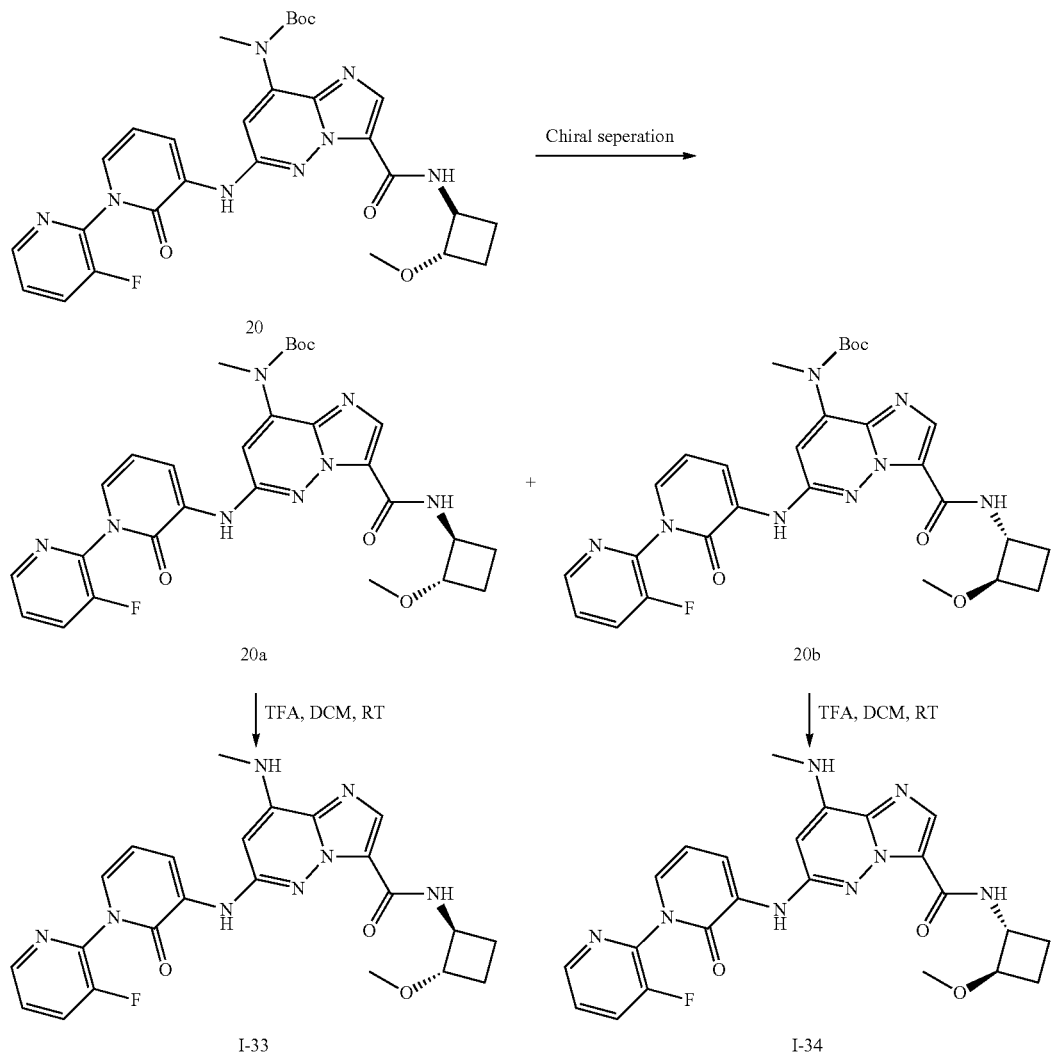

Synthesis of compound 20. Compound was synthesized as per experimental protocol of I-17 to obtain 20. (Yield: 64.77%), MS (ES): 579.24 [M+H]$^+$ Synthesis of compound 20a and 20b. Isomers of 20 (0.110 g) were separated out using column CHIRALPAK AD-H (250 mm*4.6 mm, 5 u) and 0.1% Diethyl amine in Isopropyl alcohol as co-solvent with flow rate of 4 mL/min. to get pure fraction-1 (FR-a) and fraction-2 (FR-b). FR-a was concentrated under reduced pressure at 30° C. to afford pure 20a. (0.040 g). MS(ES): m/z 579.24 [M+H]$^+$. FR-b was concentrated under reduced pressure at 30° C. to afford pure 20b. (0.041 g). MS(ES): m/z 579.24 [M+H]$^+$ Synthesis of compound I-33. The compound 20a (0.040 g, 0.069 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-33 (0.025 g, Yield: 75.58%). MS(ES): m/z 479.77 [M+H]$^+$, LCMS purity: 100%, HPLC purity: 100%, CHIRAL HPLC purity: 100%, $^1$H NMR (DMSO-d$_6$, 400 MHZ): 8.85-8.83 (d, J=8.4 Hz, 1H), 8.71 (s, 1H), 8.51-8.50 (d, J=4.4 Hz, 1H), 8.15-8.13 (d, J=6.4 Hz, 1H), 8.08-8.04 (t, J=9.2 Hz, 1H), 7.87 (s, 1H), 7.73-7.71 (m, 1H), 7.53-7.52 (d, J=5.2 Hz, 1H), 7.44-7.42 (d, J=6.8 Hz, 1H), 6.48-6.44 (t, J=7.2 Hz, 1H), 6.36 (s, 1H), 4.36-4.32 (t, J=8.4 Hz, 1H), 3.78-3.76 (d, J=7.2 Hz, 1H), 3.20 (s, 3H), 2.86-2.85 (d, J=4.4 Hz, 3H), 2.12-2.05 (m, 3H), 0.85 (bs, 1H).

Synthesis of compound I-34. The compound 20b (0.041 g, 0.070 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-34 (0.025 g, Yield: 73.7%). MS(ES): m/z 479.87 [M+H]$^+$, LCMS purity: 100%, HPLC purity: 99.44%, CHIRAL HPLC purity: 100%, $^1$H NMR (DMSO-d$_6$, 400 MHZ): 8.85-8.83 (d, J=8.4 Hz, 1H), 8.71 (s, 1H), 8.51-8.50 (d, J=4.4 Hz, 1H), 8.15-8.13 (d, J=6.4 Hz, 1H), 8.08-8.04 (t, J=9.2 Hz, 1H), 7.87 (s, 1H), 7.74-7.71 (m, 1H), 7.53-7.52 (d, J=5.2 Hz, 1H), 7.43-7.42 (d, J=6.8 Hz, 1H), 6.48-6.44 (t, J=7.2 Hz, 1H), 6.36 (s, 1H), 4.36-4.32 (t, J=8.4 Hz, 1H), 3.78-3.74 (m, 1H), 3.20 (s, 3H), 2.85-2.84 (d, J=4.4 Hz, 3H), 2.12-2.05 (m, 3H), 0.85 (bs, 1H).

Example 21: N-((1S,2S)-2-methoxycyclobutyl)-8-(methylamino)-6-((2-oxo-2H-[1,2'-bipyridin]-3-yl)amino)imidazo[1,2-b]pyridazine-3-carboxamide (I-35), N-((1R,2R)-2-methoxycyclobutyl)-8-(methylamino)-6-((2-oxo-2H-[1,2'-bipyridin]-3-yl)amino)imidazo[1,2-b]pyridazine-3-carboxamide (I-36)

Synthesis of compound 21. Compound was synthesized as per experimental protocol of I-18 to obtain 21. (Yield: 71.02%), MS (ES): 561.25 [M+H]$^+$ Synthesis of compound 21a and 21b. Isomers of 21 (0.120 g) were separated out using column CHIRALCEL OJ-H (250 mm*4.6 mm, 5 u) and 0.1% DEA in MEOH:ACN (50:50) as co-solvent with flow rate of 4 mL/min. to get pure fraction-1 (FR-a) and fraction-2 (FR-b). FR-a was concentrated under reduced pressure at 30° C. to afford pure 21a. (0.042 g). MS(ES): m/z 561.25 [M+H]$^+$. FR-b was concentrated under reduced pressure at 30° C. to afford pure 21b. (0.041 g). MS(ES): m/z 561.25 [M+H]$^+$ Synthesis of compound I-35. The compound 21a (0.042 g, 0.074 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to

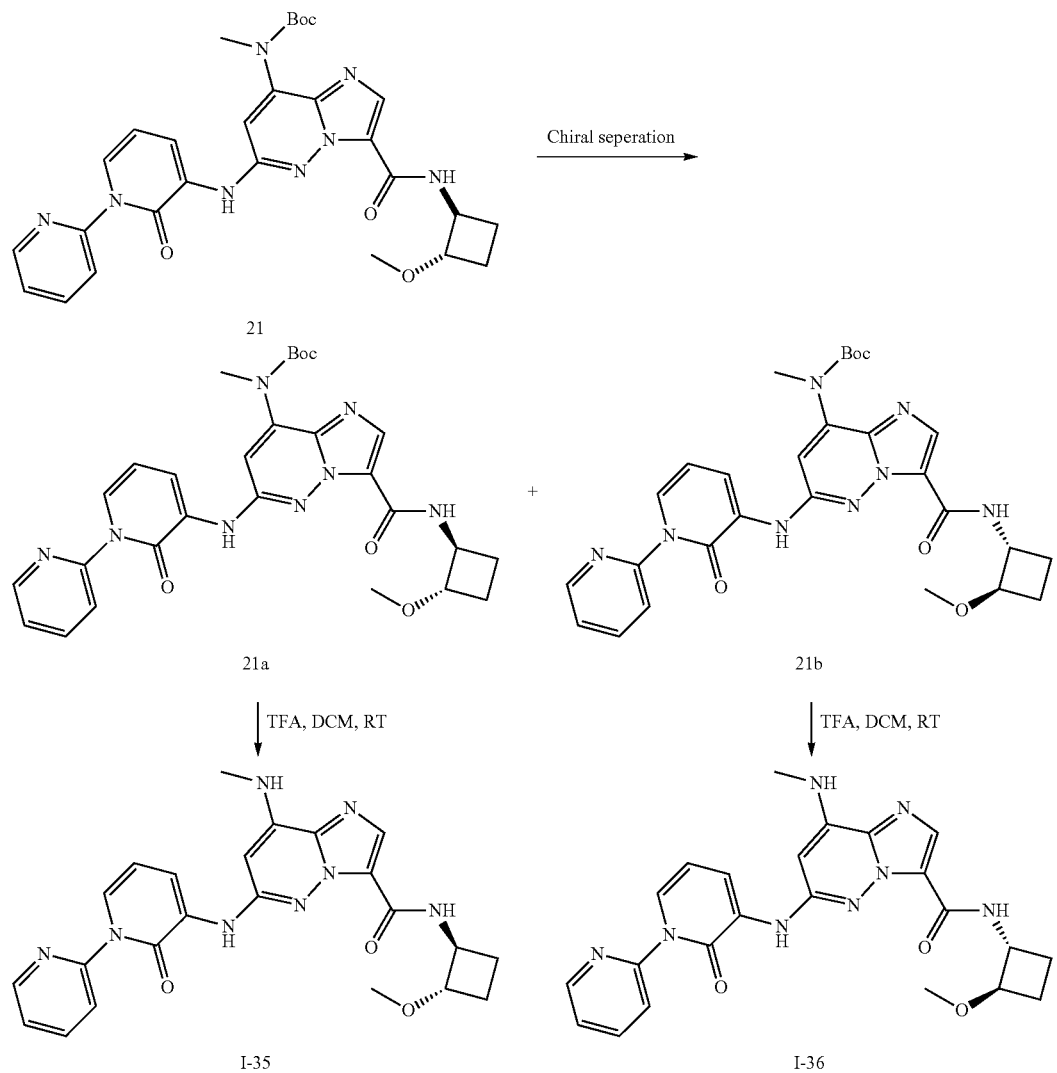

obtain pure I-35 (0.025 g, Yield: 72.46%). MS(ES): m/z 461.36 [M+H]+, LCMS purity: 100%, HPLC purity: 97.51%, CHIRAL HPLC purity: 100%, ¹H NMR (DMSO-d₆, 400 MHZ): 8.86-8.84 (d, J=8.8 Hz, 1H), 8.69 (s, 1H), 8.64-8.63 (d, J=3.6 Hz, 1H), 8.11-8.09 (d, J=7.6 Hz, 1H), 8.05-8.02 (t, J=7.6 Hz, 1H), 7.87-7.86 (d, J=4 Hz, 1H), 7.84 (s, 1H), 7.58-7.52 (m, 3H), 6.45-6.42 (t, J=7.2 Hz, 1H), 6.38 (s, 1H), 4.37-4.33 (t, J=8.4 Hz, 1H), 3.79-3.74 (m, 1H), 3.20 (s, 3H), 2.86-2.85 (d, J=4.8 Hz, 3H), 2.14-2.03 (m, 3H), 1.49-1.42 (m, 1H).

Synthesis of compound I-36. The compound 21b (0.041 g, 0.073 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-36 (0.025 g, Yield: 74.23%). MS(ES): m/z 461.77 [M+H]+, LCMS purity: 100%, HPLC purity: 100%, CHIRAL HPLC purity: 100%, ¹H NMR (DMSO-d₆, 400 MHZ): 8.86-8.84 (d, J=8.8 Hz, 1H), 8.69 (s, 1H), 8.65-8.64 (d, J=3.6 Hz, 1H), 8.11-8.09 (d, J=7.6 Hz, 1H), 8.05-8.02 (t, J=7.6 Hz, 1H), 7.87-7.86 (d, J=4 Hz, 1H), 7.84 (s, 1H), 7.58-7.52 (m, 3H), 6.46-6.42 (t, J=7.2 Hz, 1H), 6.38 (s, 1H), 4.37-4.33 (t, J=8.4 Hz, 1H), 3.79-3.74 (m, 1H), 3.20 (s, 3H), 2.86-2.85 (d, J=4.8 Hz, 3H), 2.14-2.03 (m, 3H), 1.49-1.42 (m, 1H).

Example 22: N-((1S,2S)-2-methoxycyclobutyl)-6-46'-methyl-2-oxo-2H-[1,3'-bipyridin]-3-yl)amino)-8-(methylamino)imidazo[1,2-b]pyridazine-3-carboxamide (I-37), N-((1R,2R)-2-methoxycyclobutyl)-6-46'-methyl-2-oxo-2H-[1,3'-bipyridin]-3-yl)amino)-8-(methylamino)imidazo[1,2-b]pyridazine-3-carboxamide (I-38)

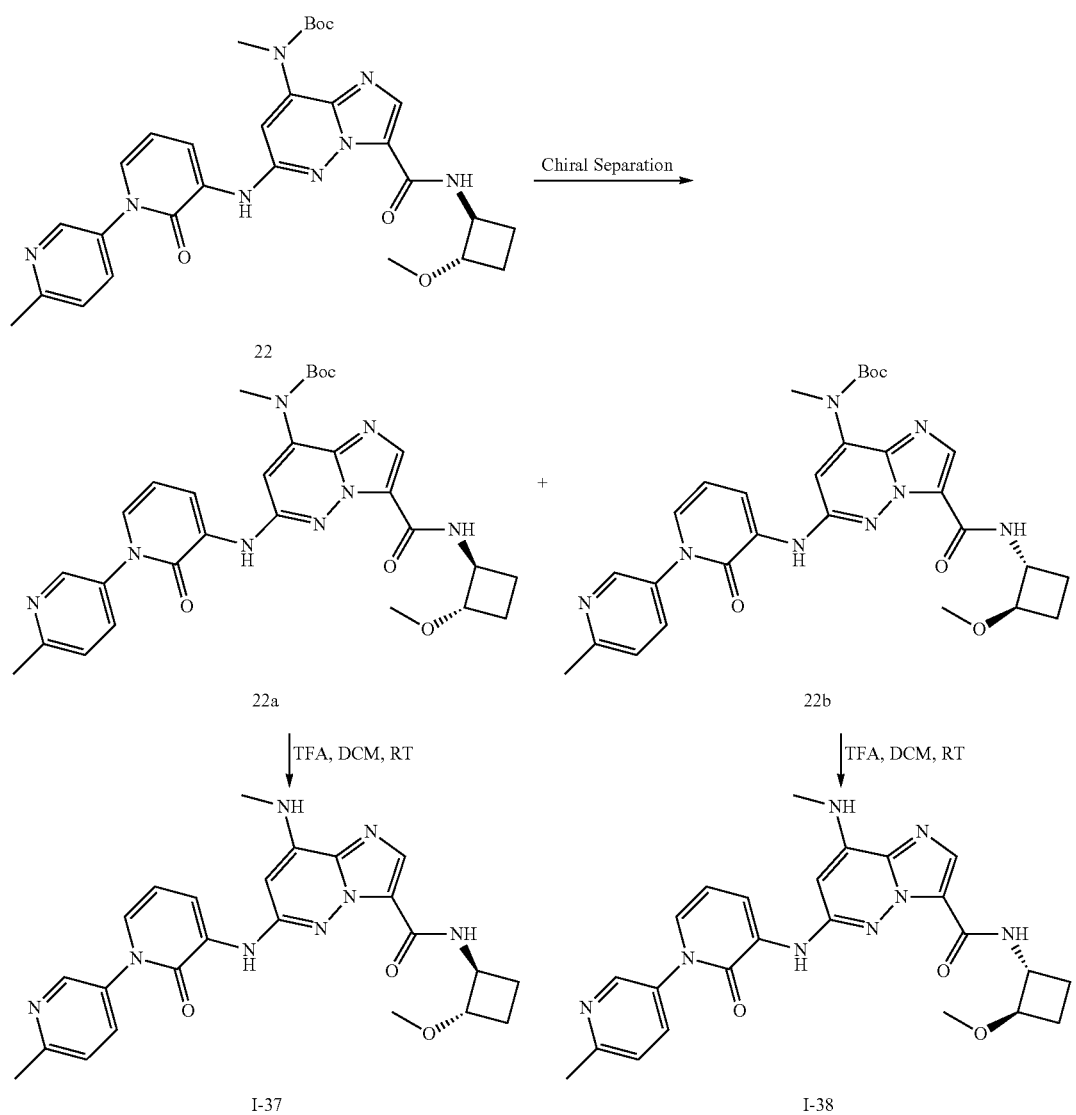

Synthesis of compound 22. Compound was synthesized as per experimental protocol of I-19 to obtain 22. (Yield: 65.21%), MS (ES): 575.27 [M+H]+

Synthesis of compound 22a and 22b. Isomers of 22 (0.102 g) were separated out using column CHIRALCEL OJ-H (250 mm*4.6 mm, 5 u) and 0.1% DEA in MEOH:ACN (50:50) as co-solvent with flow rate of 4 mL/min. to get pure fraction-1 (FR-a) and fraction-2 (FR-b). FR-a was concentrated under reduced pressure at 30° C. to afford pure 22a. (0.040 g). MS(ES): m/z 575.27 [M+H]$^+$. FR-b was concentrated under reduced pressure at 30° C. to afford pure 22b. (0.043 g). MS(ES): m/z 575.27 [M+H]$^+$ Synthesis of compound I-37. The compound 22a (0.040 g, 0.069 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-37 (0.026 g, Yield: 78.71%). MS(ES): m/z 475.56 [M+H]$^+$, LCMS purity: 100%, HPLC purity: 99.80%, CHIRAL HPLC purity: 100%, $^1$H NMR (DMSO-d$_6$, 400 MHZ): 8.84-8.82 (d, J=9.2 Hz, 1H), 8.67 (s, 1H), 8.58-8.57 (d, J=2.4 Hz, 1H), 8.12-8.11 (d, J=6 Hz, 1H), 7.87 (s, 1H), 7.86-7.85 (d, J=2 Hz, 1H), 7.52-7.51 (d, J=4.8 Hz, 1H), 7.46-7.44 (d, J=8.4 Hz, 1H), 7.38-7.36 (t, J=5.6 Hz, 1H), 6.43-6.41 (t, J=6.8 Hz, 1H), 6.39 (s, 1H), 4.37-4.33 (m, 1H), 3.79-3.77 (m, 1H), 3.21 (s, 3H), 2.85-2.84 (d, J=4.4 Hz, 3H), 2.56 (s, 3H), 2.13-2.09 (m, 3H), 1.49-1.44 (m, 1H).

Synthesis of compound I-38. The compound 22b (0.040 g, 0.074 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-38 (0.027 g, Yield: 76.04%). MS(ES): m/z 475.92 [M+H]$^+$, LCMS purity: 100%, HPLC purity: 99.81%, CHIRAL HPLC purity: 100%, $^1$H NMR (DMSO-d$_6$, 400 MHZ): 8.84-8.82 (d, J=8.8 Hz, 1H), 8.67 (s, 1H), 8.57 (s, 1H), 8.12-8.11 (d, J=6.8 Hz, 1H), 7.87 (s, 1H), 7.86 (s, 1H), 7.52-7.51 (d, J=4.8 Hz, 1H), 7.46-7.44 (d, J=8.4 Hz, 1H), 7.38-7.36 (d, J=6.8 Hz, 1H), 6.43-6.41 (t, J=7.2 Hz, 1H), 6.39 (s, 1H), 4.37-4.33 (t, J=8.4 Hz, 1H), 3.79-3.74 (m, 1H), 3.21 (s, 3H), 2.86-2.85 (d, J=4.8 Hz, 3H), 2.56 (s, 3H), 2.13-2.08 (m, 3H), 1.49-1.44 (m, 1H).

Example 23 N-((1S,2S)-2-methoxycyclobutyl)-8-(methylamino)-6-((2-oxo-1-(tetrahydro-2H-pyran-4-yl)-1,2-dihydropyridin-3-yl)amino)imidazo[1,2-b]pyridazine-3-carboxamide (I-39), N-((1R,2R)-2-methoxycyclobutyl)-8-(methylamino)-6-((2-oxo-1-(tetrahydro-2H-pyran-4-yl)-1,2-dihydropyridin-3-yl)amino)imidazo[1,2-b]pyridazine-3-carboxamide (I-40)

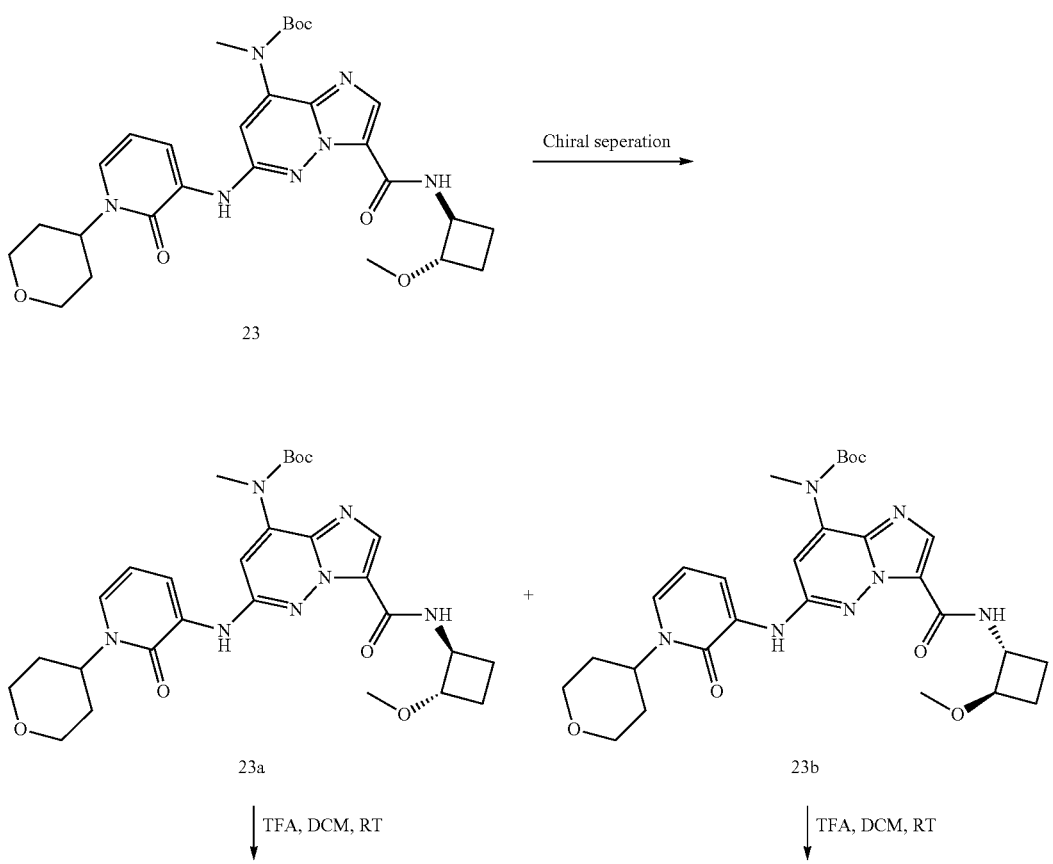

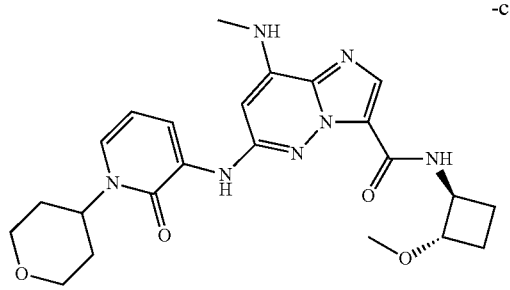

I-39

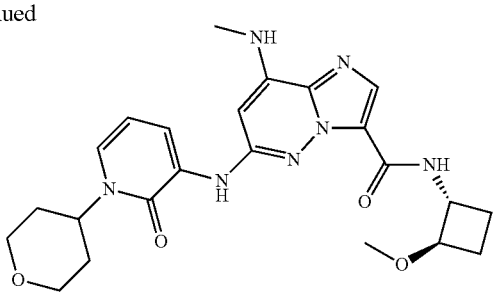

I-40

Synthesis of compound 23. Compound was synthesized as per experimental protocol of I-20 to obtain 23. (Yield: 61.89%), MS (ES): 568.28 [M+H]+

Synthesis of compound 23a and 23b. Isomers of 23 (0.125 g) were separated out using column CHIRALCEL OJ-H (250 mm*4.6 mm, 5 u) and 0.1% DEA in MEOH:ACN (50:50) as co-solvent with flow rate of 4 mL/min. to get pure fraction-1 (FR-a) and fraction-2 (FR-b). FR-a was concentrated under reduced pressure at 30° C. to afford pure 23a. (0.055 g). MS(ES): m/z 568.28 [M+H]+. FR-b was concentrated under reduced pressure at 30° C. to afford pure 23b. (0.052 g). MS(ES): m/z 568.28 [M+H]+

Synthesis of compound I-39. The compound 23a (0.055 g, 0.096 mmol, 1.0 eq) was dissolved in dichloromethane (1 mL) and trifluoroacetic acid (0.25 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-39 (0.030 g, Yield: 66.23%). MS(ES): m/z 468.82 [M+H]+, LCMS purity: 100%, HPLC purity: 98.70%, CHIRAL HPLC purity: 99.16%, $^1$H NMR (DMSO-$d_6$, 400 MHZ): 8.83-8.80 (d, J=9.2 Hz, 1H), 8.54 (s, 1H), 7.98-7.96 (d, J=6.4 Hz, 1H), 7.85 (s, 1H), 7.50-7.45 (m, 2H), 6.36-6.32 (t, J=7.2 Hz, 1H), 6.31 (s, 1H), 5.76 (s, 1H), 5.03 (bs, 1H), 4.35-4.31 (m, 1H), 3.99 (bs, 2H), 3.76-3.70 (m, 1H), 3.53-3.47 (t, J=12 Hz, 2H), 3.18 (s, 3H), 2.86-2.85 (d, J=4.8 Hz, 3H), 2.13-2.03 (m, 1H), 1.97-1.92 (m, 2H), 1.76 (bs, 1H), 1.73 (bs, 1H), 1.55-1.50 (m, 1H), 1.48-1.43 (m, 1H).

Synthesis of compound I-40. The compound 23b (0.052 g, 0.094 mmol, 1.0 eq) was dissolved in dichloromethane (1 mL) and trifluoroacetic acid (0.25 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-40 (0.028 g, Yield: 63.53%). MS(ES): m/z 468.77 [M+H]+, LCMS purity: 100%, HPLC purity: 98.34%, CHIRAL HPLC purity: 99.05%, $^1$H NMR (DMSO-$d_6$, 400 MHZ): 8.83-8.81 (d, J=9.2 Hz, 1H), 8.55 (s, 1H), 7.98-7.96 (d, J=6.4 Hz, 1H), 7.85 (s, 1H), 7.50-7.45 (m, 2H), 6.36-6.32 (t, J=7.2 Hz, 1H), 6.31 (s, 1H), 5.76 (s, 1H), 5.03 (bs, 1H), 4.35-4.28 (m, 1H), 3.99 (bs, 2H), 3.76-3.70 (m, 1H), 3.53-3.47 (t, J=12 Hz, 2H), 3.18 (s, 3H), 2.86-2.85 (d, J=4.8 Hz, 3H), 2.13-2.03 (m, 1H), 1.97-1.92 (m, 2H), 1.76 (bs, 1H), 1.73 (bs, 1H), 1.55-1.50 (m, 1H), 1.48-1.43 (m, 1H).

Example 24: N-((1S,2S)-2-methoxycyclobutyl)-6-((1-((1r,4S)-4-methoxycyclohexyl)-2-oxo-1,2-dihydropyridin-3-yl)amino)-8-(methylamino)imidazo[1,2-b]pyridazine-3-carboxamide (I-41)

N-((1R,2R)-2-methoxycyclobutyl)-6-((1-((1r,4R)-4-methoxycyclohexyl)-2-oxo-1,2-dihydropyridin-3-yl)amino)-8-(methylamino)imidazo[1,2-b]pyridazine-3-carboxamide (I-42)

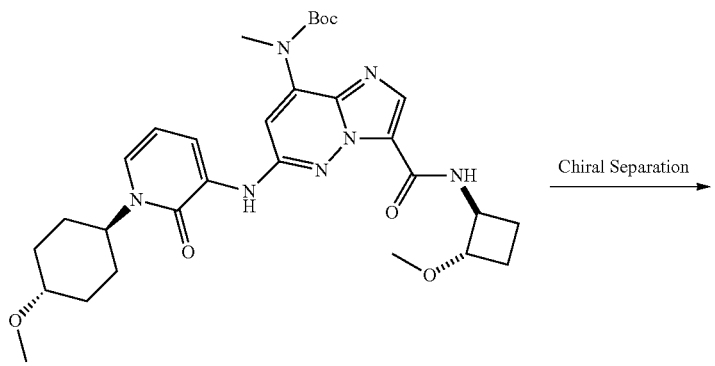

24

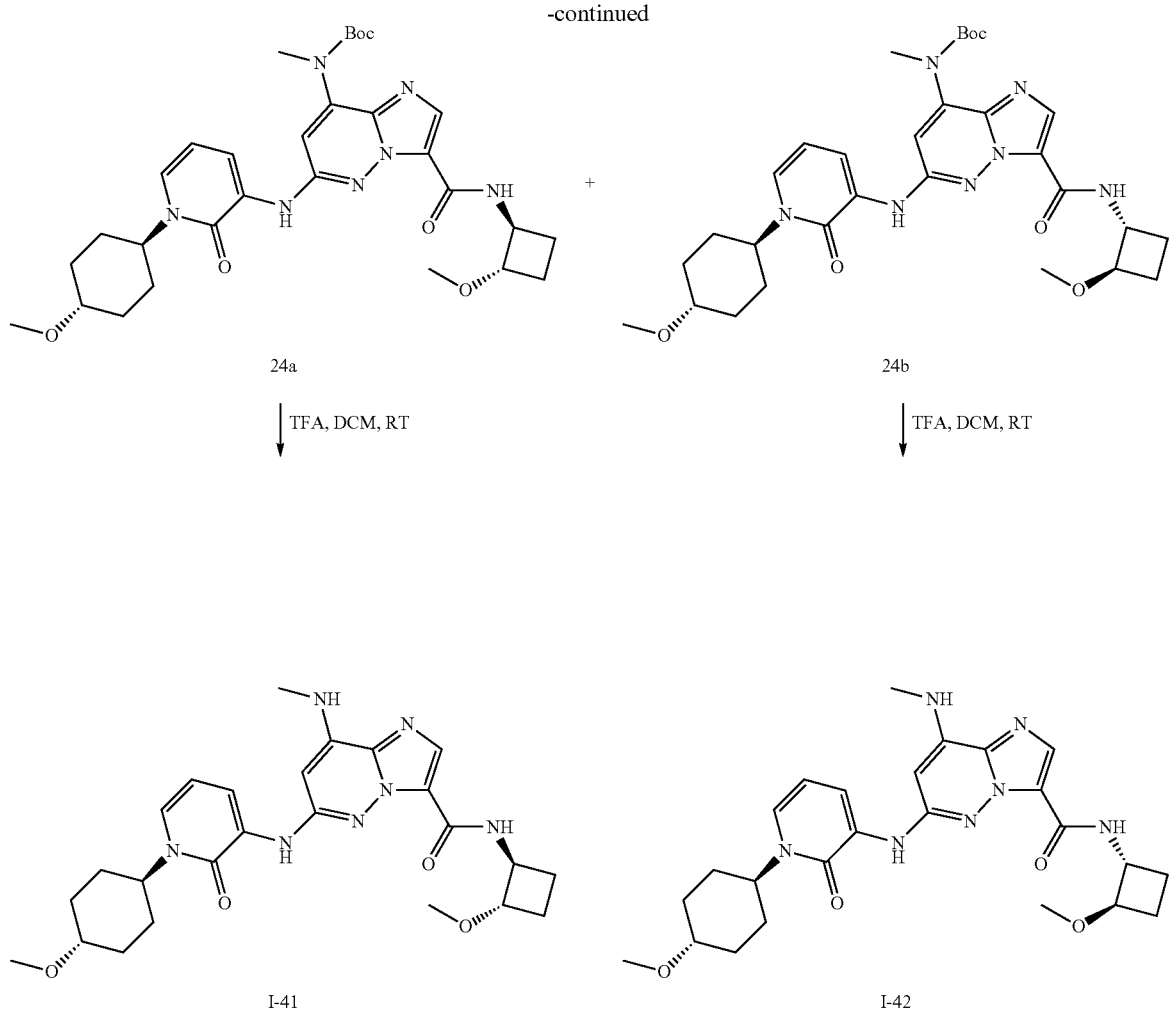

Synthesis of compound 24. Compound was synthesized as per experimental protocol of I-21 to obtain 24. (Yield: 60.16%), MS (ES): 596.32 [M+H]$^+$ Synthesis of compound 24a and 24b. Isomers of 24 (0.110 g) were separated out using column CHIRALPAK AD-H (250 mm*4.6 mm, 5 u) and 0.1% DEA in IPA:MEOH (50:50) as co-solvent with flow rate of 4 mL/min. to get pure fraction-1 (FR-a) and fraction-2 (FR-b). FR-a was concentrated under reduced pressure at 30° C. to afford pure 24a. (0.048 g). MS(ES): m/z 596.32 [M+H]$^+$. FR-b was concentrated under reduced pressure at 30° C. to afford pure 24b. (0.047 g). MS(ES): m/z 596.32 [M+H]$^+$.

Synthesis of compound I-41. The compound 24a (0.048 g, 0.080 mmol, 1.0 eq) was dissolved in dichloromethane (1 mL) and trifluoroacetic acid (0.25 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-41 (0.029 g, Yield: 72.62%). MS(ES): m/z 496.97 [M+H]$^+$, LCMS purity: 95.00%, HPLC purity: 96.95%, CHIRAL HPLC purity: 98.71%, $^1$H NMR (DMSO-d$_6$, 400 MHZ): 8.83-8.81 (d, J=8.8 Hz, 1H), 8.52 (s, 1H), 7.96-7.94 (d, J=6.8 Hz, 1H), 7.85 (s, 1H), 7.49-7.48 (d, J=4.8 Hz, 1H), 7.41-7.40 (d, J=6.8 Hz, 1H), 6.35 (s, 1H), 6.33-6.29 (t, J=7.2 Hz, 1H), 4.79 (bs, 1H), 4.34-4.30 (m, 1H), 3.74-3.70 (m, 1H), 3.27 (s, 3H), 3.18 (s, 3H), 2.86-2.85 (d, J=4.4 Hz, 3H), 2.15-2.12 (m, 3H), 2.08-2.02 (m, 2H), 1.80 (bs, 4H), 1.55-1.50 (t, J=9.2 Hz, 1H), 1.44-1.40 (m, 1H), 1.22 (bs, 2H).

Synthesis of compound I-42. The compound 24b (0.047 g, 0.078 mmol, 1.0 eq) was dissolved in dichloromethane (1 mL) and trifluoroacetic acid (0.25 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-42 (0.027 g, Yield: 69.04%). MS(ES): m/z 496.82 [M+H]$^+$, LCMS purity: 100%, HPLC purity: 100%, CHIRAL HPLC purity: 100%, $^1$H NMR (DMSO-d$_6$, 400 MHZ): 8.83-8.80 (d, J=8.8 Hz, 1H), 8.52 (s, 1H), 7.95-7.94 (d, J=6.8 Hz, 1H), 7.84 (s, 1H), 7.49-7.48 (d, J=4.8 Hz, 1H), 7.41-7.39 (d, J=6.8 Hz, 1H), 6.34 (s, 1H), 6.32-6.29 (t, J=7.2 Hz, 1H), 4.79 (bs, 1H), 4.34-4.28 (m, 1H), 3.75-3.69 (m, 1H), 3.27 (s, 3H), 3.18 (s, 3H), 2.86-2.85 (d, J=4.4 Hz, 3H), 2.15-2.12 (m, 3H), 2.08-2.02 (m, 2H), 1.79 (bs, 4H), 1.55-1.50 (t, J=9.2 Hz, 1H), 1.44-1.40 (m, 1H), 1.22 (bs, 2H).

Example 25: 6-((1-((1R,5S,6r)-3-oxabicyclo[3.1.0]hexan-6-yl)-2-oxo-1,2-dihydropyridin-3-yl)amino)-N-((1S,2S)-2-methoxycyclobutyl)-8-(methylamino)imidazo[1,2-b]pyridazine-3-carboxamide (I-43), 6-((1-((1R,5S,6r)-3-oxabicyclo[3.1.0]hexan-6-yl)-2-oxo-1,2-dihydropyridin-3-yl)amino)-N-((1R,2R)-2-methoxycyclobutyl)-8-(methylamino)imidazo[1,2-b]pyridazine-3-carboxamide (I-44)

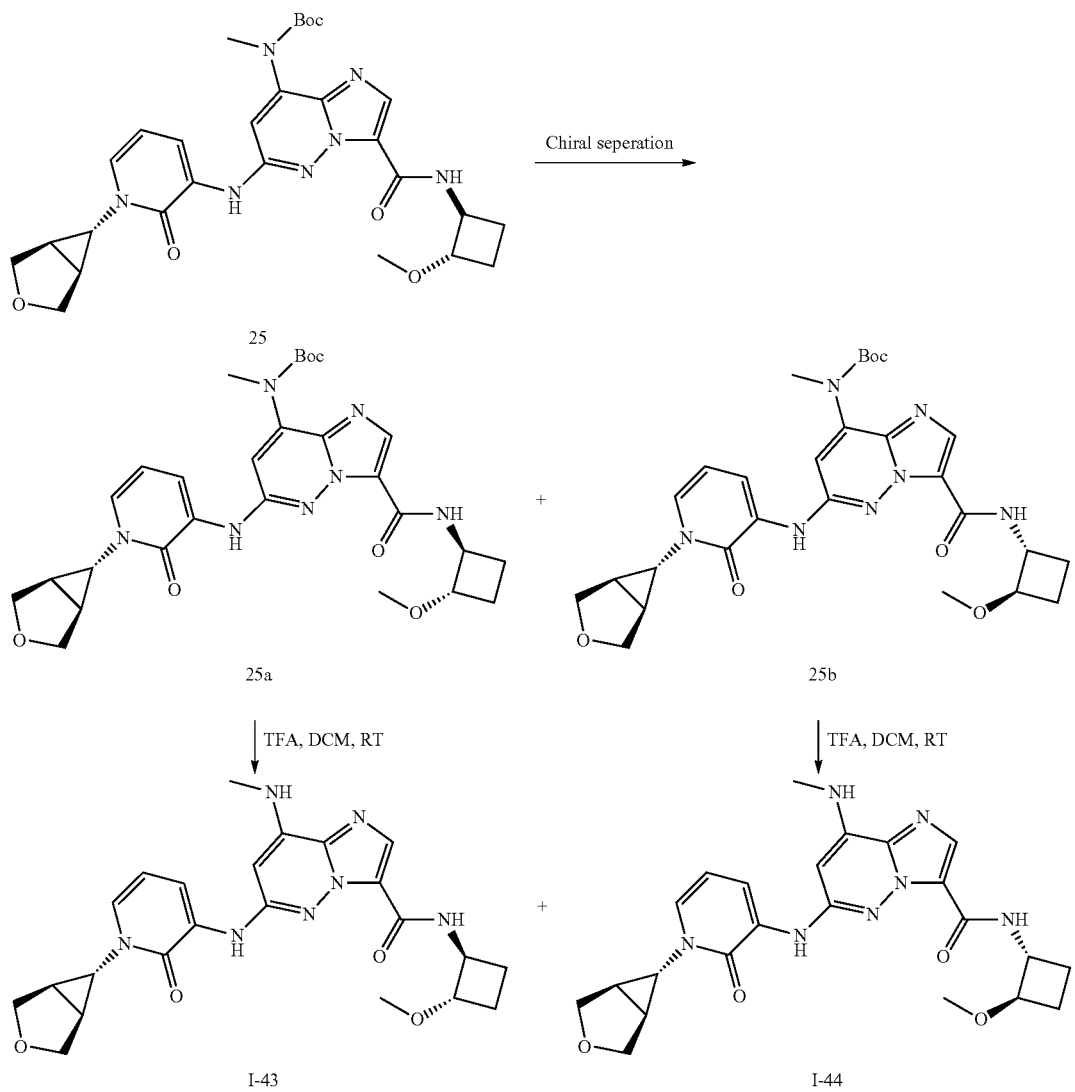

Synthesis of compound 25. Compound was synthesized as per experimental protocol of I-22 to obtain 25. (Yield: 57.97%), MS (ES): 566.27 [M+H]$^+$ Synthesis of compound 25a and 25b. Isomers of 25 (0.110 g) were separated out using column CHIRALPAK AD-H (250 mm*4.6 mm, 5 u) and 0.1% DEA in IPA:MEOH (50:50) as co-solvent with flow rate of 4 mL/min. to get pure fraction-1 (FR-a) and fraction-2 (FR-b). FR-a was concentrated under reduced pressure at 30° C. to afford pure 25a. (0.044 g). MS(ES): m/z 566.27 [M+H]$^+$. FR-b was concentrated under reduced pressure at 30° C. to afford pure 25b. (0.046 g). MS(ES): m/z 566.27 [M+H]$^+$.

Synthesis of compound I-43. The compound 25a (0.044 g, 0.077 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-43 (0.044 g, Yield: 71.80%). MS(ES): m/z 466.77 [M+H]$^+$, LCMS purity: 96.83%, HPLC purity: 97.47%, CHIRAL HPLC purity: 98.69%, $^1$H NMR (DMSO-d$_6$, 400 MHZ): 8.83-8.81 (d, J=8.8 Hz, 1H), 8.66 (s, 1H), 7.97-7.96 (d, J=7.2 Hz, 1H), 7.94 (s, 1H), 7.46 (bs, 1H), 7.29-7.28 (d, J=6.4 Hz, 1H), 6.41 (s, 1H), 6.27-6.23 (t, J=7.2 Hz, 1H), 4.35-4.30 (m, 1H), 3.73 (bs, 3H), 3.19 (bs, 3H), 3.14 (bs, 1H), 2.86-2.85 (d, J=4.4 Hz, 3H), 2.27 (bs, 2H), 2.12-2.02 (m, 2H), 1.55-1.50 (t, J=9.6 Hz, 1H), 1.42-1.38 (t, J=9.6 Hz, 1H), 1.22 (bs, 2H).

Synthesis of compound I-44. The compound 25b (0.046 g, 0.081 mmol, 1.0 eq) was dissolved in dichloromethane (1 mL) and trifluoroacetic acid (0.20 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-44 (0.046 g, Yield: 73.9%). MS(ES): m/z 466.91 [M+H]+, LCMS purity: 100%, HPLC purity: 100%, CHIRAL HPLC purity: 99.79%, $^1$H NMR (DMSO-$d_6$, 400 MHZ): 8.82-8.80 (d, J=8.8 Hz, 1H), 8.61 (s, 1H), 7.96-7.94 (d, J=7.2 Hz, 1H), 7.85 (s, 1H), 7.50-7.48 (d, J=4.8 Hz, 1H), 7.28-7.27 (d, J=6.4 Hz, 1H), 6.34 (s, 1H), 6.26-6.23 (t, J=7.2 Hz, 1H), 4.35-4.30 (m, 1H), 3.73 (bs, 3H), 3.19 (bs, 3H), 3.14 (bs, 1H), 2.86-2.85 (d, J=4.4 Hz, 3H), 2.27 (bs, 2H), 2.12-2.02 (m, 2H), 1.55-1.50 (t, J=9.6 Hz, 1H), 1.42-1.38 (t, J=9.6 Hz, 1H), 1.22 (bs, 2H).

Example 26: N-((1S,2S)-2-methoxycyclobutyl)-6-((1-((1r,3S)-3-methoxycyclobutyl)-2-oxo-1,2-dihydropyridin-3-yl)amino)-8-(methylamino)imidazo[1,2-b]pyridazine-3-carboxamide (I-45), N-((1R,2R)-2-methoxycyclobutyl)-6-((1-((1r,3R)-3-methoxycyclobutyl)-2-oxo-1,2-dihydropyridin-3-yl)amino)-8-(methylamino)imidazo[1,2-b]pyridazine-3-carboxamide (I-46)

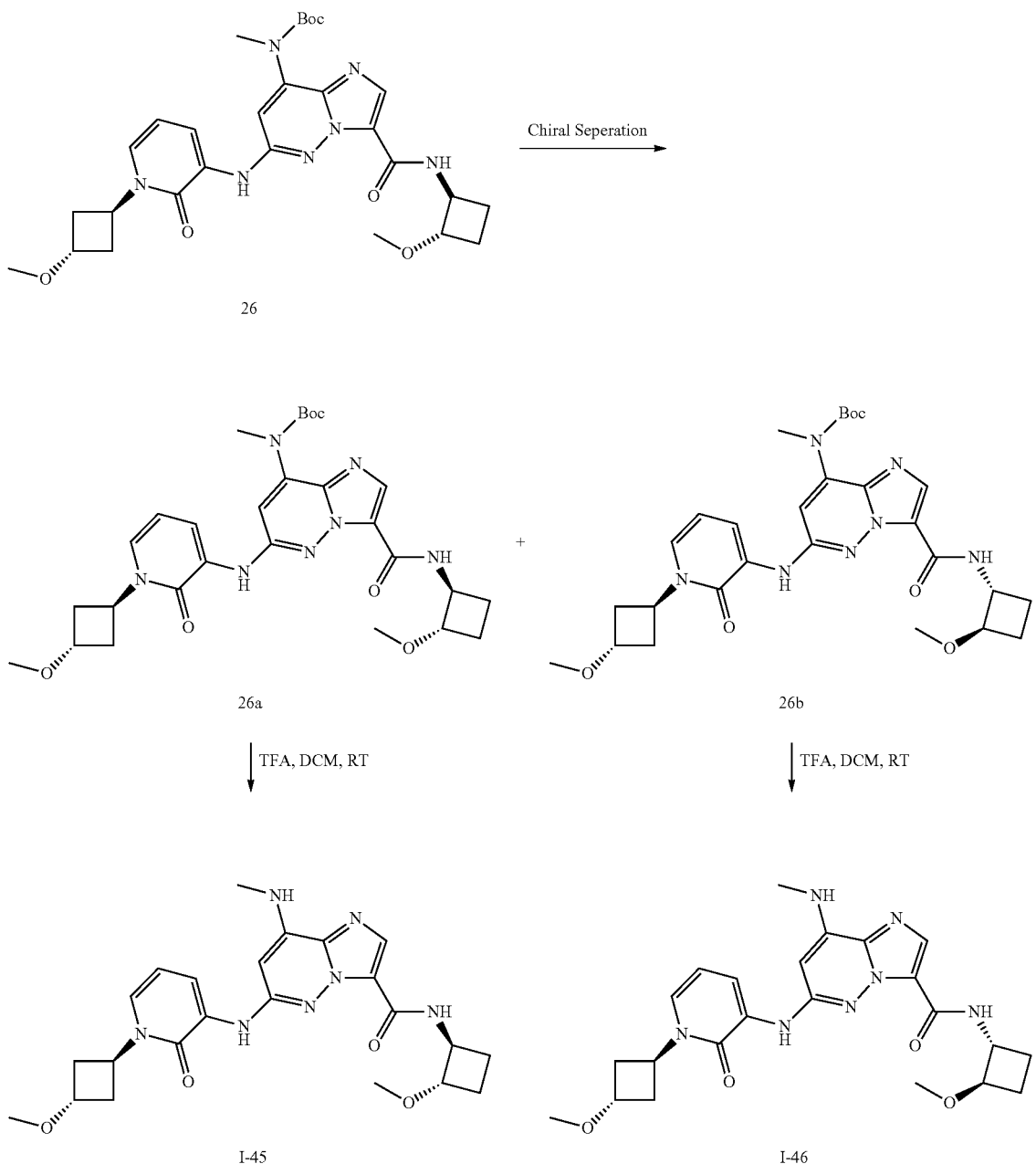

Synthesis of compound 26. Compound was synthesized as per experimental protocol of I-23 to obtain 26. (Yield: 59.83%), MS (ES): 568.28 [M+H]⁺

Synthesis of compound 26a and 26b. Isomers of 26 (0.102 g) were separated out using column CHIRALPAK AD-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 26a. (0.038 g). MS(ES): m/z 568.28 [M+H]⁺. FR-b was concentrated under reduced pressure at 30° C. to afford pure 26b. (0.032 g). MS (ES): m/z 568.28 [M+H]⁺.

Synthesis of compound I-45. The compound 26a (0.038 g, 0.066 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-45 (0.025 g, Yield: 79.88%). MS(ES): m/z 468.77 [M+H]⁺, LCMS purity: 97.08%, HPLC purity: 97.35%, CHIRAL HPLC purity: 99.55%, ¹H NMR (DMSO-d₆, 400 MHZ): 8.83-8.81 (d, J=8.8 Hz, 1H), 8.56 (s, 1H), 7.98-7.97 (d, J=7.2 Hz, 1H), 7.85 (s, 1H), 7.50-7.48 (d, J=7.2 Hz, 1H), 7.46 (bs, 1H), 6.35-6.31 (t, J=9.2 Hz, 1H), 6.31 (s, 1H), 5.31-5.25 (m, 1H), 4.35-4.31 (m, 1H), 4.05 (bs, 1H), 3.76-3.72 (m, 1H), 3.22 (s, 3H), 3.17 (s, 3H), 2.86-2.84 (d, J=4.4 Hz, 3H), 2.11-2.03 (m, 2H), 1.55-1.51 (t, J=8.8 Hz, 2H), 1.43-4.38 (t, J=9.6 Hz, 1H), 1.23 (bs, 3H).

Synthesis of compound I-46. The compound 26b (0.038 g, 0.056 mmol, 1.0 eq) was dissolved in dichloromethane (1 mL) and trifluoroacetic acid (0.15 mL) was added to the reaction mixture. The reaction was stirred at room temperature for 1 h. After completion of reaction, reaction mixture was transferred into saturated sodium bicarbonate solution and product was extracted with dichloromethane. Organic layer was combined, dried over sodium sulphate and concentrated under reduced pressure to obtain crude material. This was further purified by trituration with diethyl ether to obtain pure I-46 (0.023 g, Yield: 90.16%). MS(ES): m/z 468.77 [M+H]⁺, LCMS purity: 100%, HPLC purity: 99.69%, CHIRAL HPLC purity: 99.59%, ¹H NMR (DMSO-d₆, 400 MHZ): 8.83-8.81 (d, J=8.8 Hz, 1H), 8.56 (s, 1H), 7.98-7.97 (d, J=7.2 Hz, 1H), 7.85 (s, 1H), 7.50-7.48 (d, J=7.2 Hz, 1H), 7.46 (bs, 1H), 6.35-6.31 (t, J=9.2 Hz, 1H), 6.31 (s, 1H), 5.31-5.25 (m, 1H), 4.35-4.31 (m, 1H), 4.05 (bs, 1H), 3.76-3.72 (m, 1H), 3.22 (s, 3H), 3.19 (s, 3H), 2.86-2.84 (d, J=4.4 Hz, 3H), 2.19-2.03 (m, 2H), 1.55-1.51 (t, J=8.8 Hz, 2H), 1.43-4.38 (t, J=9.6 Hz, 1H), 1.21 (bs, 3H).

Example 27: N-(2-methoxycyclobutyl)-6-(1-((3R,4S)-4-methoxytetrahydrofuran-3-yl)-1H-pyrrolo[2,3-b]pyridin-3-yl)-8-(methylamino)imidazo[1,2-b]pyridazine-3-carboxamide (I-47)

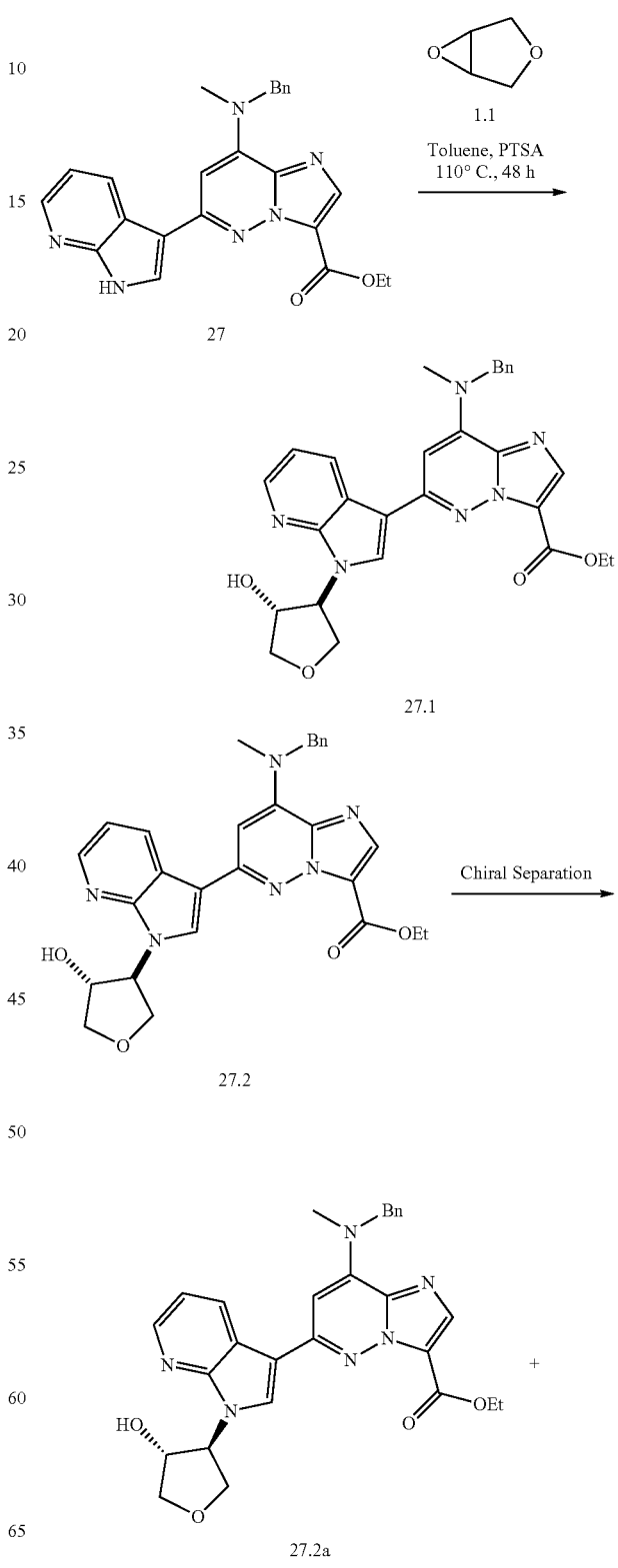

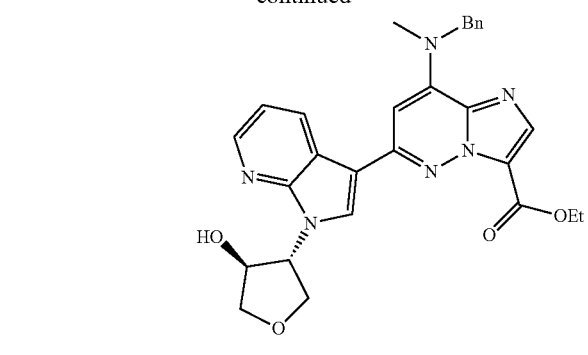

27.2b

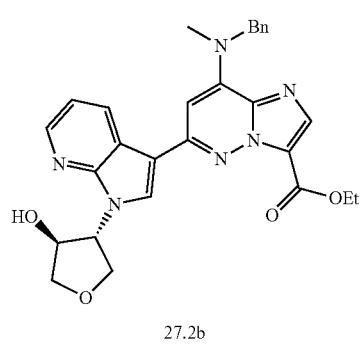

27.2b

DMF, NaH, MeI, RT

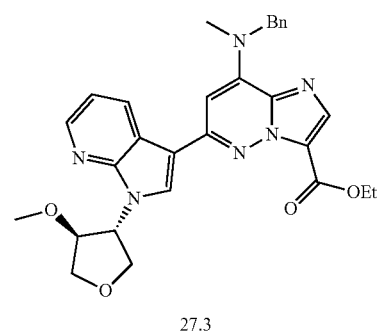

27.3

MeOH, THF
LiOH, H₂O, 50° C.

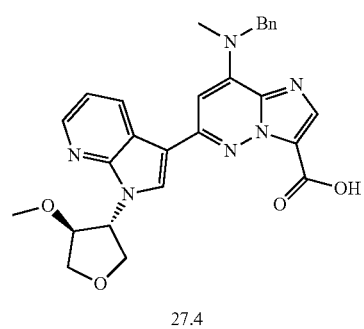

27.4

27.5

DMF, HATU, DIPEA
RT,

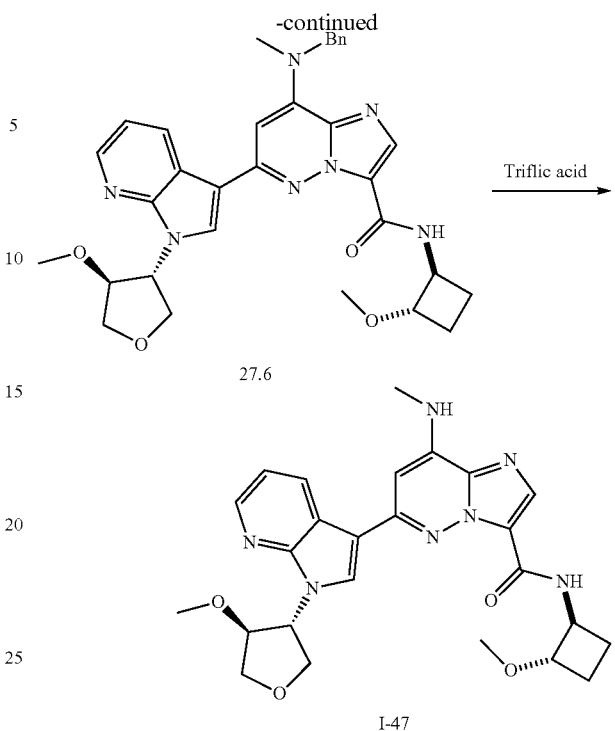

27.6

Triflic acid

I-47

Synthesis of compound 27. Compound was synthesized as per experimental protocol of I-5 to obtain 27. (Yield: 92.61%), MS (ES): m/z 427.18 [M+H]⁺

Synthesis of compound 27.2. To a solution of 27 (1.0 g, 2.34 mmol, 1.0 eq) in toluene (10 mL) was added 27.1 (0.301 g, 3.51 mmol, 1.5 eq) and p-Toluene sulfonic acid (0.040 g, 0.23 mmol, 0.1 eq). The reaction mixture was refluxed at 110° C. for 48 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.1% methanol in dichloromethane to obtain 27.2. (0.780 g, Yield: 64.90%). MS(ES): m/z 513.2 [M+H]⁺

Synthesis of compound 27.2a and 27.2b.: Isomers of 27.2 (0.780 g) were separated out using column CHIRALCEL OJ-H (250 mm*4.6 mm, 5 u) and 0.1% DEA in MEOH as co-solvent with flow rate of 4 mL/min. to get pure fraction-1 (FR-a) and fraction-2 (FR-b). FR-a was concentrated under reduced pressure at 30° C. to afford pure 27.2a (0.3 g). MS(ES): m/z 513.2 [M+H]⁺. FR-b was concentrated under reduced pressure at 30° C. to afford pure 27.2b. (0.3 g). MS(ES): m/z 513.2 [M+H]⁺

Synthesis of compound 27.3. To a suspension of sodium hydride (0.03 g, 1.16 mmol, 2 eq) in Dimethylformamide (3 mL) at 0° C. was added 27.2b (0.3 g, 0.58 mmol, 1.0 eq) and stirred for 15 min followed by addition of Methyl iodide (0.090 g, 0.63 mmol, 1.1 eq). Reaction mixture was stirred at room temperature for 2 h. After completion of reaction, reaction mixture was diluted with water extracted with diethyl ether. Organic layer was combined, dried over sodium sulphate and concentrated under reduced pressure to obtain solid which was further purified by column chromatography and the compound was eluted in 2.0% methanol in dichloromethane to obtain 27.3. (0.230 g, Yield: 74.62%). MS (ES): m/z 527.2 [M+H]⁺

Synthesis of compound 27.4. To a solution of 27.3 (0.230 g, 0.43 mmol, 1.0 eq), in tetrahydrofuran:methanol:water (4 mL, 2:1:1) was added lithium hydroxide (0.103 g, 4.3 mmol, 10.0 eq). The reaction was stirred at 50° C. for 16 h. After completion of reaction, reaction mixture was concentrated under reduced pressure to obtain residue. To this added water and acidified with 1N hydrochloric acid to adjust pH-6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 3.1% methanol in dichloromethane to obtain pure 27.4. (0.190 g, Yield: 87.26%). MS(ES): m/z 499.2 [M+H]$^+$ Synthesis of compound 27.6. Compound was synthesized using general procedure A to obtain 27.6. (0.150 g, Yield: 67.66%). MS(ES): m/z 582.28 [M+H]$^+$ Synthesis of compound I-47: A solution of 27.6 (0.040 g, 0.068 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-47 (0.025 g, Yield: 73.96%). MS(ES): m/z 492.59 [M+H]$^+$ LCMS purity: 100%, HPLC purity: 98.58%, CHIRAL HPLC: 49.13%, 49.12%, $^1$H NMR (DMSO-d$_6$, 400 MHZ): 9.26-9.24 (d, J=8.8 Hz, 1H), 8.82-8.80 (d, J=7.6 Hz, 1H), 8.55 (s, 1H), 8.24-8.23 (d, J=6 Hz, 1H), 7.99 (s, 1H), 7.70-7.69 (d, J=3.6 Hz, 1H), 7.31-7.28 (t, J=7.2 Hz, 1H), 6.68 (s, 1H), 4.18-4.10 (m, 2H), 3.85-3.80 (m, 2H), 3.45 (s, 3H), 3.24-3.23 (d, J=4.8 Hz, 3H), 3.03-3.02 (d, J=4.8 Hz, 3H), 2.09-2.05 (m, 1H), 1.55 (bs, 2H), 1.24 (bs, 3H), 0.90-0.86 (m, 2H).

Example 28: N-((1S,2S)-2-methoxycyclobutyl)-6-(1-((3R,4S)-4-methoxytetrahydrofuran-3-yl)-1H-pyrrolo[2,3-b]pyridin-3-yl)-8-(methylamino)imidazo[1,2-b]pyridazine-3-carboxamide (I-48), N-((1R,2R)-2-methoxycyclobutyl)-6-(1-((3R,4S)-4-methoxytetrahydrofuran-3-yl)-1H-pyrrolo[2,3-b]pyridin-3-yl)-8-(methylamino)imidazo[1,2-b]pyridazine-3-carboxamide (I-49)

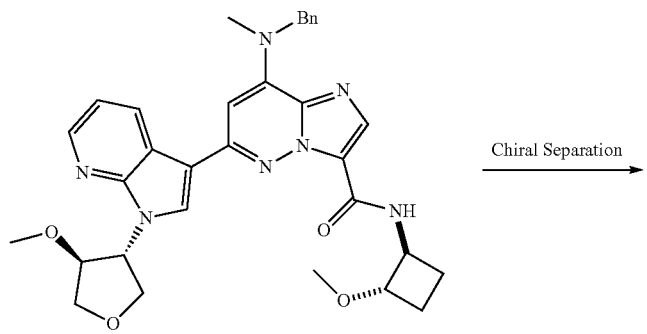

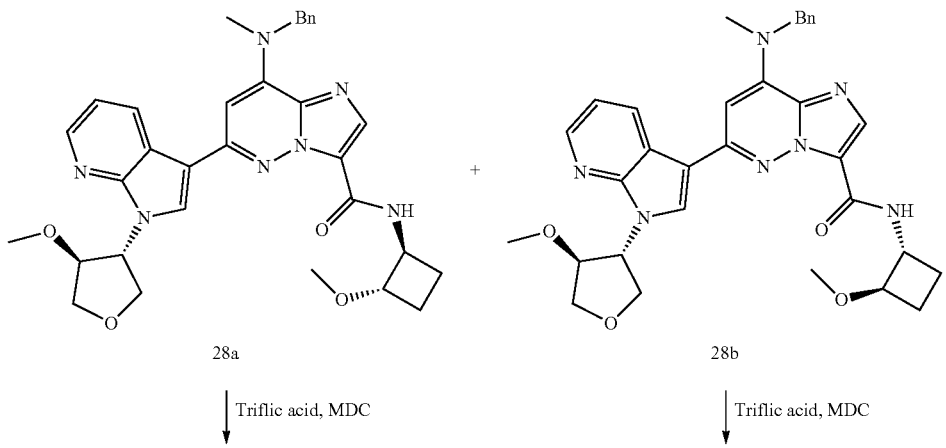

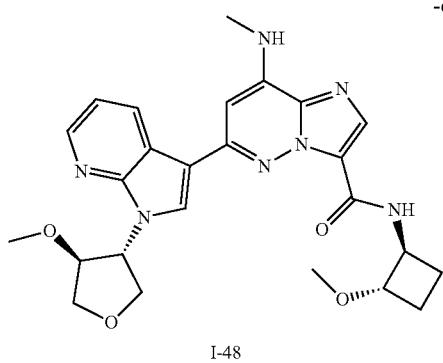

I-48

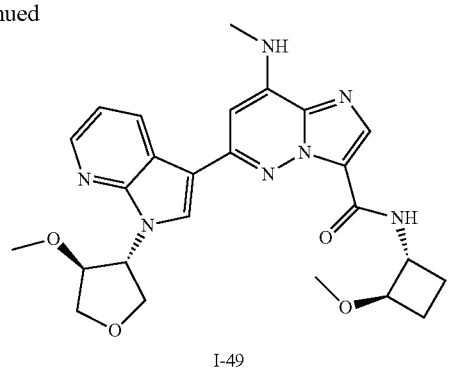

I-49

Synthesis of compound 28. Compound was synthesized as per experimental protocol of I-47 to obtain 28. (Yield: 67.66%), MS (ES): 582.28 [M+H]+

Synthesis of compound 28a and 28b. Isomers of 28 (0.110 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 28a. (0.045 g). MS(ES): m/z 582.28 [M+H]+. FR-b was concentrated under reduced pressure at 30° C. to afford pure 28b. (0.045 g). MS(ES): m/z 582.28 [M+H]+

Synthesis of compound I-48: A solution of 28a (0.045 g, 0.077 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-48 (0.031 g, Yield: 81.52%). MS(ES): m/z 492.37 [M+H]+ LCMS purity: 100%, HPLC purity: 98.07%, CHIRAL HPLC: 96.96%, $^1$H NMR (DMSO-d$_6$, 400 MHZ): 9.25-9.23 (d, J=8.4 Hz, 1H), 8.80-8.79 (d, J=7.6 Hz, 1H), 8.54 (s, 1H), 8.23-8.21 (d, J=6 Hz, 1H), 7.98 (s, 1H), 7.65-7.64 (d, J=5.2 Hz, 1H), 7.30-7.27 (t, J=6.8 Hz, 1H), 6.66 (s, 1H), 4.40-4.36 (m, 2H), 3.82-3.78 (m, 2H), 3.44 (s, 3H), 3.22 (s, 3H), 3.01-3.00 (d, J=4.4 Hz, 3H), 2.21-2.14 (m, 1H), 2.07-1.98 (m, 1H), 1.58-1.45 (s, 3H), 1.26 (s, 2H), 0.87-0.85 (m, 1H).

Synthesis of compound I-49: A solution of 28b (0.045 g, 0.077 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-49 (0.032 g, Yield: 84.15%). MS(ES): m/z 492.32 [M+H]+ LCMS purity: 100%, HPLC purity: 98.18%, CHIRAL HPLC: 100%, $^1$H NMR (DMSO-d$_6$, 400 MHZ): 9.25-9.23 (d, J=8.4 Hz, 1H), 8.81-8.79 (d, J=7.6 Hz, 1H), 8.54 (s, 1H), 8.23-8.21 (d, J=6 Hz, 1H), 7.98 (s, 1H), 7.65-7.64 (d, J=5.2 Hz, 1H), 7.30-7.27 (t, J=6.8 Hz, 1H), 6.66 (s, 1H), 4.41-4.35 (m, 2H), 3.86-3.78 (m, 2H), 3.44 (s, 3H), 3.23 (s, 3H), 3.02-3.00 (d, J=4.4 Hz, 3H), 2.20-2.16 (m, 1H), 2.08-2.04 (m, 1H), 1.58-1.45 (s, 3H), 1.24 (s, 2H), 0.87-0.85 (m, 1H).

Example 29: N-(2-methoxycyclobutyl)-6-(1-((3S,4R)-4-methoxytetrahydrofuran-3-yl)-1H-pyrrolo[2,3-b]pyridin-3-yl)-8-(methylamino)imidazo[1,2-b]pyridazine-3-carboxamide (I-50)

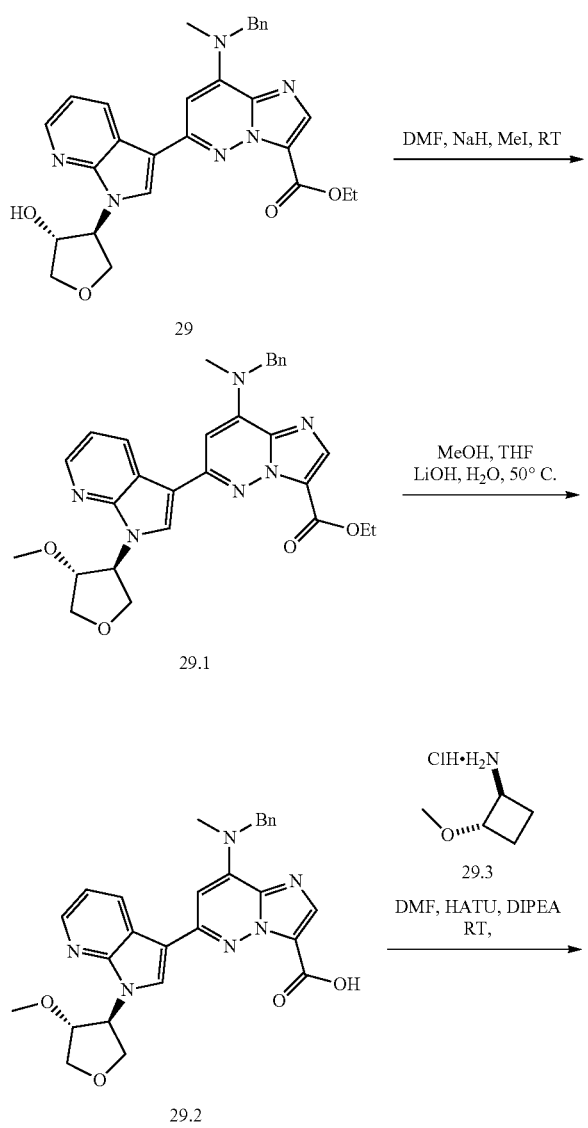

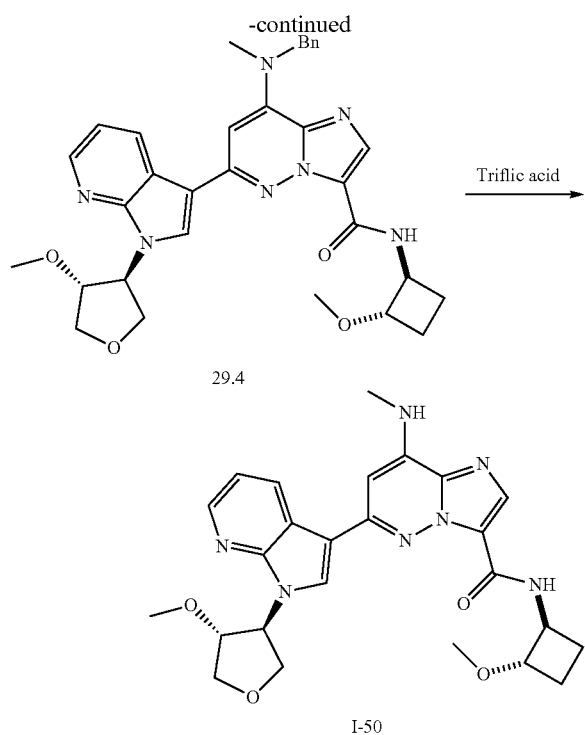

29.4

I-50

Synthesis of compound 29. Compound was synthesized as per experimental protocol of I-47 to obtain 29. MS (ES): m/z 513.2 [M+H]+

Synthesis of compound 29.1. To a suspension of sodium hydride (0.03 g, 1.16 mmol, 2 eq) in Dimethylformamide (3 mL) at 0° C. was added 29 (0.3 g, 0.58 mmol, 1.0 eq) and stirred for 15 min followed by addition of Methyl iodide, (0.090 g, 0.63 mmol, 1.1 eq). Reaction mixture was stirred at room temperature for 2 h. After completion of reaction, reaction mixture was diluted with water extracted with diethyl ether. Organic layer was combined, dried over sodium sulphate and concentrated under reduced pressure to obtain solid which was further purified by column chromatography and the compound was eluted in 2.0% methanol in dichloromethane to obtain 29.1. (0.230 g, Yield: 74.62%). MS (ES): m/z 527.2 [M+H]+

Synthesis of compound 29.2. To a solution of 29.1 (0.230 g, 0.43 mmol, 1.0 eq), in tetrahydrofuran:methanol:water (4 mL, 2:1:1) was added lithium hydroxide (0.103 g, 4.3 mmol, 10.0 eq). The reaction was stirred at 50° C. for 16 h. After completion of reaction, reaction mixture was concentrated under reduced pressure to obtain residue. To this added water and acidified with 1N hydrochloric acid to adjust pH-6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 3.1% methanol in dichloromethane to obtain pure 29.2. (0.192 g, Yield: 88.18%). MS(ES): m/z 499.2 [M+H]+

Synthesis of compound 29.4. Compound was synthesized using general procedure A to obtain 29.4. (0.150 g, Yield: 66.96%). MS(ES): m/z 582.28 [M+H]+

Synthesis of compound I-50: A solution of 29.6 (0.040 g, 0.068 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-50 (0.025 g, Yield: 73.96%). MS(ES): m/z 492.52 [M+H]+ LCMS purity: 100%, HPLC purity: 98.15%, CHIRAL HPLC: 49.13%, 49.12%, $^1$H NMR (DMSO-$d_6$, 400 MHZ): 9.26-9.24 (d, J=8.8 Hz, 1H), 8.82-8.80 (d, J=7.6 Hz, 1H), 8.55 (s, 1H), 8.24-8.23 (d, J=6 Hz, 1H), 7.99 (s, 1H), 7.70-7.69 (d, J=3.6 Hz, 1H), 7.31-7.28 (t, J=7.2 Hz, 1H), 6.68 (s, 1H), 4.15-4.12 (m, 2H), 3.85-3.80 (m, 2H), 3.45 (s, 3H), 3.24-3.23 (d, J=4.8 Hz, 3H), 3.03-3.02 (d, J=4.8 Hz, 3H), 2.09-2.05 (m, 1H), 1.55 (bs, 2H), 1.24 (bs, 3H), 0.90-0.86 (m, 2H).

Example 30: N-((1S,2S)-2-methoxycyclobutyl)-6-(1-((3S,4R)-4-methoxytetrahydrofuran-3-yl)-1H-pyrrolo[2,3-b]pyridin-3-yl)-8-(methylamino)imidazo[1,2-b]pyridazine-3-carboxamide (I-51), N-((1R, 2R)-2-methoxycyclobutyl)-6-(1-((3S,4R)-4-methoxytetrahydrofuran-3-yl)-1H-pyrrolo[2,3-b]pyridin-3-yl)-8-(methylamino)imidazo[1,2-b]pyridazine-3-carboxamide (I-52)

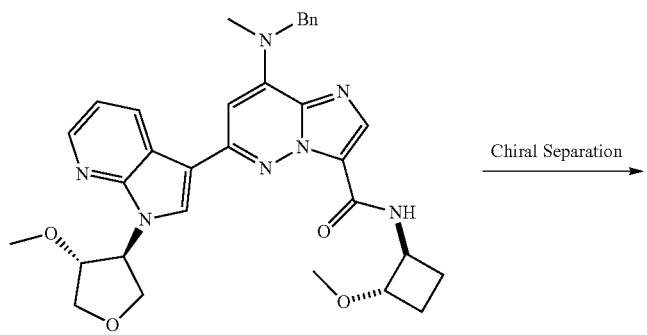

30

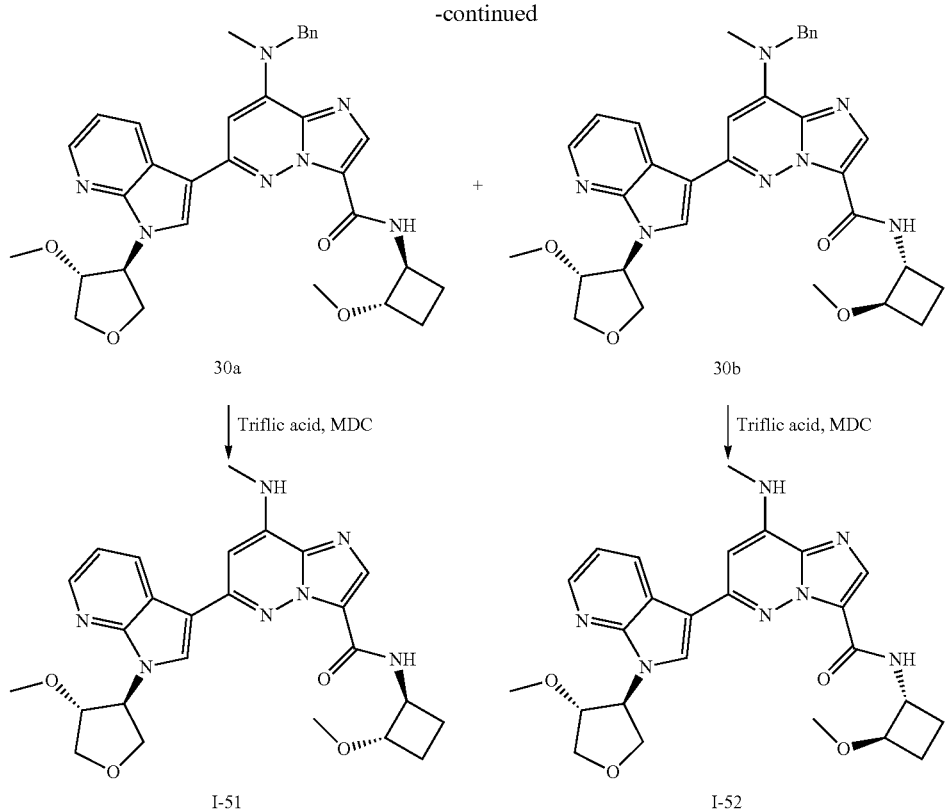

Synthesis of compound 30. Compound was synthesized as per experimental protocol of I-50 obtain 30. (Yield: 66.96%), MS (ES): 582.28 [M+H]$^+$ Synthesis of compound 30a and 30b: Isomers of 30 (0.110 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 30a. (0.045 g). MS(ES): m/z 582.28 [M+H]$^+$. FR-b was concentrated under reduced pressure at 30° C. to afford pure 30b. (0.045 g). MS(ES): m/z 582.28 [M+H]$^+$ Synthesis of compound I-51: A solution of 30a (0.045 g, 0.077 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-51 (0.031 g, Yield: 81.52%). MS(ES): m/z 492.59 [M+H]$^+$ LCMS purity: 100%, HPLC purity: 97.62%, CHIRAL HPLC: 98.94%, $^1$H NMR (DMSO-d$_6$, 400 MHZ): 9.26-9.24 (d, J=8.4 Hz, 1H), 8.82-8.80 (d, J=7.2 Hz, 1H), 8.55 (s, 1H), 8.24-8.23 (d, J=6 Hz, 1H), 7.99 (s, 1H), 7.66-7.64 (d, J=5.2 Hz, 1H), 7.31-7.28 (t, J=6.8 Hz, 1H), 6.68 (s, 1H), 4.44-4.38 (m, 2H), 3.84-3.80 (m, 2H), 3.45 (s, 3H), 3.23 (s, 3H), 3.03-3.02 (d, J=4.8 Hz, 3H), 2.20-2.18 (m, 1H), 2.09-2.05 (m, 1H), 1.60-1.46 (m, 3H), 1.24 (s, 1H), 1.12-1.08 (t, J=6.8 Hz, 2H).

Synthesis of compound I-52: A solution of 30b (0.045 g, 0.077 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-52 (0.030 g, Yield: 78.89%). MS(ES): m/z 492.47 [M+H]$^+$ LCMS purity: 99.34%, HPLC purity: 97.03%, CHIRAL HPLC: 96.96%, $^1$H NMR (DMSO-d$_6$, 400 MHZ): 9.26-9.24 (d, J=8.4 Hz, 1H), 8.82-8.80 (d, J=7.2 Hz, 1H), 8.55 (s, 1H), 8.24-8.23 (d, J=6 Hz, 1H), 7.99 (s, 1H), 7.66-7.64 (d, J=5.2 Hz, 1H), 7.32-7.28 (t, J=6.8 Hz, 1H), 6.68 (s, 1H), 4.42-4.36 (m, 2H), 3.88-3.79 (m, 2H), 3.45 (s, 3H), 3.23 (s, 3H), 3.03-3.02 (d, J=4.8 Hz, 3H), 2.19-2.17 (m, 1H), 2.09-2.05 (m, 1H), 1.60-1.46 (m, 3H), 1.24 (bs, 2H), 1.12-1.08 (t, J=6.8 Hz, 1H).

Example 31. TYK2 JH2 Domain Binding Assay

Binding constants for compounds of the present invention against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP 003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2 (JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a ≥10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. $K_d$ values were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$ values were determined using a compound top concentration of 30,000 nM. $K_d$ measurements were performed in duplicate.

Binding constants ($K_d$ values) were calculated with a standard dose-response curve using the Hill equation:

$$\text{Response} = \text{Background} + \frac{(\text{Signal} - \text{Background})}{\left(1 + \left(\frac{Kd^{\text{Hill Slope}}}{\text{Dose}^{\text{Hill Slope}}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)).

Results of the Tyk2 JH2 Domain Binding Assay are presented in Table 2. Compounds denoted as "A" had a Kd lower than 200 pM; compounds denoted as "B" had a Kd between 200 pM and 1 nM; compounds denoted as "C" had a Kd between 1 nM and 10 nM; and compounds denoted as "D" had a Kd greater than 10 nM.

TABLE 2

Results of Tyk2 JH2 Domain Binding Assay

| Compound # | hTYK2_JH2_Binding (Kd) [nM] |
|---|---|
| I-3 | A |
| I-4 | A |
| I-5 | A |
| I-6 | A |
| I-7 | A |
| I-8 | A |
| I-9 | B |
| I-10 | A |
| I-11 | A |
| I-12 | A |
| I-13 | B |
| I-14 | A |
| I-15 | A |
| I-16 | A |
| I-17 | A |
| I-18 | A |
| I-19 | A |
| I-20 | A |
| I-21 | A |
| I-22 | A |
| I-23 | A |

Example 32. Tyk2 & JAK2 Radioactive Kinase Assay

Peptide substrate, [KKSRGDYMTMQIG], (20 µM) is prepared in reaction buffer (20 mM Hepes pH 7.5, 10 mM MgCl$_2$, 1 mM EGTA, 0.02% Brij35, 0.02 mg/mL BSA, 0.1 mM Na$_3$PO$_4$, 2 mM DTT, 1% DMSO. TYK2 (Invitrogen) kinase is added, followed by compounds in DMSO. 33PATP is added to initiate the reaction in ATP at 10 µM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr] (4:1), 0.2 mg/ml is used, in the reaction carried out the same as for TYK2.

The Tyk2 and JAK2 radioactive kinase assay measures the percent inhibition at the Tyk2 kinase domain (JH1) and the percent inhibition at the JAK2 kinase domain (JH1). Results of the assay are expressed as percent inhibition at 10 µM.

Similar assays were run to measure the percent inhibition at the JAK1 and JAK3 kinase domains.

Results of the Tyk2 and JAK1, JAK2, and JAK3 Radioactive Kinase Assay are presented in Tables 3A and 3B. Compounds denoted as "A" had a percent inhibition at 10 µM lower than 50; compounds denoted as "B" had a percent inhibition at 10 µM between 50 and 70; compounds denoted as "C" had a percent inhibition at 10 µM between 70 and 90; and compounds denoted as "D" had a percent inhibition at 10 µM greater than 90.

TABLE 3A

Tyk2 & JAK2 Radioactive Kinase Assay

| Compound # | TYK2_IC50_RB (%INH_@_10 uM) at 10.0 uM [% INH] | JAK2_IC50_RB (%INH_@_10 uM) at 10.0 uM [% INH] |
|---|---|---|
| I-3  | A | A |
| I-4  | A | A |
| I-5  | A | A |
| I-6  | A | A |
| I-7  | A | A |
| I-9  |   | A |
| I-10 | A | A |
| I-12 | A | A |
| I-15 |   | A |
| I-16 | A | A |

TABLE 3B

JAK1 and JAK3 Radioactive Kinase Assay

| Compound # | JAK1_IC50_RB (% INH_@_10 uM) at 10.0 uM [% INH] | JAK3_IC50_RB (% INH_@_10 uM) at 10.0 uM [% INH] |
|---|---|---|
| I-3  | A | A |
| I-4  | A | A |
| I-5  | A | A |
| I-6  | A | A |
| I-7  | A | A |
| I-9  | A | A |
| I-10 | A | A |
| I-12 | A | A |
| I-15 | A | A |
| I-16 | A | A |

Example 33. Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Example 34. IL-12 Induced pSTAT4 in Human PBMC

Human PBMC are isolated from buffy coat and are stored frozen for assays as needed. Cells for assay are thawed and resuspended in complete media containing serum, then cells are diluted to $1.67 \times 10^6$ cells/ml so that 120 µl per well is 200,000 cells. 15 µl of compound or DMSO is added to the well at the desired concentrations and incubated at 1 hr at 37° C. 15 µl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

The IL-12 Induced pSTAT4 assay evaluates the inhibition of IL-12 induced STAT4 phophorylation mediated by Tyk2/JAK2 (heterodimeric complex).

Results of the IL-12 Induced pSTAT4 in human PBMC are presented in Table 4. Compounds denoted as "A" had an $IC_{50}$ lower than 0.1 µM; compounds denoted as "B" had an $IC_{50}$ between 0.1 and 0.5 µM; compounds denoted as "C" had an $IC_{50}$ between 0.5 and 1.0 µM; and compounds denoted as "D" had an $IC_{50}$ greater than 1.0 µM.

Compounds denoted as "*" had a percent inhibition at 0.05 µM lower than 50; compounds denoted as "" had a percent inhibition at 0.05 µM between 50 and 70; compounds denoted as "*" had a percent inhibition at 0.05 µM between 70 and 90; and compounds denoted as "****" had a percent inhibition at 0.05 µM greater than 90.

TABLE 4

IL-12 Induced pSTAT4 in human PBMC assay results.

| Compound # | PBMC_IL-12-pSTAT4 (% Inhibition_Average_ @0.05 uM) [%] | PBMC_IL-12-pSTAT4 (IC50) (µM) |
|---|---|---|
| I-3  | *** | A |
| I-4  | *   |   |
| I-5  | *** | A |
| I-6  | *   | A |
| I-10 | *** | A |
| I-11 | *** |   |
| I-12 | *   |   |
| I-14 | *** |   |
| I-15 | **  | A |
| I-16 | *   |   |
| I-17 | **  | A |
| I-18 | *** | A |
| I-19 | **  | A |
| I-20 | *** | A |
| I-21 | ****| A |
| I-22 | *** | A |
| I-23 | *** | A |

Example 35. GM-CSF Induced pSTAT5 in Human PBMC

Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

The GM-CSF Induced pSTAT5 assay is a JAK2 cellular selectivity assay which evaluates inhibition of GM-CSF induced STAT5 phopsphorylation mediated by the JAK2/JAK2 homdimeric complex.

Example 36. Ex Vivo Mouse IL-12 Induced IFNγ Studies

C57/BL6 mice are given a single oral dose of either vehicle or different doses of compound at a volume of 10 mL/kg 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 37. T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1\times10^4$ cells per well in 96-well plates. T-ALL cell lines DU.528, LOUCY, and SUP-T13 are cultured in the same medium and plated at a density of $1.5\times10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. $IC_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:
1. A method of inhibiting TYK2 in a biological sample comprising contacting the sample with a compound of formula XX:

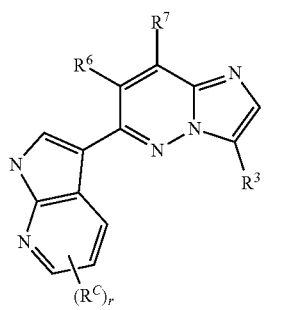

XX or a pharmaceutically acceptable salt thereof, wherein:
$R^3$ is —C(O)NH$_2$, —C(O)NHR$^{3A}$, —C(O)N(R$^{3A}$)$_2$, —C(O)OR, —C(O)NHOR, or a 5-6 membered monocyclic heteroaryl ring having 1-4 heteroatoms independently selected from nitrogen, oxygen, and sulfur, wherein said ring is substituted with m instances of R$^{3B}$,
$R^6$ is hydrogen, $R^A$, or $R^B$,
$R^7$ is hydrogen, halogen, —NH$_2$, —NHR$^{7A}$, or —NHC(O)R$^{7A}$,
or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of R$^C$;

$R^{3A}$, $R^{3B}$, and $R^{7A}$ are each independently $R^B$, and are each substituted by q instances of R$^C$, wherein two R$^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two R$^C$ substituents on adjacent carbons are optionally taken together to form a 3-6 membered saturated or partially unsaturated fused heterocyclic ring having 1-4 heteroatoms independently selected from nitrogen, oxygen, and sulfur;
each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR) NR$_2$, —N(R)S(O)$_2$NR$_2$, or —N(R)S(O)$_2$R;
each instance of $R^B$ is independently C1-6 aliphatic, phenyl, a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring, a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR) NR$_2$, —N(R)S(O)$_2$NR$_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;
each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4.

2. A method of treating a TYK2-mediated disorder, disease, or condition in a patient comprising administering to the patient a compound of formula XX:

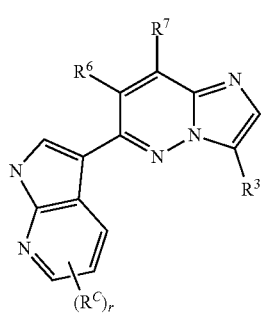

XX or a pharmaceutically acceptable salt thereof, wherein:

$R^3$ is —C(O)NH$_2$, —C(O)NHR$^{3A}$, —C(O)N(R$^{3A}$)$_2$, —C(O)OR, —C(O)NHOR, or a 5-6 membered monocyclic heteroaryl ring having 1-4 heteroatoms independently selected from nitrogen, oxygen, and sulfur, wherein said ring is substituted with m instances of $R^{3B}$, $R^6$ is hydrogen, $R^A$, or $R^B$;

$R^7$ is hydrogen, halogen, —NH$_2$, —NHR$^{7A}$, or —NHC(O)R$^{7A}$, or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$;

$R^{3A}$, $R^{3B}$, and $R^{7A}$ are each independently $R^B$, and are each substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR) NR$_2$, —N(R)S(O)$_2$NR$_2$, or —N(R)S(O)$_2$R;

each instance of $R^B$ is independently C$_{1-6}$ aliphatic, phenyl, a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring, a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR) NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4, wherein the TYK2-mediated disorder, disease, or condition is psoriasis, Crohn's disease, ulcerative colitis, inflammatory bowel disease, asthma, cutaneous lupus erythematosus, systemic lupus erythematosus, or chronic obstructive pulmonary disease.

3. The method of claim 2, wherein each of $R^{3A}$ and $R^{7A}$ is independently $R^B$, and is substituted by q instances of $R^C$, provided that neither of $R^{3A}$ or $R^{7A}$ is phenyl.

4. The method of claim 2, wherein $R^{7A}$ is C$_{1-6}$ aliphatic.

5. The method of claim 2, wherein $R^7$ is selected from —NH$_2$, —NHMe, —NHCD$_3$,

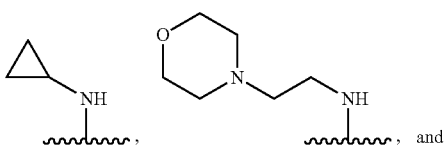

, and

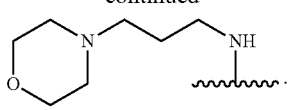
6. The method of claim 2, wherein $R^3$ is selected from
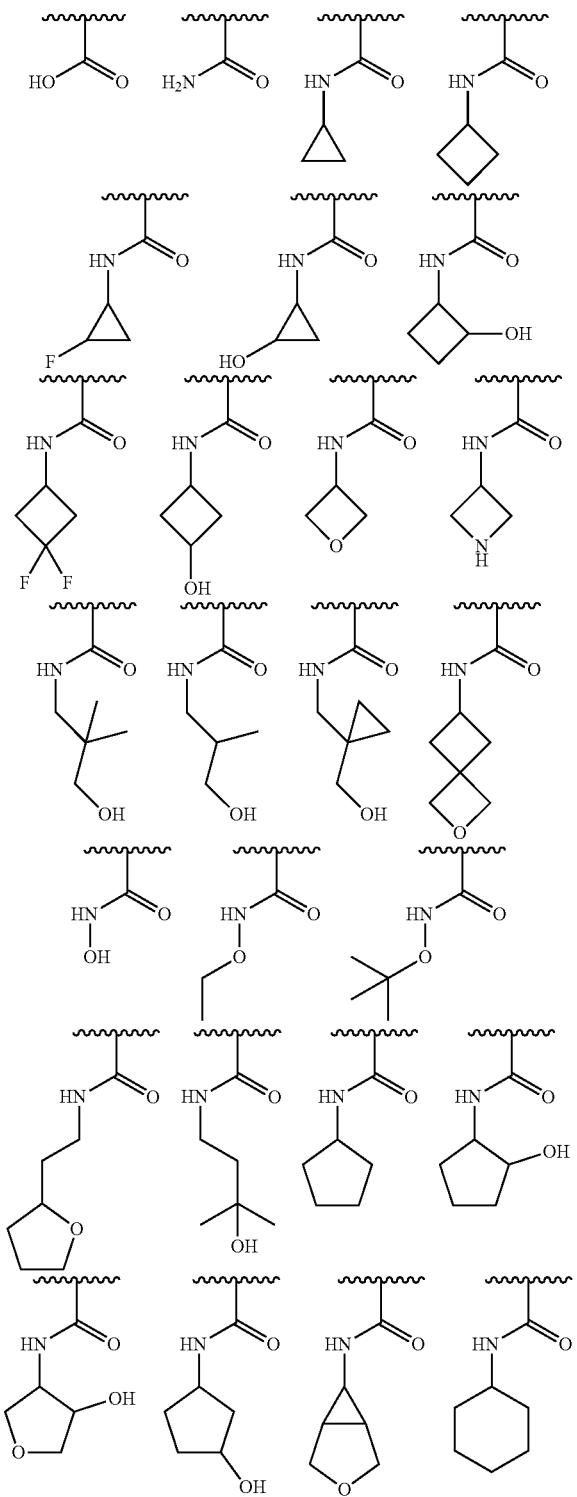
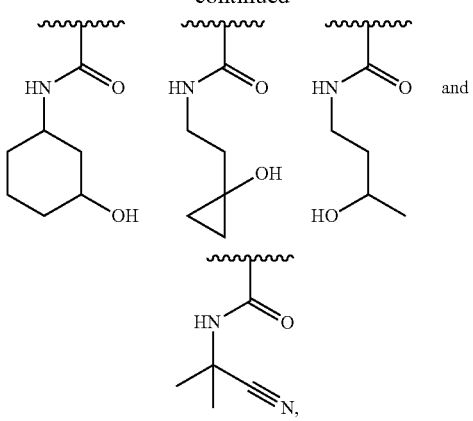
7. The method of claim 2, wherein $R^3$ is selected from
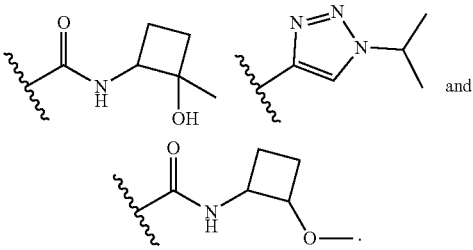
8. The method of claim 2, wherein $R^3$ is selected from
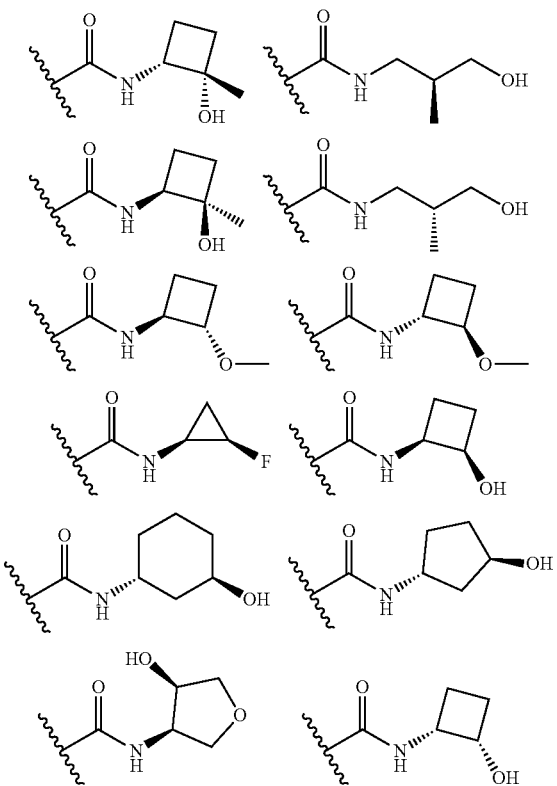

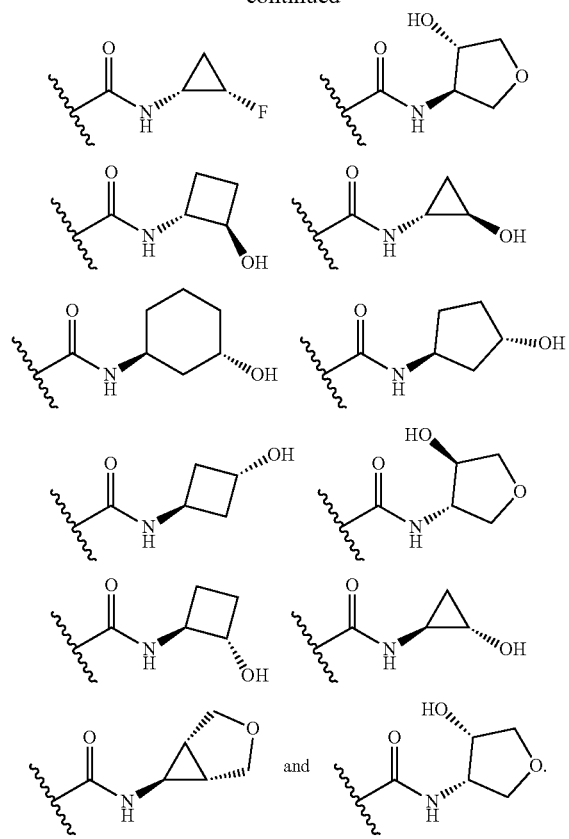
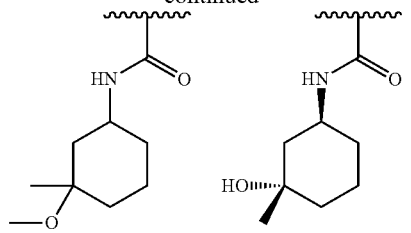
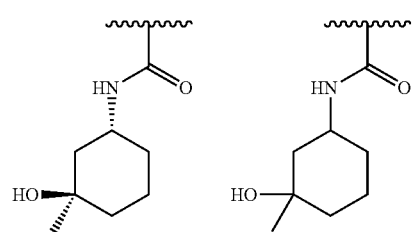
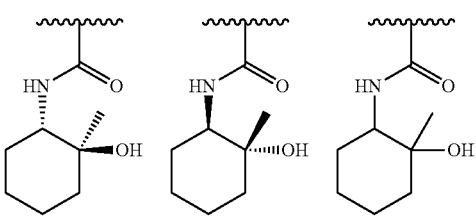
9. The method of claim 2, wherein R³ is selected from
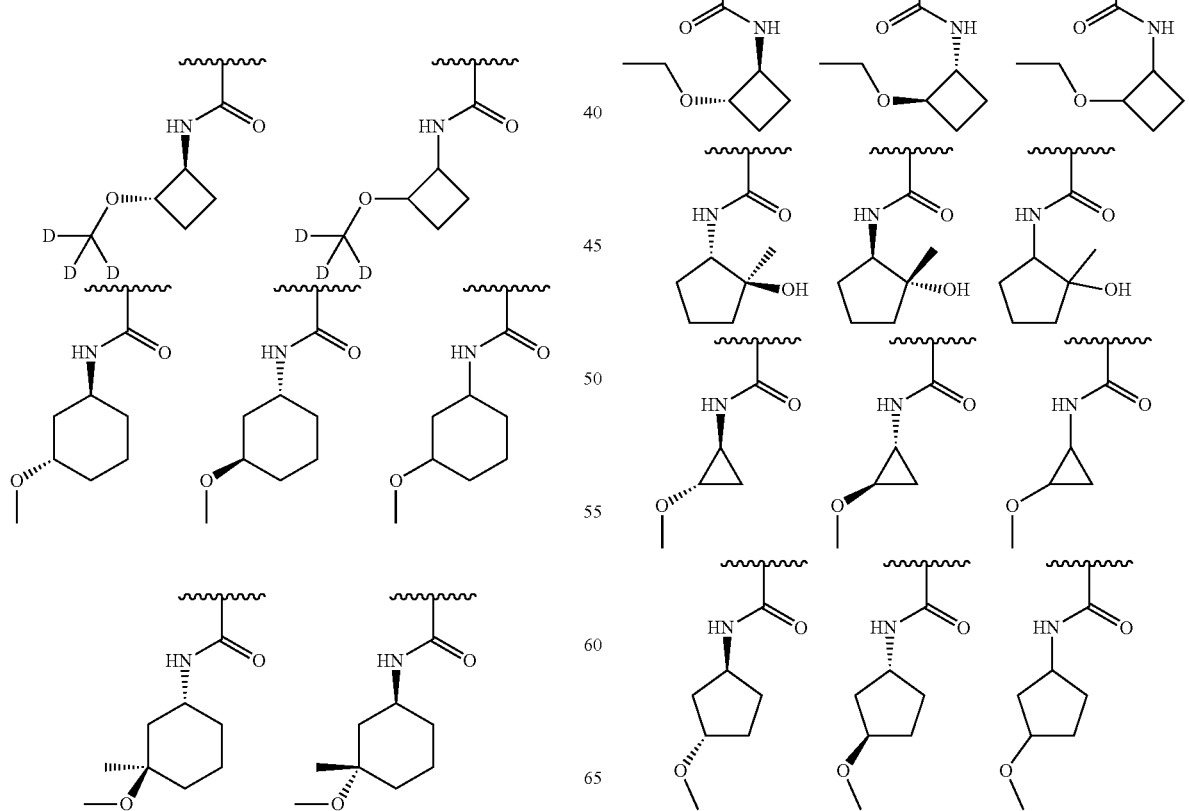

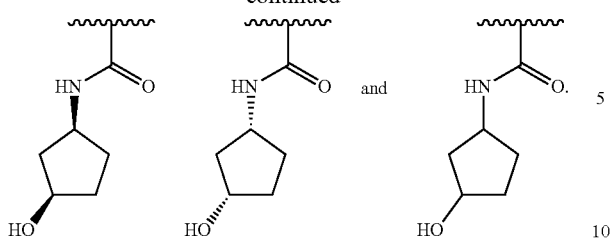
10. The method of claim 2, wherein $R^C$ is selected from
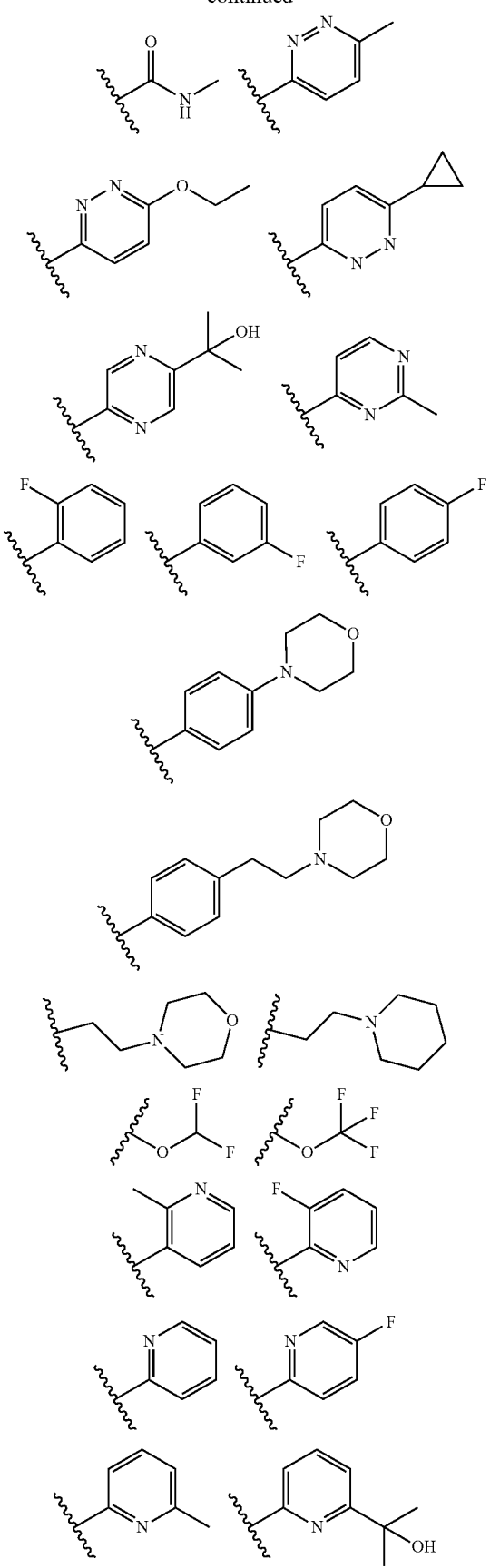

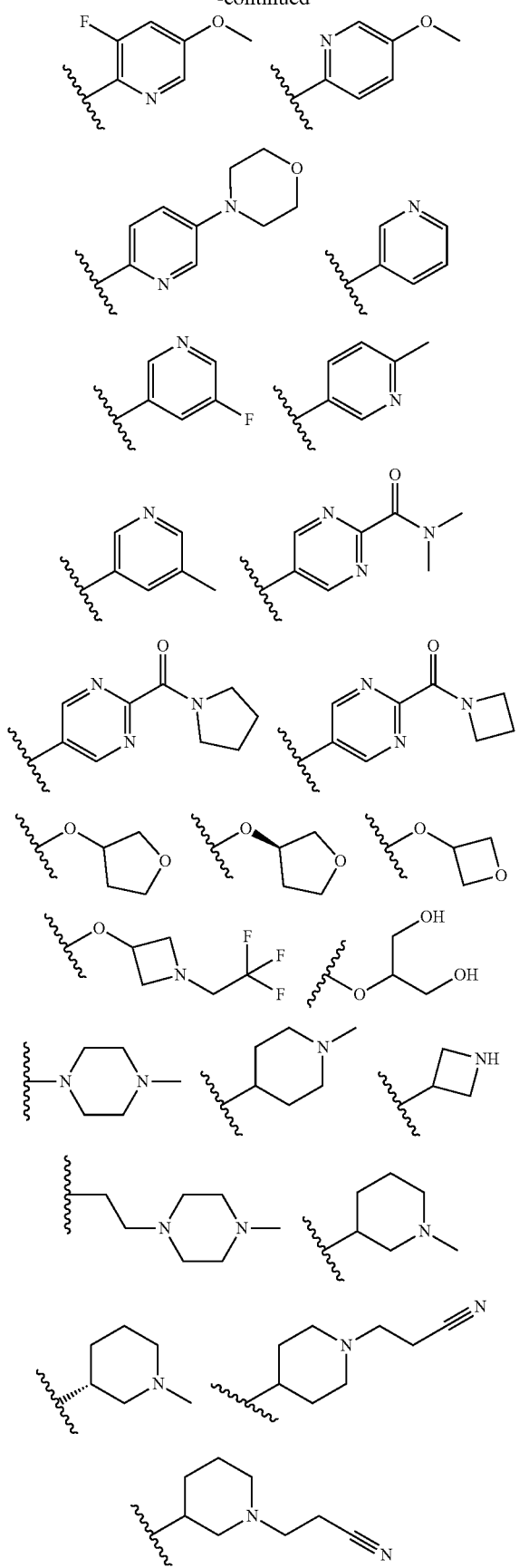
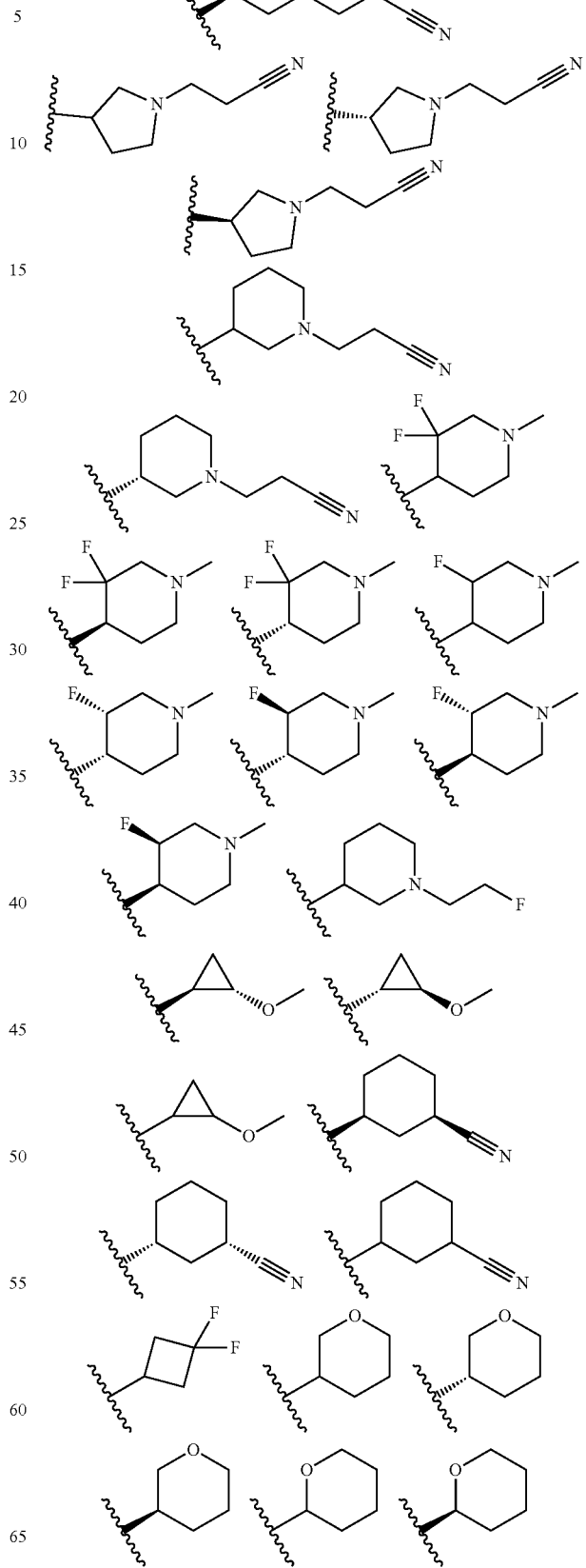

-continued
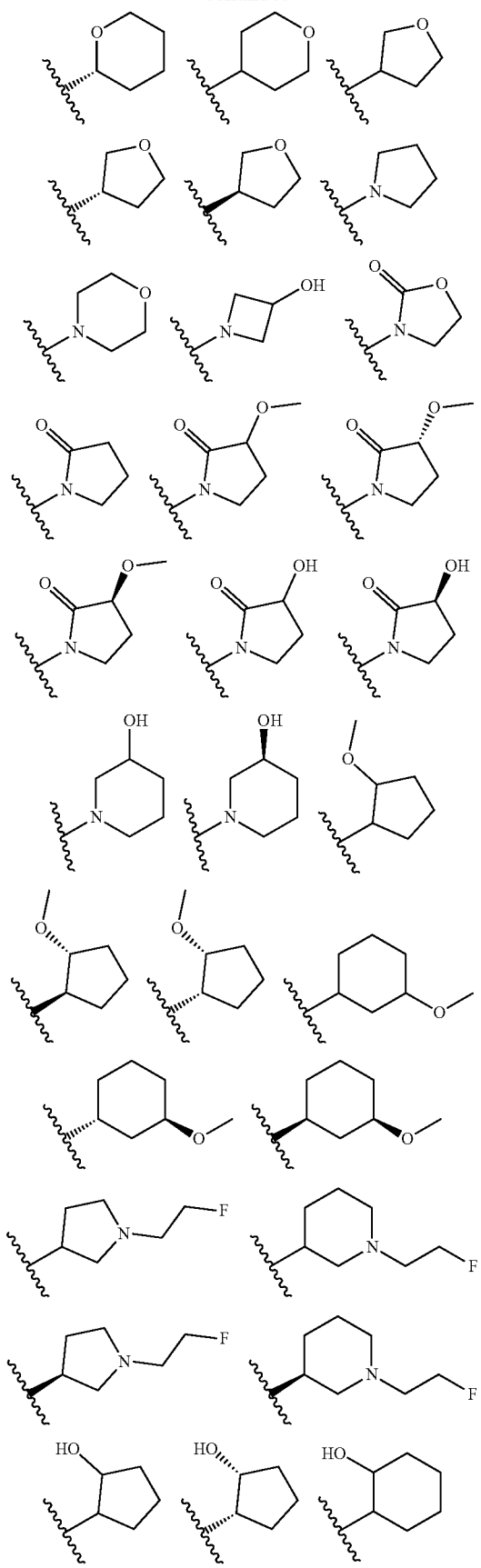
-continued
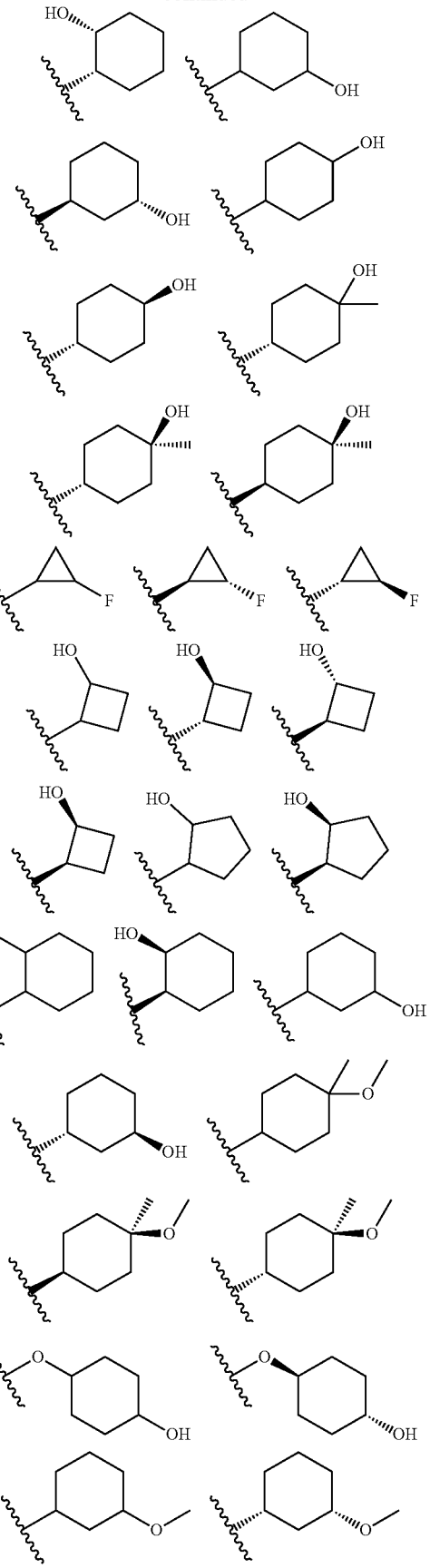

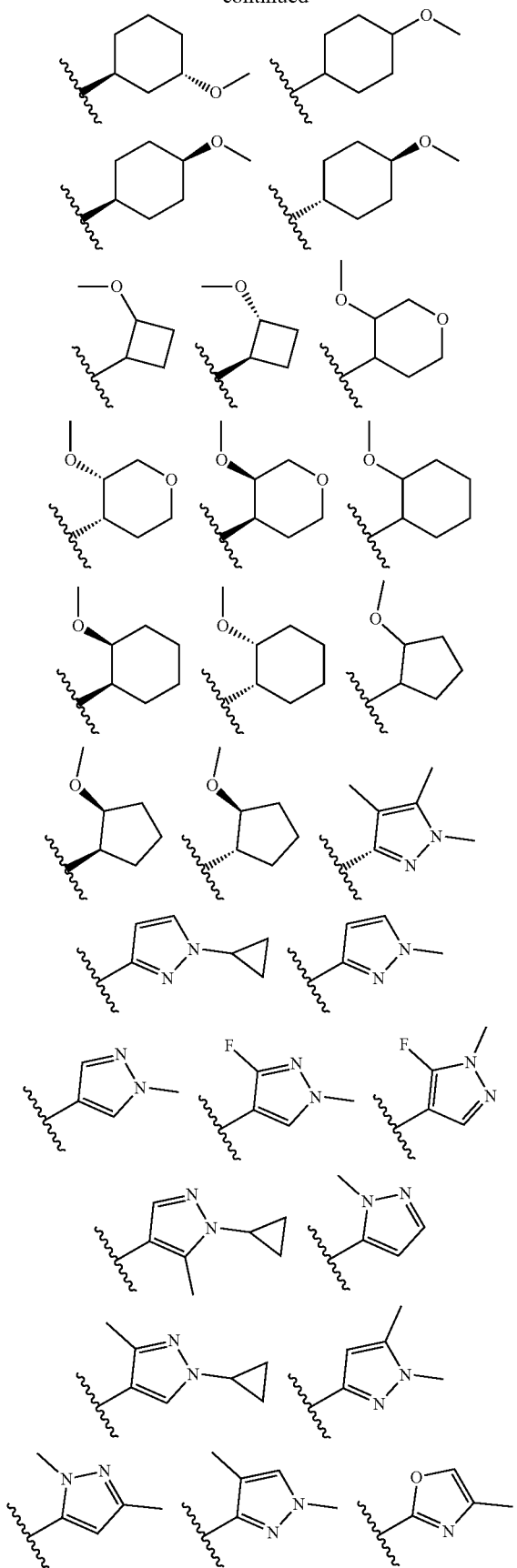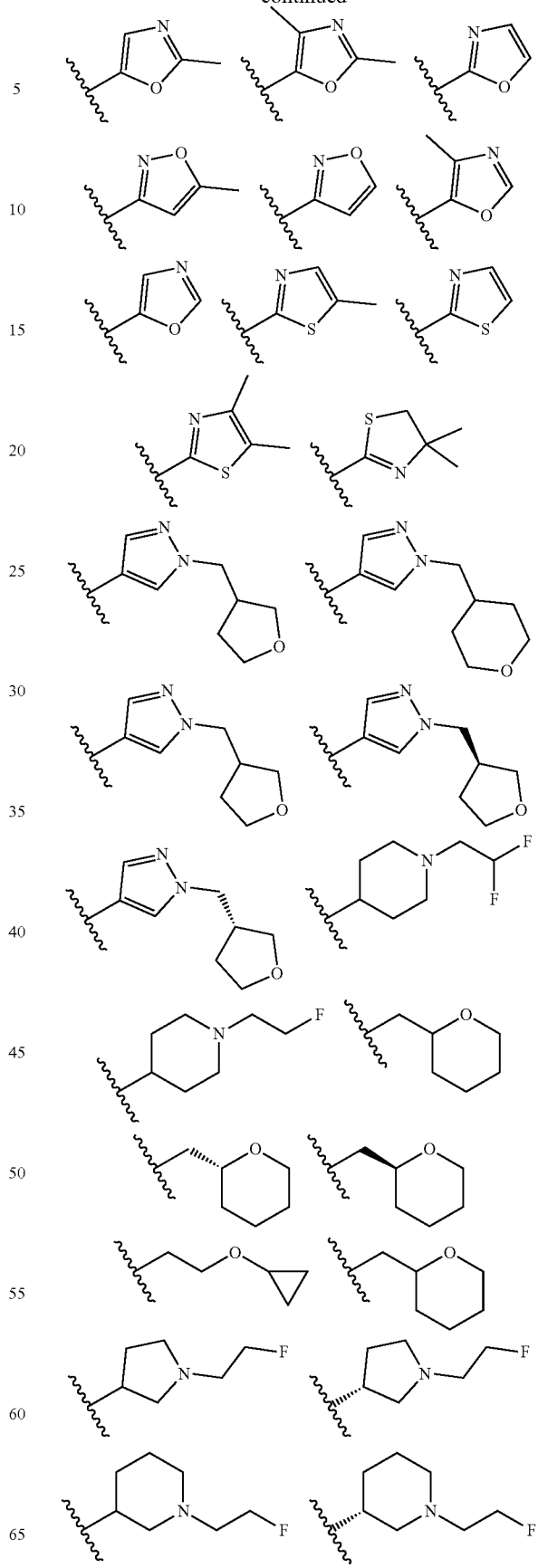

-continued
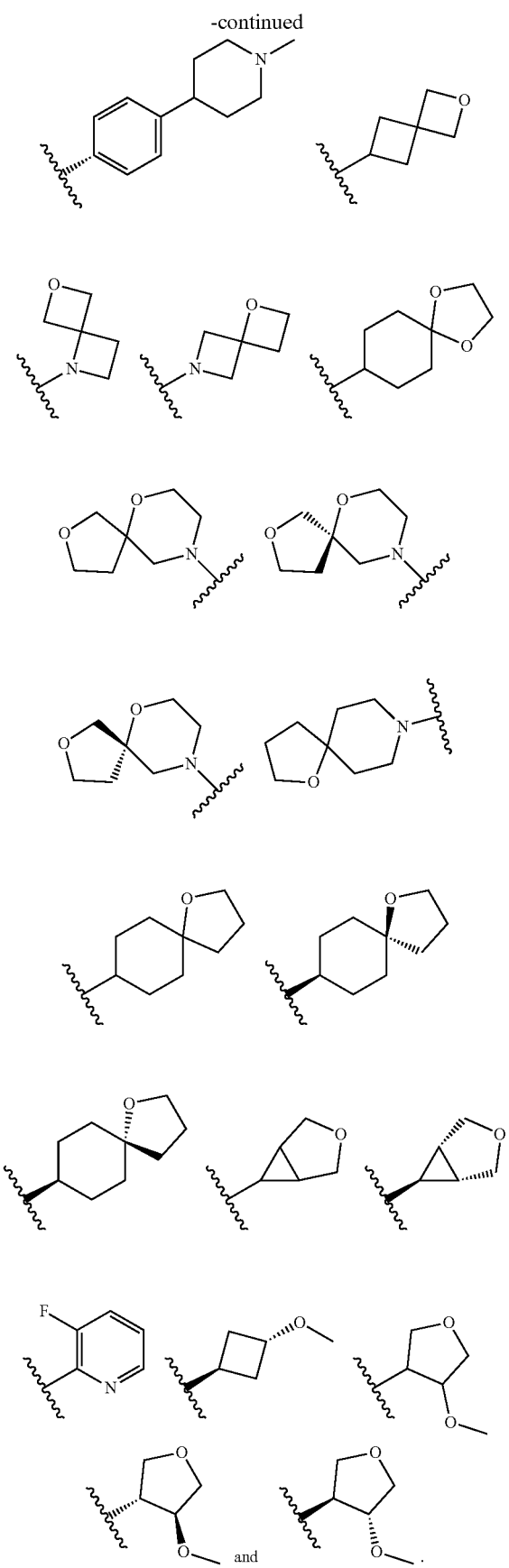
11. A compound selected from one of the following:
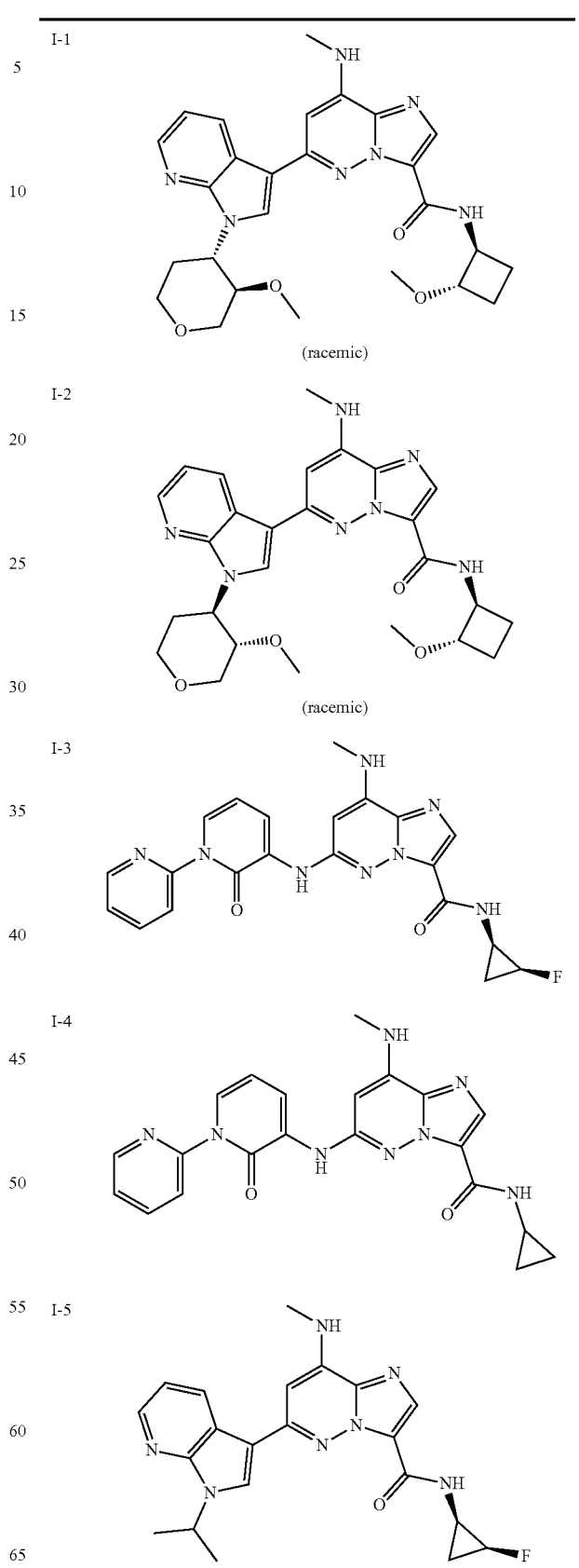

I-6
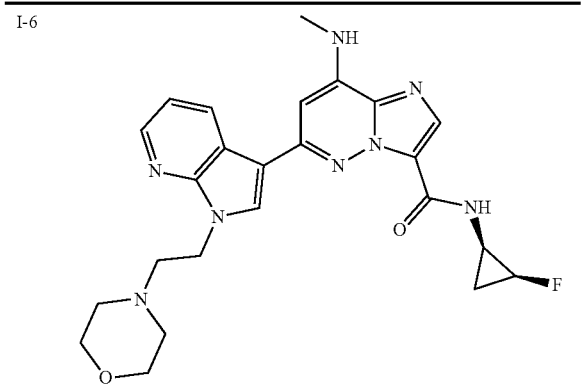
I-7
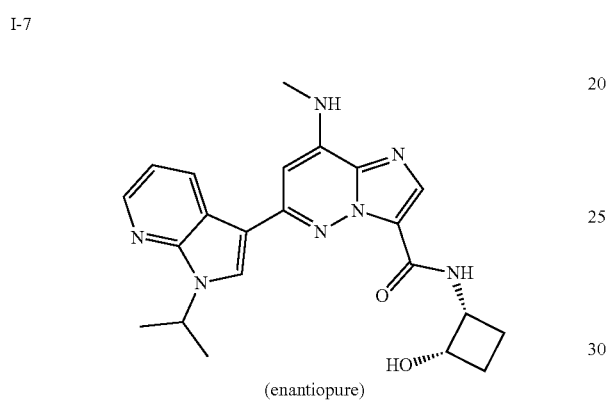
(enantiopure)
I-8
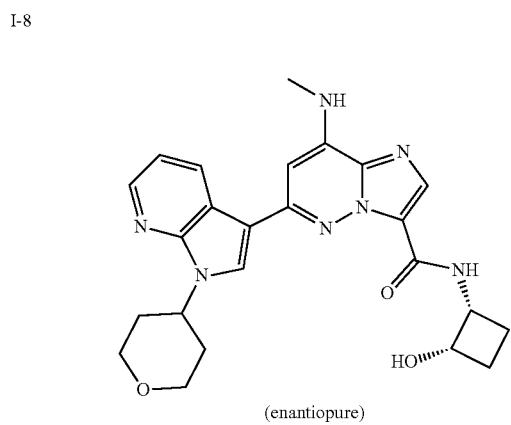
(enantiopure)
I-9
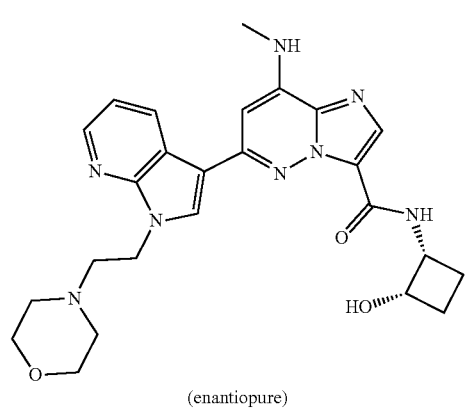
(enantiopure)
I-10
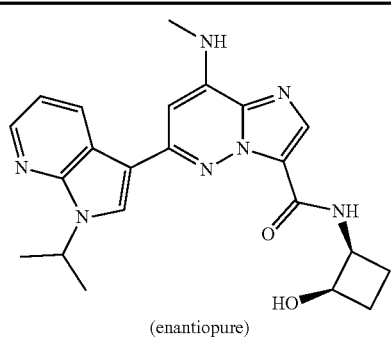
(enantiopure)
I-11
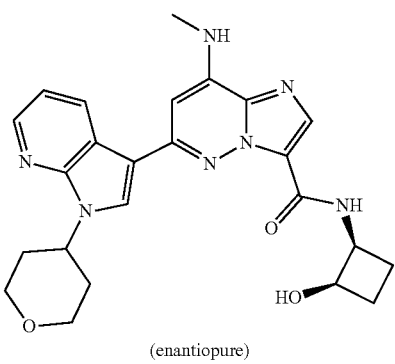
(enantiopure)
I-12
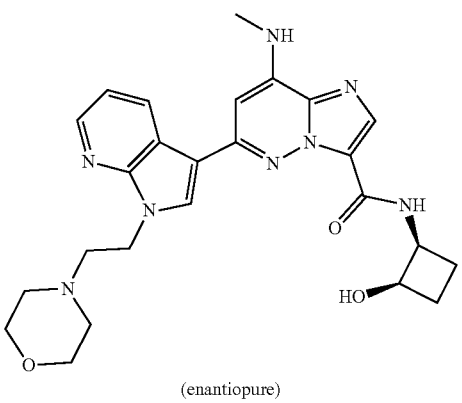
(enantiopure)
I-13
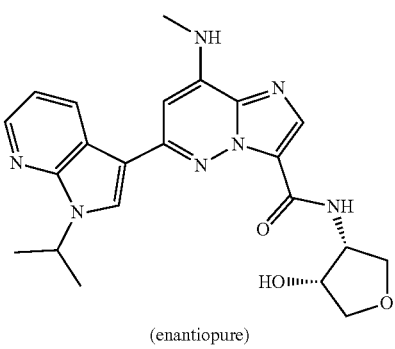
(enantiopure)

I-14
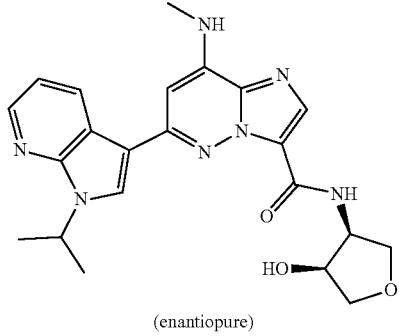
(enantiopure)
I-15
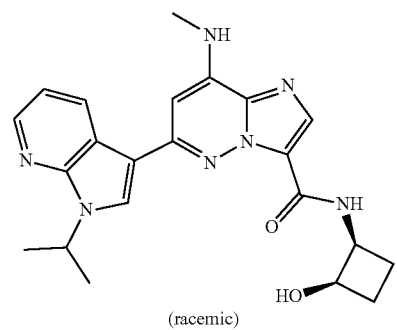
(racemic)
I-16
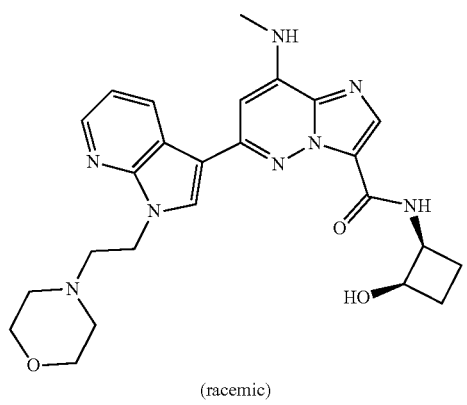
(racemic)
I-17
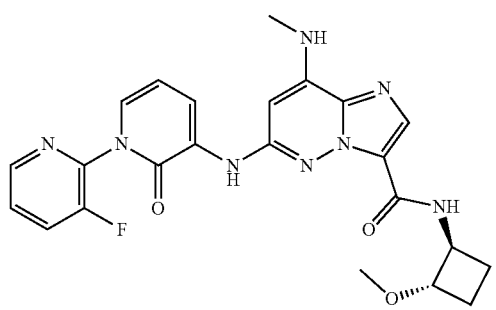 [SMILES: CNc1cc(Nc2cccn(-c3ncccc3F)c2=O)nn2c(C(=O)N[C@H]3CC[C@@H]3OC)cnc12]
I-18
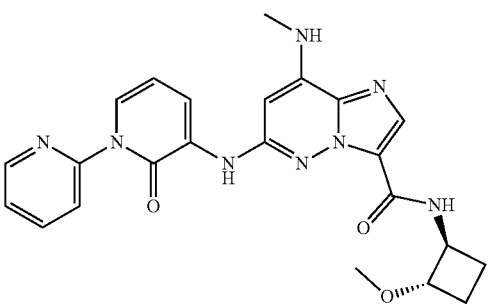 [SMILES: CNc1cc(Nc2cccn(-c3ccccn3)c2=O)nn2c(C(=O)N[C@H]3CC[C@@H]3OC)cnc12]
I-19
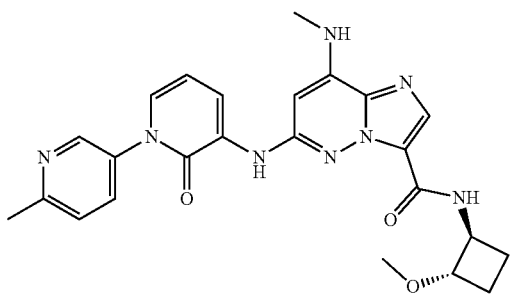 [SMILES: CNc1cc(Nc2cccn(-c3ccc(C)nc3)c2=O)nn2c(C(=O)N[C@H]3CC[C@@H]3OC)cnc12]
I-20
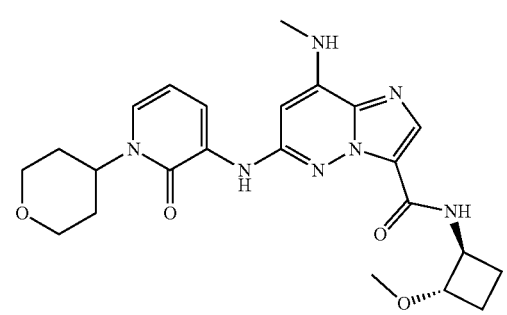 [SMILES: CNc1cc(Nc2cccn(C3CCOCC3)c2=O)nn2c(C(=O)N[C@H]3CC[C@@H]3OC)cnc12]
I-21
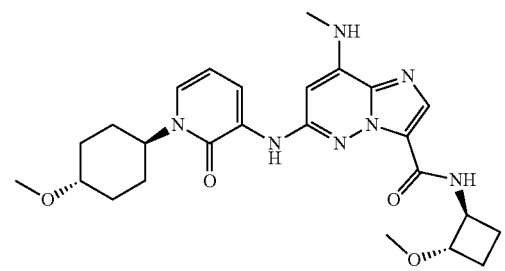 [SMILES: CNc1cc(Nc2cccn([C@H]3CC[C@H](OC)CC3)c2=O)nn2c(C(=O)N[C@H]3CC[C@@H]3OC)cnc12]
I-22
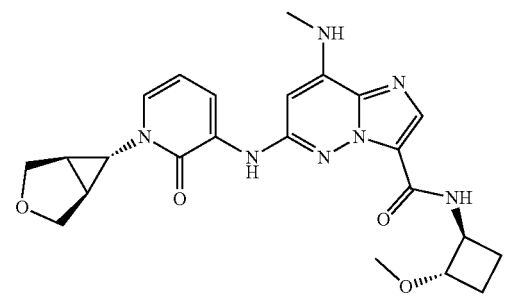 [SMILES: CNc1cc(Nc2cccn([C@H]3[C@@H]4COC[C@@H]43)c2=O)nn2c(C(=O)N[C@H]3CC[C@@H]3OC)cnc12]

I-23 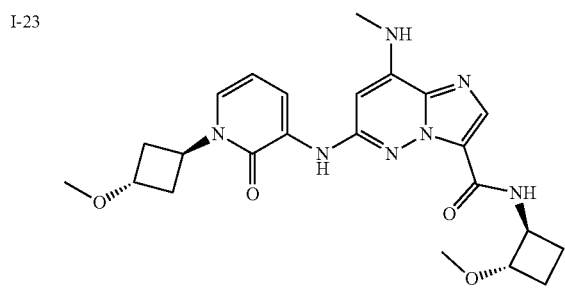
I-24 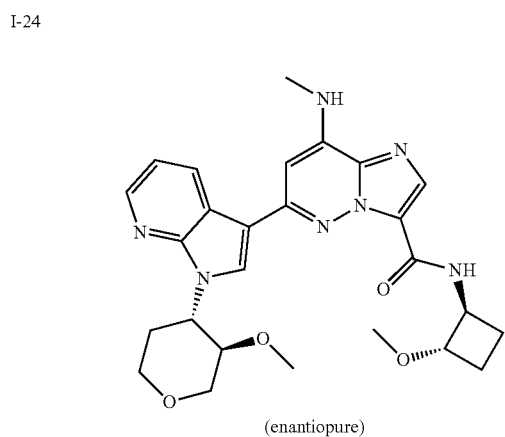
(enantiopure)
I-25 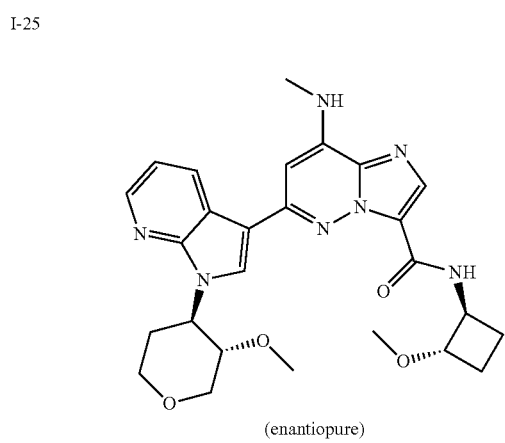
(enantiopure)
I-26 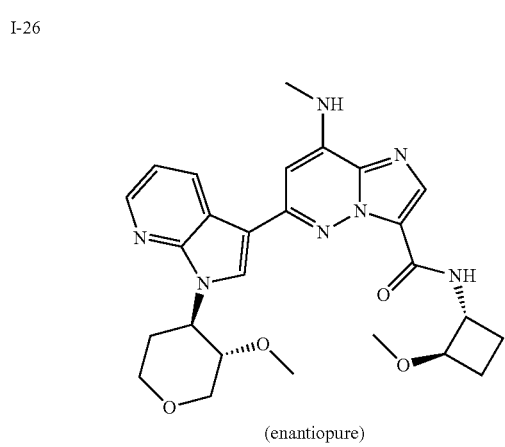
(enantiopure)
I-27 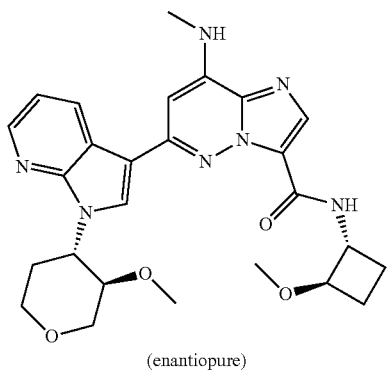
(enantiopure)
I-28 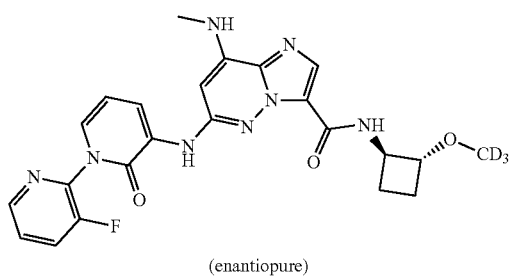
(enantiopure)
I-29 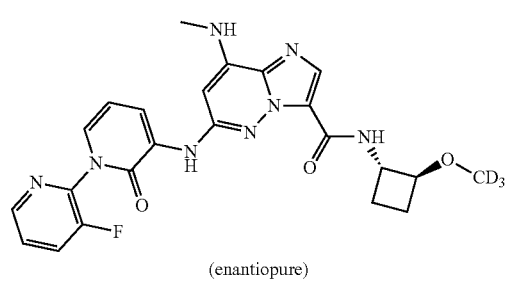
(enantiopure)
I-30 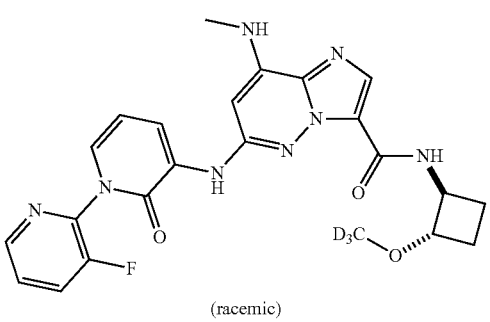
(racemic)
I-31 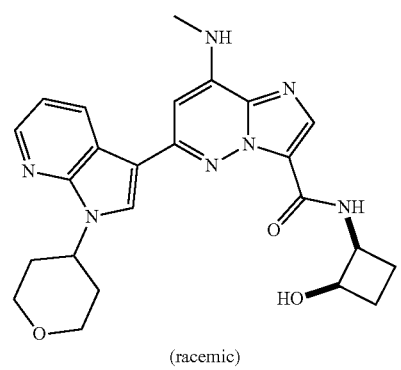
(racemic)

267
-continued
I-32
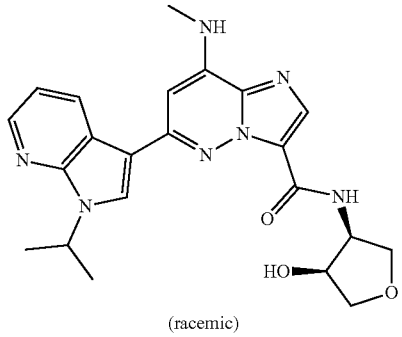
(racemic)
I-33
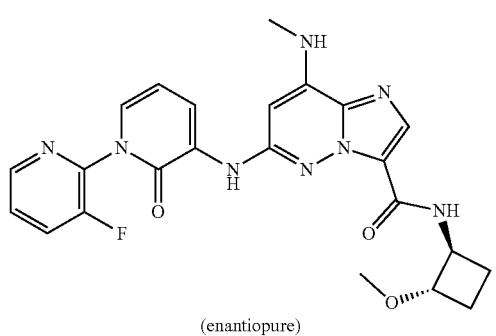
(enantiopure)
I-34
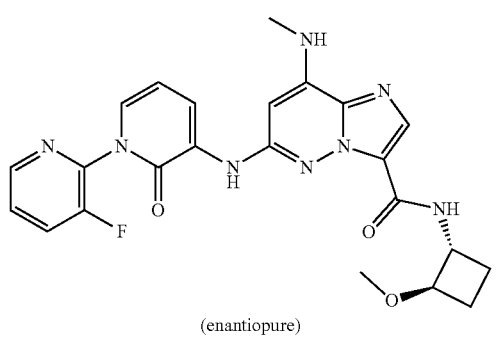
(enantiopure)
I-35
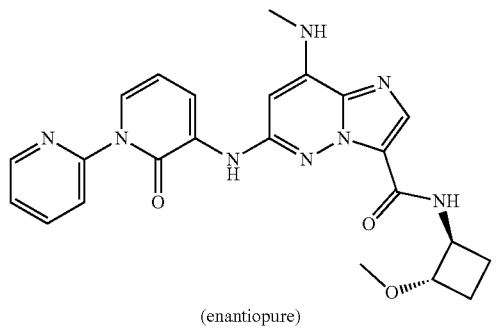
(enantiopure)
I-36
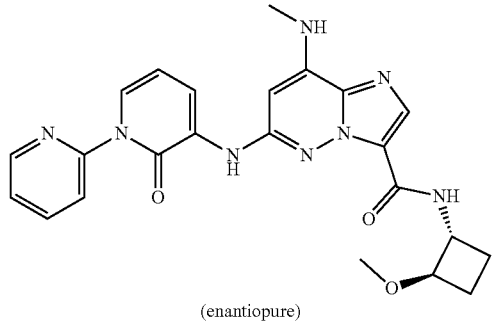
(enantiopure)
268
-continued
I-37
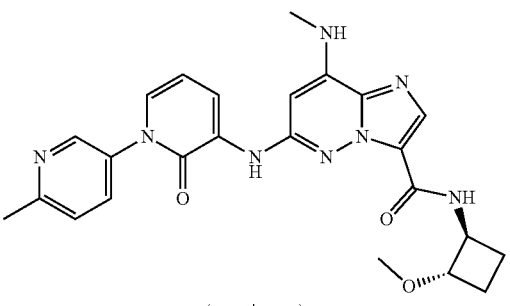
(enantiopure)
I-38
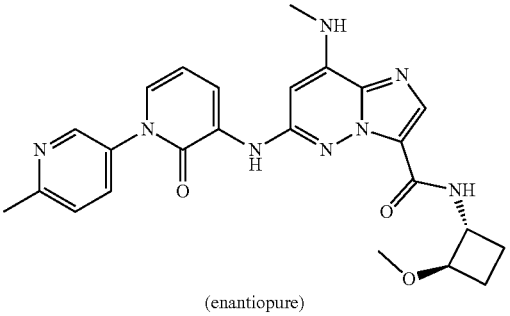
(enantiopure)
I-39
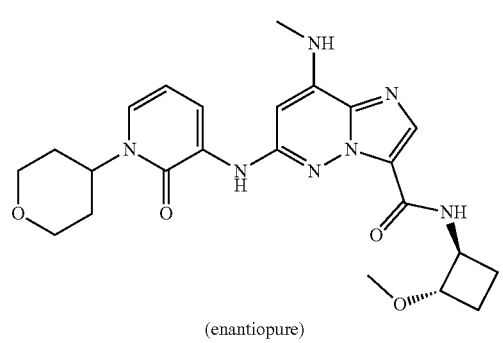
(enantiopure)
I-40
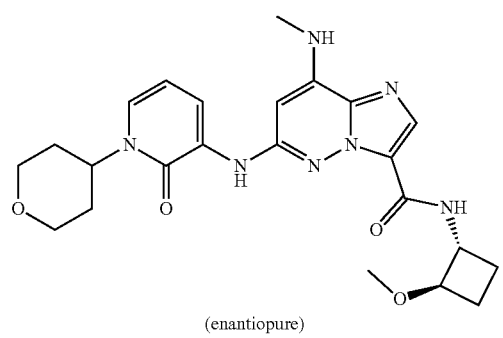
(enantiopure)
I-41
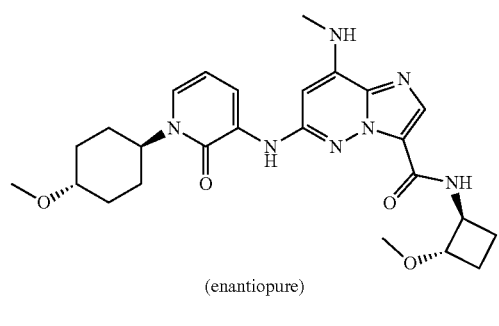
(enantiopure)

I-42
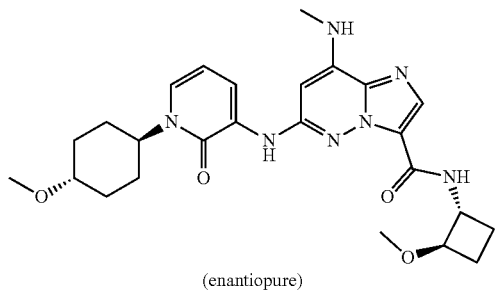
(enantiopure)
I-43
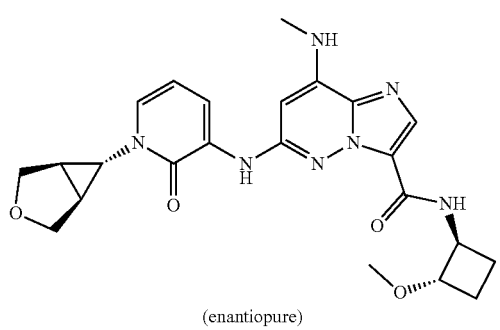
(enantiopure)
I-44
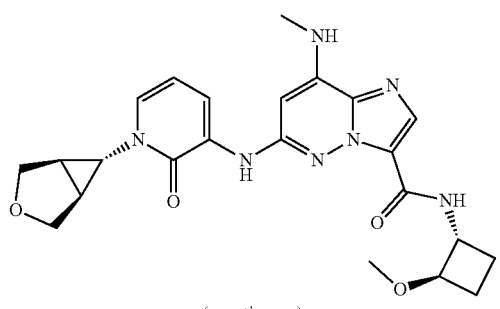
(enantiopure)
I-45
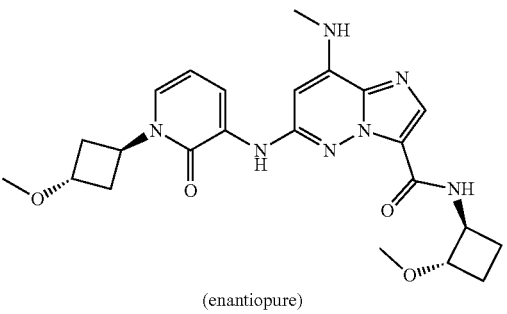
(enantiopure)
I-46
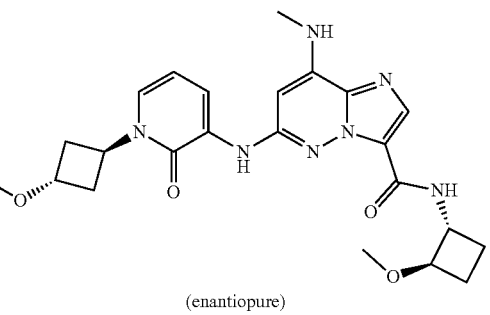
(enantiopure)
I-47
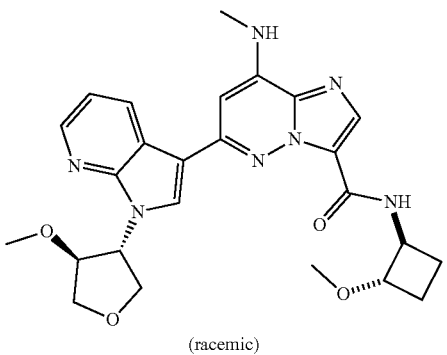
(racemic)
I-48
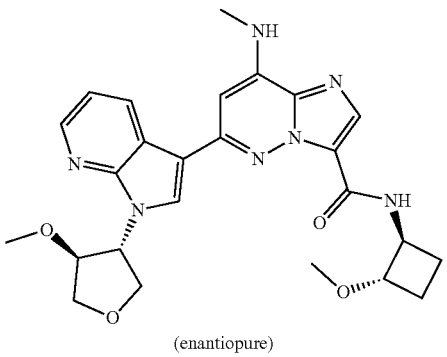
(enantiopure)
I-49
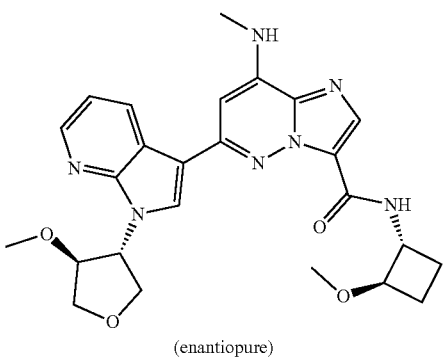
(enantiopure)

I-50

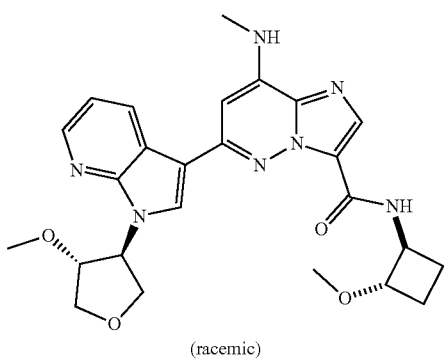

(racemic)

I-51

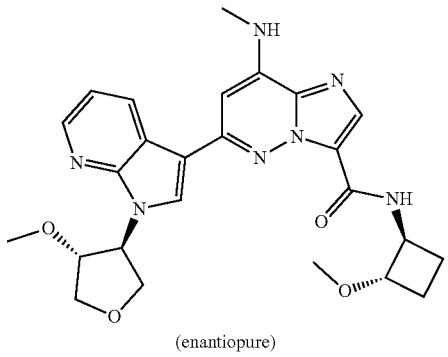

(enantiopure)

I-52

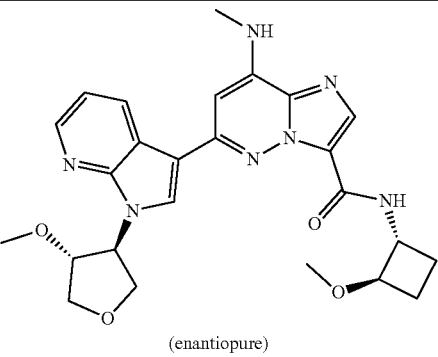

(enantiopure)

or a pharmaceutically acceptable salt thereof.

12. The method of claim 2, wherein the disorder, disease, or condition is psoriasis.

13. The method of claim 2, wherein the disorder, disease, or condition is Crohn's disease.

14. The method of claim 2, wherein the disorder, disease, or condition is ulcerative colitis.

15. The method of claim 2, wherein the disorder, disease, or condition is inflammatory bowel disease.

16. The method of claim 2, wherein the disorder, disease, or condition is systemic lupus erythematosus.

17. The method of claim 2, wherein the disorder, disease, or condition is asthma.

18. The method of claim 2, wherein the disorder, disease, or condition is chronic obstructive pulmonary disease.

19. The method of claim 2, wherein the endocrine disorder is cutaneous lupus erythematosus.

* * * * *